(12) United States Patent
Liu et al.

(10) Patent No.: US 10,301,388 B2
(45) Date of Patent: May 28, 2019

(54) ANTIBODY AGENTS SPECIFIC FOR HUMAN CD19 AND USES THEREOF

(71) Applicant: Eureka Therapeutics, Inc., Emeryville, CA (US)

(72) Inventors: Hong Liu, Emeryville, CA (US); Jingwei Lu, Emeryville, CA (US); Zhiyuan Yang, Emeryville, CA (US); Li Long, Emeryville, CA (US); Neal Cheng, Emeryville, CA (US)

(73) Assignee: Eureka Therapeutics, Inc., Emeryville, CA (US)

( * ) Notice: Subject to any disclaimer, the term of this patent is extended or adjusted under 35 U.S.C. 154(b) by 0 days.

(21) Appl. No.: 15/840,870

(22) Filed: Dec. 13, 2017

(65) Prior Publication Data

US 2018/0134787 A1 May 17, 2018

Related U.S. Application Data

(63) Continuation of application No. PCT/US2016/056325, filed on Oct. 11, 2016.

(60) Provisional application No. 62/240,624, filed on Oct. 13, 2015.

(51) Int. Cl.
| | |
|---|---|
| *C07K 16/28* | (2006.01) |
| *A61K 35/17* | (2015.01) |
| *C12N 5/0783* | (2010.01) |
| *A61P 35/00* | (2006.01) |
| *C07K 14/725* | (2006.01) |
| *C07K 14/705* | (2006.01) |
| *C07K 16/30* | (2006.01) |
| *A61K 39/00* | (2006.01) |
| *A61K 38/00* | (2006.01) |

(52) U.S. Cl.
CPC .......... *C07K 16/2803* (2013.01); *A61K 35/17* (2013.01); *A61P 35/00* (2018.01); *C07K 14/7051* (2013.01); *C07K 14/70521* (2013.01); *C07K 16/2809* (2013.01); *C07K 16/3061* (2013.01); *C12N 5/0638* (2013.01); *A61K 38/00* (2013.01); *A61K 2039/505* (2013.01); *A61K 2039/5156* (2013.01); *A61K 2039/5158* (2013.01); *C07K 2317/21* (2013.01); *C07K 2317/24* (2013.01); *C07K 2317/31* (2013.01); *C07K 2317/522* (2013.01); *C07K 2317/56* (2013.01); *C07K 2317/565* (2013.01); *C07K 2317/622* (2013.01); *C07K 2317/73* (2013.01); *C07K 2317/92* (2013.01); *C07K 2319/02* (2013.01); *C07K 2319/03* (2013.01); *C12N 2501/599* (2013.01); *C12N 2510/00* (2013.01)

(58) Field of Classification Search
CPC ............ C07K 16/2803; C07K 16/2809; A61K 35/17; A61K 2039/505; C12N 5/0638; C12N 2510/00

USPC .......... 530/387.1, 387.3; 435/325; 424/93.21
See application file for complete search history.

(56) References Cited

U.S. PATENT DOCUMENTS

| | | |
|---|---|---|
| 2006/0035320 A1 | 2/2006 | Tissot et al. |
| 2008/0118512 A1 | 5/2008 | Auf Der Maur et al. |
| 2008/0138336 A1 | 6/2008 | Damschroder et al. |
| 2009/0142349 A1 | 6/2009 | Rao-Naik et al. |
| 2010/0005543 A1 | 1/2010 | Sampson et al. |
| 2011/0286916 A1 | 11/2011 | Aste-Amezaga et al. |
| 2011/0311517 A1 | 12/2011 | Li et al. |
| 2014/0370022 A1 | 12/2014 | Kim et al. |
| 2015/0118237 A1 | 4/2015 | Kojoh et al. |
| 2015/0274828 A1 | 10/2015 | Sun et al. |

OTHER PUBLICATIONS

Sela-Culang et al. (2013) Frontiers in Immunology, vol. 4, pp. 1-13.*
Hammer (2012) Mabs, vol. 4:5, 571-577.*
Almasbak et al. (2016) J. Immunol. Res., vol. 2016.*
International Search Report in PCT/US2016/056325, dated Mar. 31, 2017, 6 pages.
Baeuerle et al., "Bispecific T-Cell Engaging Antibodies for Cancer Therapy," Cancer research 69, No. 12 (2009): 4941-4944.
Bargou et al., " Tumor Regression in Cancer Patients by Very Low Doses of a T Cell-Engaging Antibody," Science 321, No. 5891 (2008): 974-977.
Dreier et al., "T Cell Costimulus-Independent and Very Efficacious Inhibition of Tumor Growth in Mice Bearing Subcutaneous or Leukemic Human B Cell Lymphoma Xenografts by a CD19-/CD3-Bispecific Single-Chain Antibody Contruct," J Immunol 2003; 170: 4397-4402.
Hoffman, et al., "Blinatumomab, a bi-specific anti-CD19/CD3 BiTE® antibody for the treatment of acute lymphoblastic leukemia: perspectives and current pediatric applications." Frontiers in oncology 4 (2014).
Molhoj et al., "CD19-/CD3-bispecific antibody of the BiTE class is far superior to tandem diabody with respect to redirected tumor cell lysis," Molecular Immunology 44 (2007) 1935-1943.
Reichert, et al., "The future of antibodies as cancer drugs." Drug discovery today 17, No. 17 (2012): 954-963.
Suresh, et al., "New antibody approaches to lymphoma therapy." Journal of hematology & oncology 7 (2014).
Wolf et al., "BiTEs: bispecific antibody constructs with unique anti-tumor activity," Drug discovery today 10, No. 18 (2005): 1237-1244.
International Preliminary Report on Patenability in PCT/US2016/056325, international filing date Oct. 11, 2016, 9 pages.

(Continued)

*Primary Examiner* — Anne Marie S Wehbe
(74) *Attorney, Agent, or Firm* — Kilpatrick Townsend & Stockton LLP

(57) ABSTRACT

Described herein are human antibody agents and multi-specific binding agents that specifically bind human CD 19, in particular, native human CD 19. Also provided herein are methods of using the same or compositions thereof for the detection, prevention and/or therapeutic treatment of diseases characterized by CD 19 expression, in particular, B cell lymphomas and leukemias.

19 Claims, 15 Drawing Sheets
Specification includes a Sequence Listing.

(56) References Cited

OTHER PUBLICATIONS

Hammer, "CD19 as an attractive target for antibody-based Therapy," mAbs, 4:5, Sep./Oct. 2012, 571-577.

* cited by examiner

4

5

6

7

37

BL19

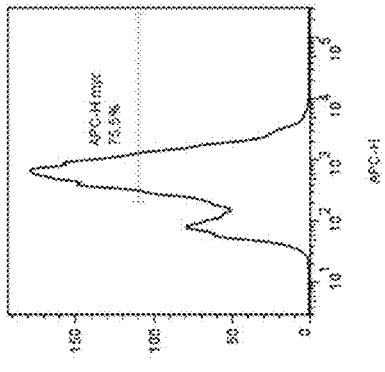
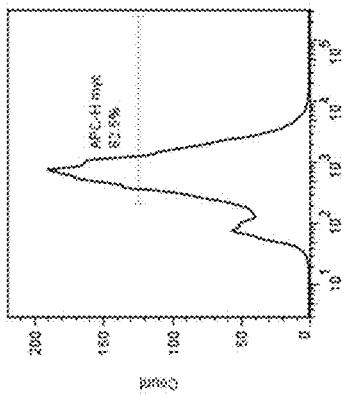
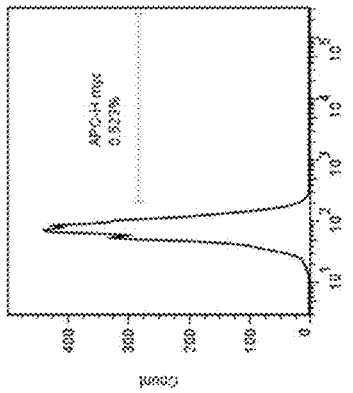
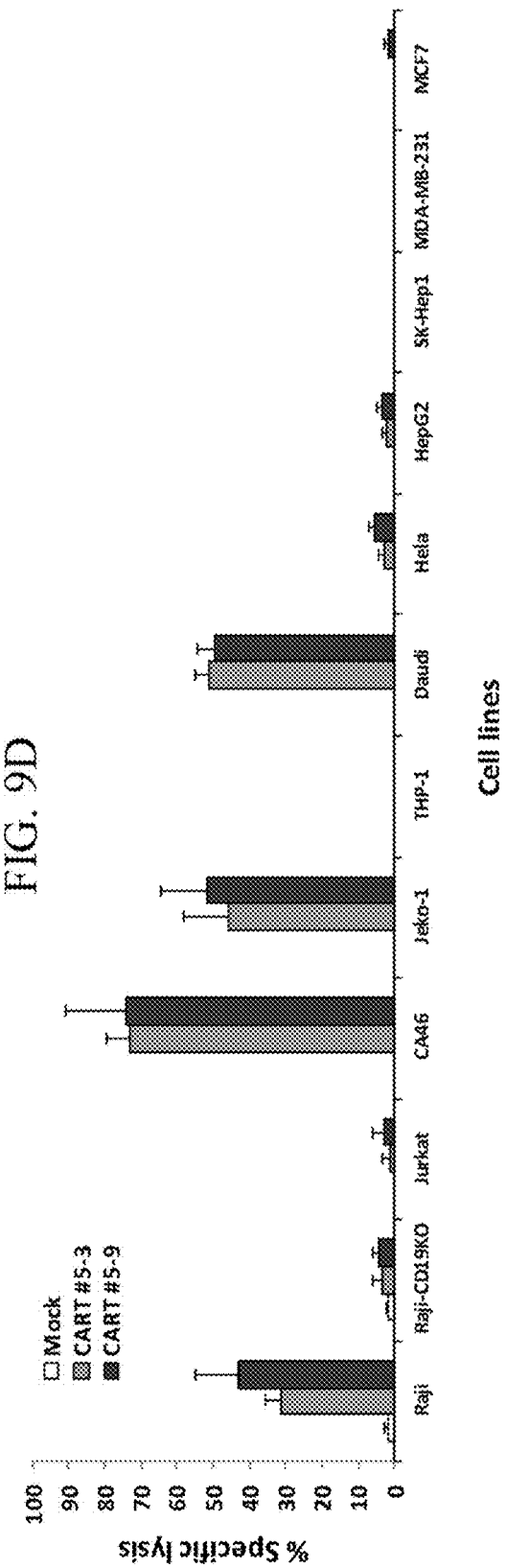

FIG. 12A
3T3 & 3T3-CD19
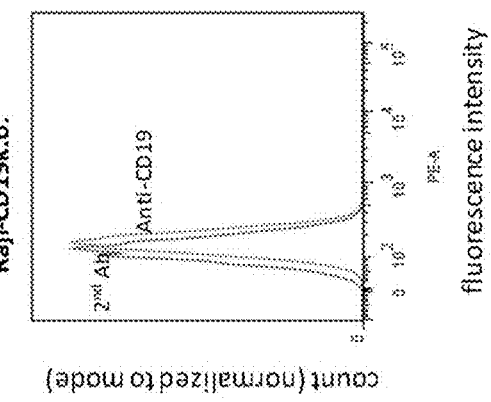
FIG. 12B            FIG. 12C
Raji & Raji-CD19k.o.
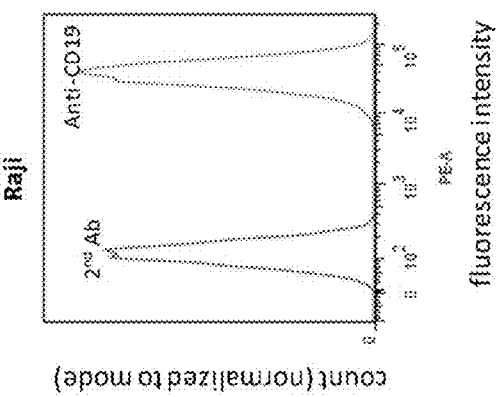
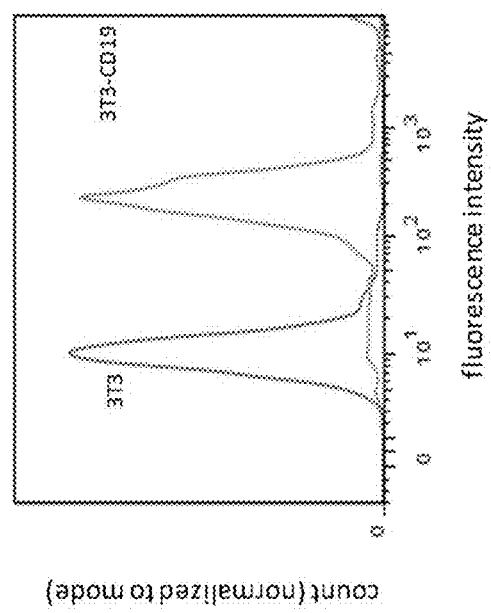

ANTIBODY AGENTS SPECIFIC FOR HUMAN CD19 AND USES THEREOF

CROSS-REFERENCE TO RELATED APPLICATIONS

This application is a continuation of PCT/US2016/056325, filed Oct. 11, 2016, which claims the benefit of U.S. Provisional Patent Application Ser. No. 62/240,624, filed Oct. 13, 2015, each of which is incorporated herein by reference in its entirety.

SEQUENCE LISTING

The present specification makes reference to a Sequence Listing submitted electronically as a .txt file named SEQ_TXT_1070348. The .txt file was generated on Dec. 11, 2017 and is 180,224 bytes in size. The entire content of the Sequence Listing is incorporated herein by reference.

BACKGROUND

With the advent of antibody-based technologies, development of new antibody-based therapeutics for the treatment of cancer has attracted tremendous interest over the last decade. Indeed, a variety of formats (e.g., chimeric, humanized, human, radiolabeled, drug-conjugated, multi-specific, etc.) continue to be developed and some have demonstrated significant promise in cancer treatment. A 2015 list, reported that nearly two dozen therapeutic antibody agents had received marketing approval or were in review in the United States or Europe for various cancer indications (see Janice M. Reichert, PhD, Reichert Biotechnology Consulting LLC, May 26, 2015). Still, development of particularly effective antibody agents remains a challenge.

SUMMARY

The present invention provides, among other things, human antibody agents, multi-specific binding agents (e.g., bi-specific antibodies) and chimeric antigen receptors that specifically bind CD19, in particular human CD19. In some embodiments, provided human antibody agents, multi-specific binding agents and chimeric antigen receptors demonstrate high specificity for human CD19 in native format (e.g., expressed on the surface of a cell) as compared to one or more reference human antibody agents, multi-specific binding agents and/or chimeric antigen receptors. In some embodiments, provided human antibody agents, multi-specific binding agents (e.g., bi-specific antibodies) and chimeric antigen receptors overcome suboptimal selectivity associated with antibody-based anti-CD19 therapeutics developed with established technologies (e.g., engineered non-human animals, phage display, humanized antibodies generated from antibodies of murine origin, etc.). In some embodiments, provided human antibody agents, multi-specific binding agents (e.g., bi-specific antibodies) and chimeric antigen receptors effectively mediate killing of cancer cells characterized by CD19 expression (e.g., lymphomas and/or leukemias).

Although embodiments employing antibody agents that contain human sequences (i.e., human heavy and light chain variable region sequences including human CDR sequences) are extensively discussed herein, the present invention also provides non-human antibody agents. In some embodiments, non-human antibody agents comprise human CDR sequences from an antibody agent as described herein and non-human framework sequences. Non-human framework sequences include, in some embodiments, any sequence that can be used for generating synthetic heavy and/or light chain variable regions using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a provided antibody agent includes an antibody agent generated by grafting one or more human CDR sequences as described herein onto a non-human framework sequence (e.g., a mouse or chicken framework sequence). In many embodiments, provided antibody agents are human antibody agents (e.g., a human monoclonal antibody or fragment thereof, human antigen-binding protein or polypeptide, human multi-specific binding agent [e.g., a human bi-specific antibody], a human polypeptide having one or more structural components of a human immunoglobulin polypeptide).

In some embodiments, the present invention provides an antibody agent that specifically binds human CD19, wherein the antibody agent comprises a heavy chain CDR1 (HC-CDR1), heavy chain CDR2 (HC-CDR2) and a heavy chain CDR3 (HC-CDR3), and a light chain CDR1 (LC-CDR1), light chain CDR2 (LC-CDR2) and a light chain CDR3 (LC-CDR3), wherein the HC-CDR1 comprises G-$X_1$-$X_2$-F-$X_3$-S-$X_4$-$X_5$ (SEQ ID NO:291), and wherein $X_1$ is F, G, Y or V, $X_2$ is S or T, $X_3$ is S or T, $X_4$ is N or Y, and $X_5$ is A, W or Y;

wherein the HC-CDR2 comprises I-$X_6$-P-$X_7$-$X_8$-$X_9$-$X_{10}$-T (SEQ ID NO:292), and wherein $X_6$ is S, D or Y, $X_7$ is E, S, G or I, $X_8$ is D, F or V, $X_9$ is G or S, and $X_{10}$ is K, E, Y, D or T;

wherein the LC-CDR1 comprises S-S-N-$X_{11}$-G-$X_{12}$-$X_{13}$-$X_{14}$ (SEQ ID NO:293) or N-I-G-S-$X_{15}$-S(SEQ ID NO:294), and wherein $X_{11}$ is I or V, $X_{12}$ is N, S or T, $X_{13}$ is N, H or K, $X_{14}$ is Y, A or T, and $X_{15}$ is K or E; and/or wherein the LC-CDR2 comprises $X_{16}$-$X_{17}$-$X_{18}$ (SEQ ID NO:295), and wherein $X_{16}$ is D, E, S, R or Y, $X_{17}$ is N or D, and $X_{18}$ is N, Y, S or D.

In some embodiments, the present invention provides a human antibody agent that specifically binds human CD19, wherein the human antibody agent comprises one or more heavy chain CDRs that each have a sequence that is at least 50% (e.g., at least about 55%, 60%, 65%, 70%, 75%, 80%, 85%, 90%, 95%, 96%, 97%, 98%, or 99%) identical to one or more heavy chain CDRs selected from Table 2, and/or one or more light chain CDRs that each have a sequence that is at least 50% (e.g., at least about 55%, 60%, 65%, 70%, 75%, 80%, 85%, 90%, 95%, 96%, 97%, 98%, or 99%) identical to one or more light chain CDRs selected from Table 3.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:73, SEQ ID NO:74 and SEQ ID NO:75, and a light chain CDR1, light chain CDR2 and light chain CDR3 that each have a sequence that is at least 95% identical to each of light chain CDR1, light chain CDR2 and light chain CDR3 set forth in SEQ ID NO:181, SEQ ID NO:182 and SEQ ID NO:183.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:76, SEQ ID NO:77 and SEQ ID NO:78, and a light chain CDR1, light chain CDR2 and light chain CDR3 that each have a sequence that is at least 95% identical to each of light chain CDR1, light chain CDR2 and light chain CDR3 set forth in SEQ ID NO:184, SEQ ID NO:185 and SEQ ID NO:186.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:79, SEQ ID NO:80 and SEQ ID NO:81, and a light chain CDR1, light chain CDR2 and light chain CDR3 that each have a sequence that is at least 95% identical to each of light chain CDR1, light chain CDR2 and light chain CDR3 set forth in SEQ ID NO:187, SEQ ID NO:188 and SEQ ID NO:189.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:82, SEQ ID NO:83 and SEQ ID NO:84, and a light chain CDR1, light chain CDR2 and light chain CDR3 that each have a sequence that is at least 95% identical to each of light chain CDR1, light chain CDR2 and light chain CDR3 set forth in SEQ ID NO:190, SEQ ID NO:191 and SEQ ID NO:192.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:85, SEQ ID NO:86 and SEQ ID NO:87, and a light chain CDR1, light chain CDR2 and light chain CDR3 that each have a sequence that is at least 95% identical to each of light chain CDR1, light chain CDR2 and light chain CDR3 set forth in SEQ ID NO:193, SEQ ID NO:194 and SEQ ID NO:195.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:88, SEQ ID NO:89 and SEQ ID NO:90, and a light chain CDR1, light chain CDR2 and light chain CDR3 that each have a sequence that is at least 95% identical to each of light chain CDR1, light chain CDR2 and light chain CDR3 set forth in SEQ ID NO:196, SEQ ID NO:197 and SEQ ID NO:198.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:91, SEQ ID NO:92 and SEQ ID NO:93, and a light chain CDR1, light chain CDR2 and light chain CDR3 that each have a sequence that is at least 95% identical to each of light chain CDR1, light chain CDR2 and light chain CDR3 set forth in SEQ ID NO:199, SEQ ID NO:200 and SEQ ID NO:201.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:94, SEQ ID NO:95 and SEQ ID NO:96, and a light chain CDR1, light chain CDR2 and light chain CDR3 that each have a sequence that is at least 95% identical to each of light chain CDR1, light chain CDR2 and light chain CDR3 set forth in SEQ ID NO:202, SEQ ID NO:203 and SEQ ID NO:204.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:97, SEQ ID NO:98 and SEQ ID NO:99, and a light chain CDR1, light chain CDR2 and light chain CDR3 that each have a sequence that is at least 95% identical to each of light chain CDR1, light chain CDR2 and light chain CDR3 set forth in SEQ ID NO:205, SEQ ID NO:206 and SEQ ID NO:207.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:100, SEQ ID NO:101 and SEQ ID NO:102, and a light chain CDR1, light chain CDR2 and light chain CDR3 that each have a sequence that is at least 95% identical to each of light chain CDR1, light chain CDR2 and light chain CDR3 set forth in SEQ ID NO:208, SEQ ID NO:209 and SEQ ID NO:210.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:103, SEQ ID NO:104 and SEQ ID NO:105, and a light chain CDR1, light chain CDR2 and light chain CDR3 that each have a sequence that is at least 95% identical to each of light chain CDR1, light chain CDR2 and light chain CDR3 set forth in SEQ ID NO:211, SEQ ID NO:212 and SEQ ID NO:213.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:106, SEQ ID NO:107 and SEQ ID NO:108, and a light chain CDR1, light chain CDR2 and light chain CDR3 that each have a sequence that is at least 95% identical to each of light chain CDR1, light chain CDR2 and light chain CDR3 set forth in SEQ ID NO:214, SEQ ID NO:215 and SEQ ID NO:216.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:109, SEQ ID NO:110 and SEQ ID NO:111, and a light chain CDR1, light chain CDR2 and light chain CDR3 that each have a sequence that is at least 95% identical to each of light chain CDR1, light chain CDR2 and light chain CDR3 set forth in SEQ ID NO:217, SEQ ID NO:218 and SEQ ID NO:219.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:112, SEQ ID NO:113 and SEQ ID NO:114, and a light chain CDR1, light chain CDR2 and light chain CDR3 that each have a sequence that is at least 95% identical to each of light chain CDR1, light chain CDR2 and light chain CDR3 set forth in SEQ ID NO:220, SEQ ID NO:221 and SEQ ID NO:222.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:115, SEQ ID NO:116 and SEQ ID NO:117, and a light chain CDR1, light chain CDR2 and light chain CDR3 that each have a sequence that is at least 95% identical to each of light chain CDR1, light chain CDR2 and light chain CDR3 set forth in SEQ ID NO:223, SEQ ID NO:224 and SEQ ID NO:225.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:118, SEQ ID NO:119 and SEQ ID NO:120, and a light chain CDR1, light chain CDR2 and light chain CDR3 that each have a sequence that is at least 95% identical to each of light chain CDR1, light chain CDR2 and light chain CDR3 set forth in SEQ ID NO:226, SEQ ID NO:227 and SEQ ID NO:228.

In some embodiments, a human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:121, SEQ ID NO:122 and SEQ ID NO:123, and a light chain CDR1, light chain CDR2 and light chain CDR3 that each have a sequence that is at least 95% identical to each of light chain CDR1, light chain CDR2 and light chain CDR3 set forth in SEQ ID NO:229, SEQ ID NO:230 and SEQ ID NO:231.

In some embodiments, a human antibody agent comprises the heavy chain CDRs of SEQ ID NO:73, SEQ ID NO:74 and SEQ ID NO:75, and the light chain CDRs of SEQ ID NO:181, SEQ ID NO:182 and SEQ ID NO:183.

In some embodiments, a human antibody agent comprises the heavy chain CDRs of SEQ ID NO:76, SEQ ID NO:77 and SEQ ID NO:78, and the light chain CDRs of SEQ ID NO:184, SEQ ID NO:185 and SEQ ID NO:186.

In some embodiments, a human antibody agent comprises the heavy chain CDRs of SEQ ID NO:79, SEQ ID NO:80 and SEQ ID NO:81 and the light chain CDRs of SEQ ID NO:187, SEQ ID NO:188 and SEQ ID NO:189.

In some embodiments, a human antibody agent comprises the heavy chain CDRs of SEQ ID NO:82, SEQ ID NO:83 and SEQ ID NO:84, and the light chain CDRs of SEQ ID NO:190, SEQ ID NO:191 and SEQ ID NO:192.

In some embodiments, a human antibody agent comprises the heavy chain CDRs of SEQ ID NO:85, SEQ ID NO:86 and SEQ ID NO:87, and the light chain CDRs of SEQ ID NO:193, SEQ ID NO:194 and SEQ ID NO:195.

In some embodiments, a human antibody agent comprises the heavy chain CDRs of SEQ ID NO:88, SEQ ID NO:89 and SEQ ID NO:90 and the light chain CDRs of SEQ ID NO:196, SEQ ID NO:197 and SEQ ID NO:198.

In some embodiments, a human antibody agent comprises the heavy chain CDRs of SEQ ID NO:91, SEQ ID NO:92 and SEQ ID NO:93, and the light chain CDRs of SEQ ID NO:199, SEQ ID NO:200 and SEQ ID NO:201.

In some embodiments, a human antibody agent comprises the heavy chain CDRs of SEQ ID NO:94, SEQ ID NO:95 and SEQ ID NO:96, and the light chain CDRs of SEQ ID NO:202, SEQ ID NO:203 and SEQ ID NO:204.

In some embodiments, a human antibody agent comprises the heavy chain CDRs of SEQ ID NO:97, SEQ ID NO:98 and SEQ ID NO:99, and the light chain CDRs of SEQ ID NO:205, SEQ ID NO:206 and SEQ ID NO:207.

In some embodiments, a human antibody agent comprises the heavy chain CDRs of SEQ ID NO:100, SEQ ID NO:101 and SEQ ID NO:102, and the light chain CDRs of SEQ ID NO:208, SEQ ID NO:209 and SEQ ID NO:210.

In some embodiments, a human antibody agent comprises the heavy chain CDRs of SEQ ID NO:103, SEQ ID NO:104 and SEQ ID NO:105, and the light chain CDRs of SEQ ID NO:211, SEQ ID NO:212 and SEQ ID NO:213.

In some embodiments, a human antibody agent comprises the heavy chain CDRs of SEQ ID NO:106, SEQ ID NO:107 and SEQ ID NO:108, and the light chain CDRs of SEQ ID NO:214, SEQ ID NO:215 and SEQ ID NO:216.

In some embodiments, a human antibody agent comprises the heavy chain CDRs of SEQ ID NO:109, SEQ ID NO:110 and SEQ ID NO:111, and the light chain CDRs of SEQ ID NO:217, SEQ ID NO:218 and SEQ ID NO:219.

In some embodiments, a human antibody agent comprises the heavy chain CDRs of SEQ ID NO:112, SEQ ID NO:113 and SEQ ID NO:114, and the light chain CDRs of SEQ ID NO:220, SEQ ID NO:221 and SEQ ID NO:222.

In some embodiments, a human antibody agent comprises the heavy chain CDRs of SEQ ID NO:115, SEQ ID NO:116 and SEQ ID NO:117, and the light chain CDRs of SEQ ID NO:223, SEQ ID NO:224 and SEQ ID NO:225.

In some embodiments, a human antibody agent comprises the heavy chain CDRs of SEQ ID NO:118, SEQ ID NO:119 and SEQ ID NO:120, and the light chain CDRs of SEQ ID NO:226, SEQ ID NO:227 and SEQ ID NO:228.

In some embodiments, a human antibody agent comprises the heavy chain CDRs of SEQ ID NO:121, SEQ ID NO:122 and SEQ ID NO:123, and the light chain CDRs of SEQ ID NO:229, SEQ ID NO:230 and SEQ ID NO:231.

In some embodiments, the present invention provides a human antibody agent that competes for binding CD19 with a human antibody agent that comprises (a) the heavy chain CDRs of SEQ ID NO:73, SEQ ID NO:74 and SEQ ID NO:75, and the light chain CDRs of SEQ ID NO:181, SEQ ID NO:182 and SEQ ID NO:183; (b) the heavy chain CDRs of SEQ ID NO:76, SEQ ID NO:77 and SEQ ID NO:78, and the light chain CDRs of SEQ ID NO:184, SEQ ID NO:185 and SEQ ID NO:186; (c) the heavy chain CDRs of SEQ ID NO:79, SEQ ID NO:80 and SEQ ID NO:81 and the light chain CDRs of SEQ ID NO:187, SEQ ID NO:188 and SEQ ID NO:189; (d) the heavy chain CDRs of SEQ ID NO:82, SEQ ID NO:83 and SEQ ID NO:84, and the light chain CDRs of SEQ ID NO:190, SEQ ID NO:191 and SEQ ID NO:192; (e) the heavy chain CDRs of SEQ ID NO:85, SEQ ID NO:86 and SEQ ID NO:87, and the light chain CDRs of SEQ ID NO:193, SEQ ID NO:194 and SEQ ID NO:195; (f) the heavy chain CDRs of SEQ ID NO:88, SEQ ID NO:89 and SEQ ID NO:90 and the light chain CDRs of SEQ ID NO:196, SEQ ID NO:197 and SEQ ID NO:198; (g) the heavy chain CDRs of SEQ ID NO:91, SEQ ID NO:92 and SEQ ID NO:93, and the light chain CDRs of SEQ ID NO:199, SEQ ID NO:200 and SEQ ID NO:201; (h) the heavy chain CDRs of SEQ ID NO:94, SEQ ID NO:95 and SEQ ID NO:96, and the light chain CDRs of SEQ ID NO:202, SEQ ID NO:203 and SEQ ID NO:204; (i) the heavy chain CDRs of SEQ ID NO:97, SEQ ID NO:98 and SEQ ID NO:99, and the light chain CDRs of SEQ ID NO:205, SEQ ID NO:206 and SEQ ID NO:207; (j) the heavy chain CDRs of SEQ ID NO:100, SEQ ID NO:101 and SEQ ID NO:102, and the light chain CDRs of SEQ ID NO:208, SEQ ID NO:209 and SEQ ID NO:210; (k) the heavy chain CDRs of SEQ ID NO:103, SEQ ID NO:104 and SEQ ID NO:105, and the light chain CDRs of SEQ ID NO:211, SEQ ID NO:212 and SEQ ID NO:213; (l) the heavy chain CDRs of SEQ ID NO:106, SEQ ID NO:107 and SEQ ID NO:108, and the light chain CDRs of SEQ ID NO:214, SEQ ID NO:215 and SEQ ID NO:216; (m) the heavy chain CDRs of SEQ ID NO:109, SEQ ID NO:110 and SEQ ID NO:111, and the light chain CDRs of SEQ ID NO:217, SEQ ID NO:218 and SEQ ID NO:219; (n) the heavy chain CDRs of SEQ ID NO:112, SEQ ID NO:113 and SEQ ID NO:114, and the light chain CDRs of SEQ ID NO:220, SEQ ID NO:221 and SEQ ID NO:222; (o) the heavy chain CDRs of SEQ ID NO:115, SEQ ID NO:116 and SEQ ID NO:117, and the light chain CDRs of SEQ ID NO:223, SEQ ID NO:224 and SEQ ID NO:225; (p) the heavy chain CDRs of SEQ ID NO:118, SEQ ID NO:119 and SEQ ID NO:120, and the light chain CDRs of SEQ ID NO:226, SEQ ID NO:227 and SEQ ID NO:228; or (q) the heavy chain CDRs of SEQ ID NO:121, SEQ ID NO:122 and SEQ ID NO:123, and the light chain CDRs of SEQ ID NO:229, SEQ ID NO:230 and SEQ ID NO:231.

In some embodiments, a human antibody agent further comprises one or more amino acid substitutions in a heavy chain CDR and/or light chain CDR.

In some embodiments, a human antibody agent further comprises at least one or up to five amino acid substitutions in a heavy chain CDR and/or light chain CDR.

In some embodiments, a human antibody agent further comprises at least one or up to three amino acid substitutions in a heavy chain CDR and/or light chain CDR.

In some embodiments, a human antibody agent comprises one or more amino acid substitutions in a heavy chain framework and/or light chain framework. In some certain embodiments, a human antibody agent comprises 1-5 amino acid substitutions in a heavy chain framework and/or light chain framework.

In some certain embodiments, one or more amino acid substitutions (e.g., 1-5 amino acid substitutions) are within a framework region (i.e., heavy and/or light chain framework) and/or a CDR (i.e., heavy and/or light chain CDR).

In some embodiments, a human antibody agent comprises one or more amino acid substitutions that appear in Table 8. In some embodiments, a human antibody agent comprises the amino acid substitution(s) found in a variant clone that appears in Table 8.

In some embodiments, the present invention provides a human antibody agent that specifically binds human CD19, wherein the human antibody agent comprises a heavy chain variable region having a sequence that is at least 50% (e.g., at least about 55%, 60%, 65%, 70%, 75%, 80%, 85%, 90%, 95%, 96%, 97%, 98%, or 99%) identical to a heavy chain variable region sequence that appears in Table 1, and a light chain variable region having a sequence that is at least 50% (e.g., at least about 55%, 60%, 65%, 70%, 75%, 80%, 85%, 90%, 95%, 96%, 97%, 98%, or 99%) identical to a light chain variable region sequence that appears in Table 1.

In some embodiments, a human antibody agent comprises a heavy chain variable region having a sequence that is at least 95% identical to the heavy chain variable region sequence that appears in SEQ ID NO:2, and a light chain variable region having a sequence that is at least 95% identical to the light chain variable region sequence that appears in SEQ ID NO:2.

In some embodiments, a human antibody agent comprises a heavy chain variable region having a sequence that is at least 95% identical to the heavy chain variable region sequence that appears in SEQ ID NO:4, and a light chain variable region having a sequence that is at least 95% identical to the light chain variable region sequence that appears in SEQ ID NO:4.

In some embodiments, a human antibody agent comprises a heavy chain variable region having a sequence that is at least 95% identical to the heavy chain variable region sequence that appears in SEQ ID NO:6, and a light chain variable region having a sequence that is at least 95% identical to the light chain variable region sequence that appears in SEQ ID NO:6.

In some embodiments, a human antibody agent comprises a heavy chain variable region having a sequence that is at least 95% identical to the heavy chain variable region sequence that appears in SEQ ID NO:8, and a light chain variable region having a sequence that is at least 95% identical to the light chain variable region sequence that appears in SEQ ID NO:8.

In some embodiments, a human antibody agent comprises a heavy chain variable region having a sequence that is at least 95% identical to the heavy chain variable region sequence that appears in SEQ ID NO:10, and a light chain variable region having a sequence that is at least 95% identical to the light chain variable region sequence that appears in SEQ ID NO:10.

In some embodiments, a human antibody agent comprises a heavy chain variable region having a sequence that is at least 95% identical to the heavy chain variable region sequence that appears in SEQ ID NO:12, and a light chain variable region having a sequence that is at least 95% identical to the light chain variable region sequence that appears in SEQ ID NO:12.

In some embodiments, a human antibody agent comprises a heavy chain variable region having a sequence that is at least 95% identical to the heavy chain variable region sequence that appears in SEQ ID NO:14, and a light chain variable region having a sequence that is at least 95% identical to the light chain variable region sequence that appears in SEQ ID NO:14.

In some embodiments, a human antibody agent comprises a heavy chain variable region having a sequence that is at least 95% identical to the heavy chain variable region sequence that appears in SEQ ID NO:16, and a light chain variable region having a sequence that is at least 95% identical to the light chain variable region sequence that appears in SEQ ID NO:16.

In some embodiments, a human antibody agent comprises a heavy chain variable region having a sequence that is at least 95% identical to the heavy chain variable region sequence that appears in SEQ ID NO:18, and a light chain variable region having a sequence that is at least 95% identical to the light chain variable region sequence that appears in SEQ ID NO:18.

In some embodiments, a human antibody agent comprises a heavy chain variable region having a sequence that is at least 95% identical to the heavy chain variable region sequence that appears in SEQ ID NO:20, and a light chain variable region having a sequence that is at least 95% identical to the light chain variable region sequence that appears in SEQ ID NO:20.

In some embodiments, a human antibody agent comprises a heavy chain variable region having a sequence that is at least 95% identical to the heavy chain variable region sequence that appears in SEQ ID NO:22, and a light chain variable region having a sequence that is at least 95% identical to the light chain variable region sequence that appears in SEQ ID NO:22.

In some embodiments, a human antibody agent comprises a heavy chain variable region having a sequence that is at least 95% identical to the heavy chain variable region sequence that appears in SEQ ID NO:24, and a light chain variable region having a sequence that is at least 95% identical to the light chain variable region sequence that appears in SEQ ID NO:24.

In some embodiments, a human antibody agent comprises a heavy chain variable region having a sequence that is at least 95% identical to the heavy chain variable region sequence that appears in SEQ ID NO:26, and a light chain variable region having a sequence that is at least 95% identical to the light chain variable region sequence that appears in SEQ ID NO:26.

In some embodiments, a human antibody agent comprises a heavy chain variable region having a sequence that is at least 95% identical to the heavy chain variable region sequence that appears in SEQ ID NO:28, and a light chain variable region having a sequence that is at least 95% identical to the light chain variable region sequence that appears in SEQ ID NO:28.

In some embodiments, a human antibody agent comprises a heavy chain variable region having a sequence that is at least 95% identical to the heavy chain variable region sequence that appears in SEQ ID NO:30, and a light chain variable region having a sequence that is at least 95% identical to the light chain variable region sequence that appears in SEQ ID NO:30.

In some embodiments, a human antibody agent comprises a heavy chain variable region having a sequence that is at least 95% identical to the heavy chain variable region sequence that appears in SEQ ID NO:32, and a light chain variable region having a sequence that is at least 95% identical to the light chain variable region sequence that appears in SEQ ID NO:32.

In some embodiments, a human antibody agent comprises a heavy chain variable region having a sequence that is at least 95% identical to the heavy chain variable region sequence that appears in SEQ ID NO:34, and a light chain variable region having a sequence that is at least 95% identical to the light chain variable region sequence that appears in SEQ ID NO:34.

In some embodiments, a human antibody agent comprises the heavy and light chain variable region sequences that appear in any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32 and SEQ ID NO:34.

In some embodiments, the present invention provides a human antibody agent that specifically binds human CD19, wherein the human antibody agent comprises one or more amino acid substitutions as compared to a parental (or reference) human antibody agent, and wherein the human antibody agent comprises (a) the heavy chain CDRs of SEQ ID NO:124, SEQ ID NO:125 and SEQ ID NO:126, and the light chain CDRs of SEQ ID NO:232, SEQ ID NO:233 and SEQ ID NO:234; (b) the heavy chain CDRs of SEQ ID NO:127, SEQ ID NO:128 and SEQ ID NO:129, and the light chain CDRs of SEQ ID NO:235, SEQ ID NO:236 and SEQ ID NO:237; (c) the heavy chain CDRs of SEQ ID NO:130, SEQ ID NO:131 and SEQ ID NO:132, and the light chain CDRs of SEQ ID NO:238, SEQ ID NO:239 and SEQ ID NO:240; (d) the heavy chain CDRs of SEQ ID NO:133, SEQ ID NO:134 and SEQ ID NO:135, and the light chain CDRs of SEQ ID NO:241, SEQ ID NO:242 and SEQ ID NO:243; (e) the heavy chain CDRs of SEQ ID NO:136, SEQ ID NO:137 and SEQ ID NO:138, and the light chain CDRs of SEQ ID NO:244, SEQ ID NO:245 and SEQ ID NO:246; (f) the heavy chain CDRs of SEQ ID NO:139, SEQ ID NO:140 and SEQ ID NO:141, and the light chain CDRs of SEQ ID NO:247, SEQ ID NO:248 and SEQ ID NO:249; (g) the heavy chain CDRs of SEQ ID NO:142, SEQ ID NO:143 and SEQ ID NO:144, and the light chain CDRs of SEQ ID NO:250, SEQ ID NO:251 and SEQ ID NO:252; (h) the heavy chain CDRs of SEQ ID NO:145, SEQ ID NO:146 and SEQ ID NO:147, and the light chain CDRs of SEQ ID NO:253, SEQ ID NO:254 and SEQ ID NO:255; (i) the heavy chain CDRs of SEQ ID NO:148, SEQ ID NO:149 and SEQ ID NO:150, and the light chain CDRs of SEQ ID NO:256, SEQ ID NO:257 and SEQ ID NO:258; (j) the heavy chain CDRs of SEQ ID NO:151, SEQ ID NO:152 and SEQ ID NO:153, and the light chain CDRs of SEQ ID NO:259, SEQ ID NO:260 and SEQ ID NO:261; (k) the heavy chain CDRs of SEQ ID NO:154, SEQ ID NO:155 and SEQ ID NO:156, and the light chain CDRs of SEQ ID NO:262, SEQ ID NO:263 and SEQ ID NO:264; (l) the heavy chain CDRs of SEQ ID NO:157, SEQ ID NO:158 and SEQ ID NO:159, and the light chain CDRs of SEQ ID NO:265, SEQ ID NO:266 and SEQ ID NO:267; (m) the heavy chain CDRs of SEQ ID NO:160, SEQ ID NO:161 and SEQ ID NO:163, and the light chain CDRs of SEQ ID NO:268, SEQ ID NO:269 and SEQ ID NO:270; (n) the heavy chain CDRs of SEQ ID NO:163, SEQ ID NO:164 and SEQ ID NO:165, and the light chain CDRs of SEQ ID NO:271, SEQ ID NO:272 and SEQ ID NO:273; (o) the heavy chain CDRs of SEQ ID NO:166, SEQ ID NO:167 and SEQ ID NO:168, and the light chain CDRs of SEQ ID NO:274, SEQ ID NO:275 and SEQ ID NO:276; (p) the heavy chain CDRs of SEQ ID NO:169, SEQ ID NO:170 and SEQ ID NO:171, and the light chain CDRs of SEQ ID NO:277, SEQ ID NO:278 and SEQ ID NO:279; (q) the heavy chain CDRs of SEQ ID NO:172, SEQ ID NO:173 and SEQ ID NO:174, and the light chain CDRs of SEQ ID NO:280, SEQ ID NO:281 and SEQ ID NO:282; (r) the heavy chain CDRs of SEQ ID NO:175, SEQ ID NO:176 and SEQ ID NO:177, and the light chain CDRs of SEQ ID NO:283, SEQ ID NO:284 and SEQ ID NO:285; or (s) the heavy chain CDRs of SEQ ID NO:178, SEQ ID NO:179 and SEQ ID NO:180, and the light chain CDRs of SEQ ID NO:286, SEQ ID NO:287 and SEQ ID NO:288. In some certain embodiments, an antibody agent as described herein comprises 1-5 amino acid substitutions as compared to a parental (or reference) antibody agent as described herein.

In some embodiments, a human antibody agent comprises a light chain variable region that comprises one or more amino acid substitutions at any of amino acid positions selected from the group consisting of 10, 16, 25, 34, 52, 54, 68, 69, 72, 75, 93, 95 and combinations thereof. In some certain embodiments, one or more amino acid substitutions includes V10M, K16E, S25N, V34I, D52N, L54Q, N68T, T69M, L72M, S75N, S93T, D95E, D95G or a combination thereof.

In some embodiments, a human antibody agent comprises a heavy chain variable region that comprises one or more amino acid substitutions at any of amino acid positions selected from the group consisting of 3, 12, 16, 17, 25, 26, 32, 63, 69, 97, 102, 106, 108, 109, 113, 116, 117 and combinations thereof. In some certain embodiments, one or more amino acid substitutions includes Q3R, K12E, E16G, S17F, S25A, G26A, Y32F, S63F, T69A, A97V, T102S, M106L, Y108N, D109E, Q113L, L116M, M117L or a combination thereof.

In some embodiments, a human antibody agent comprises a light chain variable region with amino acid substitution S75N. In some embodiments, a human antibody agent comprises a light chain variable region with amino acid substitution T69M. In some embodiments, a human antibody agent comprises a light chain variable region with amino acid substitutions D52N and D95E. In some embodiments, a human antibody agent comprises a light chain variable region with amino acid substitutions V10M and D95G. In some embodiments, a human antibody agent comprises a light chain variable region with amino acid substitution S93T, and a heavy chain variable region with amino acid substitutions S17F and T69A. In some embodiments, a human antibody agent comprises a light chain variable region with amino acid substitution N68T, and a heavy chain variable region with amino acid substitutions S17F and Y108N. In some embodiments, a human antibody agent comprises a heavy chain variable region with amino acid substitution S63F. In some embodiments, a human antibody agent comprises a heavy chain variable region with amino acid substitutions Q3R, Y32F and A97V. In some embodiments, a human antibody agent comprises a light chain variable region with amino acid substitution K16E. In some embodiments, a human antibody agent comprises a heavy chain variable region with amino acid substitution M117L.

In some embodiments, a human antibody agent comprises a light chain variable region with amino acid substitution L72M, and a heavy chain variable region with amino acid substitution S25A. In some embodiments, a human antibody agent comprises a heavy chain variable region with amino acid substitutions T102S and L116M. In some embodiments, a human antibody agent comprises a light chain variable region with amino acid substitutions S25N and V34I, and a heavy chain variable region with amino acid substitutions K12E and D109E. In some embodiments, a human antibody agent comprises a heavy chain variable region with amino acid substitution E16G. In some embodiments, a human antibody agent comprises a light chain variable region with amino acid substitution L54Q, and a heavy chain variable region with amino acid substitution M106L. In some embodiments, a human antibody agent comprises a light chain variable region with amino acid substitution S25N. In some embodiments, a human antibody agent comprises a heavy chain variable region with amino acid substitutions G26A and Q113L. In some embodiments, a human antibody agent comprises a light chain variable region with amino acid substitution L54Q. In some embodiments, a human antibody agent comprises a heavy chain variable region with amino acid substitution T102S.

In some embodiments, amino acid substitutions are selected from Table 8.

In some embodiments, the present invention provides a human antibody agent that specifically binds human CD19, wherein the human antibody agent comprises one or more amino acid substitutions (e.g., 1-5 amino acid substitutions) as compared to a parental (or reference) human antibody agent, and wherein the human antibody agent comprises the heavy and light chain variable region sequences that appear in any one of SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72. In some certain embodiments, a parental (or reference) antibody agent comprises the HCVR and LCVR of SEQ ID NO:30 or SEQ ID NO:32.

In some embodiments, a human antibody agent is a human monoclonal antibody or fragment thereof.

In some embodiments, a human antibody agent is a human monoclonal antibody that comprises a variant Fc region. In some embodiments, a variant Fc region comprises one or more amino acid substitutions as compared to a parental (or reference) Fc region. In some embodiments, a human monoclonal antibody comprises a variant glycosylation pattern as compared to a parental human monoclonal antibody that comprises a wild type (or parental, or reference) Fc region. In some embodiments, a human monoclonal antibody is an IgG1, IgG2, IgG3 or IgG4 antibody. In some certain embodiments, a human monoclonal antibody is an IgG1.

In some embodiments, a human antibody agent is conjugated to a therapeutic agent or detection agent.

In some embodiments, a human antibody agent is conjugated to a cytotoxic agent or moiety.

In some embodiments, a human antibody agent is conjugated to a radio-isotope.

In some embodiments, a human antibody agent is or comprises an immunoglobulin, Fab, F(ab')$_2$, Fd, Fv, single chain Fv (scFv) or a dAb. In some certain embodiments, a human antibody agent is or comprises an scFv. In some embodiments, an scFv comprises a linker sequence. In some embodiments, an scFv is conjugated to a therapeutic agent or detection agent. In some embodiments, an scFv is part of a chimeric antigen receptor.

In some embodiments, the present invention provides a human antibody agent as described herein for use in therapy or diagnosis.

In some embodiments, the present invention provides a human antibody agent as described herein for use in the treatment, prevention or amelioration of a disease characterized by CD19 expression.

In some embodiments, the present invention provides a human antibody agent as described herein for use in the treatment, prevention or amelioration of cancer.

In some embodiments, the present invention provides an antibody-drug conjugate comprising an antigen-binding site (or the antigen-binding sites) of a human antibody agent as described herein, and a cytotoxic agent or moiety.

In some embodiments, a cytotoxic agent or moiety is or comprises monomethyl auristatin E (MMAE), monomethyl auristatin F (MMAF) or maytansine.

In some embodiments, the present invention provides a bi-specific antibody comprising a first antigen-binding site from (or based on) a human antibody agent as described herein and a second antigen-binding site.

In some embodiments, first and/or second antigen-binding sites are selected from the group consisting of an immunoglobulin molecule, scFv, scFab, Fab, Fv and a combination thereof. In some embodiments, first and second antigen-binding sites are configured such that they form a single polypeptide chain. In some embodiments, first and second antigen-binding sites are scFvs. In some embodiments, first and second antigen-binding sites are linked by a peptide linker. In some embodiments, a second antigen-binding site is linked to the C-terminal end of a first antigen-binding site. In some embodiments, a second antigen-binding site is linked to the N-terminal end of a first antigen-binding site.

In some embodiments, a first antigen-binding site is composed of an immunoglobulin molecule and the second antigen-binding site is composed of an scFv, scFab, Fab or Fv.

In some embodiments, a second antigen-binding site binds an immune cell selected from the group consisting of a T cell, NK cell, B cell, dendritic cell, monocyte, macrophage, neutrophil, mesenchymal stem cell and neural stem cell. In some embodiments, a second antigen-binding site binds CD3 on T cells.

In some embodiments, the present invention provides a bi-specific T cell engaging monoclonal antibody comprising an antigen-binding site of a human antibody agent as described herein.

In some embodiments, the present invention provides a bi-specific antibody comprised of a first scFv that specifically binds CD19 and a second scFv that specifically binds CD3 on T cells, wherein the first scFv comprises any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

In some embodiments, the N-terminal end of a first scFv is linked to the C-terminal end of a second scFv. In some embodiments, the C-terminal end of a first scFv is linked to the N-terminal end of a second scFv.

In some embodiments, an N-terminal end of a first scFv is linked to the C-terminal end of a second scFv via a linker sequence. In some embodiments, a C-terminal end of a first scFv is linked to the N-terminal end of a second scFv via a linker sequence.

In some embodiments, the present invention provides a bi-specific antibody as described herein for use in therapy or diagnosis.

In some embodiments, the present invention provides a bi-specific antibody as described herein for use in the treatment, prevention or amelioration of a disease characterized by CD19 expression.

In some embodiments, the present invention provides a chimeric antigen receptor comprising an antigen-binding site of a human antibody agent as described herein. In some embodiments, a chimeric antigen receptor comprises an antigen-binding site of a human antibody agent as described herein and further comprises a transmembrane domain and/or an intracellular signaling domain of a native cell receptor. In some certain embodiments, a native cell receptor is a T cell receptor (TCR). In some embodiments, a chimeric antigen receptor comprises an antigen-binding site of a human antibody agent as described herein and further comprises a transmembrane domain and an intracellular signaling domain, which intracellular signaling domain comprises a CD3 (e.g., CD3ζ) intracellular signaling sequence and a CD28 intracellular signaling sequence.

In some embodiments, an antigen-binding site of a chimeric antigen receptor is or comprises an scFv.

In some embodiments, an antigen-binding site of a chimeric antigen receptor as described herein is or comprises a $V_L$ region. In some certain embodiments, a $V_L$ region comprises the light chain CDRs of (a) SEQ ID NO:181, SEQ ID NO:182 and SEQ ID NO:183; (b) SEQ ID NO:184, SEQ ID NO:185 and SEQ ID NO:186; (c) SEQ ID NO:187, SEQ ID NO:188 and SEQ ID NO:189; (d) SEQ ID NO:190, SEQ ID NO:191 and SEQ ID NO:192; (e) SEQ ID NO:193, SEQ ID NO:194 and SEQ ID NO:195; (f) SEQ ID NO:196, SEQ ID NO:197 and SEQ ID NO:198; (g) SEQ ID NO:199, SEQ ID NO:200 and SEQ ID NO:201; (h) SEQ ID NO:202, SEQ ID NO:203 and SEQ ID NO:204; (i) SEQ ID NO:205, SEQ ID NO:206 and SEQ ID NO:207; (j) SEQ ID NO:208, SEQ ID NO:209 and SEQ ID NO:210; (k) SEQ ID NO:211, SEQ ID NO:212 and SEQ ID NO:213; (l) SEQ ID NO:214, SEQ ID NO:215 and SEQ ID NO:216; (m) SEQ ID NO:217, SEQ ID NO:218 and SEQ ID NO:219; (n) SEQ ID NO:220, SEQ ID NO:221 and SEQ ID NO:222; (o) SEQ ID NO:223, SEQ ID NO:224 and SEQ ID NO:225; (p) SEQ ID NO:226, SEQ ID NO:227 and SEQ ID NO:228; (q) SEQ ID NO:229, SEQ ID NO:230 and SEQ ID NO:231; (r) SEQ ID NO:232, SEQ ID NO:233 and SEQ ID NO:234; (s) SEQ ID NO:235, SEQ ID NO:236 and SEQ ID NO:237; (t) SEQ ID NO:238, SEQ ID NO:239 and SEQ ID NO:240; (u) SEQ ID NO:241, SEQ ID NO:242 and SEQ ID NO:243; (v) SEQ ID NO:244, SEQ ID NO:245 and SEQ ID NO:246; (w) SEQ ID NO:247, SEQ ID NO:248 and SEQ ID NO:249; (x) SEQ ID NO:250, SEQ ID NO:251 and SEQ ID NO:252; (y) SEQ ID NO:253, SEQ ID NO:254 and SEQ ID NO:255; (z) SEQ ID NO:256, SEQ ID NO:257 and SEQ ID NO:258; (ab) SEQ ID NO:259, SEQ ID NO:260 and SEQ ID NO:261; (ac) SEQ ID NO:262, SEQ ID NO:263 and SEQ ID NO:264; (ad) SEQ ID NO:265, SEQ ID NO:266 and SEQ ID NO:267; (ae) SEQ ID NO:268, SEQ ID NO:269 and SEQ ID NO:270; (af) SEQ ID NO:271, SEQ ID NO:272 and SEQ ID NO:273; (ag) SEQ ID NO:274, SEQ ID NO:275 and SEQ ID NO:276; (ah) SEQ ID NO:277, SEQ ID NO:278 and SEQ ID NO:279; (ai) SEQ ID NO:280, SEQ ID NO:281 and SEQ ID NO:282; (aj) SEQ ID NO:283, SEQ ID NO:284 and SEQ ID NO:285; or (ak) SEQ ID NO:286, SEQ ID NO:287 and SEQ ID NO:288. In some certain embodiments, a $V_L$ region comprises a sequence that appears in any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

In some embodiments, an antigen-binding site of a chimeric receptor as described herein is or comprises a $V_H$ region. In some certain embodiments, a $V_H$ region comprises the heavy chain CDRs of (a) SEQ ID NO:73, SEQ ID NO:74 and SEQ ID NO:75; (b) SEQ ID NO:76, SEQ ID NO:77 and SEQ ID NO:78; (c) SEQ ID NO:79, SEQ ID NO:80 and SEQ ID NO:81; (d) SEQ ID NO:82, SEQ ID NO:83 and SEQ ID NO:84; (e) SEQ ID NO:85, SEQ ID NO:86 and SEQ ID NO:87; (f) SEQ ID NO:88, SEQ ID NO:89 and SEQ ID NO:90; (g) SEQ ID NO:91, SEQ ID NO:92 and SEQ ID NO:93; (h) SEQ ID NO:94, SEQ ID NO:95 and SEQ ID NO:96; (i) SEQ ID NO:97, SEQ ID NO:98 and SEQ ID NO:99; (j) SEQ ID NO:100, SEQ ID NO:101 and SEQ ID NO:102; (k) SEQ ID NO:103, SEQ ID NO:104 and SEQ ID NO:105; (l) SEQ ID NO:106, SEQ ID NO:107 and SEQ ID NO:108; (m) SEQ ID NO:109, SEQ ID NO:110 and SEQ ID NO:111; (n) SEQ ID NO:112, SEQ ID NO:113 and SEQ ID NO:114; (o) SEQ ID NO:115, SEQ ID NO:116 and SEQ ID NO:117; (p) SEQ ID NO:118, SEQ ID NO:119 and SEQ ID NO:120; (q) SEQ ID NO:121, SEQ ID NO:122 and SEQ ID NO:123; (r) SEQ ID NO:124, SEQ ID NO:125 and SEQ ID NO:126; (s) SEQ ID NO:127, SEQ ID NO:128 and SEQ ID NO:129; (t) SEQ ID NO:130, SEQ ID NO:131 and SEQ ID NO:132; (u) SEQ ID NO:133, SEQ ID NO:134 and SEQ ID NO:135; (v) SEQ ID NO:136, SEQ ID NO:137 and SEQ ID NO:138; (w) SEQ ID NO:139, SEQ ID NO:140 and SEQ ID NO:141; (x) SEQ ID NO:142, SEQ ID NO:143 and SEQ ID NO:144; (y) SEQ ID NO:145, SEQ ID NO:146 and SEQ ID NO:147; (z) SEQ ID NO:148, SEQ ID NO:149 and SEQ ID NO:150; (ab) SEQ ID NO:151, SEQ ID NO:152 and SEQ ID NO:153; (ac) SEQ ID NO:154, SEQ ID NO:155 and SEQ ID NO:156; (ad) SEQ ID NO:157, SEQ ID NO:158 and SEQ ID NO:159; (ae) SEQ ID NO:160, SEQ ID NO:161 and SEQ ID NO:163; (af) SEQ ID NO:163, SEQ ID NO:164 and SEQ ID NO:165; (ag) SEQ ID NO:166, SEQ ID NO:167 and SEQ ID NO:168; (ah) SEQ ID NO:169, SEQ ID NO:170 and SEQ ID NO:171; (ai) SEQ ID NO:172, SEQ ID NO:173 and SEQ ID NO:174; (aj) SEQ ID NO:175, SEQ ID NO:176 and SEQ ID NO:177; or (ak) SEQ ID NO:178, SEQ ID NO:179 and SEQ ID NO:180. In some certain embodiments, a $V_H$ region comprises a sequence that appears in any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

In some embodiments, the present invention provides a chimeric antigen receptor as described herein for use in therapy or diagnosis.

In some embodiments, the present invention provides a chimeric antigen receptor as described herein for use in the treatment, prevention or amelioration of a disease characterized by CD19 expression.

In some embodiments, the present invention provides an immune effector cell that expresses a chimeric antigen receptor (or antibody agent or bi-specific antibody) as described herein. In some embodiments, an immune effector cell is a T cell (e.g., cytotoxic T cell, helper T cell or natural killer T cell) or an NK cell.

In some embodiments, the present invention provides an immune effector cell as described herein for use in therapy or diagnosis.

In some embodiments, the present invention provides an immune effector cell as described herein for use in the treatment, prevention or amelioration of a disease characterized by CD19 expression.

In some embodiments, the present invention provides an isolated nucleic acid molecule encoding (or that encodes), in whole or in part, a human antibody agent, polypeptide chain of a bi-specific antibody or a bi-specific antibody, or a chimeric antigen receptor as described herein. In some embodiments, an isolated nucleic acid sequence includes a sequence that is codon-optimized.

In some embodiments, an isolated nucleic acid sequence is or comprises a sequence that appears in any one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69 and SEQ ID NO:71.

In some embodiments, the present invention provides a vector comprising an isolated nucleic acid molecule as described herein. In some embodiments, a vector is a recombinant, expression, lent-viral, or retroviral vector.

In some embodiments, the present invention provides a cell comprising a vector or nucleic acid molecule, or expressing an antibody agent, a bi-specific antibody or chimeric antigen receptor as described herein. In some embodiments, a cell is selected from a bacterial, yeast, insect or mammalian cell. In some embodiments, a cell is a mammalian lymphocyte (e.g., a human lymphocyte).

In some embodiments, the present invention provides a kit comprising a human antibody agent, a bi-specific antibody, a chimeric antigen receptor, an isolated nucleic acid molecule, a vector or cell as described herein.

In some embodiments, the present invention provides a kit for diagnosing a subject suffering from a CD19-related disease, or a pre-disposition thereto, or for providing a prognosis of the subject's condition, the kit comprising detection means for detecting the concentration of CD19 present in a sample from a test subject, wherein the detection means comprises an antigen-binding site of a human antibody agent as described herein, a bi-specific binding agent as described herein, a chimeric antigen receptor as described herein, or an immune effector cell as described herein, each being optionally derivatized, wherein presence of CD19 in the sample indicates that the subject suffers from a CD19-related disease.

In some embodiments, the present invention provides a vaccine comprising an isolated nucleic acid molecule as described herein.

In some embodiments, the present invention provides a composition comprising a human antibody agent, bi-specific antibody or chimeric antigen receptor as described herein. In some certain embodiments, a human antibody agent or bi-specific antibody of a composition as described herein is conjugated to a cytotoxic agent or moiety.

In some embodiments, the present invention provides a pharmaceutical composition comprising a human antibody agent, bi-specific antibody, chimeric antigen receptor, or an immune cell (or population thereof) expressing a chimeric antigen receptor as described herein, and further comprising a pharmaceutically acceptable carrier or diluent.

In some embodiments, the present invention provides a method for producing a human antibody agent, bi-specific antibody or chimeric antigen receptor (or cell expressing the chimeric antigen receptor) as described herein comprising a step of culturing a cell as described herein in a culture medium under conditions allowing the expression of the human antibody agent, bi-specific antibody or chimeric antigen receptor (or cell expressing the chimeric antigen receptor), and separating the human antibody agent, bi-specific antibody or chimeric antigen receptor (or cell expressing the chimeric antigen receptor) from the culture medium.

In some embodiments, the present invention provides a method of treating a medical condition characterized by CD19 expression in a subject, comprising a step of administering a therapeutically effective amount of a human antibody agent, bi-specific antibody, chimeric antigen receptor (or an immune effector cell expressing the chimeric antigen receptor), nucleic acid molecule, or vector as described herein to said subject.

In some embodiments, a medical condition characterized by CD19 expression is B cell lymphoma, acute lymphoblastic leukemia, chronic lymphocytic leukemia, Burkitt lymphoma, non-Hodgkin's lymphoma or acute myeloid leukemia.

In some embodiments, a medical condition characterized by CD19 expression is rheumatoid arthritis (RA), systemic lupus erythematosus (SLE), diabetes or scleroderma.

In some embodiments, the present invention provides a method of treating cancer, the method comprising a step of administering to a subject a human antibody agent, bi-specific antibody, chimeric antigen receptor (or an immune effector cell expressing the chimeric antigen receptor), nucleic acid molecule or vector as described herein.

In some embodiments, the present invention provides a method of inhibiting tumor growth, the method comprising a step of contacting tumor cells with a bi-specific antibody (or a human antibody agent as described herein, a chimeric antigen receptor as described herein, or an immune effector cell as described herein, a nucleic acid molecule as described herein, or a vector as described herein), which bi-specific antibody is composed of a first antigen-binding site based on a human antibody agent as described herein and a second antigen-binding site that binds an immune cell, the contacting being performed under conditions and for a time sufficient so that tumor cell killing is observed (or that immune cells to which the bi-specific antibody has bound inhibit growth of tumor cells).

In some embodiments, the present invention provides a method of killing tumor cells, the method comprising a step of contacting tumor cells with a bi-specific antibody (or a human antibody agent as described herein, a chimeric antigen receptor as described herein, or an immune effector cell as described herein, a nucleic acid molecule as described herein, or a vector as described herein), which bi-specific antibody is composed of a first antigen-binding site based on a human antibody agent as described herein and a second antigen-binding site that binds an immune cell, the contacting being performed under conditions and for a time sufficient so that inhibition of tumor cell growth is observed (or that immune cells to which the bi-specific antibody has bound mediate killing of tumor cells).

In some embodiments, the present invention provides a method of diagnosing a medical condition characterized by CD19 expression in a subject, the method comprising a step of administering an antibody agent (or a bi-specific antibody or chimeric antigen receptor as described herein) as described herein, and measuring binding of said antibody agent (or bi-specific antibody or chimeric antigen receptor) to a cell expressing CD19 in said subject.

In some embodiments of a method of diagnosing a medical condition, the method further comprises a step of measuring one or more activities of one or more cells of said subject. In some certain embodiments, one or more activities include cell growth and/or apoptosis.

In some embodiments, the present invention provides a bi-specific antibody composed of a first antigen-binding site based on a human antibody agent as described herein and a second antigen-binding site that binds an immune cell, for use in inhibiting tumor growth.

In some embodiments, the present invention provides a bi-specific antibody composed of a first antigen-binding site based on a human antibody agent as described herein and a second antigen-binding site that binds an immune cell, for use in killing tumor cells.

In some embodiments, an immune cell is a T cell or an NK cell.

In some embodiments, first and second antigen binding sites are scFvs.

In some embodiments, a second antigen-binding site binds CD3 on T cells.

In some embodiments, the present invention provides a method of directing T cells to kill target cells expressing CD19, the method comprising a step of contacting one or more target cells expressing CD19 with one or more T cells and/or a bi-specific antibody (or a human antibody agent as described herein, a chimeric antigen receptor as described herein or an immune effector cell as described herein), which bi-specific antibody comprises a first antigen-binding site of a human antibody agent as described herein and a second antigen-binding site that binds CD3 on T cells, the contacting being performed under conditions and for a time sufficient so that T cells to which the bi-specific antibody has bound mediate killing of the target cells expressing CD19. In some certain embodiments, first and second antigen binding sites are scFvs.

In some embodiments, the present invention provides a bi-specific antibody composed of a first antigen-binding site based on a human antibody agent as described herein and a second antigen-binding site that binds CD3 on T cells, for use in directing T cells to kill target cells expressing CD19.

In various embodiments, a linker sequence is or comprises a $(G_4S)_n$ sequence. In some embodiments, n is equal to 1, 2, 3, 4, 5, 6, 7, 8, 9, 10 or more.

In various embodiments, a linker sequence is or comprises SRGGGGSGGGGSGGGGSLEMA (SEQ ID NO:289).

In various embodiments, CD19 is human CD19.

In some embodiments, the present invention provides use of a human antibody agent, bi-specific antibody or chimeric antigen receptor (or an immune effector cell expressing the chimeric antigen receptor) as described herein for the treatment or detection of a condition related to CD19 expression.

In some embodiments, the present invention provides use of a human antibody agent, bi-specific antibody, or chimeric antigen receptor (or an immune effector cell expressing the chimeric antigen receptor) as described herein in the manufacture of a medicament for use in medicine.

In some embodiments, the present invention provides use of a human antibody agent, bi-specific antibody, or chimeric antigen receptor (or an immune effector cell expressing the chimeric antigen receptor) as described herein in the manufacture of a medicament for use in a diagnostic test or assay.

In some embodiments, the present invention provides use of a human antibody agent, bi-specific antibody, or chimeric antigen receptor (or an immune effector cell expressing the chimeric antigen receptor) as described herein in the manufacture of a medicament for use in the diagnosis or treatment of cancer.

In some embodiments, the present invention provides use of a human antibody agent, bi-specific antibody, or chimeric antigen receptor (or an immune effector cell expressing the chimeric antigen receptor) as described herein in the manufacture of a medicament for use in the diagnosis or treatment of a medical condition characterized by expression of CD19.

BRIEF DESCRIPTION OF THE DRAWING

The Drawing included herein, which is composed of the following Figures, is for illustration purposes only not for limitation.

FIG. 1A shows representative phage clone binding (in $OD_{450}$) of recombinant human CD19-Fc. FIG. 1B shows representative phage clone binding (as mean fluorescence intensity, MFI) of cell-surface expressed human CD19. Control 1: non-CD19-binding phage scFv antibody clone; Control 2: a commercial mouse anti-human CD19 antibody (Biolegend); Control 3: secondary antibody only.

FIGS. 9A-9D show representative CAR expression (top panel; FIGS. 9A-9C) and in vitro cell killing (bottom panel; FIG. 9D) of various cancer cell lines using selected anti-CD19 CAR-Ts or control T cells (mock-transduced). CD19$^+$ cells: Raji, CA46, Jeko-1 and Daudi; CD19$^-$ cells: Raji-CD19KO (i.e., Raji-CD19 k.o.), Jurkat, THP-1, HeLa, MDA-MB-231, MCF-7, SK-Hep-1 and HepG2.

FIGS. 12A-12C show FACs histograms of CD19 expression in 3T3 (left) and Raji (right) derived cells lines.

FIG. 13A: representative rainbow images of tumor-derived bioluminescence from Raji lymphoma xenografts in NSG mice treated once with phosphate-buffered saline (vehicle, n=5), T cells transduced without a CAR-encoding construct (Mock, n=6), or T cells transduced with an anti-CD19 CAR-T clone 5-13-encoding construct (CAR-T 5-13, n=7; 5×10$^6$ CAR$^+$ T cells per mouse; days are post tumor implantation; dosing was conducted on day 5). The grey-scale converted heatmap indicates total photons/second at the tumor location, which appear as dark spots overlaid on mouse images; FIG. 13B: representative quantitation of tumor growth for mock and CAR-T 5-13 treatment groups presented as total flux (p/s) versus days post implantation of Raji lymphoma xenografts in NSG mice; FIG. 13C: representative quantitation of tumor growth for mock and CAR-T 5-13 treatment groups presented as total flux (p/s) versus days post re-challenge in NSG mice re-challenged with tumor cells seven weeks post initial implantation and treatment (n=3, 0.5×10$^6$ Raji cells injected per mouse at day 35 post original implantation). Naïve mice (n=2) were implanted with Raji cells one day following an injection of 1×10$^6$ mock transduced T cells as a control.

FIG. 14A: representative rainbow images of tumor-derived bioluminescence from NALM-6 leukemia xenografts in NSG mice treated once with phosphate-buffered saline (vehicle, n=6), T cells transduced without a CAR-encoding construct (Mock, n=6), or T cells transduced with an anti-CD19 CAR-T clone 5-13-encoding construct (CAR-T 5-13, n=6; 5×10$^6$ CAR$^+$ T cells per mouse; days are post tumor implantation; dosing was conducted on day 5; days are post tumor implantation; dosing was conducted on day 5); FIG. 14B: representative quantitation of tumor growth for vehicle, mock and CAR-T 5-13 treatment groups presented as total flux (p/s) versus days post implantation of NALM-6 leukemia xenografts in NSG mice.

FIG. 15B) and in vitro cell killing (top panel; FIG. 15A) of various cancer cell lines using selected anti-CD19 CAR-Ts or control T cells (mock-transduced). CD19$^+$ cells: Raji, IM9 and Jeko-1; CD19$^-$ cells: Raji-CD19KO (i.e., Raji-CD19 k.o.) and THP-1.

DEFINITIONS

Figure 1A:
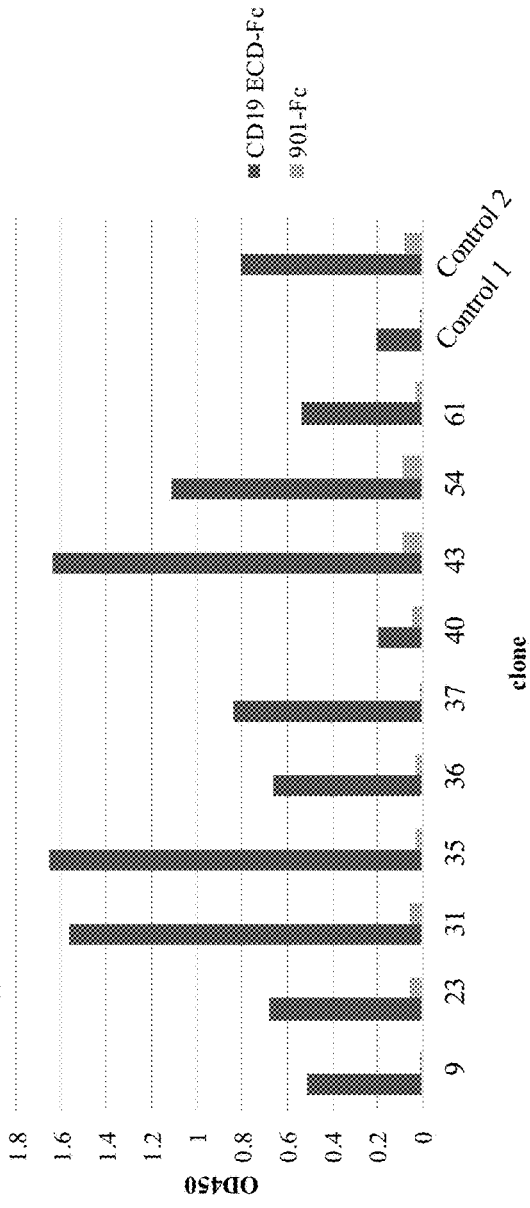
FIGS. 1A and 1B show representative phage clone binding to human CD19 for selected anti-CD19 human antibody agents.

The scope of present invention is defined by the claims appended hereto and is not limited by particular embodiments described herein; those skilled in the art, reading the present disclosure, will be aware of various modifications that may be equivalent to such described embodiments, or otherwise within the scope of the claims.

In general, terminology used herein is in accordance with its understood meaning in the art, unless clearly indicated otherwise. Explicit definitions of certain terms are provided below; meanings of these and other terms in particular instances throughout this specification will be clear to those skilled in the art from context.

In order that the present invention may be more readily understood, certain terms are first defined below. Additional definitions for the following terms and other terms are set forth throughout the specification.

Administration: As used herein, the term "administration" refers to the administration of a composition to a subject or system (e.g., to a cell, organ, tissue, organism, or relevant component or set of components thereof). Those of ordinary skill will appreciate that route of administration may vary depending, for example, on the subject or system to which the composition is being administered, the nature of the composition, the purpose of the administration, etc. For example, in certain embodiments, administration to an animal subject (e.g., to a human) may be bronchial (including by bronchial instillation), buccal, enteral, interdermal, intra-arterial, intradermal, intragastric, intrahepatic, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Affinity matured (or affinity matured antibody): As used herein, refers to an antibody with one or more alterations in one or more CDRs (or, in some embodiments, framework regions) thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al., 1992, BioTechnology 10:779-783 describes affinity maturation by $V_H$ and $V_L$ domain shuffling. Random mutagenesis of CDR and/or framework residues is described by: Barbas et al., 1994, Proc. Nat. Acad. Sci., U.S.A. 91:3809-3813; Schier et al., 1995, Gene 169: 147-155; Yelton et al., 1995. J. Immunol. 155:1994-2004; Jackson et al., 1995, J. Immunol. 154(7): 3310-9; and Hawkins et al., 1992, J. Mol. Biol. 226:889-896. Selection of binders with improved binding properties is described by Thie et al., 2009, Methods Mol. Bio. 525:309-22.

Agent: As used herein may refer to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents are provided as collections or libraries, for example that may be screened to identify or characterize active agents within them. Some particular embodiments of agents that may be utilized in accordance with the present invention include small molecules, antibodies, antibody fragments, aptamers, nucleic acids (e.g., siRNAs, shRNAs, DNA/RNA hybrids, antisense oligonucleotides, ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety.

Amelioration: As used herein, refers to the prevention, reduction or palliation of a state, or improvement of the state of a subject. Amelioration includes, but does not require complete recovery or complete prevention of a disease, disorder or condition (e.g., radiation injury).

Amino acid: As used herein, term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or post-translational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Antibody: As used herein, has its art understood meaning and refers to an immunoglobulin (Ig) that binds specifically to a particular antigen. As is known by those of ordinary skill in the art, antibodies produced in nature are typically comprised of four polypeptide chains, two heavy (H) chains and two light (L) chains. Each heavy and light chain is comprised of a variable region (abbreviated herein as HCVR or $V_H$ and LCVR or $V_L$, respectively) and a constant region. The constant region of a heavy chain comprises a $C_H1$, $C_H2$ and $C_H3$ domain (and optionally a $C_H4$ domain in the case of IgM and IgE). The constant region of a light chain is comprised of one domain, CL. The $V_H$ and $V_L$ regions further contain regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgM, IgD, IgG, IgA and IgE), class (e.g., IgG1, IgG2, IgG3, IgG4, IgA1 and IgA2) or subclass.

Antibody agent: As used herein, the term "antibody agent" refers to an agent that specifically binds to a particular antigen. In some embodiments, the term encompasses any polypeptide with immunoglobulin structural elements sufficient to confer specific binding. In various embodiments, suitable antibody agents may include, but are not limited to, monoclonal antibodies, polyclonal antibodies, humanized antibodies, primatized antibodies, chimeric antibodies, human antibodies, bi-specific or multi-specific antibodies, single domain antibodies (e.g., shark single domain antibodies (e.g., IgNAR or fragments thereof)), conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody fragments, etc. In some embodiments, the term can refer to a stapled peptide. In some embodiments, the term can refer to an antibody-like binding peptidomimetic. In some embodiments, the term can refer to an antibody-like binding scaffold protein. In some embodiments, the term can refer to monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody (e.g., a parental antibody). In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR is substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain, which is homologous or largely homologous to an immunoglobulin-binding domain. In some embodiments, an antibody agent is or comprises a polypeptide that includes all CDRs found in a particular reference antibody chain or chains (e.g., heavy chain and/or light chain).

Antibody component: As used herein, refers to a polypeptide element (that may be a complete polypeptide, or a portion of a larger polypeptide, such as for example a fusion polypeptide as described herein) that specifically binds to an epitope or antigen and includes one or more immunoglobulin structural features. In general, an antibody component is any polypeptide whose amino acid sequence includes elements characteristic of an antibody-binding region (e.g., an antibody light chain or variable region or one or more complementarity determining regions ("CDRs") thereof, or an antibody heavy chain or variable region or one more CDRs thereof, optionally in presence of one or more framework regions). In some embodiments, an antibody component is or comprises a full-length antibody. In some embodiments, an antibody component is less than full-length but includes at least one binding site (comprising at least one, and preferably at least two sequences with structure of known antibody "variable regions"). In some embodiments, the term "antibody component" encompasses any protein having a binding domain, which is homologous or largely homologous to an immunoglobulin-binding domain. In particular embodiments, an included "antibody component" encompasses polypeptides having a binding domain that shows at least 99% identity with an immunoglobulin-binding domain. In some embodiments, an included "antibody component" is any polypeptide having a binding domain that shows at least 70%, 75%, 80%, 85%, 90%, 95% or 98% identity with an immunoglobulin-binding domain, for example a reference immunoglobulin-binding domain. An included "antibody component" may have an amino acid sequence identical to that of an antibody (or a portion thereof, e.g., an antigen-binding portion thereof) that is found in a natural source. An antibody component may be monospecific, bi-specific, or multi-specific. An antibody component may include structural elements characteristic of any immunoglobulin class, including any of the human classes: IgG, IgM, IgA, IgD, and IgE. It has been shown that the antigen-binding function of an antibody can be performed by fragments of a full-length antibody. Such antibody embodiments may also be bi-specific, dual specific, or multi-specific formats; specifically binding to two or more different antigens. Examples of binding fragments encompassed within the term "antigen-binding portion" of an antibody include (i) a Fab fragment, a monovalent fragment consisting of the $V_H$, $V_L$, $C_H1$ and CL domains; (ii) a $F(ab')_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al, 1989, Nature 341:544-546), which comprises a single variable domain; and (vi) an isolated complementarity determining region (CDR). Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al., 1988, Science 242:423-426; and Huston et al., 1988, Proc. Natl. Acad. Sci. U.S.A. 85:5879-5883). In some embodiments, an "antibody component", as described herein, is or comprises such a single chain antibody. In some embodiments, an "antibody component" is or comprises a diabody. Diabodies are bivalent, bi-specific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., 1993, Proc. Natl. Acad. Sci. U.S.A. 90:6444-6448; Poljak, R. J., et al., 1994, Structure 2:1121-1123). Such antibody binding portions are known in the art (Kontermann and Dubel eds., Antibody Engineering, 2001, Springer-Verlag. New York. 790 pp. ISBN 3-540-41354-5). In some embodiments, an antibody component is or comprises a single chain "linear antibody" comprising a pair of tandem Fv segments ($V_H$-$C_H1$-$V_H$-$C_H1$) which, together with complementary light chain polypeptides, form a pair of antigen binding regions (Zapata et al., 1995, Protein Eng. 8(10):1057-1062; and U.S. Pat. No. 5,641,870). In some embodiments, an antibody component may have structural elements characteristic of chimeric, humanized or human antibodies. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some embodiments, an antibody component may have structural elements characteristic of a human antibody. In some embodiments, an antibody component may be included in a chimeric molecule, which chimeric molecule further comprises one or more additional polypeptides or polypeptide fragments (e.g., a signaling component, transmembrane component, etc.).

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc.

Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain, which is homologous or largely homologous to an immunoglobulin-binding domain. In particular embodiments, "antibody polypeptides" encompasses polypeptides having a binding domain that shows at least 99% identity with an immunoglobulin-binding domain. In some embodiments, "antibody polypeptide" is any protein having a binding domain that shows at least 70%, 80%, 85%, 90%, or 95% identity with an immunoglobulin-binding domain, for example a reference immunoglobulin-binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')$_2$, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, an antibody polypeptide may be a humanized antibody. Humanized antibody polypeptides include may be chimeric immunoglobulins, immunoglobulin chains or antibody polypeptides (such as Fv, Fab, Fab', F(ab')$_2$ or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity.

Antigen-binding fragment: The term "antigen-binding fragment", as used herein, refers to one or more fragments of an antibody that retain the ability to bind to an antigen. It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, CL and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR), e.g., $V_H$ CDR3 comprising or not additional sequence (linker, framework region(s) etc.) and (vii) a combination of two to six isolated CDRs comprising or not additional sequence (linker, framework region(s) etc.). Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain $C_H2$ constant region fused to the hinge region, and (iii) an immunoglobulin heavy chain $C_H3$ constant region fused to the $C_H2$ constant region. The hinge region may be modified by replacing one or more cysteine residues with serine residues so as to prevent dimerization. Such binding-domain immunoglobulin fusion proteins are further disclosed in U.S. Patent Application Publication No. 2003/0118592 A1 and U.S. Patent Application Publication No. 2003/0133939 A1. Antibody fragments are obtained using conventional techniques known to those with skill in the art, and fragments are screened for utility in the same manner as are intact antibodies. Furthermore, antigen-binding fragments include divalent (or bivalent) single-chain variable fragments (di-scFvs, bi-scFvs) or, alternatively, so-called diabodies that can be engineered by standard molecular biological means.

Biological activity: As used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Bi-specific antibody: As used herein, refers to a bi-specific binding agent in which at least one, and typically both, of the binding moieties is or comprises an antibody component. A variety of different bi-specific antibody structures are known in the art. In some embodiments, each binding moiety in a bi-specific antibody that is or comprises an antibody component includes $V_H$ and/or $V_L$ regions; in some such embodiments, the $V_H$ and/or $V_L$ regions are those found in a particular monoclonal antibody. In some embodiments, where the bi-specific antibody contains two antibody component-binding moieties, each includes $V_H$ and/or $V_L$ regions from different monoclonal antibodies.

Bi-specific binding agent: As used herein, refers to a polypeptide agent with two discrete binding moieties, each of which binds a distinct target. In some embodiments, a bi-specific binding agent is a single polypeptide; in some embodiments, a bi-specific binding agent is or comprises a plurality of peptides which, in some such embodiments may be covalently associated with one another, for example by cross-linking. In some embodiments, the two binding moieties of a bi-specific binding agent recognize different sites (e.g., epitopes) of the same target (e.g., antigen); in some embodiments, they recognize different targets. In some embodiments, a bi-specific binding agent is capable of binding simultaneously to two targets, which are of different structure.

Carrier: As used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

CDR: As used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Boundaries of CDRs have been defined differently depending on the system, of which several are known in the art (e.g., Kabat, Chothia, IMGT, etc.).

Chimeric antigen receptors (CARs): Antibody agents of the present invention, including single chain variable fragments (scFv), may be used for the preparation of chimeric antigen receptors, the preparation and use of which is generally known in the art. A chimeric antigen receptor (CAR) typically is an artificially constructed hybrid protein or polypeptide containing an antigen-binding domain of an scFv, or other antibody agent, linked to immune cell (e.g., T cell or NK cell) signaling domains. Characteristics of CARs include their ability to redirect immune cell (e.g., T cell or NK cell) specificity and reactivity toward a selected target in either MHC-restricted (in case of TCR-mimic antibodies) or non-MHC-restricted (in case of antibodies against cell surface proteins) manners, exploiting the antigen-binding properties of monoclonal antibodies. The non-MHC-restricted antigen recognition gives immune cells (e.g., T cells or NK cells) expressing CARs the ability to recognize antigen independent of antigen processing, thus bypassing a major mechanism of tumor escape.

Chimeric antigen receptor (CAR) therapy (or adoptive cell therapy): As used herein, refers to the use of chimeric antigen receptors for therapeutic treatment, including for example for adoptive cell therapy. Adoptive cell therapy is a therapeutic approach that typically includes isolation and ex vivo expansion and/or manipulation of immune cells (e.g., NK cells or T cells) and subsequent administration of these cells to a patient, for example for the treatment of cancer. Administered cells may be autologous or allogeneic. Cells may be manipulated to express chimeric antigen receptors in any one of the known ways, including, for example, by using RNA and DNA transfection, viral transduction, electroporation, all of which are technologies known in the art.

Comparable: As used herein, refers to two or more agents, entities, situations, sets of conditions, etc. that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Control: As used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. As used herein, a "control" may refer to a "control antibody". A "control antibody" may be a human, chimeric, humanized, CDR-grafted, multi-specific, or bi-specific antibody as described herein, an antibody that is different as described herein, an antibody fragment or antibody component, or a parental antibody. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Corresponding to: As used herein designates the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

Detection entity/agent: As used herein, refers to any element, molecule, functional group, compound, fragment or moiety that is detectable. In some embodiments, a detection entity is provided or utilized alone. In some embodiments, a detection entity is provided and/or utilized in association with (e.g., joined to) another agent. Examples of detection entities include, but are not limited to: various ligands, radionuclides (e.g., $^3$H, $^{14}$C, $^{18}$F, $^{19}$F, $^{32}$P, $^{35}$S, $^{135}$I, $^{125}$I, $^{123}$I, $^{64}$Cu, $^{187}$Re, $^{111}$In, $^{90}$Y, $^{99}$mTc, $^{177}$Lu, $^{89}$Zr etc.), fluorescent dyes (for specific exemplary fluorescent dyes, see below), chemiluminescent agents (such as, for example, acridinium esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, digoxigenin, haptens, and proteins for which antisera or monoclonal antibodies are available.

Effector function: As used herein refers a biochemical event that results from the interaction of an antibody Fc region with an Fc receptor or ligand. Effector functions include but are not limited to antibody-dependent cell-mediated cytotoxicity (ADCC), antibody-dependent cell-mediated phagocytosis (ADCP), and complement-mediated cytotoxicity (CMC). In some embodiments, an effector function is one that operates after the binding of an antigen, one that operates independent of antigen binding, or both.

Effector cell: As used herein refers to a cell of the immune system that mediates one or more effector functions. In some embodiments, effector cells may include, but may not be limited to, one or more of monocytes, macrophages, neutrophils, dendritic cells, eosinophils, mast cells, platelets, large granular lymphocytes, Langerhans' cells, natural killer (NK) cells, T-lymphocytes, B-lymphocytes and may be from any organism including but not limited to humans, mice, rats, rabbits, and monkeys.

Engineered: As used herein refers, in general, to the aspect of having been manipulated by the hand of man. For example, in some embodiments, a polynucleotide may be considered to be "engineered" when two or more sequences that are not linked together in that order in nature are manipulated by the hand of man to be directly linked to one another in the engineered polynucleotide. In some particular such embodiments, an engineered polynucleotide may comprise a regulatory sequence that is found in nature in operative association with a first coding sequence but not in operative association with a second coding sequence, is linked by the hand of man so that it is operatively associated with the second coding sequence. Alternatively or additionally, in some embodiments, first and second nucleic acid sequences that each encode polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed). As is common practice and is understood by those in the art, progeny of an engineered polynucleotide or cell are typically still referred to as "engineered" even though the actual manipulation was performed on a prior entity. Furthermore, as will be appreciated by those skilled in the art, a variety of methodologies are available through which "engineering" as described herein may be achieved. For example, in some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc.). Alternatively or additionally, in some embodiments, "engineering" may involve use of in vitro chemical synthesis methodologies and/or recombinant nucleic acid technologies such as, for example, nucleic acid amplification (e.g., via the polymerase chain reaction) hybridization, mutation, transformation, transfection, etc., and/or any of a variety of controlled mating methodologies. As will be appreciated by those skilled in the art, a variety of established such techniques (e.g., for recombinant DNA, oligonucleotide synthesis, and tissue culture and transformation (e.g., electroporation, lipofection, etc.)) are well known in the art and described in various general and more specific references that are cited and/or discussed throughout the present specification. See e.g., Sambrook et al., Molecular Cloning: A Laboratory Manual (2d ed., Cold Spring Harbor Laboratory Press, Cold Spring Harbor, N.Y., 1989).

Epitope: As used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Excipient: As used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Fc ligand: As used herein refers to a molecule, preferably a polypeptide, from any organism that binds to the Fc region of an antibody to form an Fc-ligand complex. Fc ligands include but are not limited to FcγRIIA (CD32A), FcγRIIB (CD32B), FcγRIIIA (CD16A), FcγRIIIB (CD16B), FcγRI (CD64), FcεRII (CD23), FcRn, C1q, C3, staphylococcal protein A, streptococcal protein G, and viral FcγR. Fc ligands may include undiscovered molecules that bind Fc.

Framework or framework region: As used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

Host cell: As used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, a host cell is a human, monkey, ape, hamster, rat, or mouse cell. In some embodiments, a host cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, a host cell comprises one or more viral genes, e.g., a retinal cell that expresses a viral gene (e.g., a PER.C6™ cell).

Human antibody: As used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example, that may (originally) have been introduced by random or site-specific mutagenesis in vitro or by somatic mutation in vivo), for example in one or more CDRs and in particular CDR3.

Humanized: As is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$ hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

Hydrophilic: As used herein, the term "hydrophilic" and/or "polar" refers to a tendency to mix with, or dissolve easily in, water.

Hydrophobic: As used herein, the term "hydrophobic" and/or "non-polar", refers to a tendency to repel, not combine with, or an inability to dissolve easily in, water.

Improve, increase or reduce: As used herein, or grammatical equivalents thereof, indicate values that are relative to a baseline measurement, such as a measurement in the same individual prior to initiation of a treatment described herein, or a measurement in a control individual (or multiple control individuals) in the absence of the treatment described herein. A "control individual" is an individual afflicted with the same form of disease or injury as the individual being treated.

In vitro: As used herein refers to events that occur in an artificial environment, e.g., in a test tube or reaction vessel, in cell culture, etc., rather than within a multi-cellular organism.

In vivo: As used herein refers to events that occur within a multi-cellular organism, such as a human and a non-human animal. In the context of cell-based systems, the term may be used to refer to events that occur within a living cell (as opposed to, for example, in vitro systems).

Isolated: As used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

$K_D$: As used herein, refers to the dissociation constant of a binding agent (e.g., an antibody agent or binding component thereof) from a complex with its partner (e.g., the epitope to which the antibody agent or binding component thereof binds).

$k_{off}$: As used herein, refers to the off rate constant for dissociation of a binding agent (e.g., an antibody agent or binding component thereof) from a complex with its partner (e.g., the epitope to which the antibody agent or binding component thereof binds).

$k_{on}$: As used herein, refers to the on rate constant for association of a binding agent (e.g., an antibody agent or binding component thereof) with its partner (e.g., the epitope to which the antibody agent or binding component thereof binds).

Linker: As used herein, is used to refer to that portion of a multi-element polypeptide that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al., 1993, Proc. Natl. Acad. Sci. U.S.A. 90:6444-6448; Poljak, R. J. et al., 1994, Structure 2:1121-1123).

Multivalent binding agent (or multi-specific binding agent): As used herein, refers a binding agent capable of binding to two or more antigens, which can be on the same molecule or on different molecules. Multivalent binding agents as described herein are, in some embodiments, engineered to have the two or more antigen binding sites, and are typically not naturally occurring proteins. Multivalent binding agents as described herein refer to binding agents capable of binding two or more related or unrelated targets. Multivalent binding agents may be composed of multiple copies of a single antibody component or multiple copies of different antibody components. Such binding agents are capable of binding to two or more antigens and are tetravalent or multivalent binding agents. Multivalent binding agents may additionally comprise a therapeutic agent, such as, for example, an immunomodulator, toxin or an RNase. Multivalent binding agents as described herein are, in some embodiments, capable of binding simultaneously to at least two targets that are of different structure, e.g., two different antigens, two different epitopes on the same antigen, or a hapten and/or an antigen or epitope. In many embodiments, multivalent binding agents of the present invention are proteins engineered to have characteristics of multivalent binding agents as described herein. Multivalent binding agents of the present invention may be monospecific (capable of binding one antigen) or multi-specific (capable of binding two or more antigens), and may be composed of two heavy chain polypeptides and two light chain polypeptides. Each binding site, in some embodiments, is composed of a heavy chain variable domain and a light chain variable domain with a total of six CDRs involved in antigen binding per antigen binding site.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Operably linked: As used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with a gene of interest and expression control sequences that act in trans or at a distance to control said gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

Peptide: The term "peptide" refers to two or more amino acids joined to each other by peptide bonds or modified peptide bonds. In particular embodiments, "peptide" refers to a polypeptide having a length of less than about 100 amino acids, less than about 50 amino acids, less than 20 amino acids, or less than 10 amino acids.

Physiological conditions: As used herein, has its art-understood meaning referencing conditions under which cells or organisms live and/or reproduce. In some embodiments, the term refers to conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Polypeptide: As used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30 to 40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least three to four and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice-versa, and/or fragments may be present in a different order in the polypeptide of interest than in the parent), so that the polypeptide of interest is a derivative of its parent polypeptide.

Prevent or prevention: As used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Recombinant: As used herein, is intended to refer to polypeptides (e.g., antibodies or antibody components, or multi-specific binding agents as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., 1997, TIB Tech. 15:62-70; Azzazy H., and Highsmith W. E., 2002, Clin. Biochem. 35:425-45; Gavilondo J. V., and Larrick J. W., 2002, BioTechniques 29:128-45; Hoogenboom H., and Chames P., 2000, Immunol. Today 21:371-8), antibodies isolated from an animal (e.g., a mouse) that is transgenic for human immunoglobulin genes (see e.g., Taylor, L. D., et al., 1992, Nucl. Acids Res. 20:6287-95; Kellermann S-A., and Green L. L., 2002, Curr. Opin. Biotech. 13:593-7; Little, M. et al., 2000, Immunol. Today 21:364-70; Murphy, A. J. et al., 2014, Proc. Natl. Acad. Sci. U.S.A. 111(14):5153-8) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant antibody polypeptide is comprised of sequences found in the germline of a source organism of interest (e.g., human, mouse, etc.). In some embodiments, a recombinant antibody has an amino acid sequence that resulted from mutagenesis (e.g., in vitro or in vivo, for example in a transgenic animal), so that the amino acid sequences of the $V_H$ and $V_L$ regions of the recombinant antibodies are sequences that, while originating from and related to germline $V_H$ and $V_L$ sequences, may not naturally exist within the germline antibody repertoire in vivo.

Reference: As used herein describes a standard, control, or other appropriate reference against which a comparison is made as described herein. For example, in some embodiments, a reference is a standard or control agent, animal, individual, population, sample, sequence, series of steps, set of conditions, or value against which an agent, animal, individual, population, sample, sequence, series of steps, set of conditions, or value of interest is compared. In some embodiments, a reference is tested and/or determined substantially simultaneously with the testing or determination of interest. In some embodiments, a reference is a historical reference, optionally embodied in a tangible medium. Typically, as would be understood by those skilled in the art, a reference is determined or characterized under conditions comparable to those utilized in the assessment of interest.

Specific binding: As used herein, refers to a binding agent's ability to discriminate between possible partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations. In some embodiments, specific binding is assessed by determining the difference in binding affinity between cognate and non-cognate targets. For example, a binding agent may have a binding affinity for a cognate target that is about 3-fold, 4-fold, 5-fold, 6-fold, 7-fold, 8-fold, 9-fold, 10-fold or more than binding affinity for a non-cognate target.

Specificity: As is known in the art, "specificity" is a measure of the ability of a particular ligand to distinguish its binding partner from other potential binding partners.

Subject: As used herein, means any mammal, including humans. In certain embodiments of the present invention the subject is an adult, an adolescent or an infant. In some embodiments, terms "individual" or "patient" are used and are intended to be interchangeable with "subject." Also contemplated by the present invention are the administration of the pharmaceutical compositions and/or performance of the methods of treatment in utero.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial sequence homology: As used herein, the phrase "substantial homology" to refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized as follows:

| Alanine | Ala | A | Nonpolar | Neutral | 1.8 |
| Arginine | Arg | R | Polar | Positive | -4.5 |
| Asparagine | Asn | N | Polar | Neutral | -3.5 |
| Aspartic acid | Asp | D | Polar | Negative | -3.5 |
| Cysteine | Cys | C | Nonpolar | Neutral | 2.5 |
| Glutamic acid | Glu | E | Polar | Negative | -3.5 |
| Glutamine | Gln | Q | Polar | Neutral | -3.5 |
| Glycine | Gly | G | Nonpolar | Neutral | -0.4 |
| Histidine | His | H | Polar | Positive | -3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | -3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | -1.6 |
| Serine | Ser | S | Polar | Neutral | -0.8 |
| Threonine | Thr | T | Polar | Neutral | -0.7 |
| Tryptophan | Trp | W | Nonpolar | Neutral | -0.9 |
| Tyrosine | Tyr | Y | Polar | Neutral | -1.3 |
| Valine | Val | V | Nonpolar | Neutral | 4.2 |

| Ambiguous Amino Acids | 3-Letter | 1-Letter |
| --- | --- | --- |
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, J. Mol. Biol., 215(3):403-410; Altschul et al., 1996, Meth. Enzymology 266:460-480; Altschul et al., 1997, Nucleic Acids Res. 25:3389-3402; Baxevanis et al, Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial identity: As used herein, the phrase "substantial identity" refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al, 1990, J. Mol. Biol., 215(3):403-410, 1990; Altschul et al, 1996, Methods in Enzymology 266:460-480; Altschul et al, 1997, Nucleic Acids Res. 25:3389-3402; Baxevanis et al, Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of a CDR, reference to "substantial identity" typically refers to a CDR having an amino acid sequence at least 80%, preferably at least 85%, at least 90%, at least 95%, at least 98% or at least 99% identical to that of a reference CDR.

Surface plasmon resonance: As used herein, refers to an optical phenomenon that allows for the analysis of specific binding interactions in real-time, for example through detection of alterations in protein concentrations within a biosensor matrix, such as by using a BIAcore system (Pharmacia Biosensor AB, Uppsala, Sweden and Piscataway, N.J.). For further descriptions, see Jonsson, U. et al., 1993, Ann. Biol. Clin. 51:19-26; Jonsson, U. et al., 1991, Biotechniques 11:620-627; Johnsson, B. et al., 1995, J. Mol. Recognit. 8:125-131; and Johnnson, B. et al., 1991, Anal. Biochem. 198:268-277.

Therapeutic agent: As used herein, generally refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically effective amount: As used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Transformation: As used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Treatment: As used herein, the term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 insertions or deletions, and often has no insertions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

Vector: As used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Wild type: As used herein, the term "wild type" has its art-understood meaning that refers to an entity having a structure and/or activity as found in nature in a "normal" (as contrasted with mutant, variant, diseased, altered, etc.) state or context. Those of ordinary skill in the art will appreciate that wild type genes and polypeptides often exist in multiple different forms (e.g., alleles).

DETAILED DESCRIPTION OF CERTAIN EMBODIMENTS

The present invention is based, in part, on the recognition that human antibody agents (e.g., human monoclonal antibodies) that have high specificity for CD19, in particular, human CD19, can be made having preferential binding to CD19 in native format (i.e., form expressed on a cell surface). Further, such human antibody agents are generally associated with better in vivo properties as compared to antibody agents that preferentially bind to recombinant or immobilized forms of CD19 (e.g., plate-bound CD19). The present invention is also based on the recognition that human antibody agents developed from naïve repertoires may, in some embodiments, not provide human antibody agents having specificity for clinically relevant epitopes. To give but one example, the present disclosure specifically demonstrates that anti-CD19 human antibody agents described herein, in particular, a human antibody agent developed using an antibody library generated from sequences obtained from an autoimmune disease subject, demonstrated binding to CD19 expressed on the surface of cells, but not to recombinant human CD19 in the context of a fusion protein. Thus, provided human antibody agents can be characterized, in some embodiments, by high specificity to native human CD19 and not non-native forms of human CD19 that potentially have little to no therapeutic relevance.

The present invention demonstrates, among other things, the successful production of multi-specific binding agents (e.g., bi-specific antibodies) that bind human CD19 expressed on the surface of several cancer cell lines and primary human B cells. In particular, the present invention specifically provides multi-specific binding agents (e.g., bi-specific antibodies) that bind several cancer cell lines in a CD19-specific manner and mediate a high efficiency of target cell lysis. Such multi-specific binding agents are characterized by high specificity and potency in cytotoxicity assays.

The present invention also demonstrates the successful production of chimeric antigen receptors (CARs) using provided human antibody agents and subsequent expression in transduced T cells, thereby creating engineered CAR-T cells (CAR-Ts). In particular, the present disclosure provides CAR-Ts that specifically recognize human CD19 expressed on the surface of various cancer cell lines. As described herein, provided anti-CD19 CAR-Ts demonstrate efficient target cell killing that is, in some embodiments, superior to CAR-Ts generated from other anti-CD19 antibody components. Further, as described herein, provided anti-CD19 CAR-Ts effectively eradicate tumors from animals implanted with human lymphoma xenografts. Thus, the present disclosure, at least in some embodiments, embraces the development of human antibody agents having high specificity for native human CD19 for use in cancer diagnosis and treatment, and provide a source of antibody components for the generation of multi-specific binding agents and CAR-expressing immune cells for use in humans.

CD19

Cluster of Differentiation 19, or CD19, is a transmembrane glycoprotein that is expressed on B cells, in particular, a broad number of B cell lineages with the exception of plasma cells. CD19 is also expressed on a number of malignant B cells. CD19 functions as a co-receptor on the surface of B cells in regulating the stimulation threshold for antigen-BCR interaction. CD19 also interacts with other molecules on the cell surface such as CD21, CD81 and CD82. Activation of CD19 (i.e., phosphorylation of cytoplasmic domain) triggers various signal transduction pathways involving various kinases (e.g., Src-family) and leads to various immune cell processes. CD19 has been implicated in various cancers and autoimmune diseases. Indeed, CD19 has been intensely investigated as a target for the development of antibody-based therapeutics for the treatment of cancer (see, e.g., Hammer, 2012, mAbs 4:5, 571-577; Reichert, J. M. and E. Dhimolea, 2012, Drug Discovery Today 17(17/18):954-963; Suresh, T. et al., 2014, J. Hematol. 7:58); however, most such antibody-based therapeutics are humanized and/or chimeric versions of murine antibodies. Ideally, fully human antibody agents are preferred for treatment of human patients. The amino acid sequence of human CD19 is set forth below (signal sequence is underlined).

| human CD19 polypeptide (SEQ ID NO: 290) | MPPPRLLFFLLFLTPMEVRPEEPLVVKVEEGDNAVLQCLKG TSDGPTQQLTWSRESPLKPFLKLSLGLPGLGIRMRPLAIWLF IFNVSQQMGGFYLCQPGPPSEKAWQPGWTVNVEGSGELFR WNVSDLGGLGCGLKNRSSEGPSSPSGKLMSPKLYVWAKDR PEIWEGEPPCLPPRDSLNQSLSQDLTMAPGSTLWLSCGVPPD SVSRGPLSWTHVHPKGPKSLLSLELKDDRPARDMWVMETG LLLPRATAQDAGKYYCHRGNLTMSFHLEITARPVLWHWLL RTGGWKVSAVTLAYLIFCLCSLVGILHLQRALVLRRKRKR MTDPTRRFFKVTPPPGSGPQNQYGNVLSLPTPTSGLGRAQR WAAGLGGTAPSYGNPSSDVQADGALGSRSPPGVGPEEEEG EGYEEPDSEEDSEFYENDSNLGQDQLSQDGSGYENPEDEPL GPEDEDSFSNAESYENEDEELTQPVARTMDFLSPHGSAWDP SREATSLGSQSYEDMRGILYAAPQLRSIRGQPGPNHEEDAD SYENMDNPDGPDPAWGGGRMGTWSTR |
|---|---|

Anti-CD19 Antibody Agents

While anti-CD19 antibodies are known and have shown promise as therapeutic agents for the treatment of cancer and autoimmune disorders in humans, many are of murine origin. The use of human antibody agents is preferred in this context, among other things, because it reduces the likelihood of an immune response against the administered antibody. Thus, the present invention provides fully human antibody agents (e.g., human monoclonal antibodies and fragments thereof) developed from human B cell libraries that demonstrate high specificity for human CD19 and, in some embodiments, overcome the limitations associated with existing humanized and/or chimeric versions of antibodies of non-human origin (e.g., murine).

The present invention provides methods and compositions for treating CD19-associated diseases, disorder and conditions and related malignances, based on administration of anti-CD19 human antibody agents (e.g., monoclonal antibodies), and, in some embodiments, multi-specific binding agents (e.g., bi-specific antibodies) having a first antigen-binding site that binds human CD19 and a second antigen-binding site that binds an immune cell (e.g., a T cell).

The present invention specifically provides certain human antibody sequences, and also certain affinity-matured antibody sequences, that bind human CD19, and particularly to its native form (i.e., cell surface expressed). For example, particularly exemplified herein are human antibody agents (e.g., full-length antibodies, fragments thereof, single chain antibodies, bi-specific antibodies, or other antibody agent formats as described herein or otherwise known in the art) that include polypeptides containing sequence elements described herein.

Exemplary human antibody agents (e.g., scFvs) that bind human CD19 are presented in Table 1 (light chain variable region sequences (DNA and amino acid) are presented as bold text; heavy chain variable region sequences (DNA and amino acid) are presented as italicized text; linker sequences are presented as underlined text).

TABLE 1

9 DNA
CAGACTGTGGTGACTCAGGAGCCCTCAGTGTCTGCGGCCCCAGGACAGA
AGGTCACCATCTCCTGCTCTGGAAGCAGCTCCAACATTGGGAATAATTA
TGTATCCTGGTACCAGCAGCTCCCAGGAACAGCCCCCAAACTCCTCATT
TATGACAATAATAAGCGACCCTCAGGGATTCCTGACCGATTCTCTGGCT
CCAAGTCTGGCACGTCAGCCACCCTGGGCATCACCGGACTCCAGACTGG
GGACGAGGCCGATTATTACTGCGGAACATGGGATAGCAGCCTGAGTGCT
GGTGTCTTCGGAACTGGGACCAAGCTGACCGTCCTAGGT<u>TCTAGAGGTG
GTGGTGGTAGCGGCGGCGGCGGCTCTGGTGGTGGTGGATCCCTCGAGAT
GGCC</u>*CAGGTGCAGCTGGTGGAGACTGGGGGAGGCTTGGTACAGCCTGGG*

TABLE 1-continued

*GGGTCCCTGAGACTCTCCTGTGCAGCCTCTGGATTCACCTTTAGCAGCT
ATGCCATGAGCTGGGTCCGCCAGGCTCCAGGGAAGGGGCTGGAGTGGGT
CTCAGCTATTAGTGGTAGTGGTGGTAGCACATACTACGCAGACTCCGTG
AAGGGCCGGTTCACCATCTCCAGAGACAATTCCAAGAACACGCTGTATC
TGCAAATGAACAGCCTGAGAGCCGAGGACACGGCCGTATATTACTGTGC
GCGCTACTACTACTCTCGTCTGGATTACTGGGGTCAAGGTACTCTGGTG
ACCGTCTCCTCA* (SEQ ID NO: 1)

9 Amino Acid
**QTVVTQEPSVSAAPGQKVTISCSGSSSNIGNNYVSWYQQLPGTAPKLLI
YDNNKRPSGIPDRFSGSKSGTSATLGITGLQTGDEADYYCGTWDSSLSA
GVFGTGTKLTVLG**<u>SRGGGGSGGGGSGGGGSLEMA</u>*QVQLVETGGGLVQPG
GSLRLSCAASGFTFSSYAMSWVRQAPGKGLEWVSAISGSGGSTYYADSV
KGRFTISRDNSKNTLYLQMNSLRAEDTAVYYCARYYYSRLDYWGQGTLV
TVSS* (SEQ ID NO: 2)

23 DNA
CAGTCTGTGCTGACGCAGCCGCCCTCAGTGTCTGCGGCCCCAGGACAGA
AGGTCACCATCTCCTGCTCTGGAAGCAGCTCCAACATTGGGAATAATTA
TGTATCCTGGTACCGGCAACTCCCAGGAACAGCCCCCAAACTCCTCATC
TATGAAAATAATAAGCGACCCTCAGGGATTCCTGACCGATTCTCTGGCT
CCAAGTCTGGCACGTCAGCCACCCTGGGCATCACCGGACTCCAGACTGG
GGACGAGGCCGATTATTACTGCGGAACATGGGATAGCAGCCTGCGTGCT
GGGGTCTTCGGAACTGGGACCAAGGTCACCGTCCTAGGT<u>TCTAGAGGTG
GTGGTGGTAGCGGCGGCGGCGGCTCTGGTGGTGGTGGATCCCTCGAGAT
GGCC</u>*CAGGTGCAGCTGGTGGAGTCTGGGGGAGGCTTGGTACAGCCTGGG
GGGTCCCTGAGACTCTCCTGTGCAGCCTCTGGATTCACCTTTAGCAGCT
ATGCCATGAGCTGGGTCCGCCAGGCTCCGGGGAAGGGGCTGGAGTGGGT
CTCAGGTATTAGTGCTAGTGGTGGTAGCACATACTACGCAGACTCCGTG
AAGGGCCGCTTCACCATCTCCAGAGACAATTCCAAGAATACGCTGTATC
TGCAAATGAACAGCCTGAGAGCCGAGGACACGGCCGTATATTACTGTGC
GCGCTACTACCTGTCTCAGATCGATTCTTGGGGTCAAGGTACTCTGGTG
ACCGTCTCCTCA* (SEQ ID NO: 3)

23 Amino Acid
**QSVLTQPPSVSAAPGQKVTISCSGSSSNIGNNYVSWYRQLPGTAPKLLI
YENNKRPSGIPDRFSGSKSGTSATLGITGLQTGDEADYYCGTWDSSLRA
GVFGTGTKVTVLG**<u>SRGGGGSGGGGSGGGGSLEMA</u>*QVQLVESGGGLVQPG
GSLRLSCAASGFTFSSYAMSWVRQAPGKGLEWVSGISASGGSTYYADSV
KGRFTISRDNSKNTLYLQMNSLRAEDTAVYYCARYYLSQIDSWGQGTLV
TVSS* (SEQ ID NO: 4)

TABLE 1-continued

31 DNA
CAGTCTGTGTTGACTCAGCCACCCTCAGCGTCTGGGACCCCCGGGCAGA
GGGTCACCATCTCTTGTTCTGGAAGCAGCTCCAACATCGGAAGTAATAC
TGTAAACTGGTACCAGCAGCTCCCAGGAACGGCCCCCCAAACTCCTCATC
TATAGTAATAATCAGCGGCCCTCAGGGGTCCCTGACCGATTCTCTGGCT
CCAAGTCTGGCACCTCAGCCTCCTGGCCATCAGTGGGCTCCAGTCTGA
GGATGAGGCTGATTATTACTGTGCAGCATGGGATGACAGCCTGAATGGC
CATGTGGTATTCGGCGGAGGGACCAAGCTGACCGTCCTAGGTTCTAGAG
GTGGTGGTGGTAGCGGCGGCGGCGGCTCTGGTGGTGGTGGATCCCTCGA
GATGGCCGAGGTCCAGCTGGTGCAGTCTGGGGCTGAGGTGAAGAAGCCT
GGGGCTACAGTGAAAATCTCCTGCAAGGTTTCTGGATACACCTTCACCG
ACTACTACATGCACTGGGTGCAACAGGCCCCTGGAAAAGGGCTTGAGTG
GATGGGACTTGTTGATCCTGAAGATGGTGAAACAATATACGCAGAGAAG
TTCCAGGGCAGAGTCACCATAACCGCGGACACGTCTACAGACACAGCCT
ACATGGAGCTGAGCAGCCTGAGATCTGAGGACACGGCCGTGTATTACTG
TGCAACCGGAATCTATAGCAGACCTCTGGGCTACTGGGGCCAGGGAACC
CTGGTCACCGTCTCCTCA (SEQ ID NO: 5)

31 Amino Acid
QSVLTQPPSASGTPGQRVTISCSGSSSNIGSNTVNWYQQLPGTAPKLLI
YSNNQRPSGVPDRFSGSKSGTSASLAISGLQSEDEADYYCAAWDDSLNG
HVVFGGGTKLTVLGSRGGGGSGGGGSGGGGSLEMAEVQLVQSGAEVKKP
GATVKISCKVSGYTFTDYYMHWVQQAPGKGLEWMGLVDPEDGETIYAEK
FQGRVTITADTSTDTAYMELSSLRSEDTAVYYCATGIYSRPLGYWGQGT
LVTVSS (SEQ ID NO: 6)

35 DNA
TCCTATGTGCTGACTCAGCCACCCTCAGCGTCTGGGACCCCCGGGCAGA
GGGTCACCATCTCTTGTTCTGGAAGCAGCTCCAACATCGGAAGTAATAC
TGTAAACTGGTACCAGCAGCTCCCAGGAACGGCCCCCAAACTCCTCATC
TATAGTAATAATCAGCGGCCCTCAGGGGTCCCTGACCGATTCTCTGGCT
CCAAGTCTGGCACCTCAGCCTCCTGGCCATCAGTGGGCTCCAGTCTGA
GGATGAGGCTGATTATTACTGTGCAGCATGGGATGACAGCCTGAATGGT
TATGTCTTCGGAACTGGGACCAAGGTCACCGTCCTAGGTTCTAGAGGTG
GTGGTGGTAGCGGCGGCGGCGGCTCTGGTGGTGGTGGATCCCTCGAGAT
GGCCGAGGTGCAGCTGGTGGAGACTGGGGGAGGCTTGGTACAGCCTGGG
GGGTCCCTGAGACTCTCCTGTGCAGCCTCTGGATTCACCTTTAGCAGCT
ATGCCATGAGCTGGGTCCGCCAGGCTCCAGGGAAGGGGCTGGAGTGGGT
CTCAGCTATTAGTGGTAGTGGTGGTAGCACATACTACGCAGACTCCGTG
AAGGGCCGATTCACCATCTCCAGAGACAATTCCAAGAACACGCTGTATC
TTCAAATGAACAGCCTGAGAGCTGAGGACACGGCCGTGTATTACTGTGC
GCGCTCTGACGGTAAACATTTCTGGCAGCAGTACGATGCTTGGGGTCAA
GGTACTCTGGTGACCGTCTCCTCA (SEQ ID NO: 7)

35 Amino Acid
SYVLTQPPSASGTPGQRVTISCSGSSSNIGSNHTVNWYQQLPGTAPKLLI
YSNNQRPSGVPDRFSGSKSGTSASLAISGLQSEDEADYYCAAWDDSLNG
YVFGTGTKVTVLGSRGGGGSGGGGSGGGGSLEMAEVQLVETGGGLVQPG
GSLRLSCAASGFTFSSYAMSWVRQAPGKGLEWVSAISGSGGSTYYAD
SVKGRFTISRDNSKNTLYLQMNSLRAEDTAVYYCARSDGKHFWQQYDAW
GQGTLVTVSS (SEQ ID NO: 8)

36 DNA
GACATCCAGTTGACCCAGTCTCCATCCTCCCTGTCTGCATATGTGGGAG
ACAGAGTCACCATCACTTGTCGGGCGAGTCAGGGCATTACCAATTCTTT
AGCCTGGTATCAGCAGAAGCCAGGGAAAGCCCCTAAGCTCCTGCTACAT
GCTGCATCCAGATTGGAGTCTGGGGTCCCATCAAGGTTCAGCGGCAGTG
GATTTGGGACGGATTTCACTCTCACCATCAGCAGCCTGCAGCCTGAAGA
TTTTGCAGTTTATTACTGTCAACACTATTTAGGTACCCCGTACTCTTTT
GGCCAGGGGACCAAGGTGGAGATCAAACGTTCTAGAGGTGGTGGTGGTA
GCGGCGGCGGCGGCTCTGGTGGTGGTGGATCCCTCGAGATGGCCGAGGT
GCAGCTGGTGGAGTCTGGAGGAGGCTTGGTCCAGCCTGGGGGTCCCTG
AGACTCTCCTGTGCAGCCTCTGGGTTCACCGTCAGTGGCAACTACATGA
GCTGGGTCCGCCAGGCTCCAGGGAAGGGGCTGGAGTGGGTCTCAGCTAT
TAGTGGTAGTGGTGGTAGCACATACTACGCAGACTCCGTGAAGGGCCGG
TTCACCATCTCCAGAGACAATTCCAAGAACACGCTGTATCTGCAAATGA
ACAGCCTGAGAGCCGAGGACACGGCCGTATATTACTGTGCGCGCATGAA
CATCGATTACTGGGGTCAAGGTACTCTGGTGACCGTCTCCTCA
(SEQ ID NO: 9)

36 Amino Acid
DIQLTQSPSSLSAYVGDRVTITCRASQGITNSLAWYQQKPGKAPKLLHL
AASRLESGVPSRFSGSGFGTDFTLTISSLQPEDFAVYYCQHYLGTPYSF
GQGTKVEIKRSRGGGGSGGGGSGGGGSLEMAEVQLVESGGGLVQPGGSL
RLSCAASGFTVSSNYMSWVRQAPGKGLEWVSAISGSGGSTYYADSVKGR
FTISRDNSKNTLYLQMNSLRAEDTAVYYCARMNIDYWGQGTLVTVSS
(SEQ ID NO: 10)

37 DNA
GAAATTGTGCTGACTCAGTCTCCATCCTCCCTGTCTGCATCTGTAGGAG
ACAGAGTCACCATCTCTTGCCGGGCAAGTCAGAGCGTTAGCAGATTTTT
AAATTGGTATCAGCAGAAACCCGGGTAAAGCCCCTAAGCTCCTGATCTAT
GGTGTATCCACTTTGGAACGTGGGGTCCCTTCAAGGTTCAGTGGCAGTG
GATCTGGGACAGATTTCACTCTCACCATCAGCAGTCTGCAACCTGAAGA
TTTTGCAACTTACTACTGTCAAGAGAGTTACATTATCCCGCTCACTTTC
GGCGGAGGGACCAAGCTGGAGATCAAACGTTCTAGAAGGTGGTGGTGTA
GCGGCGGCGGCGGCTCTGGTGGTGGTGGATCCCTCGAGATGGCCGAGGT
GCAGCTGGTGCAGTCTGGAGCAGAGGTGAAAAGGCCCGGGGAGTCTCTG
ACGATCTCCTGTAAGGGTTCTGAATACAGCTTTGCCAGCTACTGGATCA
CCTGGGTGCGCCAGATGCCCGGGAAAGGCCTGGAGTGGATGGGGAGGAT
TGATCCTAGTGACTCTTATACCAACTACGCCCGTCCTTCCAAGGCCAC
GTCACCATCTCAGCTGACAAGTCCATCAGCACTGCCTACTTGCAGTGGA
GCAGCCTGAAGGCCTCGGACACCGCCATATATTACTGTGCGAGACCTTT
TCAGTACGACTACGGTGGTTACTCCGATGCTTTTGATATCTGGGGCCAA
GGGACAATGGTCACCGTCTCTTCA (SEQ ID NO: 11)

37 Amino Acid
EIVLTQSPSSLSASVGDRVTISCRASQSVSRFLNWYQQKPGKAPKWYGV
STLERGVPSRFSGSGSGTDFTLTISSLQPEDFATYYCQESYIIPLTFG
GGTKLEIKRSRGGGGSGGGGSGGGGSLEMAEVQLVQSGAEVKRPGESLTI
SCKGSEYSFASYWITWVRQMPGKGLEWMGRIDPSDSYTNYSPSFQGHVT
ISADKSISTAYLQWSSLKASDTAIYYCARPFQYDYGGYSDAFDIWQGT
MVTVSS (SEQ ID NO: 12)

40 DNA
GAAATTGTGATGACGCAGTCTCCACTCTCCCTGTCCGTCACCCCTGGAG
AGCCGGCCTCCATCTCCTGCAGGTCTAGTCAGAGCCTTGGACAGCAA
TGGATTCAACTCTTTGGATTGGTACCTGCAGAAGCCAGGGCAGTCTCCA
CAACTCCTGATCCATTTAGGTTCTGATCGGGCCTCCGGGGTCCCTGACA
GGTTCAGCGGCAGTGGATCAGGCACAGATTTTACACTGAAAATCAGCAG
AGTGGAGGCTGTTGAAAATTATTACTGCATGCAGTCTCTACAA
ATTCCGACGTTCGGCCAAGGGACCAAGGTGGAAATCAAACGTTCTAGAG
GTGGTGGTGGTAGCGGCGGCGGCGGCTCTGGTGGTGGTGGATCCCTCGA
GATGGCCCAGATGCAGCTGGTGCAATCTGGGGCTGAGGTGAAGAAGGCT
GGGTCCTCGGTGAAGGTCTCCTGCGAGACTTCTGGAGGCACCTTCAGCA
GCTACTAGTGTCAACTGGGTGCAGGCCCCTGGACAAGGGCTTGAGTG
GATGGGAGGAATCATCCCTATCGTTGGAACACCAAACTACGCACAGAAG
TTCCAGGAGCAGAGTCACGATTACCGCGGTCGAATCACCTTTACAGCCT
ACATGGAGCTGAGCGGCCTGAGATCTGAGGACACGGCCGTTTATTACTG
TGCGCGGGGGGGATATCGCGACTATATGGATGTCTGGGGCAGAGGGACC
ACGGTCACCGTCTCCTCA (SEQ ID NO: 13)

40 Amino Acid
EIVMTQSPLSLSVTPGEPASISCRSSQSLLDSNGFNSLDWYLQKPGQSP
QLLIHLGSDRASGVPDRFSGSGSGTDFTLKISRVEAEDVGIYYCMQSLQ
IPTFGQGTKVEIKRSRGGGGSGGGGSGGGGSLEMAQMQLVQSGAEVKKA
GSSVKVSCETSGGTFSSSSVNWVRQAPGQGLEWMGGHPIVGTPNYAQKF
QDRVTITAVESTFTAYMELSGLRSEDTAVYYCARGGYRDYMDVWGRGTT
VTVSS(SEQ ID NO: 14)

43 DNA
TCCTATGAGCTGACTCAGCCACCCTCAGCGTCTGGGACCCCCGGGCAGA
GGGTCACCATCTCTTGTTCTGGAAGCAGCTCCAACATCGGAAGTAATTA
TGTATACTGGTACCAGCAGCTCCCAGGAACGGCCCCCAAACTCCTCATC
TATAGGAATAATCAGCGGCCCTCAGGGGTCCCTGACCGATTCTCTGGCT
CCAAGTCTGGCACCTCAGCCTCCTGGCCATCAGTGGGCTCCGGTCCGA
GGATGAGGCTGATTATTACTGTGCAGCATGGGATGACAGCCTGAGTGGT
TATGTCTTCGGAACTGGGACCAAGGTCACCGTCCTAGGTTCTAGAGGTG
GTGGTGGTAGCGGCGGCGGCGGCTCTGGTGGTGGTGGATCCCTCGAGAT
GGCCGAGGTGCAGCTGTGGAGGAGGCTTGGTACAGCCTGGGAGGGTCCCTGAGACTCTCCTGTGCAGCCTCTGGGTTCACCGTCAGTAGCA
ACTACATGAGCTGGGTCCGCCAGGCTCCAGGGAAGGGGCTGGAGTGGGT
CTCAGTTATTTATAGCGGTGGTAGCACATACTACGCAGACTCCGTGAAG
GGCCGATTCACCATCTCCAGAGACAATTCCAAGAACACGCTGTATCTTC
AAATGAACAGCCTGAGAGCCGAGGACACGGCCGTGTATTACTGTGCGAG
GGGGGGTTTGGAGCTGAATTTGACTACTGGGGCCAGGGAACCCTGGTC
ACCGTCTCCTCA (SEQ ID NO: 15)

43 Amino Acid
SYELTQPPSASGTPGQRVTISCSGSSSNIGSNYVYWYQQLPGTAPKLLI
YRNNQRPSGVPDRFSGSKSGTSASLAISGLRSEDEADYYCAAWDDSLSG
YVFGTGTKVTVLGSRGGGGSGGGGSGGGGSLEMAEVQLVESGGGLIQPG
GSLRLSCAASGFTVSSNYMSWVRQAPGKGLEWVSVIYSGGSTYYADSVK
GRFTISRDNSKNTLYLQMNSLRAEDTAVYYCARGGFGAEFDYWGQGTLV
TVSS (SEQ ID NO: 16)

TABLE 1-continued

54 DNA
TCCTATGTGCTGACTCAGCCACCCTCAGTGTCCGTGTCCCCAGGACAGA
CAGCCAGCATCACCTGCTCTGGAGATAAATTGGGGGATAAATATGCTTC
CTGGTATCAGCAGAAGCCAGGCCAGTCCCCTGTACTGGTCATCTATCAA
GATAACAAGCGGCCCTCAGGGATCCCTGAGCGATTCTCTGGCTCCAACT
CTGGGAACACAGCCACTCTGACCATCAGCGGGACCCAGGCTATGGATGA
GGCTGACTATTACTGTCAGGCGTGGGACAGCAGCACTGAGGATGTCTTC
GGACCTGGGACCAAGGTCACCGTCCTAGGTTCTAGAGGTGGTGGTGGTA
GCGGCGGCGGCGGCTCTGGTGGTGGTGGATCCCTCGAGATGGCCGAGGT
GCAGCTGGTGGAGTCTGGAGGAGGCTTGATCCAGCCTGGGGGGTCCCTG
AGACTCTCCTGTGCAGCCTCTGGGTTCACCGTCAGTAGCAACTACATGA
GCTGGGTCCGCCAGGCTCCAGGGAAGGGGCTGGAGTGGGTCTCAGTTAT
TTATAGCGGTGGTAGCACATACTACGCAGACTCCGTGAAGGGCCGATTC
ACCATCTCCAGAGACAATTCCAAGAACACGCTGTATCTTCAAATGAACA
GCCTGAGAGCCGAGGACACGGCCGTGTATTACTGTGCGAGAGGTGGTAT
TTCGGACGATTACTATGGTTCGGGGAGTTATGATAACTGGGGCCAGGGA
ACCCTGGTCACCGTCTCCTCA (SEQ ID NO: 17)

54 Amino Acid
SYVLTQPPSVSVSPGQTASITCSGDKLGDKYASWYQQKPGQSPVLVIYQ
DNKRPSGIPERFSGSNSGNTATLTISGTQAMDEADYYCQAWDSSTEDVF
GPGTKVTVLGSRGGGGSGGGGSGGGGSLEMAEVQLVESGGGLIQPGGSL
RLSCAASGFTVSSNYMSWVRQAPGKGLEWVSVIYSGGSTYYADSVKGRF
TISRDNSKNTLYLQMNSLRAEDTAVYYCARGGISDDYYGSGSYDNWGQG
TLVTVSS(SEQ ID NO: 18)

61 DNA
GACATCCAGTTGACCCAGTCTCCATCCTCCCTGTCTGCATCTGTAGGAG
ACAGAGTCACCATCACTTGCCGGGCAAGTCAGAGCATTAGCAGCTATTT
AAATTGGTATCAGCAGAAACCAGGGAAAGCCCCTAAGCTCCTGATCTAT
GCTGCATCCAGTTTGCAAAGTGGGGTCCCATCAAGGTTCAGTGGCAGTG
GATCTGGGACAGATTTCACTCTCACCATCAGCAGTCTGCAACCTGAAGA
TTTTGCAACTTACTACTGTCAACAGAGTTACAGTACCCCCTTCACTTTC
GGCGGAGGGACCAAGGTGGAGATCAAACGTTCTAGAGGTGGTGGTGGTA
GCGGCGGCGGCGGCTCTGGTGGTGGTGGATCCCTCGAGATGGCCGAGGT
GCAGCTGGTGGAGTCTGGGGGAGGCTTGGTCCAGCCTGGGGGGTCCCTG
AGACTCTCCTGTGCAGCCTCTGGATTCACCGTCAGTAGCAACTACATGA
GCTGGGTCCGCCAGGCTCCAGGGAAGGGGCTGGAGTGGGTCTCAGTTAT
TTATAGCGGTGGTAGCACATACTACGCAGACTCCGTGAAGGGCCGATTC
ACCATCTCCAGAGACAATTCCAAGAACACGCTGTATCTTCAAATGAACA
GCCTGAGAGCCGAGGACACGGCCGTGTATTACTGTGCGAGAGAAAGGGG
GATGGGATATGCTTTTGATATCTGGGGCCAAGGGACAATGGTCACCGTC
TCTTCA (SEQ ID NO: 19)

61 Amino Acid
DIQLTQSPSSLSASVGDRVTITCRASQSISSYLNVVYQQKPGKAPKLLI
YAASSLQSGVPSRFSGSGSGTDFTLTISSLQPEDFATYYCQQSYSTPFT
FGGGTKVEIKRSRGGGGSGGGGSGGGGSLEMAEVQLVESGGGLVQPGGS
LRLSCAASGFTVSSNYMSWVRQAPGKGLEWVSVIYSGGSTYYADSVKGR
FTISRDNSKNTLYLQMNSLRAEDTAVYYCARERGMGYAFDIWGQGTMVT
VSS (SEQ ID NO: 20)

1 DNA
GACATCCAGATGACCCAGTCTCCATCCTCCCTGTCTGCATCTGTAGGAG
ACAGAGTCACCATCACTTGCCGGGCCAGTCAGGGCATTGGCAGTTATTT
AGCCTGGTATCAGCAAAAACCAGGGAAAGCCCCTAAACTCCTGATCTAT
CCTGCATCCAGTTGCAAAGTGGGGTCCCATCAAGGTTCAGCGGCAGTG
GATCTGGGACAGAATTCACTCTCACAATCAGCAGCCTGCAGCCTGAAGA
TTTTGCAACTTATTACTGTCAACAACTTAATAGTCTCTTCGGCCAAGGG
ACACGACTGGAGATTAAACGTTCTAGAGGTGGTGGTGGTAGCGGCGGCG
GCGGCTCTGGTGGTGGTGGATCCCTCGAGATGGCCCAGCTGCAGCTGCA
GGAGTCGGGCCCAGGACTGGTGAAGCCTTCGGAGACCCTGTCCCTCACC
TGCTCTGTCTCTGGTGTCTCCATGAGTGAAAACTACTGGAGCTGGATCC
GGCAGCCCCCAGGGAAGCGACTGGAGTGGATTGGGTGTGCCCATTACAC
TGGGGACACCCACTACAACCCCTCCCTCAAGGGTCGAGTCACCATATCA
CTAGACACGTCCATGAACCAGTTCTCCCTGAGGCTGAACTCTGTGACCG
CTGCGGACACGGCCGTCTATTACTGTGCGAGTTATCATCCCTTTAACTA
CTGGGGCCAGGGAACCCTGGTCACCGTCTCCTCA
(SEQ ID NO: 21)

1 Amino Acid
DIQMTQSPSSLSASVGDRVTITCRASQGIGSYLAWYQQKPGKAPKWYPA
STLQSGVPSRFSGSGSGTEFTLTISSLQPEDFATYYCQQLNSLFGQGTR
LEIKRSRGGGGSGGGGSGGGGSLEMAQLQLESGPGLVKPSETLSLTCS
VSGVSMSENYWSWIRQPPGKRLEWIGCAHYTGDTHYNPSLKGRVTISLD
TSMNQFSLRLNSVTAADTAVYYCASYHPFNYWGQGTLVTVSS
(SEQ ID NO: 22)

2 DNA
CAGGCTGTGCTGACTCAGCCACCCTCGGCGTCTGGGACCCCCGGGCAGA
GGGTCACCATCTCTTGTTCTGGAAGCAGCTCCAACATCGGAACTAAAAC
TGTAAACTGGTATCAGGTGCTCCCAGGAACGGCCCCCAAACTCCTCATC
TATAGTAATTATCGCCGGCCCTCAGGGGTCCCTGACCGATTCTCTGGCT
CCAAGTCTGGCACCTCAGCCTCCCTGGCCATCAGTGGGCTCCAGTCTGA
CGATGAGGCTGATTATTACTGTGCACTATGGGATGACAGCCTGGATGGT
TATGTCTTCGGAACTGGGACCAAGGTCACCGTCCTAGGTTCTAGAGGTG
GTGGTGGTAGCGGCGGCGGCTCTGGTGGTGGTGGATCCCTCGAGAT
GGCCGAGGTCCAGCTGGTGCAGTCTGGGGCTGAGGTGAGGAGGCCTGGG
GCTACAGTGAAAATCTCCTGCAAGGTTTCTGGATACACCTTCAACGACT
TCTACTTACACTGGGTGCGACAGGCCCCTGGAAAAGGGCTTGAGTGGAT
GGGACGTATTGATCCTGAAGATGGTAAAACAAGATATGCAGAGAAGTTC
CAGGGCAGACTCACCATTACCGCGGACACGTCTACAGACACTCTTTACA
TGCAACTGGGCGGCCTGACATCTGACGACACGGCCGTCTATTACTGTAC
AACTGATTGGGGCTATAGCAGTTCCCTACGTGAGGAGGACATCTGGTAC
GACTGCTGGGGCCAGGGAACCCTGGTCACCGTCTCCTCA
(SEQ ID NO: 23)

2 Amino Acid
QAVLTQPPSASGTPGQRVTISCSGSSSNIGTKTVNWYQVLPGTAPKLLI
YSNYRRPSGVPDRFSGSKSGTSASLAISGLQSDDEADYYCALWDDSLDG
YVFGTGTKVTVLGSRGGGGSGGGGSGGGGSLEMAEVQLVQSGAEVRRPG
ATVKISCKVSGYTFNDFYLHWVRQAPGKGLEWMGRIDPEDGKTRYAEKF
QGRLTITADTSTDTLYMQLGGLTSDDTAVYYCTTDWGYSSSLREEDIWY
DCWGQGTLVTVSS (SEQ ID NO: 24)

3 DNA
TCCTATGAGCTGACTCAGCCACCCTCAGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCATCTATTAT
GATAGCGACCGGCCCTCAGGGATCCCTGAGCGATTCTCTGGCTCCAACT
CTGGGAACACGGCCACCCTGACCATCAGCAGGGTCGAAGCCGGGGATGA
GGCCGACTATTACTGTCAGGTGTGGGATAGTAGTGATCATTATGTC
TTCGGAACTGGGACCAAGGTCACCGTCCTAGGTTCTAGAGGTGGTGGTG
GTAGCGGCGGCGGCGGCTCTGGTGGTGGTGGATCCCTCGAGATGGCCGA
GGTGCAGCTGGTGCAGTCTGGGGCTGAGGTGAAGAAGCCTGGGTCCTCG
GTGAAGGTCTCCTGCAAGGCTTCTGGAGGCACCTTCAGCAGCTATGCTA
TCAGCTGGGTGCGACAGGCCCCTGGACAAGGGCTTGAGTGGATGGGAGG
GATCATCCCTATCTTTGGTACAGCAAACTACGCACAGAAGTTCCAGGGC
AGAGTCACGATTACCGCGGACGAATCCACGAGCACAGCCTACATGGAGC
TGAGCAGCCTGAGATCTGAGGACACGGCCGTGTATTACTGTGCAGAGA
TTATGGCTACGGTGACTACGGTGATGCTTTTGATATCTGGGGCCAAGGG
ACAATGGTCACCGTCTCTTCA (SEQ ID NO: 25)

3 Amino Acid
SYELTQPPSVSVAPGKTARITCGGNNIGSKSVHWYQQKPGQAPVLVIYY
DSDRPSGIPERFSGSNSGNTATLTISRVEAGDEADYYCQVWDSSSDHYV
FGTGTKVTVLGSRGGGGSGGGGSGGGGSLEMAEVQLVQSGAEVKKPGSS
VKVSCKASGGTFSSYAISWVRQAPGQGLEWMGGHPIFGTANYAQKFQGR
VTITADESTSTAYMELSSLRSEDTAVYYCARDYGYGDYGDAFDIWGQGT
MVTVSS(SEQ ID NO: 26)

4 DNA
TCCTATGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAGGCCAGGCCAGGCCCCTGTGCTGGTCGTCTATGAT
GATAGCGACCGGCCCTCAGGGATCCCTGAGCGATTCTCTGGCTCCAACT
CTGGAAACACGGCACCCTGACCATCAGCAGGGTCGAAGCCGGGGATGA
GGCCGACTATTCCTGTCAGGTGTGGGATAGCAGTAGTGATCATTATGTC
TTCGGACCTGGGACCAAGGTCACCGTCCTAGGTTCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTACTGGA
TCGCTGGGTGCGCCAGATGCCCGGGAAAGGCCTGGAGTGGATGGGGAT
CATCTATCCTGGTGACTCTGATACCAGATACAGCCCGTCCTTCAAGGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCGT
TGTTGGTACTATCTACTCTATGCAGTACGATGTTTGGGGTCAAGGTACT
CTGGTGACCGTCTCCTCA (SEQ ID NO: 27)

4 Amino Acid
SYVLTQPPSVSVAPGKTARITCGGNNIGSKSVHWYQQRPGQAPVLVVYD
DSDRPSGIPERFSGSNSGNTATLTISRVEAGDEADYSCQVWDSSSDHYV
FGPGTKVTVLGSRGGGGSGGGGSGGGGSLEMAEVQLVQSGAEVKKPGES
LKISCKGSGYSFTSYWIGWVRQMPGKGLEWMGHPGDSDTRYSPSFQGQ
VTISADKSISTAYLQWSSLKASDTAMYYCARVVGTIYSMQYDVWGQG
TLVTVSS(SEQ ID NO: 28)

TABLE 1-continued

5 DNA
CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGAACACGGCCACCCTGACCATCAGCAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGTTCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 29)

5 Amino Acid
LPVLTQPPSVSVAPGKTARITCGGNNIGSKSVHWYQQKPGQAPVLVVYD
DSDRPSGIPERFSGSNSGNTATLTISRVEAGDEADYYCQVWDSSSDYVV
FGGGTKLTVLGSRGGGGSGGGGSGGGGSLEMAEVQLVQSGAEVKKPGES
LKISCKGSGYSFTSYWIGWVRQMPGKGLEWMGHYPGDSDTRYSPSFQGQ
VTISADKSISTAYLQWSSLKASDTAMYYCARQVWGWQGGMYPRSNWW
YNMDSWGQGTLVTVSS (SEQ ID NO: 30)

6 DNA
CAGGCTGTGCTGACTCAGCCACCCTCGGTGTCTGAAGCCCCCAGGCAGA
GGGTCACCATCTCCTGTTCTGGAAGCAGCTCCAACGTCGGAAATAATGC
TGTAAACTGGTACCAGCAGGTCCCAGGAAAGGCTCCCAAACTCCTCATC
TATTATGATGATCTGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
CCGGTATTCGGCGGAGGGACCAAGCTGACCGTCCTAGGTTCTAGAGGTG
GTGGTGGTAGCGGCGGCGGCGGCTCTGGTGGTGGTGGATCCCTCGAGAT
GGCCGAAGTGCAGCTGGTGCAGTCTGGAGCAGAGGTGAAAAAGCCCGGG
GAGTCTCTGAAGATCTCCTGTAAGGGTTCTGGATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCCGTCCTTC
CAAGGCCAGGTCACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTACTTGGGACTCTATGTACATGGATTACTGGGGTCAA
GGTACTCTGGTGACCGTCTCCTCA (SEQ ID NO: 31)

6 Amino Acid
QAVLTQPPSVSEAPRQRVTISCSGSSSNVGNNAVNWYQQVPGKAPKLLI
YYDDLLSSGVSDRFSGSKSGTSASLAISGLQSEDEADYYCAAWDDSLNG
PVFGGGTKLTVLGSRGGGGSGGGGSGGGGSLEMAEVQLVQSGAEVKKPG
ESLKISCKGSGYSFTSYWIGWVRQMPGKGLEWMGHYPGDSDTRYSPSFQ
GQVTISADKSISTAYLQWSSLKASDTAMYYCARWSSTWDSMYMDYWG
QGTLVTVSS (SEQ ID NO: 32)

7 DNA
CAGCCTGTGCTGACTCAGCCACCCTCAGTGTCAGTGGCCCCAGGAAAGA
CGGCCAGGATCACCTGTGGAGGAAACAACATTGGAAGTGAAAGTGTGCA
CTGGTACCAGCAGAAGCCAGGCCAGGCCCCTATGGTGGTCATCTATTAT
GATAGCAACCGGCCCTCAGGGATCCCTGAGCGATTCTCTGGCTCCAACT
CTGGGAACACGGCCACCCTGACCGTCAGCAGGGTCGAAGCCGAGGATGA
GGCCGACTATTACTGTCAGGTGTGGAATAGTAGTAGTGATCATCGAGGA
GTGTTCGGCGGAGGGACCAAGCTGACCGTCCTAGGTTCTAGAGGTGGTG
GTGGTAGCGGCGGCGGCGGCTCTGGTGGTGGTGGATCCCTCGAGATGGC
CGAAGTGCAGCTGGTGCAGTCTGGAGCAGAGGTGAAAAAGCCCGGGGAG
TCTCTGAAGATCTCCTGTAAGGGTTCTGGATACAGCTTTACCAGCTACT
GGATCGGCTGGGTGCGCCAGATGCCCGGGAAAGGCCTGGAGTGGATGGG
GATCATCTATCCTGGTGACTCTGATACCAGATACAGCCCGTCCTTCCAA
GGCCAGGTCACCATCTCAGCCGACAAGTCCATCAGCACCGCCTACCTGC
AGTGGAGCAGCCTGAAGGCCTCGGACACCGCCATGTATTACTGTGCGCG
CGTTACTTACTCTATGGACTACTACTTCGATTCTTGGGGTCAAGGT
ACTCTGGTGACCGTCTCCTCA (SEQ ID NO: 33)

7 Amino Acid
QPVLTQPPSVSVAPGKTARITCGGNNIGSESVHWYQQKPGQAPMVVIYY
DSNRPSGIPERFSGSNSGNTATLTVSRVEAEDEADYYCQVWNSSSDHRG
VFGGGTKLTVLGSRGGGGSGGGGSGGGGSLEMAEVQLVQSGAEVKKPGE
SLRISCKGSGYSFTSYWIGWVRQMPGKGLEWMGHYPGDSDTRYSPSFQG
QVTISADKSISTAYLQWSSLKASDTAMYYCARVTYSMDSYYFDSWGQ
GTLVTVSS (SEQ ID NO: 34)

5-1 DNA
CTGCCTGTGCTTACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGAACACGGCCACCCTGACCATCAACAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGTTCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACTGTCTCCTCA
(SEQ ID NO: 35)

5-1 Amino Acid
LPVLTQPPSVSVAPGKTARITCGGNNIGSKSVHWYQQKPGQAPVLVVYD
DSDRPSGIPERFSGSNSGNTATLTINRVEAGDEADYYCQVWDSSSDYVV
FGGGTKLTVLGSRGGGGSGGGGSGGGGSLEMAEVQLVQSGAEVKKPGES
LKISCKGSGYSFTSYWIGWVRQMPGKGLEWMGHYPGDSDTRYSPSFQGQ
VTISADKSISTAYLQWSSLKASDTAMYYCARQVWGWQGGMYPRSNWW
YNMDSWGQGTLVTVSS (SEQ ID NO: 36)

5-10 DNA
CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGAACACGGCCACCCTGACCATCAGCAGGGTCGAAGCCGGGGATGA
GGCCGACTATTACTGTCAGGTGTGGGATAGTAGTAGTGATTATGTGGTA
TTTGGCGGAGGGACCAAGCTGACCGTCCTAGGTTCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTCTGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTAACCGTCTCCTCA
(SEQ ID NO: 37)

5-10 Amino Acid
LPVLTQPPSVSVAPGKTARITCGGNNIGSKSVHWYQQKPGQAPVLVVYD
DSDRPSGIPERFSGSNSGNTATLTISRVEAGDEADYYCQVWDSSSDYVV
FGGGTKLTVLGSRGGGGSGGGGSGGGGSLEMAEVRLVQSGAEVKKPGES
LKISCKGSGYSFTSFWIGWVRQMPGKGLEWMGHYPGDSDTRYSPSFQGQ
VTISADKSISTAYLQWSSLKASDTAMYYCVRQVWGWQGGMYPRSNWW
YNMDSWGQGTLVTVSS (SEQ ID NO: 38)

5-11 DNA
CTGCCTGTGCTGACTCAGCCACCCTCGGTGTCAGTGGCCCCAGGAGAGA
CGGCCAGGATTACCTGTGGGGGAAACAACATTGGAAGTAAAAGTGTGCA
CTGGTACCAGCAGAAGCCAGGCCAGGCCCCCTGTGCTGGTCGTCTATGAT
GATAGCGACCGGCCCTCAGGGATCCCTGAGCGATTCTCTGGCTCCAACT
CTGGGAACACGGCCACCCTGACCATCAGCAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGTTCTAGAGGTGGTGGTG
GTAGCGGCGGCGGCTCTGGTGGTGGTGGATCCCTCGAGATGGCCGAGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 39)

5-11 Amino Acid
LPVLTQPPSVSVAPGETARITCGGNNIGSKSVHWYQQKPGQAPVLVVYD
DSDRPSGIPERFSGSNSGNTATLTISRVEAGDEADYYCQVWDSSSDYVV
FGGGTKLTVLGSRGGGGSGGGGSGGGGSLEMAEVQLVQSGAEVKKPGES
LKISCKGSGYSFTSYWIGWVRQMPGKGLEWMGHYPGDSDTRYSPSFQGQ
VTISADKSISTAYLQWSSLKASDTAMYYCARQVWGWQGGMYPRSNWW
YNMDSWGQGTLVTVSS (SEQ ID NO: 40)

TABLE 1-continued 5-13 DNA
CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGAACACGGCCACCCTGACCATCAGCAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGT<u>TCTAGAGGTGGTGGTG
GTAGCGGCGGCGGCGGCTCTGGCGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 41)

5-13 Amino Acid
**LPVLTQPPSVSVAPGKTARITCGGNNIGSKSVHWYQQKPGQAPVLVVYD
DSDRPSGIPERFSGSNSGNTATLTISRVEAGDEADYYCQVWDSSSDYVV
FGGGTKLTVLG**<u>SRGGGGSGGGGSGGGGSLEMA</u>*EVQLVQSGAEVKKPGES
LKISCKGSGYSFTSYWIGWVRQMPGKGLEWMGIIYPGDSDRYSPSFQGQ
VTISADKSISTAYLQWSSLKASDTAIVIYYCARQVWGWQGGMYPRSNWW
YNLDSWGQGTLVTVSS* (SEQ ID NO: 42)

5-15 DNA
CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGAACACGGCCACCATGACCATCAGCAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGT<u>TCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTGCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 43)

5-15 Amino Acid
**LPVLTQPPSVSVAPGKTARITCGGNNIGSKSVHWYQQKPGQAPVLVVYD
DSDRPSGIPERFSGSNSGNTATMTISRVEAGDEADYYCQVWDSSSDYVV
FGGGTKLTVLG**<u>SRGGGGSGGGGSGGGGSLEMA</u>*EVQLVQSGAEVKKPGES
LKISCKGAGYSFTSYWIGWVRQMPGKGLEWMGIIYPGDSDRYSPSFQGQ
VTISADKSISTAYLQWSSLKASDTAMYYCARQVWGWQGGMYPRSNWW
YNMDSWGQGTLVTVSS* (SEQ ID NO: 44)

5-2 DNA
CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGAACATGGCCACCCTGACCATCAGCAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGT<u>TCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 45)

5-2 Amino Acid
**LPVLTQPPSVSVAPGKTARITCGGNNIGSKSVHWYQQKPGQAPVLVVYD
DSDRPSGIPERFSGSNSGNMATLTISRVEAGDEADYYCQVWDSSSDYVV
FGGGTKLTVLG**<u>SRGGGGSGGGGSGGGGSLEMA</u>*EVQLVQSGAEVKKPGES
LKISCKGSGYSFTSYWIGWVRQMPGKGLEWMGIIYPGDSDRYSPSFQGQ
VTISADKSISTAYLQWSSLKASDTAMYYCARQVWGWQGGMYPRSNWW
YNMDSWGQGTLVTVSS* (SEQ ID NO: 46)

5-3 DNA
CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCAACCGGCCCTCAGGGATCCCTGAGCGATTCTCTGGCTCCAACT
CTGGGAACACGGCCACCCTGACCATCAGCAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGT<u>TCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGTCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 47)

5-3 Amino Acid
**LPVLTQPPSVSVAPGKTARITCGGNNIGSKSVHWYQQKPGQAPVLVVYD
DSNRPSGIPERFSGSNSGNTATLTISRVEAGDEADYYCQVWDSSSEYVV
FGGGTKLTVLG**<u>SRGGGGSGGGGSGGGGSLEMA</u>*EVQLVQSGAEVKKPGES
LKISCKGSGYSFTSYWIGWVRQMPGKGLEWMGIIYPGDSDRYSPSFQGQ
VTISADKSISTAYLQWSSLKASDTAMYYCARQVWGWQGGMYPRSNWW
YNMDSWGQGTLVTVSS* (SEQ ID NO: 48)

5-4 DNA
CTGCCTGTGCTGACTCAGCCACCCTCGATGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGAACACGGCCACCCTGACCATCAGCAGGGTCGAAGCCGGGGATGA
GGCCGACTATTACTGTCAGGTGTGGGATAGTAGTAGTGGTTATGTGGTA
TTCGGCGGAGGGACCAAGCTGACCGTCCTAGGT<u>TCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTGCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 49)

5-4 Amino Acid
**LPVLTQPPSMSVAPGKTARITCGGNNIGSKSVHWYQQKPGQAPVLVVYD
DSDRPSGIPERFSGSNSGNTATLTISRVEAGDEADYYCQVWDSSSGYVV
FGGGTKLTVLG**<u>SRGGGGSGGGGSGGGGSLEMA</u>*EVQLVQSGAEVKKPGES
LKISCKGSGYSFTSYWIGWVRQMPGKGLEWMGIIYPGDSDRYSPSFQGQ
VTISADKSISTAYLQWSSLKASDTAMYYCARQVWGWQGGMYPRSNWWY
NMDSWGQGTLVTVSS* (SEQ ID NO: 50)

5-5 DNA
CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTACGAT
GATAGCGACCGGCCCTCAGGGATCCCTGAGCGATTCTCTGGCTCCAACT
CTGGGAACACGGCCACCCTGACCATCAGCAGGGTCGAAGCCGGGGATGA
GGCCGACTATTACTGTCAGGTGTGGGATACTAGTGATTATGTGGTA
TTCGGCGGAGGGACCAAGCTGACCGTCCTAGGT<u>TCTAGAGGTGGTGGTG
GTAGCGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTTT
CTGAAGATCTCCTGTAAGGGTTCTGGATACAGCTTCACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCGCCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 51)

5-5 Amino Acid
**LPVLTQPPSVSVAPGKTARITCGGNNIGSKSVHWYQQKPGQAPVLVVYD
DSDRPSGIPERFSGSNSGNTATLTISRVEAGDEADYYCQVWDSTSDYVV
FGGGTKLTVLG**<u>SRGGGGSGGGGSGGGGSLEMA</u>*EVQLVQSGAEVKKPGEF*

TABLE 1-continued

LKISCKGSYSFTSYWIGWVRQMPGKGLEWMGHYPGDSDTRYSPSFQGQ
VAISADKSISTAYLQWSSLKASDTAMYYCARQVWGWQGGMYPRSNWWYN
MDSWGQGTLVTVSS (SEQ ID NO: 52)

5-7 DNA
**CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGACCACTGCCACCCTGACCATCAGCAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGT**TCTAGAGGTGGTGGTG
GTAGCGGCGGCGGCGGCTCTGGTGGTGGTGGATCCCTCGAGATGGCCGA
AGTGCAGCTAGTGCAGTCTGGAGCAGAGGTGAAAAAGCCCGGGGAGTCT
CTGAAGATCTCCTGTAAGGGTTCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTCCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGAACCCGCGTTCTAACTGGTGGTAC
AACATGGATTCTTGGGGTCAAGGTACTCTGGTGACCGTCTCCTCA
(SEQ ID NO: 53)

5-7 Amino Acid
**LPVLTQPPSVSVAPGKTARITCGGNNIGSKSVHWYQQKPGQAPVLVVYD
DSDRPSGIPERFSGSNSGTTATLTISRVEAGDEADYYCQVWDSSSDYVV
FGGGTKLTVLGSRGGGGSGGGGSGGGGSLEMAEVQLVQSGAEVKKPGES
LKISCKGSYSFTSYWIGWVRQMPGKGLEWMGHYPGDSDTRYSPSFQGQ
VTISADKSISTAYLQWSSLKASDTAMYYCARQVWGWQGGMNPRSNWWYN
MDSWGQGTLVTVSS** (SEQ ID NO: 54)

5-9 DNA
**CTGCCTGTGCTGACTCAGCCACCCTCGGTGTCAGTGGCCCCAGGAAAGA
CGGCCAGGATTACCTGTGGGGGAAACAACATTGGAAGTAAAAGTGTGCA
CTGGTACCAGCAGAAGCCAGGCCAGGCCCCTGTGCTGGTCGTCTATGAT
GATAGCGACCGGCCCTCAGGGATCCCTGAGCGATTCTCTGGCTCCAACT
CTGGGAACCACTGCCACCTTGACCATCAGCAGGGTCGAAGCCGGGGATGA
GGCCGACTATTACTGTCAGGTGTGGGATAGTAGTAGTGATTATGTGGTA
TTCGGCGGAGGGACCAAGCTGACCGTCCTAGGT**TCTAGAGGTGGTGGTG
GTAGTGGCGGCGGCGGCTCTGGTGGTGGTGGATCCCTCGAGATGGCCGA
AGTGCAGCTGGTGCAGTCTGGAGCAGAGGTGAAAAAGCCCGGGGAGTCT
CTGAAGATCTCCTGTAAGGGTTCTGGATACAGCTTTACCAGCTACTGGA
TCGGCTGGGTGCGCCAGATGCCCGGGAAAGGCCTGGAGTGGATGGGGAT
CATCTATCCTGGTGACTCTGATACCAGATACAGCCCGTTCTTCCAAGGC
CAGGTCACCATCTCAGCCGACAAGTCCATCAGCACCGCCTACCTGCAGT
GGAGCAGCCTGAAGGCCTCGGACACCGCCATGTATTACTGTGCGCGCCA
GGTTTGGGGTTGGCAGGGTGGTATGTACCCGCGTTCTAACTGGTGGTAC
AACATGGATTCTTGGGGTCAAGGTACTCTGGTGACCGTCTCCTCA
(SEQ ID NO: 55)

5-9 Amino Acid
**LPVLTQPPSVSVAPGKTARITCGGNNIGSKSVHWYQQKPGQAPVLVVYD
DSDRPSGIPERFSGSNSGNTATLTISRVEAGDEADYYCQVWDSSSDYVV
FGGGTKLTVLGSRGGGGSGGGGSGGGGSLEMAEVQLVQSGAEVKKPGE
SLKISCKGSYSFTSYWIGWVRQMPGKGLEWMGHYPGDSDTRYSPFFQGQ
VTISADKSISTAYLQWSSLKASDTAMYYCARQVWGWQGGMYPRSNWWYN
MDSWGQGTLVTVSS** (SEQ ID NO: 56)

6-1 DNA
**CAGGCTGTGCTGACTCAGCCACCCTCGGTGTCTGAAGCCCCCAGGCAGA
GGGTCACCATCTCCTGTTCTGGAAGCAGCTCCAACGTCGGAAATAATGC
TGTAAACTGGTACCAGCAGGTCCCAGGAAAGGCTCCCAAACTCCTCATC
TATTATGATGATCTGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
CCGGTATTCGGCGGAGGGACCAAGCTGACCGTCCTAGGT**TCTAGAGGTG
GTGGTGGTAGCGGCGGCGGCGGCTCTGGTGGTGGTCCCGAGCAGAGGTGGATCCCTCGAGAT
GGCCGAAGTGCAGCTGGTGCAGTCCGGAGCAGAGGTGAAAAAGCCCGGG
GAGTCTCTGAAGATCTCCTGTAAGGGTTCTGGATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCGTCCTTC
CAAGGCCAGGTCACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTTCTTGGGACTCTATGTACATGGATTACTGGGGTCAA
GGTACTATGGTGACCGTCTCCTCA (SEQ ID NO: 57)

6-1 Amino Acid
**QAVLTQPPSVSEAPRQRVTISCSGSSSNVGNNAVNWYQQVPGKAPKLLI
YYDDLLSSGVSDRFSGSKSGTSASLAISGLQSEDEADYYCAAWDDSLNG
PVFGGGTKLTVLGSRGGGGSGGGGSGGGGSLEMAEVQLVQSGAEVKKPG ESLKISCKGSYSFTSYWIGWVRQMPGKGLEWMGHYPGDSDTRYSPSFQ
GQVTISADKSISTAYLQWSSLKASDTAMYYCARWSSSWDSMYMDYWGQG
TMVTVSS** (SEQ ID NO: 58)

6-2 DNA
**CAGGCTGTGCTTACTCAGCCACCCTCGGTGTCTGAAGCCCCCAGGCAGA
GGGTCACCATCTCCTGTTCTGGAAACAGCTCCAACGTCGGAAATAATGC
TATAAACTGGTACCAGCAGGTCCCAGGAAAGGCTCCCAAACTCCTCATC
TATTATGATGATCTGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
CCGGTATTCGGCGGAGGGACCAAGCTGACCGTCCTAGGT**TCTAGAGGTG
GTGGTGGTAGCGGCGGCGGCGGCTCTGGTGGTGGTGGATCCCTCGAGAT
GGCCGAAGTGCAGCTGGTGCAGTCTGGAGCAGAGGTGGAAAAGCCCGGG
GAGTCTCTGAAGATCTCCTGTAAGGGTTCTGGATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCCGTCCTTC
CAAGGCCAGGTCACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTACTTGGGACTCTATGTACATGGAATACTGGGGTCAA
GGTACTCTGGTGACCGTCTCCTCA (SEQ ID NO: 59)

6-2 Amino Acid
**QAVLTQPPSVSEAPRQRVTISCSGNSSNVGNNAINWYQQVPGKAPKLLI
YYDDLLSSGVSDRFSGSKSGTSASLAISGLQSEDEADYYCAAWDDSLNG
PVFGGGTKLTVLGSRGGGGSGGGGSGGGGSLEMAEVQLVQSGAEVEKPG
ESLKISCKGSYSFTSYWIGWVRQMPGKGLEWMGHYPGDSDTRYSPSFQ
GQVTISADKSISTAYLQWSSLKASDTAMYYCARWSSTWDSMYMEYWGQG
TLVTVSS** (SEQ ID NO: 60)

6-4 DNA
**CAGGCTGTGCTGACTCAGCCACCCTCGGTGTCTGAAGCCCCCAGGCAGA
GGGTCACCATCTCCTGTTCTGGAAGCAGCTCCAACGTCGGAAATAATGC
TGTAAACTGGTACCAGCAGGTCCCAGGAAAAGGCTCCCAAACTCCTCATC
TATTATGATGATCTGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
CCGGTATTCGGCGGAGGGACCAAGCTGACCGTCCTAGGT**TCTAGAGGTG
GTGGTGGTAGCGGCGGCGGCGGCTCTGGTGGTGGTGGATCCCTCGAGAT
GGCCGAAGTGCAGCTGGTGCAGTCTGGAGCAGAGGTGAAAAAGCCCGGG
GGGTCTCTGAAGATCTCCTGTAAGGGTTCTGGATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCCGTCCTTC
CAAGGCCAGGTCACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTACTTGGGACTCTATGTACATGGATTACTGGGGTCAA
GGTACTCTGGTGACCGTCTCCTCAA (SEQ ID NO: 61)

6-4 Amino Acid
**QAVLTQPPSVSEAPRQRVTISCSGSSSNVGNNAVNWYQQVPGKAPKLLI
YYDDLLSSGVSDRFSGSKSGTSASLAISGLQSEDEADYYCAAWDDSLNG
PVFGGGTKLTVLGSRGGGSGGGGSGGGGSLEMAEVQLVQSGAEVKKPG
GSLKISCKGSYSFTSYWIGWVRQMPGKGLEWMGHYPGDSDTRYSPSFQ
GQVTISADKSISTAYLQWSSLKASDTAMYYCARWSSTWDSMYMDYWGQG
TLVTVSS** (SEQ ID NO: 62)

6-5 DNA
**CAGGCTGTGCTGACTCAGCCACCCTCGGTGTCTGAAGCCCCCAGGCAGA
GGGTCACCATCTCCTGTTCTGGAAGCAGCTCCAACGTCGGAAATAATGC
TGTAAACTGGTACCAGCAGGTCCCAGGAAAGGCTCCCAAACTCCTCATC
TATTATGATGATCAGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
CCGGTATTCGGCGGAGGGACCAAGCTGACCGTCCTAGGT**TCTAGAGGTG
GTGGTGGTAGCGGCGGCGGCGGCTCTGGTGGTGGTGGATCCCTCGAGAT
GGCCGAAGTGCAGCTGGTGCAGTCTGGAGCAGAGGTGAAAAAGCCCGGG
GAGTCTCTGAAGATCTCCTGTAAGGGTTCTGGATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCCGTCCTTC
CAAGGCCAGGTCACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTACTTGGGACTCTTTGTACATGGATTACTGGGGTCAA
GGTACTCTGGTGACCGTCTCCTCA (SEQ ID NO: 63)

6-5 Amino Acid
**QAVLTQPPSVSEAPRQRVTISCSGSSSNVGNNAVNWYQQVPGKAPKLLI
YYDDQLSSGVSDRFSGSKSGTSASLAISGLQSEDEADYYCAAWDDSLNG
PVFGGGTKLTVLGSRGGGGSGGGGSGGGGSLEMAEVQLVQSGAEVKKPG TABLE 1-continued

*ESLKISCKGSYSFTSYWIGWVRQMPGKGLEWMGHYPGDSDTRYSPSFQ*
*GQVTISADKSISTAYLQWSSLKASDTAMYYCARWSSTWDSLYMDYWGQG*
*TLVTVSS* (SEQ ID NO: 64)

6-6 DNA
CAGGCTGTGCTGACTCAGCCACCCTCGGTGTCTGAAGCCCCCAGGCAGA
GGGTCACCATCTCCTGTTCTGGAAACAGCTCCAACGTCGGAAATAATGC
TGTAAACTGGTACCAGCAGGTCCCAGGAAAGGCTCCCAAACTTCTCATC
TATTATGATGATCTGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
CCGGTATTCGGCGGAGGGACCAAGCTGACCGTCCTAGGT<u>TCTAGAGGTG
GTGGTGGTAGCGGCGGCGGCGGCTCTGGTGGTGGTGGATCCCTCGAGAT
GGCC</u>GAAGTGCAGCTGGTGCAGTCTGGAGCAGAGGTGAAAAAGCCCGGG
GAGTCTCTGAAGATCTCCTGTAAGGGTTCTGGATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCCGTCCTTC
CAAGGCCAGGTCACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTACTTGGGACTCTATGTACATGGATTACTGGGGTCAA
GGTACTCTGGTGACCGTCTCCTCA (SEQ ID NO: 65)

6-6 Amino Acid
*QAVLTQPPSVSEAPRQRVTISCSGNSSNVGNNAVNWYQQVPGKAPKLLI*
*YYDDLLSSGVSDRFSGSKSGTSASLAISGLQSEDEADYYCAAWDDSLNG*
*PVFGGGTKLTVLG*<u>SRGGGGSGGGGSGGGGS</u>*LEMAEVQLVQSGAEVKKPG*
*ESLKISCKGSYSFTSYWIGWVRQMPGKGLEWMGHYPGDSDTRYSPSFQ*
*GQVTISADKSISTAYLQWSSLKASDTAMYYCARWSSTWDSMYMDYWGQG*
*TLVTVSS* (SEQ ID NO: 66)

6-7 DNA
CAGGCTGTGCTGACTCAGCCACCCTCGGTGTCCGAAGCCCCCAGGCAGA
GGGTCACCATCTCCTGTTCTGGAAGCAGCTCCAACGTCGGAAATAATGC
TGTAAACTGGTACCAGCAGGTCCCAGGAAAGGCTCCCAAACTTCTCATC
TATTATGATGATCTGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
ACCGGTATTCGGCGGAGGGCCAAGCTGACCGTCCTAGGT<u>TCTAGAGGTG
GTGGTGGTAGCGGCGGCGGCGGCTCTGGTGGTGGTGGTTCCCTCGAGAT
GGCC</u>GAAGTACAGCTGGTGCAGTCAGGAGCAGAGGTGAAAAAGCCCGGG
GAATCTCTGAAGATCTCCTGTAAGGGTTCTGCATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCCGTCCTTC
CAAGGCCAGGTCACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTACTTGGGACTCTATGTACATGGATTACTGGGGTCTA
GGTACTCTGGTGACCGTCTCCTCA (SEQ ID NO: 67)

6-7 Amino Acid
*QAVLTQPPSVSEAPRQRVTISCSGSSSNVGNNAVNWYQQVPGKAPKLLI*
*YYDDLLSSGVSDRFSGSKSGTSASLAISGLQSEDEADYYCAAWDDSLNG*
*PVFGGGTKLTVLG*<u>SRGGGGSGGGGSGGGGS</u>*LEMAEVQLVQSGAEVKKPG*
*ESLKISCKGSAYSFTSYWIGWVRQMPGKGLEWMGHYPGDSDTRYSPSFQ*
*GQVTISADKSISTAYLQWSSLKASDTAMYYCARWSSTWDSMYMDYWGLG*
*TLVTVSS* (SEQ ID NO: 68)

6-8 DNA
CAGGCTGTGCTGACTCAACCACCCTCGGTGTCTGAAGCCCCCAGGCAGA
GGGTCACCATCTCCTGTTCTGGAAGCAGCTCCAACGTCGGAAATAATGC
TGTAAACTGGTACCAGCAGGTCCCAGGAAAGGCTCCCAAACTTCTCATC
TATTATGATGATCAGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
CCGGTATTCGGCGGAGGGACCAAGCTGACCGTCCTAGGT<u>TCTAGAGGTG
GTGGTGGTAGCGGCGGCGGCGGCTCTGGTGGTGGTGGATCCCTCGGGAT
GGCC</u>GAAGTGCAGCTGGTGCAGTCTGGAGCAGAGGTGAAAAAGCCCGGG
TGAGTCTCTGAAGATCTCCTGTAAGGGTCTGGATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCCGTCCTTC
CAAGGCCAGGTTACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTACTTGGGACTCTATGTACATGGATTACTGGGGTCAA
GGTACTCTGGTAACCGTCTCCTCA (SEQ ID NO: 69)

6-8 Amino Acid
*QAVLTQPPSVSEAPRQRVTISCSGSSSNVGNNAVNWYQQVPGKAPKLLI*
*YYDDQLSSGVSDRFSGSKSGTSASLAISGLQSEDEADYYCAAWDDSLNG*
*PVFGGGTKLTVLG*<u>SRGGGGSGGGGSGGGGS</u>*LGMAEVQLVQSGAEVKKPG*

TABLE 1-continued

*ESLKISCKGSYSFTSYWIGWVRQMPGKGLEWMGHYPGDSDTRYSPSFQ*
*GQVTISADKSISTAYLQWSSLKASDTAMYYCARWSSTWDSMYMDYWGQG*
*TLVTVSS* (SEQ ID NO: 70)

6-9 DNA
CAGGCTGTGCTGACTCAGCCACCCTCGGTGTCTGAAGCCCCCAGGCAGA
GGGTCACCATCTCCTGTTCTGGAAGCAGCTCCAACGTCGGTAATAATGC
TGTAAACTGGTACCAGCAGGTCCCAGGAAAGGCTCCCAAACTCCTCATC
TATTATGATGATCTGCTGTCCTCAGGGGTCTCTGACCGATTCTCTGGCT
CCAAGTCTGGCACCTCAGCCTCCCTGGCCATCAGTGGGCTCCAGTCTGA
GGATGAGGCCGATTATTATTGTGCAGCATGGGATGACAGCCTGAATGGT
CCGGTATTCGGCGAGGGACCAAGCTGACCGTCCTAGGT<u>TCTAGAGGTG
GTGGTGGTAGCGGCGGCGGCGGCTCTGGTGGTGGTGATCCCTCGAGAT
GGCC</u>GAAGTGCAGCTGGTGCAGTCTGGAGCAGAGGTGAAAAAGCCCGGG
GAGTCTCTGAAGATCTCCTGTAAGGGTTCTGGATACAGCTTTACCAGCT
ACTGGATCGGCTGGGTGCGCCAGATGCCCGGGAAAGGCCTGGAGTGGAT
GGGGATCATCTATCCTGGTGACTCTGATACCAGATACAGCCCGTCCTTC
CAAGGCCAGGTCACCATCTCAGCCGACAAGTCCATCAGCACCGCCTACC
TGCAGTGGAGCAGCCTGAAGGCCTCGGACACCGCCATGTATTACTGTGC
GCGCTGGTCTTCTTCTTGGGACTCTATGTACATGGATTACTGGGGTCAA
GGTACTCTGGTGACCGTCTCCTCA (SEQ ID NO: 71)

6-9 Amino Acid
*QAVLTQPPSVSEAPRQRVTISCSGSSSNVGNNAVNWYQQVPGKAPKLLI*
*YYDDLLSSGVSDRFSGSKSGTSASLAISGLQSEDEADYYCAAWDDSLNG*
*PVFGGGTKLTVLG*<u>SRGGGGSGGGGSGGGGS</u>*LEMAEVQLVQSGAEVKKPG*
*ESLKISCKGSYSFTSYWIGWVRQMPGKGLEWMGHYPGDSDTRYSPSFQ*
*GQVTISADKSISTAYLQWSSLKASDTAMYYCARWSSSWDSMYMDYWGQG*
*TLVTVSS* (SEQ ID NO: 72)

In various embodiments, an anti-CD19 human antibody agent according to the present invention is composed of heavy and light chain variable regions, wherein the heavy chain variable region has a sequence that is at least about 50% (e.g., at least about 55%, 60%, 65%, 70%, 75%, 80%, 85%, 90%, 95%, 96%, 97%, 98%, or 99%) identical to a heavy chain variable region that appears in Table 1.

In various embodiments, an anti-CD19 human antibody agent according to the present invention is composed of heavy and light chain variable regions, wherein the heavy chain variable region has a sequence that is substantially identical or identical to a heavy chain variable region that appears in Table 1.

In various embodiments, an anti-CD19 human antibody agent according to the present invention is composed of heavy and light chain variable regions, wherein the light chain variable region has a sequence that is at least about 50% (e.g., at least about 55%, 60%, 65%, 70%, 75%, 80%, 85%, 90%, 95%, 96%, 97%, 98%, or 99%) identical to a light chain variable region that appears in Table 1.

In various embodiments, an anti-CD19 human antibody agent according to the present invention is composed of heavy and light chain variable regions, wherein the light chain variable region has a sequence that is substantially identical or identical to a light chain variable region that appears in Table 1.

In various embodiments, an anti-CD19 human antibody agent according to the present invention is composed of heavy and light chain variable regions, which heavy chain variable region has a sequence that is at least about 50% (e.g., at least about 55%, 60%, 65%, 70%, 75%, 80%, 85%, 90%, 95%, 96%, 97%, 98%, or 99%) identical to a heavy chain variable region that appears in Table 1, and which light chain variable region has a sequence that is at least about 50% (e.g., at least about 55%, 60%, 65%, 70%, 75%, 80%, 85%, 90%, 95%, 96%, 97%, 98%, or 99%) identical to a light chain variable region that appears in Table 1.

In various embodiments, an anti-CD19 human antibody agent according to the present invention is composed of heavy and light chain variable regions, which heavy chain variable region has a sequence that is substantially identical or identical to a heavy chain variable region that appears in Table 1, and which light chain variable region has a sequence that is substantially identical or identical to a light chain variable region that appears in Table 1.

In various embodiments, an anti-CD19 human antibody agent according to the present invention is composed of heavy and light chain variable regions that are selected from heavy and light chain variable region sequences that appear in Table 1.

In various embodiments, an anti-CD19 human antibody agent according to the present invention is or comprises a single chain variable fragment (scFv), which scFv comprises a sequence that is at least about 50% (e.g., at least about 55%, 60%, 65%, 70%, 75%, 80%, 85%, 90%, 95%, 96%, 97%, 98%, or 99%) identical to an scFv that appears in Table 1.

In various embodiments, an anti-CD19 human antibody agent according to the present invention is or comprises a single chain variable fragment (scFv), which scFv comprises a sequence that is substantially identical or identical to an scFv that appears in Table 1.

In various embodiments, an anti-CD19 human antibody agent according to the present invention is or comprises a single chain variable fragment (scFv), which scFv is selected from Table 1.

Provided antibody agents, including antibodies and/or characteristic portions thereof, or nucleic acids encoding them, may be produced by any available means. For example, protocols for antibody production are described by Harlow and Lane, Antibodies: A Laboratory Manual, (1988). Technologies for generating antibodies (e.g., monoclonal antibodies and/or polyclonal antibodies) are well known in the art. It will be appreciated that a wide range of animal species can be used for the production of antisera, including rabbit, mouse, rat, hamster, guinea pig or goat. The choice of animal may be decided upon the ease of manipulation, costs or the desired amount of sera, as would be known to one of skill in the art. It will be appreciated that antibody agents can also be produced transgenically through the generation of a mammal or plant that is transgenic for the immunoglobulin heavy and light chain sequences of interest (e.g., a transgenic rodent transgenic for human immunoglobulin heavy and light chain genes). In connection with the transgenic production in mammals, antibodies can be produced in, and recovered from, the milk of goats, cows, or other mammals (see, e.g., U.S. Pat. Nos. 5,827,690, 5,756, 687, 5,750,172, and 5,741,957; herein incorporated by reference in their entireties). Typically, antibodies can be generated in mouse, rat, guinea pig, hamster, camel, llama, shark, or other appropriate host. Alternatively, antibodies may be made in chickens, producing IgY molecules (Schade et al., 1996, ALTEX 13(5):80-85). In some embodiments, antibodies suitable for the present invention are subhuman primate antibodies. For example, general techniques for raising therapeutically useful antibodies in baboons may be found, for example, in International Patent Application Publication No. 1991/11465 and in Losman et al., 1990, Int. J. Cancer 46:310. In some embodiments, monoclonal antibodies may be prepared using hybridoma methods (Milstein and Cuello, 1983, Nature 305(5934):537-40). In some embodiments, monoclonal antibodies may also be made by recombinant methods (see, e.g., U.S. Pat. No. 4,166,452).

Many of the difficulties associated with generating monoclonal antibodies by B-cell immortalization can be overcome by engineering and expressing antibody fragments in E. coli (or yeast), using phage display. To ensure the recovery of high affinity, monoclonal antibodies a combinatorial immunoglobulin library must typically contain a large repertoire size. A typical strategy utilizes mRNA obtained from lymphocytes or spleen cells of immunized mice to synthesize cDNA using reverse transcriptase. The heavy and light chain genes are amplified separately by PCR and ligated into phage cloning vectors. Two different libraries are produced, one containing the heavy chain genes and one containing the light chain genes. The libraries can be naïve or they can be semi-synthetic, wherein the heavy chain CDR3 is synthesized, with all amino acids (with the exception of cysteine) equally likely to be present at any given position in the heavy chain CDR3 region. Phage DNA is isolated from each library, and the heavy and light chain sequences are ligated together and packaged to form a combinatorial library. Each phage contains a random pair of heavy and light chain cDNAs and upon infection of E. coli directs the expression of the antibody chains in infected cells. To identify an antibody that recognizes the antigen of interest (e.g., CD19), the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Alternatively, identification of an antibody that recognizes the antigen of interest (e.g., CD19) may be achieved by iterative binding of phage to the antigen, which is bound to a solid support, for example, beads or mammalian cells followed by removal of non-bound phage and by elution of specifically bound phage. In such embodiments, antigens are first biotinylated for immobilization to, for example, streptavidin-conjugated Dynabeads M-280. The phage library is incubated with the cells, beads or other solid support and non-binding phage is removed by washing. Antibody phage clones that bind the antigen of interest are selected and tested for further characterization.

Once selected, positive scFv clones are tested for their binding to the antigen of interest expressed on the surface of live cells by indirect flow cytometry. Briefly, phage clones are incubated with cells (e.g., engineered to express the antigen of interest, or those that naturally express the antigen) that either do or do not express the antigen. The cells are washed and then labeled with a mouse anti-M13 coat protein monoclonal antibody. Cells are washed again and labeled with a fluorescent-conjugated secondary antibody (e.g., FITC-goat (Fab)$_2$ anti-mouse IgG) prior to flow cytometry. Cloning and expression vectors that are useful for producing a human immunoglobulin phage library can be obtained, for example, from Stratagene Cloning Systems (La Jolla, Calif.).

A similar strategy can be employed to obtain high-affinity scFv (see, e.g., Vaughn et al., 1996, Nat. Biotechnol., 14:309-314). An scFv library with a large repertoire can be constructed by isolating V-genes from non-immunized human donors using PCR primers corresponding to all known $V_H$, $V_\kappa$ and $V\lambda$, gene families. Following amplification, the $V_\kappa$ and $V\lambda$, pools are combined to form one pool. These fragments are ligated into a phagemid vector. An scFv linker (e.g., $(G_4S)_n$) is then ligated into the phagemid upstream of the $V_L$ fragment (or upstream of the $V_H$ fragment as so desired). The $V_H$ and linker-$V_L$ fragments (or $V_L$ and linker-$V_H$ fragments) are amplified and assembled on the $J_H$ region. The resulting $V_H$-linker-$V_L$ (or $V_L$-linker-$V_H$) fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris* (see, e.g., Ridder et al., 1995, Biotechnology, 13:255-260). Additionally, following isolation of an appropriate scFv, antibody fragments with higher binding affinities and slower dissociation rates can be obtained through affinity maturation processes such as CDR3 mutagenesis and chain-shuffling (see, e.g., Jackson et al., 1998, Br. J. Cancer, 78:181-188); Osbourn et al., 1996, Immunotechnology, 2:181-196).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, e.g., Larrick et al., 1991, Methods: A Companion to Methods in Enzymology 2:106; Courtenay-Luck, "Genetic Manipulation of Monoclonal Antibodies," in Monoclonal Antibodies: Production, Engineering And Clinical Application, Ritter et al., eds., p. 166-179, Cambridge University Press 1995; and Ward et al., "*Genetic Manipulation and Expression of Antibodies*," in Monoclonal Antibodies: Principles And Applications, Birch et al., eds., p. 137-185, Wiley-Liss, Inc. 1995).

Human antibodies can be produced using various techniques, including phage display libraries (Hoogenboom et al., 1991, Mol. Immunol. 28(9):1027-37; Marks et al., 1991, J. Mol. Biol. 222(3):581-97) and the preparation of human monoclonal antibodies (Reisfeld and Sell, 1985, Cancer Surv. 4(1):271-90). Similarly, introducing human Ig genes into transgenic animals in which the endogenous Ig genes have been partially or completely inactivated can be exploited to synthesize human antibodies (see, e.g., Fishwild et al., 1996, Nat. Biotechnol. 14(7):845-51; Lonberg et al., 1994, Nature 368(6474):856-9; Lonberg and Huszar, 1995, Int. Rev. Immunol. 13:65-93; Taylor, L. D., et al., 1992, Nucl. Acids Res. 20:6287-95; Kellermann S-A., and Green L. L., 2002, Curr. Opin. Biotechnol. 13:593-7; Little, M. et al., 2000, Immunol. Today 21:364-70; Murphy, A. J. et al., 2014, Proc. Natl. Acad. Sci. U.S.A. 111(14):5153-8). Upon challenge, human antibody production is observed. In some embodiments, anti-CD19 human antibodies are made by immunization of non-human animals engineered to make human antibodies in response to antigen challenge with human CD19.

Provided human antibody agents (including antibodies and/or characteristic portions) may be produced, for example, by utilizing a host cell system engineered to express an inventive antibody-encoding nucleic acid. Alternatively or additionally, provided human antibody agents may be partially or fully prepared by chemical synthesis (e.g., using an automated peptide synthesizer or gene synthesis of antibody agent-encoding nucleic acids).

Human antibody agents of interest can be expressed using any appropriate vector. A variety of vectors (e.g., viral vectors) are known in the art; cells into which such vectors have been introduced (or progeny of such cells) can be cultured as known in the art (e.g., using continuous or fed-batch culture systems). In some embodiments, cells may be genetically engineered; technologies for genetically engineering cells to express engineered polypeptides (e.g., antibody agent polypeptides, as described herein) are well known in the art (see, e.g., Ausabel et al., eds., 1990, Current Protocols in Molecular Biology (Wiley, New York)).

In some embodiments, provided human antibody agents may be purified, if desired, using filtration, centrifugation and/or a variety of chromatographic technologies such as HPLC or affinity chromatography. In some embodiments, fragments of provided human antibody agents are obtained by methods that include digestion with enzymes, such as pepsin or papain, and/or by cleavage of disulfide bonds by chemical reduction.

In some embodiments, as described herein, provided human antibody agents can be or include, e.g., a polyclonal antibody; a monoclonal antibody or antigen binding fragment thereof; a modified antibody such as an affinity-matured antibody, variant antibody (e.g., having one or more amino acid substitutions as compared to a reference antibody), or fragment thereof (e.g., Fab', Fab, F(ab')$_2$); or a biosynthetic antibody, e.g., a single chain antibody, single domain antibody (DAB), Fv, single chain Fv (scFv), multi-specific binding agents (e.g., bi-specific antibodies), chimeric antigen receptors (CARs) or the like.

It will be appreciated that provided human antibody agents may be engineered, produced, and/or purified in such a way as to improve characteristics and/or activity of the antibody agents. For example, improved characteristics of provided antibody agents include, but are not limited to, increased stability, improved binding affinity and/or avidity, increased binding specificity, increased production, decreased aggregation, decreased nonspecific binding, among others.

In some embodiments, provided human antibody agents may comprise one or more amino acid substitutions (e.g., in a framework region in the context of an immunoglobulin or fragment thereof [e.g., an scFv]) that improve protein stability, antigen binding, expression level or provides a site or location for conjugation of a therapeutic, diagnostic or detection agent.

In some embodiments, a provided human antibody agents is or comprises an immunoglobulin (i.e., an antibody) that is a member of an antibody class (i.e., isotype) selected from the group consisting of IgG, IgM, IgA, IgD, IgE, or a fragment thereof.

In some embodiments, provided human antibody agents include human monoclonal antibodies that comprise a variant Fc region, wherein said variant Fc region comprises at least one amino acid modification relative to a reference Fc region (or parental Fc region). In such embodiments, human antibody agents comprising variant Fc regions may demonstrate an altered affinity for an Fc receptor (e.g., an FcγR), provided that said variant Fc regions do not have a substitution at positions that make a direct contact with Fc receptor based on crystallographic and structural analysis of Fc-Fc receptor interactions such as those disclosed by Sondermann et al., 2000, Nature, 406:267-273. Examples of positions within the Fc region that make a direct contact with an Fc receptor such as an FcγR are amino acids 234-239 (hinge region), amino acids 265-269 (B/C loop), amino acids 297-299 (C'/E loop), and amino acids 327-332 (F/G) loop. In some embodiments, provided human antibody agents of the present invention comprising variant Fc regions comprise a modification of at least one residue that makes a direct contact with an FcγR based on structural and crystallographic analysis.

In some embodiments, a provided human antibody agent is an anti-CD19 human monoclonal antibody having a variant Fc region with one or more amino acid modifications as compared to a reference Fc region (or parental Fc region). Amino acid modifications in Fc regions to create variant Fc regions that, e.g., alter affinity for activating and/or inhibitory receptors, lead to improved effector function such as, e.g., Antibody-Dependent Cell-Mediated Cytotoxicity (ADCC) and Complement Dependent Cytotoxicity (CDC), increase binding affinity for C1q, reduce or eliminate FcR binding, increase half-life are known in the art (see, e.g., U.S. Pat. Nos. 9,051,373, 9,040,041, 8,937,158, 8,883,973, 8,883,147, 8,858,937, 8,852,586, 8,809,503, 8,802,823, 8,802,820, 8,795,661, 8,753,629, 8,753,628, 8,735,547, 8,735,545, 8,734,791, 8,697,396, 8,546,543, 8,475,792, 8,399,618, 8,394,925, 8,388,955, 8,383,109, 8,367,805, 8,362,210, 8,338,574, 8,324,351, 8,318,907, 8,188,231, 8,124,731, 8,101,720, 8,093,359, 8,093,357, 8,088,376, 8,084,582, 8,039,592, 8,012,476, 7,799,900, 7,790,858, 7,785,791, 7,741,072, 7,704,497, 7,662,925, 7,416,727, 7,371,826, 7,364,731, 7,335,742, 7,332,581, 7,317,091, 7,297,775, 7,122,637, 7,083,784, 6,737,056, 6,538,124, 6,528,624 and 6,194,551).

In some embodiments, a provided human antibody agent is an anti-CD19 human monoclonal antibody having an Fc region with variant glycosylation as compared to a parent Fc region (e.g., aglycosylated). In some embodiments, variant glycosylation results from expression in an engineered cell line (see, e.g., Umana, P. et al., 1999, Nat. Biotechnol. 17(2):176-80; Yamane-Ohnuki, N. et al., 2004, Biotechnol. Bioeng. 87(5):614-22; von Horsten, H. H. et al., 2010, Glycobiol. 20(12):1607-18; Beck, A. et al., 2010, Expert Opin. Drug Discov. 5(1):95-111; and U.S. Pat. Nos. 8,080,415 and 8,084,222; all of which are hereby incorporated by reference). In some embodiments, the present invention provides multi-specific binding agents having a human anti-CD19 antibody component that comprises a variant Fc region. In some embodiments a provided multi-specific binding agent includes an antibody component that shows variant glycosylation (e.g., is aglycosylated) as compared with a parent antibody from which the component may be derived.

In some embodiments, the present invention provides and/or utilizes antibodies or antibody agents comprising a variant Fc region (i.e., an Fc region includes one or more additions, deletions, and/or substitutions relative to an appropriate reference Fc) that are characterized in that alter (e.g., increase and/or decrease) effector function and/or affinity for an FcR is enhanced or diminished relative to a reference Fc. These variations are within the skill of a person in the art.

Therefore, among other things, the present invention provides antibody agents and multi-specific binding agents (e.g., antibody agents) comprising variant Fc regions that bind with a greater affinity to one or more FcγRs. Such agents preferably mediate effector function more effectively as discussed infra. In some embodiments, the present invention provides antibody agents and multi-specific binding agents (e.g., bi-specific antibodies) comprising a variant Fc region that bind with a weaker affinity to one or more FcγRs. Reduction or elimination of effector function is desirable in certain cases for example in the case of antibodies whose mechanism of action involves blocking or antagonism but not killing of the cells bearing a target antigen. Further, elimination of effector function is desirable, in some embodiments, when making bi-specific antibodies as discussed infra. Reduction or elimination of effector function would be desirable in cases of autoimmune disease where one would block FcγR activating receptors in effector cells (This type of function would be present in the host cells). Generally, increased effector function may be directed to tumor and cells expressing foreign antigens; in some embodiments, effector function may be directed away from tumor cells.

Fc variants for use in accordance with the present invention may be combined with other Fc modifications, including, for example, modifications that alter effector function. The present invention includes combining an Fc variant as described herein with other Fc modifications to provide additive, synergistic, or novel properties in antibodies or Fc fusions. In some such embodiments, Fc variants may enhance the phenotype of the modification with which they are combined. For example, if an Fc variant is combined with a mutant known to bind FcγRIIIA with a higher affinity than a comparable molecule comprising a wild type Fc region, the combination with the mutant results in a greater fold enhancement in FcγRIIIA affinity.

In some embodiments, in accordance with the present invention Fc variants as described herein are incorporated into an antibody or Fc fusion to generate an engineered agent that comprises one or more Fc glycoforms (i.e., one or more Fc polypeptides to which one or more carbohydrates is covalently attached) to a molecule comprising an Fc region wherein the carbohydrate composition of the glycoform differs chemically from that of a parent molecule comprising an Fc region.

In some embodiments, a multi-specific binding agent (e.g., an antibody agent) as described herein may include an Fc variant that shows variant glycosylation and/or may be expressed in a glycosylation deficient cell line such that an Fc region of the agent is produced lacking glycosylation as compared to an appropriate reference Fc region (e.g., a parent Fc region), or an Fc region expressed in a cell line not deficient in glycosylation.

In some embodiments, antibodies utilized in accordance with the present invention, may have a modified glycosylation site relative to an appropriate reference antibody that binds to an antigen of interest (e.g., CD19), preferably without altering the functionality of the antibody, e.g., binding activity to the antigen. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform that lacks certain oligosaccharides including fucose and terminal N-acetylglucosamine may be produced in special CHO cells and exhibit enhanced ADCC effector function.

In some embodiments, the present invention encompasses methods of modifying the carbohydrate content of an antibody as described herein by adding or deleting a glycosylation site. Methods for modifying the carbohydrate content of antibodies are well known in the art and are included within the present disclosure (see, e.g., U.S. Pat. Nos. 6,218,149, 6,472,511; U.S. Patent Publication Nos. 2003-0115614 A1, 2002-0028486 A1; International Patent Application Publication WO 2003/035835; European Patent No. 0 359 096 B1). In some embodiments, the present invention provides methods of modifying the carbohydrate content of an antibody (or relevant portion or component thereof) by deleting one or more endogenous carbohydrate moieties of the antibody.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example N-acetylglucosaminyltransferase I (GnTI), by expressing a molecule comprising an Fc region (or variant Fc region) in various organisms or cell lines from various organisms, or by modifying carbohydrate(s) after the molecule comprising Fc region has been expressed. Methods for generating engineered glycoforms are known in the art, and include but are not limited to those described in Umana et al., 1999, Nat. Biotechnol. 17:176-180; Davies et al., 2001, Biotechnol. Bioeng. 74:288-294; Shields et al., 2002, J. Biol. Chem. 277:26733-26740; Shinkawa et al., 2003, J. Biol. Chem. 278:3466-3473; U.S. Pat. No. 6,602,684; U.S. Patent Publication Application Nos. 2003-0157108 A1, 2003-0003097 A1; International Patent Publication Nos. WO 2000/61739, WO 2001/292246, WO 2002/311140 and WO 2002/30954; POTILLEGENT™ technology (Biowa, Inc. Princeton, N.J.); GLYCOMAB™ glycosylation engineering technology (GLYCART biotechnology AG, Zurich, Switzerland). See, e.g., Okazaki et al., 2004, JMB, 336:1239-49; U.S. Patent Publication No. 2003-0115614 A1; International Patent Publication No. WO 2000/061739.

Specific Exemplary
Embodiments—Immunoglobulin Heavy and Light
Chain Combinations In some embodiments, a human antibody agent of the present invention includes an immunoglobulin heavy chain variable region that appears in SEQ ID NO:2 and/or an immunoglobulin light chain variable region that appears in SEQ ID NO:2. In some embodiments, a human antibody agent is an antibody that includes the immunoglobulin heavy chain variable region that appears in SEQ ID NO:2 and the immunoglobulin light chain variable region that appears in SEQ ID NO:2.

In some embodiments, a human antibody agent of the present invention includes an immunoglobulin heavy chain variable region that appears in SEQ ID NO:4 and/or an immunoglobulin light chain variable region that appears in SEQ ID NO:4. In some embodiments, a human antibody agent is an antibody that includes the immunoglobulin heavy chain variable region that appears in SEQ ID NO:4 and the immunoglobulin light chain variable region that appears in SEQ ID NO:4.

In some embodiments, a human antibody agent of the present invention includes an immunoglobulin heavy chain variable region that appears in SEQ ID NO:6 and/or an immunoglobulin light chain variable region that appears in SEQ ID NO:6. In some embodiments, a human antibody agent is an antibody that includes the immunoglobulin heavy chain variable region that appears in SEQ ID NO:6 and the immunoglobulin light chain variable region that appears in SEQ ID NO:6.

In some embodiments, a human antibody agent of the present invention includes an immunoglobulin heavy chain variable region that appears in SEQ ID NO:8 and/or an immunoglobulin light chain variable region that appears in SEQ ID NO:8. In some embodiments, a human antibody agent is an antibody that includes the immunoglobulin heavy chain variable region that appears in SEQ ID NO:8 and the immunoglobulin light chain variable region that appears in SEQ ID NO:8.

In some embodiments, a human antibody agent of the present invention includes an immunoglobulin heavy chain variable region that appears in SEQ ID NO:10 and/or an immunoglobulin light chain variable region that appears in SEQ ID NO:10. In some embodiments, a human antibody agent is an antibody that includes the immunoglobulin heavy chain variable region that appears in SEQ ID NO:10 and the immunoglobulin light chain variable region that appears in SEQ ID NO:10.

In some embodiments, a human antibody agent of the present invention includes an immunoglobulin heavy chain variable region that appears in SEQ ID NO:12 and/or an immunoglobulin light chain variable region that appears in SEQ ID NO:12. In some embodiments, a human antibody agent is an antibody that includes the immunoglobulin heavy chain variable region that appears in SEQ ID NO:12 and the immunoglobulin light chain variable region that appears in SEQ ID NO:12.

In some embodiments, a human antibody agent of the present invention includes an immunoglobulin heavy chain variable region that appears in SEQ ID NO:14 and/or an immunoglobulin light chain variable region that appears in SEQ ID NO:14. In some embodiments, a human antibody agent is an antibody that includes the immunoglobulin heavy chain variable region that appears in SEQ ID NO:14 and the immunoglobulin light chain variable region that appears in SEQ ID NO:14.

In some embodiments, a human antibody agent of the present invention includes an immunoglobulin heavy chain variable region that appears in SEQ ID NO:16 and/or an immunoglobulin light chain variable region that appears in SEQ ID NO:16. In some embodiments, a human antibody agent is an antibody that includes the immunoglobulin heavy chain variable region that appears in SEQ ID NO:16 and the immunoglobulin light chain variable region that appears in SEQ ID NO:16.

In some embodiments, a human antibody agent of the present invention includes an immunoglobulin heavy chain variable region that appears in SEQ ID NO:18 and/or an immunoglobulin light chain variable region that appears in SEQ ID NO:18. In some embodiments, a human antibody agent is an antibody that includes the immunoglobulin heavy chain variable region that appears in SEQ ID NO:18 and the immunoglobulin light chain variable region that appears in SEQ ID NO:18.

In some embodiments, a human antibody agent of the present invention includes an immunoglobulin heavy chain variable region that appears in SEQ ID NO:20 and/or an immunoglobulin light chain variable region that appears in SEQ ID NO:20. In some embodiments, a human antibody agent is an antibody that includes the immunoglobulin heavy chain variable region that appears in SEQ ID NO:20 and the immunoglobulin light chain variable region that appears in SEQ ID NO:20.

In some embodiments, a human antibody agent of the present invention includes an immunoglobulin heavy chain variable region that appears in SEQ ID NO:22 and/or an immunoglobulin light chain variable region that appears in SEQ ID NO:22. In some embodiments, a human antibody agent is an antibody that includes the immunoglobulin heavy chain variable region that appears in SEQ ID NO:22 and the immunoglobulin light chain variable region that appears in SEQ ID NO:22.

In some embodiments, a human antibody agent of the present invention includes an immunoglobulin heavy chain variable region that appears in SEQ ID NO:24 and/or an immunoglobulin light chain variable region that appears in SEQ ID NO:24. In some embodiments, a human antibody agent is an antibody that includes the immunoglobulin heavy chain variable region that appears in SEQ ID NO:24 and the immunoglobulin light chain variable region that appears in SEQ ID NO:24.

In some embodiments, a human antibody agent of the present invention includes an immunoglobulin heavy chain variable region that appears in SEQ ID NO:26 and/or an immunoglobulin light chain variable region that appears in SEQ ID NO:26. In some embodiments, a human antibody agent is an antibody that includes the immunoglobulin heavy chain variable region that appears in SEQ ID NO:26 and the immunoglobulin light chain variable region that appears in SEQ ID NO:26.

In some embodiments, a human antibody agent of the present invention includes an immunoglobulin heavy chain variable region that appears in SEQ ID NO:28 and/or an immunoglobulin light chain variable region that appears in SEQ ID NO:28. In some embodiments, a human antibody agent is an antibody that includes the immunoglobulin heavy chain variable region that appears in SEQ ID NO:28 and the immunoglobulin light chain variable region that appears in SEQ ID NO:28.

In some embodiments, a human antibody agent of the present invention includes an immunoglobulin heavy chain variable region that appears in SEQ ID NO:30 and/or an immunoglobulin light chain variable region that appears in SEQ ID NO:30. In some embodiments, a human antibody agent is an antibody that includes the immunoglobulin heavy chain variable region that appears in SEQ ID NO:30 and the immunoglobulin light chain variable region that appears in SEQ ID NO:30.

In some embodiments, a human antibody agent of the present invention includes an immunoglobulin heavy chain variable region that appears in SEQ ID NO:32 and/or an immunoglobulin light chain variable region that appears in SEQ ID NO:32. In some embodiments, a human antibody agent is an antibody that includes the immunoglobulin heavy chain variable region that appears in SEQ ID NO:32 and the immunoglobulin light chain variable region that appears in SEQ ID NO:32.

In some embodiments, a human antibody agent of the present invention includes an immunoglobulin heavy chain variable region that appears in SEQ ID NO:34 and/or an immunoglobulin light chain variable region that appears in SEQ ID NO:34. In some embodiments, a human antibody agent is an antibody that includes the immunoglobulin heavy chain variable region that appears in SEQ ID NO:34 and the immunoglobulin light chain variable region that appears in SEQ ID NO:34.

Specific Exemplary Embodiments—Specific Amino Acid Substitutions

In some embodiments, a human antibody agent of the present invention includes an immunoglobulin heavy chain variable region that comprises one or more amino acid substitutions at any of amino acid positions 3, 12, 16, 17, 25, 26, 32, 63, 69, 97, 102, 106, 108, 109, 113, 116, 117 and combinations thereof. In some embodiments, a human antibody agent of the present invention includes an immunoglobulin heavy chain variable region that comprises at least one and up to five amino acid substitutions in a framework and/or CDR region.

In some embodiments, a human antibody agent of the present invention includes an immunoglobulin heavy chain variable region that appears in a SEQ ID NO. selected from the group consisting of SEQ ID NO:2, 4, 6, 8, 10, 12, 14, 16, 18, 20, 22, 24, 26, 28, 30, 32 and 34, and further comprises one or more amino acid substitutions at any of amino acid positions 3, 12, 16, 17, 25, 26, 32, 63, 69, 97, 102, 106, 108, 109, 113, 116, 117 and combinations thereof.

In some embodiments, a human antibody agent of the present invention includes an immunoglobulin heavy chain variable region that comprises one or more substitutions selected from the group consisting of Q3R, K12E, E16G, S17F, S25A, G26A, Y32F, S63F, T69A, A97V, T102S, M106L, Y108N, D109E, Q113L, L116M, M117L and combinations thereof.

In some embodiments, a human antibody agent of the present invention includes an immunoglobulin heavy chain variable region that comprises one or more substitutions as compared to a reference immunoglobulin heavy chain variable region, and which immunoglobulin heavy chain variable region has a sequence that appears in any one of SEQ ID NO:36, 38, 40, 42, 44, 46, 48, 50, 52, 54, 56, 58, 60, 62, 64, 66, 68, 70 and 72.

In some embodiments, a human antibody agent of the present invention includes an immunoglobulin light chain variable region that comprises one or more amino acid substitutions at any of amino acid positions 10, 16, 25, 34, 52, 54, 68, 69, 72, 75, 93, 95 and combinations thereof. In some embodiments, a human antibody agent of the present invention includes an immunoglobulin light chain variable region that comprises at least one and up to five amino acid substitutions in a framework and/or CDR region.

In some embodiments, a human antibody agent of the present invention includes an immunoglobulin light chain variable region that appears in a SEQ ID NO. selected from the group consisting of SEQ ID NO:2, 4, 6, 8, 10, 12, 14, 16, 18, 20, 22, 24, 26, 28, 30, 32 and 34, and further comprises one or more amino acid substitutions at any of amino acid positions 10, 16, 25, 34, 52, 54, 68, 69, 72, 75, 93, 95 and combinations thereof.

In some embodiments, a human antibody agent of the present invention includes an immunoglobulin light chain variable region that comprises one or more substitutions selected from the group consisting of V10M, K16E, S25N, V34I, D52N, L54Q, N68T, T69M, L72M, S75N, S93T, D95E, D95G and combinations thereof.

In some embodiments, a human antibody agent of the present invention includes an immunoglobulin light chain variable region that comprises one or more substitutions as compared to a reference immunoglobulin light chain variable region, and which immunoglobulin light chain variable region has a sequence that appears in any one of SEQ ID NO:36, 38, 40, 42, 44, 46, 48, 50, 52, 54, 56, 58, 60, 62, 64, 66, 68, 70 and 72.

In some embodiments, a human antibody agent of the present invention includes immunoglobulin heavy and light chain variable regions that together comprise at least one and up to five amino acid substitutions in a framework and/or CDR region.

Among other things, the present disclosure demonstrates that presence of such amino acid substitutions in an anti-CD19 human antibody agent of the present invention increases the human antibody agent's binding affinity and/or specificity to human CD19 relative to a parental human antibody agent. That is, introduction of such amino acid substitutions into an anti-CD19 human antibody agent improves its binding affinity to CD19, and particularly to native CD19 (i.e., cell surface expressed).

Persons of skill in the art are aware of a variety of technologies know in the art for accomplishing such introduction, or for otherwise preparing, providing, or manufacturing polypeptides containing such sequences. Exemplary technologies useful in this regard are provided, for instance, in Green & Sambrook, Molecular Cloning: A Laboratory Manual, Cold Spring Harbor Laboratory Press 2012.

Specific Exemplary Embodiments—Specific CDRs

As is generally known in the art, monoclonal antibodies are made of two heavy chains and two light chains, each comprising variable regions and constant regions. The heavy chain variable region usually comprises three CDRs, identified herein as HCDR1, HCDR2 and HCDR3, flanked by framework regions (see, e.g., William E. Paul, Fundamental Immunology (7th ed.), Lippincott Williams & Wilkins 2013). The light chain variable region usually comprises three complementary determining regions (CDRs), identified herein as LCDR1, LCDR2 and LCDR3, flanked by framework regions.

The present invention provides human antibody agents including CDRs set forth in Tables 2 (HCDRs) and 3 (LCDRs) in any possible combination. By example, which is not meant to be limiting, the present invention includes human antibody agents including a HCDR1, HCDR2, HCDR3, LCDR1, LCDR2 and LCDR3 that are SEQ ID NO:73, SEQ ID NO:74, SEQ ID NO:75, SEQ ID NO:181, SEQ ID NO:182 and SEQ ID NO:183, respectively.

The manufacture of antibodies having desired CDRs and/or framework regions is generally known in the art and described in, for example, Strohl & Strohl, Therapeutic Antibody Engineering, Woodhead Publishing Limited 2012.

TABLE 2

| Clone | HCDR1 | HCDR2 | HCDR3 |
|---|---|---|---|
| 9 | GFTFSSYA (SEQ ID NO: 73) | ISGSGGST (SEQ ID NO: 74) | ARYYYSRLDY (SEQ ID NO: 75) |
| 23 | GFTFSSYA (SEQ ID NO: 76) | ISASGGST (SEQ ID NO: 77) | ARYYLSQIDS (SEQ ID NO: 78) |
| 31 | GYTFTDYY (SEQ ID NO: 79) | VDPEDGET (SEQ ID NO: 80) | ATGIYSRPLGY (SEQ ID NO: 81) |
| 35 | GFTFSSYA (SEQ ID NO: 82) | ISGSGGST (SEQ ID NO: 83) | ARSDGKHFWQQYDA (SEQ ID NO: 84) |
| 36 | GFTVSSNY (SEQ ID NO: 85) | ISGSGGST (SEQ ID NO: 86) | ARMNIDY (SEQ ID NO: 87) |
| 37 | EYSFASYW (SEQ ID NO: 88) | IDPSDSYT (SEQ ID NO: 89) | ARPFQYDYGGYSDAFDI (SEQ ID NO: 90) |
| 40 | GGTFSSSS (SEQ ID NO: 91) | IIPIVGTP (SEQ ID NO: 92) | ARGGYRDYMDV (SEQ ID NO: 93) |
| 43 | GFTVSSNY (SEQ ID NO: 94) | IYSGGST (SEQ ID NO: 95) | ARGGFGAEFDY (SEQ ID NO: 96) |
| 54 | GFTVSSNY (SEQ ID NO: 97) | IYSGGST (SEQ ID NO: 98) | ARGGISDDYYGSGSYDN (SEQ ID NO: 99) |
| 61 | GFTVSSNY (SEQ ID NO: 100) | IYSGGST (SEQ ID NO: 101) | ARERGMGYAFDI (SEQ ID NO: 102) |
| 1 | GVSMSENY (SEQ ID NO: 103) | AHYTGDT (SEQ ID NO: 104) | ASYHPFNY (SEQ ID NO: 105) |
| 2 | GYTFNDFY (SEQ ID NO: 106) | IDPEDGKT (SEQ ID NO: 107) | TTDWGYSSSLREEDIWYDC (SEQ ID NO: 108) |
| 3 | GGTFSSYA (SEQ ID NO: 109) | IIPIFGTA (SEQ ID NO: 110) | ARDYGYGDYGDAFDI (SEQ ID NO: 111) |
| 4 | GYSFTSYW (SEQ ID NO: 112) | IYPGDSDT (SEQ ID NO: 113) | ARVVGTIYSMQYDV (SEQ ID NO: 114) |
| 5 | GYSFTSYW (SEQ ID NO: 115) | IYPGDSDT (SEQ ID NO: 116) | ARQVWGWQGGMYPRSMDS (SEQ ID NO: 117) |
| 6 | GYSFTSYW (SEQ ID NO: 118) | IYPGDSDT (SEQ ID NO: 119) | ARWSSTWDSMYMDY (SEQ ID NO: 120) |
| 7 | GYSFTSYW (SEQ ID NO: 121) | IYPGDSDT (SEQ ID NO: 122) | ARVTYSMDSYYFDS (SEQ ID NO: 123) |
| 5-1 | GYSFTSYW (SEQ ID NO: 124) | IYPGDSDT (SEQ ID NO: 125) | ARQVWGWQGGMYPRSMDS (SEQ ID NO: 126) |
| 5-2 | GYSFTSYW (SEQ ID NO: 127) | IYPGDSDT (SEQ ID NO: 128) | ARQVWGWQGGMYPRSNWWYNMDS (SEQ ID NO: 129) |
| 5-3 | GYSFTSYW (SEQ ID NO: 130) | IYPGDSDT (SEQ ID NO: 131) | ARQVWGWQGGMYPRSNWWYNMDS (SEQ ID NO: 132) |

TABLE 2-continued

| Clone | HCDR1 | HCDR2 | HCDR3 |
|---|---|---|---|
| 5-4 | GYSFTSYW (SEQ ID NO: 133) | IYPGDSDT (SEQ ID NO: 134) | ARQVWGWQGGMYPRSNWWYNMDS (SEQ ID NO: 135) |
| 5-5 | GYSFTSYW (SEQ ID NO: 136) | IYPGDSDT (SEQ ID NO: 137) | ARQVWGWQGGMYPRSNWWYNMDS (SEQ ID NO: 138) |
| 5-7 | GYSFTSYW (SEQ ID NO: 139) | IYPGDSDT (SEQ ID NO: 140) | ARQVWGWQGGMNPRSNWWYNMDS (SEQ ID NO: 141) |
| 5-9 | GYSFTSYW (SEQ ID NO: 142) | IYPGDSDT (SEQ ID NO: 143) | ARQVWGWQGGMYPRSNWWYNMDS (SEQ ID NO: 144) |
| 5-10 | GYSFTSFW (SEQ ID NO: 145) | IYPGDSDT (SEQ ID NO: 146) | VRQVWGWQGGMYPRSNWWYNMDS (SEQ ID NO: 147) |
| 5-11 | GYSFTSYW (SEQ ID NO: 148) | IYPGDSDT (SEQ ID NO: 149) | ARQVWGWQGGMYPRSNWWYNMDS (SEQ ID NO: 150) |
| 5-13 | GYSFTSYW (SEQ ID NO: 151) | IYPGDSDT (SEQ ID NO: 152) | ARQVWGWQGGMYPRSNWWYNLDS (SEQ ID NO: 153) |
| 5-15 | GYSFTSYW (SEQ ID NO: 154) | IYPGDSDT (SEQ ID NO: 155) | ARQVWGWQGGMYPRSNWWYNMDS (SEQ ID NO: 156) |
| 6-1 | GYSFTSYW (SEQ ID NO: 157) | IYPGDSDT (SEQ ID NO: 158) | ARWSSSWDSMYMDY (SEQ ID NO: 159) |
| 6-2 | GYSFTSYW (SEQ ID NO: 160) | IYPGDSDT (SEQ ID NO: 161) | ARWSSTWDSMYMEY (SEQ ID NO: 162) |
| 6-4 | GYSFTSYW (SEQ ID NO: 163) | IYPGDSDT (SEQ ID NO: 164) | ARWSSTWDSMYMDY (SEQ ID NO: 165) |
| 6-5 | GYSFTSYW (SEQ ID NO: 166) | IYPGDSDT (SEQ ID NO: 167) | ARWSSTWDSLYMDY (SEQ ID NO: 168) |
| 6-6 | GYSFTSYW (SEQ ID NO: 169) | IYPGDSDT (SEQ ID NO: 170) | ARWSSTWDSMYMDY (SEQ ID NO: 171) |
| 6-7 | AYSFTSYW (SEQ ID NO: 172) | IYPGDSDT (SEQ ID NO: 173) | ARWSSTWDSMYMDY (SEQ ID NO: 174) |
| 6-8 | GYSFTSYW (SEQ ID NO: 175) | IYPGDSDT (SEQ ID NO: 176) | ARWSSTWDSMYMDY (SEQ ID NO: 177) |
| 6-9 | GYSFTSYW (SEQ ID NO: 178) | IYPGDSDT (SEQ ID NO: 179) | ARWSSSWDSMYMDY (SEQ ID NO: 180) |

TABLE 3

| Clone | LCDR1 | LCDR2 | LCDR3 |
|---|---|---|---|
| 09 | SSNIGNNY (SEQ ID NO: 181) | DNN (SEQ ID NO: 182) | GTWDSSLSAGV (SEQ ID NO: 183) |
| 23 | SSNIGNNY (SEQ ID NO: 184) | ENN (SEQ ID NO: 185) | GTWDSSLRAGV (SEQ ID NO: 186) |
| 31 | SSNIGSNT (SEQ ID NO: 187) | SNN (SEQ ID NO: 188) | AAWDDSLNGHVV (SEQ ID NO: 189) |
| 35 | SSNIGSHT (SEQ ID NO: 190) | SNN (SEQ ID NO: 191) | AAWDDSLNGYV (SEQ ID NO: 192) |
| 36 | QGITNS (SEQ ID NO: 193) | AAS (SEQ ID NO: 194) | QHYLGTPYS (SEQ ID NO: 195) |
| 37 | QSVSRF (SEQ ID NO: 196) | GVS (SEQ ID NO: 197) | QESYIIPLT (SEQ ID NO: 198) |
| 40 | QSLLDSNGFNS (SEQ ID NO: 199) | LGS (SEQ ID NO: 200) | MQSLQIPT (SEQ ID NO: 201) |

TABLE 3-continued

| Clone | LCDR1 | LCDR2 | LCDR3 |
|---|---|---|---|
| 43 | SSNIGSNY (SEQ ID NO: 202) | RNN (SEQ ID NO: 203) | AAWDDSLSGYV (SEQ ID NO: 204) |
| 54 | KLGDKY (SEQ ID NO: 205) | QDN (SEQ ID NO: 206) | QAWDSSTEDV (SEQ ID NO: 207) |
| 61 | QSISSY (SEQ ID NO: 208) | AAS (SEQ ID NO: 209) | QQSYSTPFT (SEQ ID NO: 210) |
| 1 | QGIGSY (SEQ ID NO: 211) | PAS (SEQ ID NO: 212) | QQLNSL (SEQ ID NO: 213) |
| 2 | SSNIGTKT (SEQ ID NO: 214) | SNY (SEQ ID NO: 215) | ALWDDSLDGYV (SEQ ID NO: 216) |
| 3 | NIGSKS (SEQ ID NO: 217) | YDS (SEQ ID NO: 218) | QVWDSSSDHYV (SEQ ID NO: 219) |
| 4 | NIGSKS (SEQ ID NO: 220) | DDS (SEQ ID NO: 221) | QVWDSSSDHYV (SEQ ID NO: 222) |
| 5 | NIGSKS (SEQ ID NO: 223) | DDS (SEQ ID NO: 224) | QVWDSSSDYVV (SEQ ID NO: 225) |
| 6 | SSNVGNNA (SEQ ID NO: 226) | YDD (SEQ ID NO: 227) | AAWDDSLNGPV (SEQ ID NO: 228) |
| 7 | NIGSES (SEQ ID NO: 229) | YDS (SEQ ID NO: 230) | QVWNSSSDHRGV (SEQ ID NO: 231) |
| 5-1 | NIGSKS (SEQ ID NO: 232) | DDS (SEQ ID NO: 233) | QVWDSSSDYVV (SEQ ID NO: 234) |
| 5-2 | NIGSKS (SEQ ID NO: 235) | DDS (SEQ ID NO: 236) | QVWDSSSDYVV (SEQ ID NO: 237) |
| 5-3 | NIGSKS (SEQ ID NO: 238) | DDS (SEQ ID NO: 239) | QVWDSSSEYVV (SEQ ID NO: 240) |
| 5-4 | NIGSKS (SEQ ID NO: 241) | DDS (SEQ ID NO: 242) | QVWDSSSGYVV (SEQ ID NO: 243) |
| 5-5 | NIGSKS (SEQ ID NO: 244) | DDS (SEQ ID NO: 245) | QVWDSTSDYVV (SEQ ID NO: 246) |
| 5-7 | NIGSKS (SEQ ID NO: 247) | DDS (SEQ ID NO: 248) | QVWDSSSDYVV (SEQ ID NO: 249) |
| 5-9 | NIGSKS (SEQ ID NO: 250) | DDS (SEQ ID NO: 251) | QVWDSSSDYVV (SEQ ID NO: 252) |
| 5-10 | NIGSKS (SEQ ID NO: 253) | DDS (SEQ ID NO: 254) | QVWDSSSDYVV (SEQ ID NO: 255) |
| 5-11 | NIGSKS (SEQ ID NO: 256) | DDS (SEQ ID NO: 257) | QVWDSSSDYVV (SEQ ID NO: 258) |
| 5-13 | NIGSKS (SEQ ID NO: 259) | DDS (SEQ ID NO: 260) | QVWDSSSDYVV (SEQ ID NO: 261) |
| 5-15 | NIGSKS (SEQ ID NO: 262) | DDS (SEQ ID NO: 263) | QVWDSSSDYVV (SEQ ID NO: 264) |
| 6-1 | SSNVGNNA (SEQ ID NO: 265) | YDD (SEQ ID NO: 266) | AAWDDSLNGPV (SEQ ID NO: 267) |
| 6-2 | SSNVGNNA (SEQ ID NO: 268) | YDD (SEQ ID NO: 269) | AAWDDSLNGPV (SEQ ID NO: 270) |
| 6-4 | SSNVGNNA (SEQ ID NO: 271) | YDD (SEQ ID NO: 272) | AAWDDSLNGPV (SEQ ID NO: 273) |
| 6-5 | SSNVGNNA (SEQ ID NO: 274) | YDD (SEQ ID NO: 275) | AAWDDSLNGPV (SEQ ID NO: 276) |
| 6-6 | SSNVGNNA (SEQ ID NO: 277) | YDD (SEQ ID NO: 278) | AAWDDSLNGPV (SEQ ID NO: 279) |

TABLE 3-continued

| Clone | LCDR1 | LCDR2 | LCDR3 |
|---|---|---|---|
| 6-7 | SSNVGNNA (SEQ ID NO: 280) | YDD (SEQ ID NO: 281) | AAWDDSLNGPV (SEQ ID NO: 282) |
| 6-8 | SSNVGNNA (SEQ ID NO: 283) | YDD (SEQ ID NO: 284) | AAWDDSLNGPV (SEQ ID NO: 285) |
| 6-9 | SSNVGNNA (SEQ ID NO: 286) | YDD (SEQ ID NO: 287) | AAWDDSLNGPV (SEQ ID NO: 288) |

In various embodiments, a human antibody agent of the present invention includes at least one of the HCDRs that appears in Table 2 and/or at least one of the LCDRs that appears in Table 3.

In various embodiments, a human antibody agent of the present invention includes at least two of the HCDRs that appears in Table 2 and/or at least two of the LCDRs that appears in Table 3.

In various embodiments, a human antibody agent of the present invention includes any three HCDRs that appear in Table 2 and/or any three LCDRs that appear in Table 3.

In various embodiments, a human antibody agent of the present invention includes a set of three HCDRs that appear in Table 2 and/or a corresponding set of three LCDRs that appear in Table 3.

In various embodiments, a human antibody agent of the present invention includes three HCDRs, which three HCDRs each have a sequence that is at least about 50% (e.g., at least about 55%, 60%, 65%, 70%, 75%, 80%, 85%, 90%, 95%, 96%, 97%, 98%, or 99%) identical to three HCDRs that appear in Table 2.

In various embodiments, a human antibody agent of the present invention includes three LCDRs, which three LCDRs each have a sequence that is at least about 50% (e.g., at least about 55%, 60%, 65%, 70%, 75%, 80%, 85%, 90%, 95%, 96%, 97%, 98%, or 99%) identical to three LCDRs that appear in Table 3.

In various embodiments, a human antibody agent of the present invention includes three HCDRs and three LCDRs, which three HCDRs each have a sequence that is at least about 50% (e.g., at least about 55%, 60%, 65%, 70%, 75%, 80%, 85%, 90%, 95%, 96%, 97%, 98%, or 99%) identical to three HCDRs that appear in Table 2, and which three LCDRs each have a sequence that is at least about 50% (e.g., at least about 55%, 60%, 65%, 70%, 75%, 80%, 85%, 90%, 95%, 96%, 97%, 98%, or 99%) identical to three LCDRs that appear in Table 3.

In various embodiments, a human antibody agent of the present invention includes three HCDRs and/or three LCDRs, which HCDRs and LCDRs each have a sequence that is substantially identical or identical to HCDRs and LCDRs that appear in Tables 2 and 3, respectively.

In various embodiments, a human antibody agent of the present invention is or comprises an immunoglobulin (e.g., a monoclonal antibody) that comprises HCDRs and LCDRs selected from Tables 2 and 3, respectively.

Single Chain Fv (scFv)

Single chain Fvs (scFvs) are widely known and used in the art. A single-chain Fv is a fusion protein of the variable regions of the heavy ($V_H$) and light chains ($V_L$) of immunoglobulins, sometimes connected by a short linker peptide (see, e.g., see, e.g., Benny K. C. Lo (ed.), Antibody Engineering—Methods and Protocols, Humana Press 2004, and references cited therein).

The present invention provides single chain Fvs (scFvs) that specifically bind human CD19 and, in some embodiments, provided scFvs contain a linker sequence. In some embodiments, $V_H$ and $V_L$ regions of scFvs provided herein include a linker sequence that is or comprises SRGGGGSGGGGSGGGGSLEMA (SEQ ID NO:289). In some embodiments, a linker sequence is or comprises a $(G_4S)_n$ sequence, wherein n is equal to 1, 2, 3, 4, 5, 6, 7, 8, 9, 10 or more.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to a polypeptide (e.g., first and/or second binding components).

In some embodiments, a provided scFv polypeptide comprises a sequence that appears in any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

In various embodiments, a human antibody agent of the present invention is or comprises a single chain variable fragment (scFv), which scFv comprises HCDRs and LCDRs selected from Tables 2 and 3, respectively.

In various embodiments, a human antibody agent of the present invention is or comprises a single chain variable fragment (scFv), which scFv comprises a heavy and/or light chain variable region sequence that appears in Table 1.

In some embodiments, a provided scFv polypeptide is conjugated to a therapeutic or detection agent.

As is known to the skilled artisan, generation of scFvs and their modification in accordance with the present invention is known in the art (see, e.g., Benny K. C. Lo (ed.), Antibody Engineering—Methods and Protocols, Humana Press 2004, and references cited therein).

Multi-Specific Binding Agents

As those skilled in the art are aware, a multi-specific binding agent is a molecular entity or complex that includes binding components that bind specifically to two or more targets (e.g., epitopes). Such multi-specific binding agents find a variety of uses in the art, including therapeutic uses. To give but one example, as those skilled in the art are aware, multi-specific binding agents have been engineered to facilitate killing of tumor cells by directing (or recruiting) cytotoxic T cells to a tumor site. Examples of tumor antigens include, but are not limited to, alpha fetoprotein (AFP), CA15-3, CA27-29, CA19-9, CA-125, calretinin, carcinoembryonic antigen, CD34, CD99, CD117, chromogranin, cytokeratin, desmin, epithelial membrane protein (EMA), Factor VIII, CD31 FL1, glial fibrillary acidic protein (GFAP), gross cystic disease fluid protein (GCDFP-15), HMB-45, human chorionic gonadotropin (hCG), inhibin, keratin, CD45, a lymphocyte marker, MART-1 (Melan-A), Myo D1, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, tumor M2-PK, and vimentin.

In some embodiments, multi-specific binding agents for use in accordance with the present invention are bi-specific binding agents. In many embodiments, such bi-specific binding agents are capable of binding to tumor cells. In many embodiments, such bi-specific binding agents are capable of binding to CD19$^+$ cells, or cells that express a CD19 polypeptide on the cell surface (e.g., a tumor cell).

In some embodiments, multi-specific binding agents (e.g., bi-specific binding agents) provided herein are or comprise antibody components. A variety of technologies are known in the art for designing, constructing, and/or producing multi-specific binding agents comprising antibody components.

For example, multi-specific binding agents have been constructed that either utilize the full immunoglobulin framework (e.g., IgG), single chain variable fragment (scFv), or combinations thereof. Bi-specific binding agents composed of two scFv units in tandem has been shown to be a clinically successful bi-specific antibody format. In the case of anti-tumor immunotherapy, bi-specific binding agents that comprise two single chain variable fragments (scFvs) in tandem have been designed such that an scFv that binds a tumor antigen is linked with an scFv that engages T cells by binding CD3 (e.g., CD3γ, CD3δ, CD3ε, CD3ζ, etc.). In this way, T cells are recruited to a tumor site in the hope that they can mediate killing of the tumor cells by the cytotoxic properties that certain T cells have. An example of such a bi-specific binding agent has been made that targets CD19 and CD3 for lymphoma (termed Bi-specific T cell Engaging, or BiTE; e.g., see Dreier et al., 2003, J. Immunol. 170:4397-4402; Wolf, E. et al., 2005, Drug Discovery Today 10(18):1237-1244; Molhoj, M. et al. 2007, Mol. Immunol. 44:1935-43; Bargou et al., 2008, Science 321:974-977; Baeuerle, P. A. and C. Reinhardt, 2009, Cancer Res. 69(12): 4941-44; Hoffman, L. M and L. Gore, Frontiers in Oncol. 4(Art. 63), 5 pages), which has been successful in preventing tumor growth in animal xenograft studies. In human studies, this bi-specific binding agent demonstrated objective tumor response, including five partial and two complete remissions.

Exemplary bi-specific binding agents include those with a first antibody component specific for a tumor antigen (e.g., CD19) and a second antibody component specific for an immune cell (e.g., a T cell, NK cell, etc.). Bi-specific binding agents can be made, for example, by combining heavy chains and/or light chains that recognize different epitopes of the same or different antigen. In some embodiments, by molecular function, a bi-specific binding agent binds one antigen (or epitope) on one of its two binding arms (one $V_H/V_L$ pair), and binds a different antigen (or epitope) on its second arm (a different $V_H/V_L$ pair). By this definition, a bi-specific binding agent has two distinct antigen binding arms (in both specificity and CDR sequences), and is monovalent for each antigen to which it binds.

In some embodiments, bi-specific binding agents of the present invention are characterized by the ability to bind simultaneously to two targets that are of different structure. In some embodiments, bi-specific binding agents of the present invention have at least one component that specifically binds to, for example, a B-cell, T-cell, myeloid, plasma, or a mast cell antigen or epitope and at least one other component that specifically binds CD19, in particular, CD19 expressed on the surface of a cell.

In various embodiments, a bi-specific binding agent (e.g., a bi-specific antibody) according to the present invention is composed of a first binding component and a second binding component. In many embodiments, first and second binding components of a bi-specific binding agent as described herein are each composed of antibody components characterized by different specificities. In many embodiments, antibody components are selected from Table 1.

In various embodiments, a bi-specific binding agent according to the present invention comprises a first binding component and a second binding component. In various embodiments, a bi-specific binding agent according to the present invention comprises a first binding component, a second binding component and a linker that is connected to both the first and second binding component (e.g., positioned between the first and second binding components).

In various embodiments, first and/or second binding components as described herein comprise or are antibody components. In various embodiments, first and/or second binding components as described herein comprise a linker sequence or are connected via a linker sequence.

In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide (e.g., first and/or second binding components). In some embodiments, a linker is employed in a bi-specific binding agent described herein based on specific properties imparted to the bi-specific binding agent such as, for example, a reduction in aggregation and/or an increase in stability. In some embodiments, a bi-specific binding agent of the present invention comprises a G4S linker. In some certain embodiments, a bi-specific binding agent of the present invention comprises a $(G_4S)_n$ linker, wherein n is 1, 2, 3, 4, 5, 6, 7, 8, 9, 10, 11, 12, 13, 14, 15 or more.

In some embodiments, first and/or second binding components as described herein are or comprise immunoglobulins (e.g., IgGs). In some embodiments, first and/or second binding components binding components as described herein are or comprise antibody fragments (e.g., scFvs). In some embodiments, first binding components as described herein are or comprise antibody fragments and second binding components are or comprise immunoglobulins. In some embodiments, first binding components as described herein are or comprise immunoglobulins and second binding components are or comprise antibody fragments. In some certain embodiments, first binding components are immunoglobulins and second binding components are antibody fragments. In some certain embodiments, first binding components are IgGs and second binding components are scFvs.

In some certain embodiments, a bi-specific binding agent according to the present invention comprises a first and a second scFv. In some certain embodiments, a first scFv is linked to the C-terminal end of a second scFv. In some certain embodiments, a second scFv is linked to the C-terminal end of a first scFv. In some certain embodiments, scFvs are linked to each other via a linker sequence. In some certain embodiments, scFvs are linked to each other without a linker sequences.

In some embodiments, a bi-specific binding agent of the present invention includes two different heavy chains or heavy chain variable regions and two different light chains or light chain variable regions.

In some embodiments, a bi-specific binding agent of the present invention has two specificities, one of which binds human CD19 and the other binds human CD3 (e.g., CD3γ, CD3δ, CD3ε, CD3ζ, etc.) on T cells.

In some embodiments, a bi-specific binding agent of the present invention comprises one or more sequences that are at least about 50% (e.g., at least about 55%, 60%, 65%, 70%, 75%, 80%, 85%, 90%, 95%, 96%, 97%, 98%, or 99%) identical to one or more sequences that appear in Table 1.

In some embodiments, a bi-specific binding agent of the present invention comprises one or more sequences that are substantially identical or identical to one or more sequences that appear in Table 1.

In various embodiments, a first binding component of a bi-specific binding agent as described herein comprises one or more HCDRs and one or more LCDRs, which one or more HCDRs each have a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to one or more HCDRs that appear in Table 2, and which one or more LCDRs each have a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to one or more LCDRs that appear in Table 3.

In various embodiments, a first binding component of a bi-specific binding agent as described herein comprises three HCDRs and three LCDRs, which three HCDRs each have a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to three HCDRs that appear in Table 2, and which three LCDRs each have a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to three LCDRs that appear in Table 3.

In various embodiments, a first binding component of a bi-specific binding agent as described herein comprises a set of three HCDRs and a set of three LCDRs, which set of three HCDRs each have a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to a set of three HCDRs that appear in Table 2, and which set of three LCDRs each have a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to a set of three LCDRs that appear in Table 3.

In various embodiments, a first binding component of a bi-specific binding agent as described herein comprises a set of three HCDRs that appear in Table 2 and a set of three LCDRs that appear in Table 3.

In various embodiments, a first binding component of a bi-specific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 1.

In various embodiments, a first binding component of a bi-specific binding agent as described herein comprises an antibody component having a sequence that is substantially identical or identical to an antibody component that appears in Table 1.

In various embodiments, a second binding component of a bi-specific binding agent as described herein comprises an antibody component that binds a T cell. Exemplary T cell markers that can be employed as targets for a second binding component of a bi-specific binding agent as described herein include CD3 (e.g., CD3γ, CD3δ, CD3ε, CD3ζ, etc.), CD4, CD8, CD28, OX40 (TNFRSF4 or CD134), GITR (TNFRSF18 or CD357), CD137 (TNFRSF9 or 4-1BB), CD27 (TNFRSF7), CD40L (TNFSF5 or CD154), HVEM (TNFRSF14 or CD270), etc. In some embodiments, a second binding component of a bi-specific binding agent as described herein comprises an antibody component that binds CD3. In some certain embodiments, a second binding component of a bi-specific binding agent as described herein comprises an antibody component that binds CD3ε. Exemplary anti-CD3 antibody components that can be employed in bi-specific binding agents of the present invention are known in the art and can be found in, e.g., Routledge et al., 1991, Eur. J. Immunol. 21:2717-25; Adair et al., 1994, Hum. Antibodies Hybridomas 5:41-7; Norman et al., 2000, Clin. Transplant. 70(12):1707-12; Chatenoud, 2003, Nat. Rev. Immunol. 3(2):123-32; Cheadle, 2006, Curr. Opin. Mol. Ther. 8(1):62-8; Herold et al., 2009, Clin. Immunol. 132: 166-73; Heiss and Murawa, 2010, Int. J. Cancer 127(9): 2209-21; Keymeulen et al., 2010, Diabetologia, 53: 614-23; Silke and Gires, 2011, MAbs, 3(1):31-7; Cioffi, M. et al., 2012, Clin. Cancer Res. 18:465-474; Dean et al., 2012, Swiss Med. Wkly. 142:w13711; Labrijn et al., 2013, Proc. Nat. Acad. Sci. U.S.A. 110(13):5145-50; Portell et al., 2013, Clin. Pharmacol. 5:5-11; U.S. Pat. Nos. 7,112,324, 7,575, 923, 8,076,459, 8,101,722, all of which are herein incorporated by reference in their entireties.

Alternatively, existing non-human (e.g., murine) anti-CD3 antibody components provide a valuable source of antibody components for employing in bi-specific binding agents of the present invention (see, e.g., murine OKT3 light chain in EMBL accession A22259.1 GL641464, and murine OKT3 heavy chain at EMBL accession A22261.1 GL21727144). While such non-human antibody components are useful, humanized forms thereof are preferred in the treatment of human subjects because, among other things, it reduces the likelihood of immune reactions against the administered antibody (or bi-specific binding agent). Methods for making humanized antibodies are generally known in the art.

Chimeric Antigen Receptors

The present invention also provides chimeric antigen receptors comprising a human antibody agent and/or multi-specific binding agent as described herein. CARs may be constructed by methods known in the art (see, e.g., International Patent Application Publication Nos. 2012/079000, 2013/126726, 2015/177789 and 2015/080981; U.S. Patent Application Publication No. 2012/0213783 A1, U.S. Pat. Nos. 7,446,179 and 5,912,172; Milone, M. C. et al., 2009, Mol. Therapy 17(8):1453-64; Kochenderfer, J. N. et al., 2010, Blood 116(19):3875-86; 2011, N. Engl. J. Med. 365 (20):1937-9; Grupp, S. A. et al., 2013, N. Engl. J. Med. 368(16):1509-18; Romas, C. A. et al., 2014, Cancer J. 20(2):112-18; Singh, H. et al., 2014, Immunol. Rev. 257(1): 181-90; Fujiwara, H., 2014, Pharmaceuticals 7:1049-68; Maude, S. L. et al., 2015, Blood 125(26):4017-23; all of which are incorporated herein by reference). Immune effector cells (e.g., T cells, NK cells, etc.) may be engineered to express a chimeric antigen receptor that contains an antibody component as described herein, thereby creating anti-tumor immune effector cells that overcome the surveillance mechanisms of the immune system employed by cancer cells to evade detection. In some embodiments, the present invention provides an immune cell that expresses a chimeric antigen receptor, which chimeric antigen receptor comprises one or more antigen-binding sites of a human antibody agent or multi-specific binding agent as described herein. In some embodiments, immune cells include T cells engineered to express an antigen-binding site of a human antibody agent described herein. In some embodiments, an antigen-binding site is or comprises an antibody component as described herein.

In some embodiments, immune cells include a chimeric antigen receptor that is human and/or engineered by the hand of man (e.g., includes one or more amino acid substitutions). In some embodiments, a chimeric antigen receptor comprises one, two, three, four, five, or more components (e.g., antibody components, binding components, signaling components, etc.). In some embodiments, a chimeric antigen receptor comprises a transmembrane component and/or an intracellular signaling component. In some embodiments, a chimeric antigen receptor comprises components native to an immune cell from which said chimeric antigen receptor is expressed (e.g., a native immune cell receptor). In some embodiments, a chimeric antigen receptor comprises one or more transmembrane and/or one or more intracellular components of a T cell receptor (TCR) polypeptide.

The term "T cell receptor," or "TCR," as used herein refers to a heterodimeric receptor composed of $\alpha\beta$ or $\gamma\delta$ chains that pair on the surface of a T cell. Each $\alpha$, $\beta$, $\gamma$, and $\delta$ chain is composed of two Ig-like domains: a variable domain (V) that confers antigen recognition through TCR's CDRs, followed by a constant domain (C) that is anchored to cell membrane by a connecting peptide and a transmembrane (TM) region, which in turn connects to a cytoplasmic sequence/intracellular component. The TM region associates with the invariant subunits of the CD3 signaling apparatus. Each of the TCR V domains has three CDRs. These CDRs interact with a complex between an antigenic peptide bound to a protein encoded by the major histocompatibility complex (pMHC) (see, e.g., Davis and Bjorkman, 1988, Nature 334:395-402; Davis et al., 1998, Annu. Rev. Immunol. 16:523-44; Murphy, Kenneth P. Janeway's Immunobiology. 8$^{th}$ Edition. New York: Garland Science, Taylor & Francis Group, LLC, 2012. Print. Chapters 5 & 6). TCR V domain and CDR sequences are typically very different from antibody V domain and CDR sequences.

In some embodiments, a provided chimeric antigen receptor (CAR) is composed of a heterodimer of first and second polypeptides, with the first polypeptide comprising an anti-CD19 heavy chain variable region as described herein and the TM region of a TCR $\gamma$ chain, and the second polypeptide comprising an anti-CD19 light chain variable region as described herein and the TM region of a TCR $\delta$ chain. In some embodiments, a first polypeptide of the CAR heterodimer comprises an anti-CD19 heavy chain variable region as described herein and the TM region of a TCR $\delta$ chain, and the second polypeptide comprising an anti-CD19 light chain variable region as described herein and the TM region of a TCR $\gamma$ chain. In some embodiments, a provided chimeric antigen receptor comprises the TM region of TCR $\alpha\beta$ chains. In some embodiments, a provided chimeric antigen receptor comprises an intracellular domain of a TCR. In particular embodiments, a provided chimeric antigen receptor comprises both the TM region and the intracellular region of a TCR.

In some embodiments, components of a chimeric antigen receptor as described herein facilitate binding of an immune cell to a CD19$^+$ cell. In some embodiments, a chimeric antigen receptor as described herein comprises an antibody component that is or is based on an antibody agent as described herein. In some embodiments, a chimeric antigen receptor as described herein comprises an antibody component that binds human CD19, and further comprises one or more cytoplasmic signaling domains, in whole or in part, and one or more co-stimulatory molecules, in whole or in part. In some embodiments, an antibody component of a chimeric antigen receptor as described herein is or comprises an scFv; in some certain embodiments, an scFv is selected from Table 1.

Targets

Among other things, the present invention encompasses the recognition that multi-specific binding agents (and/or chimeric antigen receptors), and particularly bi-specific binding agents such as bi-specific antibodies, are particularly useful and/or effective to facilitate cell killing. In particular, the present invention demonstrates that activity of multi-specific binding agents that bind specifically to both a target-cell-associated epitope (e.g., CD19 on cancer cells) and a lymphocyte-associated epitope (e.g., a T cell surface protein) can be an effective immunotherapy for B cell-associated disease and malignancies.

For example, in some embodiments of the present invention, a multi-specific binding agent binds specifically to a tumor-cell-associated epitope and a T-cell epitope. In accordance with such embodiments, the multi-specific binding agent can facilitate binding of the agent to one or both of its target epitopes and/or can enhance killing of the target tumor cell as mediated by the target T cell. To give but another example, in some embodiments of the present invention, a chimeric antigen receptor binds CD19 on a cancer cell. In accordance with such embodiments, an immune cell can facilitate killing of the CD19$^+$ cell after engagement of the chimeric antigen receptor with its target epitope.

In some embodiments, target cells to be killed include, for example, cells that express CD19 (e.g., lymphoma or leukemia cell). Those of ordinary skill in the art will be aware of appropriate target epitopes on such cells to which multi-specific binding agents as described herein desirably bind.

In some embodiments, lymphocyte cells that can mediate killing of target cells as described herein include T cells (e.g., CD8$^+$ T cells), natural killer (NK) cells, macrophages, granulocytes and antibody-dependent cytotoxic cells. Those of ordinary skill in the art will be aware of appropriate target epitopes on such lymphocytes to which multi-specific binding agents as described herein desirably bind. Representative such epitopes can be found on antigens such as, for example, Fc receptor of IgG (e.g., Fc$\gamma$RIIB), CD1d, CD3 (e.g., CD3$\gamma$, CD38, CD3$\epsilon$, CD3$\zeta$, etc.), CD4, CD7, CD8, CD13, CD14, CD16, CD27, CD28, CD31, CD38, CD40L, CD56, CD68, MAC-1/MAC-3, IL-2Ra, OX40, GITR, HVEM, Ly49, and CD94, CD137.

Nucleic Acid Construction and Expression

Human antibody agents (e.g., human monoclonal antibodies, scFvs, etc.) multi-specific binding agents (e.g., bi-specific antibodies) and chimeric antigen receptors as described herein may be produced from nucleic acid molecules using molecular biological methods known to the art. Nucleic acid molecules are inserted into a vector that is able to express the fusion proteins when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al., Molecular Cloning, A Laboratory Manual, Cold Spring Harbor Laboratory; Current Protocols in Molecular Biology, Eds. Ausubel, et al, Greene Publ. Assoc., Wiley-Interscience, NY).

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs include regions that encode multi-specific binding proteins (or chimeric antigen receptors) generated from antibodies and/or antibody components. Typically, such multi-specific binding proteins (or chimeric antigen receptors) will be generated from $V_H$ and/or $V_L$ regions. After identification and selection of antibodies exhibiting desired binding and/or functional properties, variable regions of each antibody are isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids. The antibodies and/or antibody components may be generated from human, non-human (e.g., rodent), humanized or chimeric antibodies.

Nucleic acid constructs of the present invention are inserted into an expression vector or viral vector by methods known to the art, and nucleic acid molecules are operatively linked to an expression control sequence.

Where appropriate, nucleic acid sequences that encode human antibody agents, multi-specific binding agents, and chimeric antigen receptors as described herein may be modified to include codons that are optimized for expression in a particular cell type or organism (e.g., see U.S. Pat. Nos. 5,670,356 and 5,874,304). Codon-optimized sequences are synthetic sequences, and preferably encode the identical polypeptide (or a biologically active fragment of a full length polypeptide which has substantially the same activity as the full length polypeptide) encoded by the non-codon-optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, the coding sequence for a human heavy (or light) chain variable region as described herein may be optimized for expression in a bacterial cells. Alternatively, the coding sequence may be optimized for expression in a mammalian cell (e.g., a CHO). Such a sequence may be described as a codon-optimized sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a COS or CHO cell). Host cells transformed with an expression vector are grown under conditions permitting production of a human antibody agent, multi-specific binding agent, or chimeric antigen receptor of the present invention followed by recovery of the human monoclonal antibody, multi-specific binding agent or chimeric antigen receptor. In some embodiments, host cells include those that exhibit a variant glycosylation pattern in one or more expressed polypeptides (see, e.g., U.S. Pat. Nos. 8,080,415 and 8,084,222).

Human antibody agents and/or multi-specific binding agents of the present invention may be purified by any technique, which allows for the subsequent formation of a stable antibody or binding agent molecule. For example, not wishing to be bound by theory, human antibody agents and/or multi-specific binding agents may be recovered from cells either as soluble polypeptides or as inclusion bodies, from which they may be extracted quantitatively by 8M guanidinium hydrochloride and dialysis. In order to further purify human antibody agents and/or multi-specific binding agents of the present invention, conventional ion exchange chromatography, hydrophobic interaction chromatography, reverse phase chromatography or gel filtration may be used. Human antibody agents and/or multi-specific binding agents of the present invention may also be recovered from conditioned media following secretion from eukaryotic or prokaryotic cells.

Chimeric antigen receptors expressed on an immune cell surface may be achieved by methods known in the art. Typically, an expression vector carrying the nucleic acid sequence that encodes the chimeric antigen receptor polypeptide is transformed into a host cell for expression. As described above, such a host cell can be a cell line or primary human cell isolates, such as T cells from PBMC. The expression vector may also include a sequence that encodes a signal peptide and/or a transmembrane domain and/or a signaling domain such that the expression of the chimeric antigen receptor is targeted to a cell membrane. Such signal peptides are known by persons of skill in the art. The expression vector that encodes the chimeric antigen receptor polypeptide is introduced into a host cell by methods known in the art, which include, for example, DNA transfection, electroporation, transfection and infection (e.g., with a virus such as an adenovirus or retrovirus).

In some embodiments, nucleic acid molecules encoding a chimeric antigen receptor as described herein provide for expression in a T cell thereby generating chimeric antigen receptor T cells (CAR-Ts). The nucleic acid molecule encoding the chimeric antigen receptor can be included in one or more vectors (e.g., a lenti-viral or retroviral vector) for expression in a host immune effector cell, such as a T cell. Exemplary immune cells include T cells, Natural Killer (NK) cells, cytotoxic T lymphocytes (CTLs), and regulatory T cells. Methods of generating nucleic acid molecules encoding chimeric antigen receptors and T cells including such chimeric antigen receptors are known in the art (see, e.g., Till, B. G. et al., 2008, Blood 112(6):2261-71; Brentjens, R. et al., 2010, Molecular Therapy 18(4):666-8; Morgan, R. A. et al., 2010, Molecular Therapy 18(4):843-51; Park, T. S. et al., 2011, Trends Biotechnol. 29(11):550-7; Grupp, S. A. et al., 2013, N. Engl. J. Med. 368(16):1509-18; Han, E. Q. et al., 2013, J. Hematol. Oncol. 6:47; WO 2012/079000, WO 2013/126726; and U.S. Patent Application Publication No. 2012/0213783).

Conjugates

Several technologies for the attachment or conjugation of a therapeutic or detection agent to an antibody agent are known in the art. Some attachment technologies involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (see, e.g., U.S. Pat. Nos. 4,472,509 and 4,938,948). Provided human antibody agents may also be reacted with an enzyme in the presence of a coupling agent such as glutaraldehyde or periodate. Conjugates with fluorescein markers, for example, are prepared in the presence of these coupling agents or by reaction with an isothiocyanate.

In some embodiments, a human antibody agent as described herein is associated with a payload entity. In some embodiments, a payload entity is or comprises a therapeutic agent; in some embodiments, a payload entity is or comprises a detection agent.

Protecting Groups

Human antibody agents (or multi-specific binding agents or chimeric antigen receptors) of the present invention may be provided with protecting groups, which are known in the art. Without wishing to be bound by any particular theory, addition of a protecting group may, in some embodiments, improve one or more characteristics of a polypeptide or peptide to which it is added such as, for example, stability and/or efficacy. In some embodiments, human antibody agents (or multi-specific binding agents or chimeric antigen receptors) described herein may bear one or more (e.g., one, two, three, four, five or more) protecting groups. Protecting groups may be coupled to the N- and/or C-terminal end of a polypeptide or polypeptide chain of a human antibody agent (or multi-specific binding agent or chimeric antigen receptor) as described herein. Protecting groups suitable for use in accordance with the present invention include those described in U.S. Provisional Patent Application Ser. No. 62/131,128, which is herein incorporated by reference.

Therapeutic Agents

Therapeutic agents can be or comprise any class of chemical entity including, for example, but not limited to, proteins, carbohydrates, lipids, nucleic acids, small organic molecules, non-biological polymers, metals, ions, radioisotopes, etc. In some embodiments, therapeutic agents for use in accordance with the present invention may have a biological activity relevant to the treatment of one or more symptoms or causes of cancer. In some embodiments, therapeutic agents for use in accordance with the present invention may have a biological activity relevant to modulation of the immune system and/or enhancement of T-cell mediated cytotoxicity. In some embodiments, therapeutic agents for use in accordance with the present invention have one or more other activities.

In some embodiments, a conjugated therapeutic agent is a radioisotope, a drug conjugate, a nanoparticle, an immunetoxin, or any other therapeutic payload.

Detection Agents

A detection agent comprises any moiety that may be detected using an assay, for example due to its specific functional properties and/or chemical characteristics. Non-limiting examples of such agents include enzymes, radiolabels, haptens, fluorescent labels, phosphorescent molecules, chemiluminescent molecules, chromophores, luminescent molecules, photoaffinity molecules, colored particles or ligands, such as biotin.

Many detection agents are known in the art, as are systems for their attachment to antibodies (see, for e.g., U.S. Pat. Nos. 5,021,236; 4,938,948; and 4,472,509). Examples of such detection agents include paramagnetic ions, radioactive isotopes, fluorochromes, NMR-detectable substances, X-ray imaging agents, among others. For example, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

The radioactive isotope may be one or more of actinium-225, astatine-211, bismuth-212, carbon-14, chromium-51, chlorine-36, cobalt-57, cobalt-58, copper-67, Europium-152, gallium-67, hydrogen-3, iodine-123, iodine-124, iodine-125, iodine-131, indium-111, iron-59, lead-212, lutetium-177, phosphorus-32, radium-223, radium-224, rhenium-186, rhenium-188, selenium-75, sulphur-35, technicium-99m, thorium-227, yttrium-90, and zirconium-89. Radioactively labeled human antibody agents may be produced according to well-known technologies in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Provided human antibody agents may be labeled with technetium-99m by ligand exchange process, for example, by reducing pertechnate with stannous solution, chelating the reduced technetium onto a Sephadex column and applying the antibody to this column. In some embodiments, provided human antibody agents are labeled using direct labeling techniques, e.g., by incubating pertechnate, a reducing agent such as $SNCl_2$, a buffer solution such as sodium-potassium phthalate solution, and the antibody. In some embodiments, provided human antibody agents may be conjugated to intermediary functional groups. Intermediary functional groups are often used to bind radioisotopes, which exist as metallic ions, to antibodies. Radioactive isotopes may be detected by, for example, dosimetry.

A fluorescent label may be or may comprise one or more of Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

In some embodiments, a conjugated detection agent is a diagnostic or imaging agent.

Screening, Detection and Therapeutic Methods

Human antibody agents, multi-specific binding agents and/or chimeric antigen receptors of the present invention may also be used in in vitro or in vivo screening methods where it is desirable to detect and/or measure one or more activities of a cell or cells (e.g., apoptosis or cell growth). Screening methods are well known to the art and include cell-free, cell-based, and animal assays. In vitro assays can be either solid state or soluble target molecule detection may be achieved in a number of ways known to the art, including the use of a label or detectable group capable of identifying a human antibody agent, multi-specific binding agent, or chimeric antigen receptor which is bound to a target molecule (e.g., cell surface antigen). Detectable labels may be used in conjunction with assays using human antibody agents, multi-specific binding agents or chimeric antigen receptors of the present invention.

The ability of human antibody agents, multi-specific binding agents and/or chimeric antigen receptors of the present invention to exhibit high affinity and/or specificity for CD19 makes them therapeutically useful for efficiently targeting cells expressing CD19 (e.g., a lymphoma or leukemia cell). Thus, in some embodiments, it may be desirable to increase the affinity of a human antibody agent or multi-specific binding agent for one target antigen (e.g., CD19) and not the other target antigen that is also bound by the multi-specific binding agent (or an Fc receptor in the case of a human monoclonal antibody). For example, in the context of tumor killing, certain conditions may benefit from an increase in affinity to a tumor antigen (e.g., CD19) but not to an antigen on the surface of a cell capable of mediating killing of the tumor (e.g., a T cell). Thus, it may be beneficial to increase the binding affinity and/or specificity of a human antibody agent, multi-specific binding agent or chimeric antigen receptor to a tumor antigen in a patient having a tumor that expresses the tumor antigen through the use of a human antibody agent, multi-specific binding agent or chimeric antigen receptor as described herein.

The present invention provides a human antibody agent, multi-specific binding agent and/or chimeric antigen receptor as described herein as a therapeutic for the treatment of patients having a tumor that expresses an antigen that is capable of being bound by the same. Such human antibody agents, multi-specific binding agents and/or chimeric antigen receptors may be used in a method of treatment of the human or animal body, or in a method of diagnosis.

In some embodiments, a provided human antibody agent, multi-specific binding agent, or chimeric antigen receptor is useful in medicine. In some embodiments, a provided human antibody agent, multi-specific binding agent, or chimeric antigen receptor is useful (e.g., as a prophylactic agent) in the treatment or prevention of CD19-associated disease or malignancies. In some embodiments, a provided human antibody agent, multi-specific binding agent, or chimeric antigen receptor is useful in the treatment of patients that exhibit negative ramifications associated or correlated with CD20-associated disease or malignancies (e.g., inefficient internalization). In some embodiments, a provided human antibody agent, multi-specific binding agent, or chimeric antigen receptor is useful in therapeutic applications, for example in individuals suffering from or susceptible to CD19-associated disease or malignancies.

Administration

The present invention provides methods of administering an effective amount of a therapeutic active described herein (e.g., a human antibody agent, multi-specific binding agent, or chimeric antigen receptor) to a subject in need of treatment.

Human antibody agents, multi-specific binding agents, or chimeric antigen receptor as described herein may be administered through various methods known in the art for the therapeutic delivery of agents, such as proteins or nucleic acids can be used for the therapeutic delivery of a human antibody agent, multi-specific binding agent or chimeric antigen receptor or a nucleic acid encoding a human antibody agent, multi-specific binding agent, or chimeric antigen receptor of the present invention for killing or inhibiting growth of target cells in a subject, e.g., cellular transfection, gene therapy, direct administration with a delivery vehicle or pharmaceutically acceptable carrier, indirect delivery by providing recombinant cells comprising a nucleic acid encoding a human antibody agent, multi-specific binding agent, or chimeric antigen receptor of the present invention.

Various delivery systems are known and can be used to administer a human antibody agent, multi-specific binding agent, or chimeric antigen receptor of the present invention, e.g., encapsulation in liposomes, microparticles, microcapsules, recombinant cells capable of expressing said antibody agent, multi-specific binding agent, or chimeric antigen receptor, receptor-mediated endocytosis (see, e.g., Wu and Wu, 1987, J. Biol. Chem. 262:4429-32), construction of a nucleic acid as part of a retroviral or other vector, etc. Routes of administration can be enteral or parenteral and include, but are not limited to, intravenous, subcutaneous, intramuscular, parenteral, transdermal, or transmucosal (e.g., oral or nasal). In some embodiments, human antibody agents, multi-specific binding agents, or chimeric antigen receptors of the present invention are administered intravenously. In some embodiments, human antibody agents, multi-specific binding agents, or chimeric antigen receptors of the present invention are administered subcutaneously. In some embodiments, human antibody agents, multi-specific binding agents, or chimeric antigen receptors of the present invention are administered together with one or more biologically active agents.

Pharmaceutical Compositions

The present invention further provides pharmaceutical compositions comprising human antibody agents, multi-specific binding agents, or chimeric antigen receptors of the present invention and a pharmaceutically acceptable carrier or excipient. The composition, if desired, can also contain one or more additional therapeutically active substances.

In some embodiments, pharmaceutical compositions comprising a chimeric antigen receptor may be provided as a virus (e.g., a lenti-virus or a retrovirus) used to infect autologous T cells isolated from a subject. In such embodiments, autologous T cells are infected with a virus that has been engineered to express a chimeric antigen receptor as described herein, thereby creating chimeric antigen receptor T cells for reinfusion into the subject (e.g., a human patient).

In some embodiments, pharmaceutical compositions comprising a chimeric antigen receptor may be provided a host cell (or populations thereof) expressing said chimeric antigen receptor, and a pharmaceutically acceptor carrier. Exemplary host cells include T cells or NK cells and may be autologous or allogeneic. Thus, host cells expressing a chimeric antigen receptor as described herein can be formulated into a pharmaceutical composition for administration to a subject (e.g., a human). Such pharmaceutical compositions may comprise a population of host cells expressing the same or different (two, three, four, etc.) chimeric antigen receptors as described herein. Alternatively, a pharmaceutical composition comprising a host cell expressing a chimeric antigen receptor as described herein may further comprise one or more additional pharmaceutically active agents or drugs, such as, e.g., chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In various embodiments, a pharmaceutical composition comprising a chimeric antigen receptor as described herein is provided as a host cell expressing said chimeric antigen receptor or populations thereof.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Pharmaceutical compositions may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

Formulations of pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition of the present invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the present invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans. In some embodiments, an excipient is approved for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody-based compositions for longer than the specified time results in degradation of the antibody-based entity.

Liquid dosage forms and/or reconstituted solutions may comprise particulate matter and/or discoloration prior to administration. In some embodiments, a solution should not be used if discolored or cloudy and/or if particulate matter remains after filtration.

General considerations in the formulation and/or manufacture of pharmaceutical agents may be found, for example, in Remington: The Science and Practice of Pharmacy 21st ed., Lippincott Williams & Wilkins, 2005.

Kits

The present invention further provides a pharmaceutical pack or kit comprising one or more containers filled with at least one human antibody agent, multi-specific binding agent (e.g., a bi-specific antibody), or chimeric antigen receptor (or chimeric antigen receptor immune effector cell) as described herein. Kits may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Other features of the invention will become apparent in the course of the following descriptions of exemplary embodiments, which are given for illustration of the invention and are not intended to be limiting thereof. All patent and non-patent literature cited herein are incorporated herein by reference in their entireties.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Generation and Selection of Human Antibody Agents Specific for Human CD19

This example demonstrates the production of human antibody agents specific for human CD19. In particular, this example demonstrates the production of human single chain variable fragments (scFvs) that specifically bind human CD19 in native format. Human antibody agents described herein were developed using naïve or semi-synthetic human antibody libraries developed from normal donors and/or autoimmune diseases donors and selected based on high specificity for human CD19 via panning on cell surface expressed human CD19 in its native conformation. Thus, such human antibody agents provide a valuable source of antibody components for construction of, among other things, full-length IgG, multi-specific binding agents and chimeric antigen receptors that may otherwise be deleted from repertoires found in nature.

Briefly, an exemplary outline for the development of anti-human CD19 antibody agents is set forth in Table 4. The process started with identification of human CD19-specific and biologically active antibody agents from the Eureka ALPHA™ phage library. Top antibody agent candidates underwent affinity maturation to generate antibody agents with improved binding affinity and better cytotoxicity against target cancer cells.

A collection of human scFv antibody phage display libraries (diversity=$10 \times 10^{10}$) constructed at Eureka Therapeutics, named as ALPHA™ phage libraries, was used for the selection of human antibody agents specific to human CD19. ALPHA™ phage libraries included naive libraries consisting of fully naïve human heavy and light chain repertoires, and semi-synthetic libraries containing fully naïve human light chain repertoires and semi-synthetic heavy chain with completely randomized heavy chain CDR3 regions. The naïve antibody repertoires were cloned from PBMCs and spleens of healthy donors or from PBMCs of autoimmune disease donors (such as systemic lupus erythematosus and rheumatoid arthritis). The scFv libraries were used in panning against recombinant human CD19 ECD-Fc fusion protein and human CD19 positive cells including Raji and 3T3-CD19 cells (described below). For protein panning, Fc fusion protein was directly coated onto 96-well plates and mixed with human scFv phage libraries. After extended washing with PBS buffer, the bound clones were eluted and used to infect E. coli XL1-Blue. For cell panning, 3T3-CD19 or Raji cells were first mixed with human scFv phage libraries. After extended washing with PBS, cells with bound scFv antibody phage were spun down. The bound clones were then eluted and used to infect E. coli XL1-Blue cells. The phage clones were expressed in bacteria and purified. The panning was performed for three to four rounds to enrich for scFv phage clones that specifically bound the extracellular region of human CD19.

As shown in Table 5 (ALPHA™ Phage Display Summary), when protein panning was included in panning steps and ELISA binding against recombinant human CD19 ECD-Fc fusion protein was employed as the primary phage clone screening method, only a single unique antibody clone was identified as a cell-surface human CD19 binder after screening 762 phage clones from the panning enriched phage pools. The inventors then performed cell panning only and using a human CD19 positive cell line in a FACS assay as the primary screening method. Seven additional unique clones that bound cell-surface human CD19 were identified from the 690 clones screened using this panning campaign.

For the ELISA assay, standard ELISA plates were coated with human CD19 ECD-Fc or negative control 901-Fc, respectively. Individual phage clones from enriched phage display panning pools were incubated in the coated plates. Binding of the phage clones was detected by HRP-conjugated anti-M13 antibodies and developed using HRP substrate. The absorbance was read at 450 nm. Multiple human CD19 ELISA-specific phage clones were identified and exemplary clones were shown in FIG. 1A. Among 762 phage clones screened, 85 unique antibody clones were found to be hCD19 specific as determined by ELISA assay.

Figure 1B:
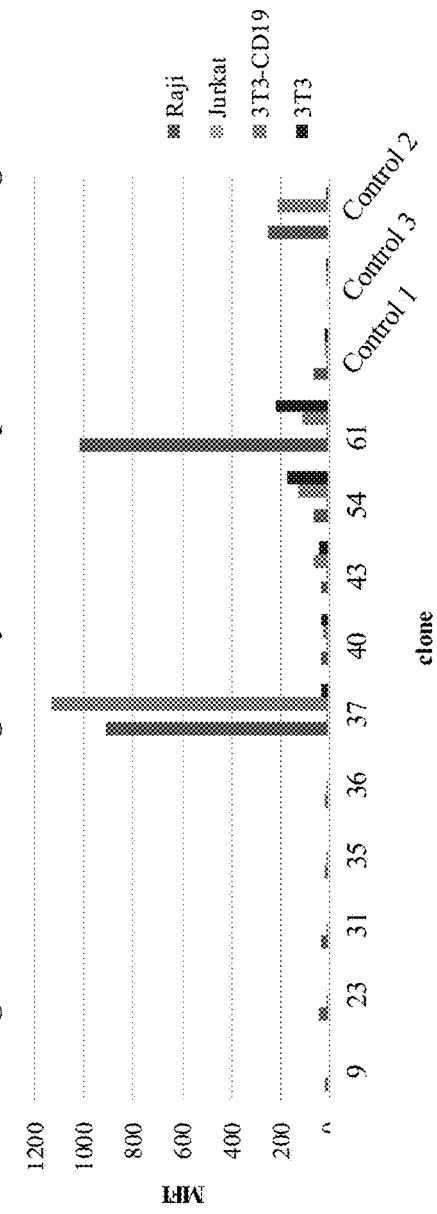

ELISA-positive phage clones were then tested for cell-surface human CD19 binding by flow cytometry using human CD19-positive Raji and 3T3-hCD19 cell lines, and human CD19 negative Jurkat and 3T3 cell lines (FIG. 1B). Cells were first stained with purified scFv phage clones, followed by mixing with a mouse anti-M13 monoclonal antibody, and finally a R-PE conjugated horse anti-mouse IgG (Vector Labs). Each step of staining was performed between 30-60 minutes on ice and cells were washed twice between stainings. One unique clone, 37, was identified to specifically bound human CD19$^+$ Raji and 3T3-CD19 cells and not hCD19$^-$ Jurkat and 3T3 (FIG. 1B).

Figure 2:
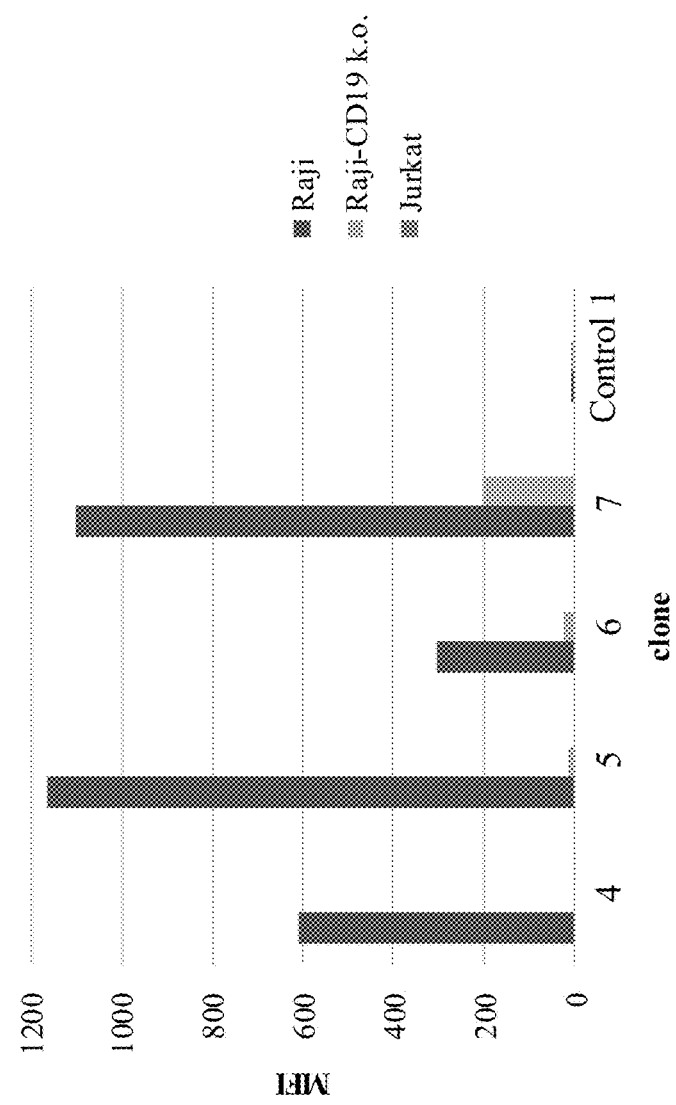
FIG. 2 shows representative mean fluorescent intensity (MFI) of phage clone binding of human CD19 positive Raji cells (Raji), CD19 knock-out Raji cells (Raji-CD19 k.o.) and human CD19 negative Jurkat cells (Jurkat) in a flow cytometry assay for selected anti-CD19 human antibody agents. Control 1: secondary antibody only, including anti-M13 mouse antibody and PE-labeled anti-mouse antibody.

Hits from the second screen where phage clones were selected by cell panning only were tested for cell-surface human CD19 binding directly, without employing an ELISA binding screen. As shown in FIG. 2, exemplary clones 4, 5 and 6 demonstrated specific binding to Raji cells, while clone 7 also demonstrated some detectable binding to Raji-CD19 knockout cells.

As shown in this example, phage-panning efficiency of human CD19 antibody was very low, since only eight specific and unique (by sequence) clones were identified among 1452 individual phage clones identified from the primary screens. One clone (37) was generated from auto-immune disease naïve library, and seven other clones were generated from naïve or semi-synthetic human antibody libraries made from normal donor B cells.

TABLE 4

| Stage | Methodology |
| --- | --- |
| Primary panning with ALPHA™ phage library | Protein and cell panning<br>ELISA and/or FACs screening of phage clones |
| Clone Characterization | Target cancer cell killing<br>Human B cell binding |
| Affinity Maturation | Affinity matured phage library construction<br>Cell panning<br>FACs screening of phage clones |
| Clone Characterization | $K_D$ measurement<br>Target cancer cell killing |

TABLE 5

| Protein/Cell Panning | | Cell Panning | |
| --- | --- | --- | --- |
| No. of clones (ELISA Screening) | 762 | No. of clones (FACS Screening) | 690 |
| Cell-surface CD19 binding clones | 1 | Cell-surface CD19 binding clones | 7 |

Example 2. Generation of Bi-Specific Antibody Constructs Using Human CD19 Antibody Agents This example demonstrates the construction of multi-specific binding agents using human scFv fragments specific for human CD19. In particular, this example specifically demonstrates the construction of bi-specific antibodies having a first antigen-binding site that binds human CD19 in native format (cell-surface expressed) and a second antigen-binding site that binds CD3 on T cells. Thus, the present example illustrates that, in some embodiments, using multi-specific binding agents that contain antibody components as described herein, T cells can be directed to kill target cells that express human CD19.

Figure 3:
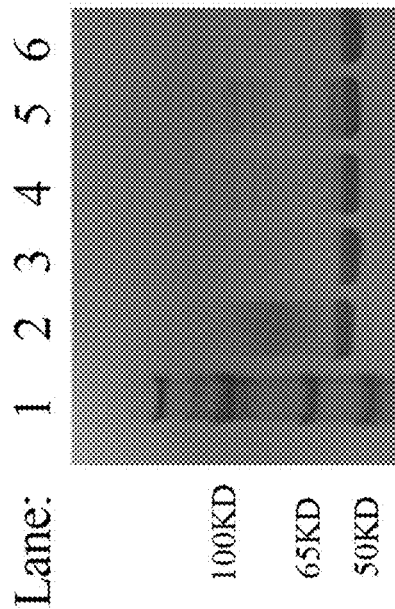
FIG. 3 shows a representative image of an SDS-PAGE illustrating selected bi-specific antibodies described in Example 2. Lane numbers are indicated at the top of the gel image. Lane 1: marker; Lane 2: CD19×CD3 bi-specific antibody using clone 2; Lane 3: CD19×CD3 bi-specific antibody using clone 3; Lane 4: CD19×CD3 bi-specific antibody using clone 4; Lane 5: CD19×CD3 bi-specific antibody using clone 37; Lane 6: BL19 (comparator bi-specific antibody; see SEQ ID NO:30 of U.S. Pat. No. 7,635,472).
Figure 4A:
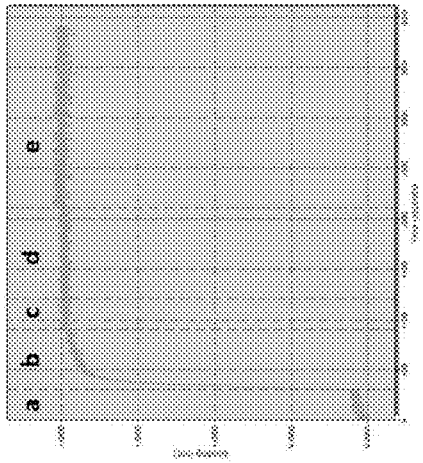
FIGS. 4A-4F show representative octet association/dissociation curves for binding (y-axis, in nm) of exemplary bi-specific antibody molecules to recombinant human CD19 ECD-Fc fusion protein over time (x-axis, in seconds). Kinetic steps (separated by vertical dashed lines) are indicated above each sensorgram. a: baseline; b: biotinylated human CD19-Fc (5 µg/mL); c: re-equilibration; d: antibody binding to human CD19-Fc (10 µg/mL); e: antibody dissociation. Bi-specific antibodies tested included CD19×CD3 bi-specific antibody based on phage clones 4, 5, 6, 7, 37 and BL19 (a comparator bi-specific antibody; see SEQ ID NO:30 of U.S. Pat. No. 7,635,472).
Figure 4B:
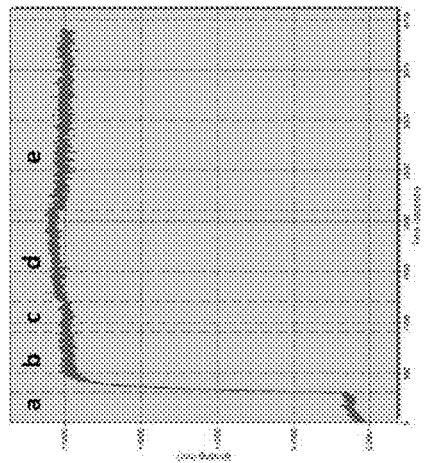
Figure 4C:
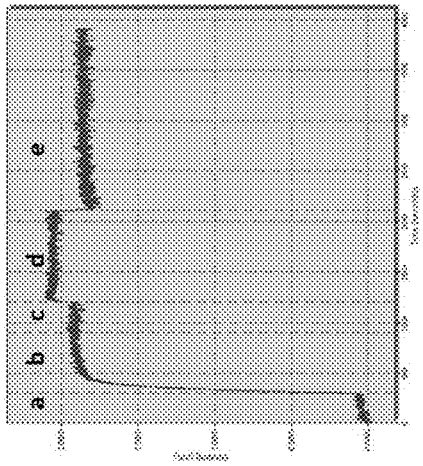
Figure 4D:
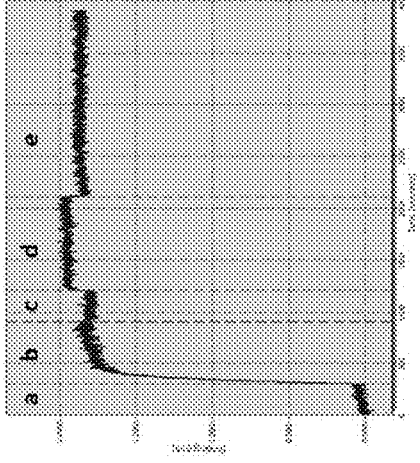
Figure 4E:
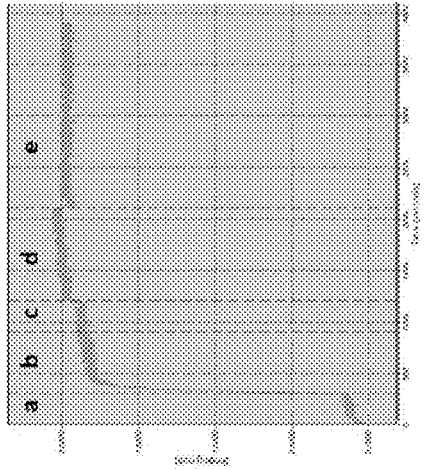
Figure 4F:
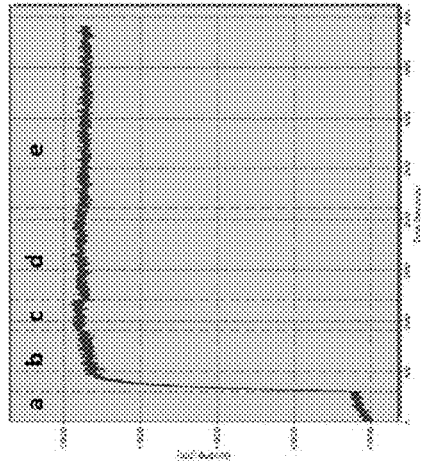

Bi-specific antibodies were generated using scFv sequences of the human CD19-specific phage clones. The bi-specific antibodies were constructed using a single-chain format comprising the $V_L$-$V_H$ scFv sequence of a human CD19-specific phage clone at the N-terminal end and an anti-human CD3ε mouse monoclonal scFv at the C-terminal end (e.g., see Brischwein, K. et al., *Mol. Immunol.* 43:1129-1143, 2006). The DNA fragments encoding the human CD19 scFv and the anti-human CD3ε scFv were synthesized by Genewiz or Genscript and subcloned into a mammalian expression vector pQD-T (Eureka Therapeutics, Inc.) using standard recombinant DNA technology. A hexhistamine tag was inserted at the C-terminal end for purification and detection. HEK293 cells were transfected with the bi-specific antibody expression vector and cultured for seven days for bi-specific antibody production. Bi-specific antibodies were purified from HEK293 cell supernatants using HisTrap HP column (GE healthcare) by FPLC AKTA system. HEK293 cell culture was clarified and loaded onto the column with low imidazole concentration (20 mM), and then an isocratic high imidazole concentration elution buffer (500 mM) was used to elute bound bi-specific antibodies. Molecular weights of purified human CD19 bi-specific antibodies were measured under non-reducing conditions by gel electrophoresis. Protein (4 μg) was mixed with 2.54, of the NuPAGE LDS Sample Buffer (Life Technologies, NP0008) and brought up to 104, with deionized water. Samples were heated to 70° C. for 10 minutes and loaded onto gels. Gel electrophoresis was performed at 180V for 1 hour. Bands (~55 kD) corresponding to the bi-specific antibodies were observed as the major species on the gel (FIG. 3).

Taken together, this example demonstrates the successful construction of bi-specific molecules having a first antigen-binding site that is specific for human CD19 expressed on the cell surface (i.e., native format) and a second antigen-binding site that is specific for CD3. Further characterization of such bi-specific molecules is described in the following examples.

Example 3. Characterization of Human CD19 Bi-Specific Antibodies

This example demonstrates the CD19 binding profile for selected bi-specific molecules. In particular, this example specifically describes the binding profile of selected bi-specific antibody molecules for recombinant human CD19 (i.e., human CD19 ECD-Fc) in solution.

Binding to Recombinant Human CD19 ECD-Fc Fusion Protein.

Phage clones that were identified as specific binders to cell surface human CD19 were tested for binding to recombinant human CD19 ECD-Fc fusion protein in solution using Fortebio Octet. Biotinylated human CD19 ECD-Fc fusion proteins (5 μg/mL) were loaded onto a streptavidin biosensor. After washing off excess antigen, bi-specific antibodies were tested at 10 μg/mL in PBS buffer for association and dissociation. None of the tested clones, which recognized cell surface expressed human CD19, demonstrated binding to recombinant human CD19 ECD-Fc fusion protein, including clone 37, which was an ELISA-positive clone. FIGS. 4A-4F show the Octet hCD19 binding data of exemplary clones and BL19, a comparator anti-CD19 bi-specific antibody. Thus, the inventors reasoned that recombinant hCD19 protein may have a distinct structural conformation as compared to native human CD19 (i.e., on the cell surface) as well as ELISA-plate-bound human CD19. Coating an ELISA plate with recombinant human CD19 may force the formation of a certain conformation(s) that mimic the native hCD19, yet with extremely low efficiency. Only one of 85 human CD19 ELISA-specific antibody clones demonstrated specificity for cell-surface human CD19. Cell panning with human CD19-expressing cells yielded more positive antibody clones that were specific to cell surface expressed human CD19.

Binding to Primary Human B Cells.

Human B cells were tested for anti-CD19 antibody binding by co-staining human PBMC's with PerCP-conjugated anti-human CD20 antibody, APC-labeled anti-human CD3 antibody and anti-CD19 bi-specific antibodies. After a round of brief washing with PBS buffer, FITC-labeled anti-His tag antibody was added to the mixture as the secondary antibody for detection of the bi-specific antibody. For the flow cytometry assay, human B cells were gated by positive CD20 staining and negative CD3 staining (see box in FIG. 5A). The anti-CD19 bi-specific antibodies were evaluated for their ability to recognize human CD19 expressed on these $CD20^+CD3^-$ cells.

The level of anti-CD19 binding to $CD20^+CD3^-$ cells was measured by the mean fluorescence intensity (MFI) in the FITC channel. As shown in Table 6, negative control bi-specific antibody (NC-ET901) did not bind human B cells. In contrast, all anti-human CD19 bi-specific antibody clones tested recognized human B cells and demonstrated positive binding signals.

T-Cell Killing Assay.

Tumor cytotoxicity was assayed using an LDH Cytotoxicity Assay (Promega). Human T cells (AllCells) or Ficoll-purified cells from whole blood (Blood Centers of the Pacific) were activated and expanded with CD3/CD28 Dynabeads (Invitrogen) according to manufacturer's specifications. Activated T cells were cultured and maintained in RPMI1640 medium with 10% FBS plus 100 U/mL IL-2, and used at day 7-14 post-activation. T cells were >99% $CD3^+$ by FACS analysis. Activated T cells and target cells were co-cultured at a 5:1 ratio with bi-specific antibodies for 16 hours. Cytotoxicity was determined by measuring LDH activity in culture supernatants.

Figure 5B:
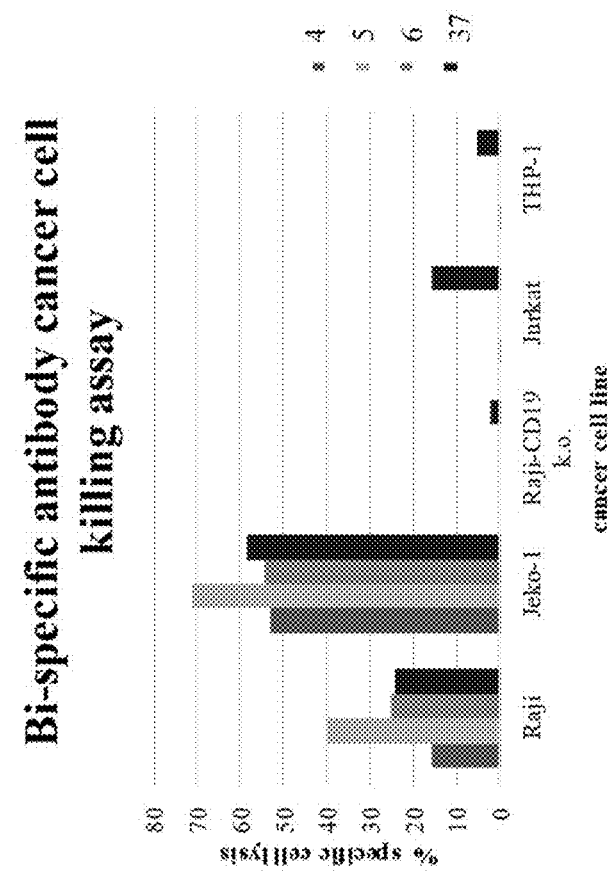
FIG. 5B shows representative cancer cell killing (in % specific cell lysis, y-axis) of various cells lines for exemplary bi-specific antibody molecules based on clones 4, 5, 6 and 37.
Figure 5A:
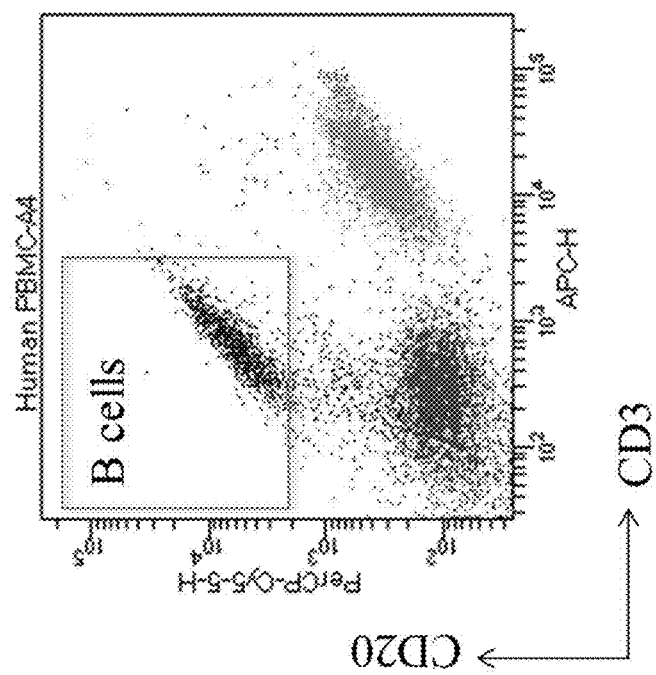
FIG. 5A shows a representative flow cytometry analysis of human PBMCs stained with CD20 (y-axis) and CD3 (x-axis) and the B cell population gate used for the analysis of bi-specific antibody binding in FIG. 5B.

As shown in FIG. 5B, bi-specific antibody molecules based on clones 4, 5 and 6, at 0.2 μg/ml, effectively mediated killing of cancer cells in a human CD19-specific manner. Also, bi-specific antibody molecule based on clone 37 exhibited some detectable killing towards a CD19 negative cell lines (Jurkat and THP-1). In the context of an scFv, clone 37 did not demonstrate binding to Jurkat cells by flow cytometry (FIG. 1B).

TABLE 6

| CD19 × CD3<br>Bi-specific antibody clone | Mean Fluorescence Intensity<br>(MFI) in FITC channel |
|---|---|
| 4 | 545 |
| 5 | 1271 |
| 6 | 2195 |

TABLE 6-continued

| CD19 × CD3 Bi-specific antibody clone | Mean Fluorescence Intensity (MFI) in FITC channel |
|---|---|
| 7 | 1880 |
| 37 | 2083 |
| NC-ET901 | 144 |

(NC-ET901: control)

Example 4. Affinity Maturation of Anti-Human CD19 Antibody Agents

This example demonstrates the affinity maturation of anti-human CD19 antibody agents. In particular, this example specifically demonstrates the generation of a series of antibody variants by incorporation of random mutations into selected anti-human CD19 antibody agents (clones 4, 5 and 6) followed by screening and characterization of the antibody variants.

Generation of Variant Phage Libraries.

DNA encoding anti-human CD19 scFvs were subjected to random mutagenesis using GeneMorph II Random Mutagenesis kit (Agilent Technologies) according to the manufacturer's specifications. After mutagenesis, DNA sequences were cloned into an scFv-expressing phagemid vector to build variant antibody phage libraries. Mutation libraries were built for each anti-human CD19 specific clone separately. Each mutation library contained about $5\times10^8$ unique phage clones. On average, variant clones have two nucleotide mutations compared with parental anti-human CD19 clones, ranging from 1 to 4 nucleotide mutations, per scFv sequence. Three libraries were built upon parental clones 4, 5 and 6 (Table 7). Exemplary mutations in the $V_H$ and $V_L$ regions of selected affinity matured anti-human CD19 antibody agents as compared to respective parental clones are set forth in Table 8.

Figure 6A:
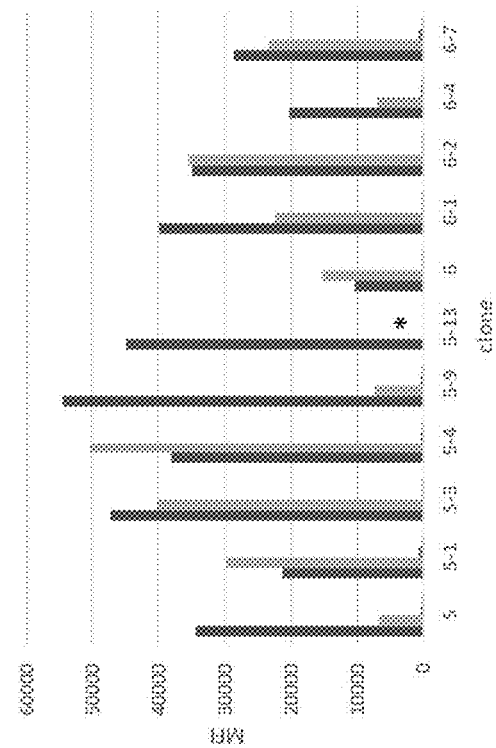
FIG. 6A shows representative cell binding (as measured by MFI in a flow cytometry assay) of exemplary variant antibody phage clones generated by affinity maturation of selected parental antibody phage clones. Variant clones are denoted with a hyphen (i.e., clones 5-1, 5-3, 5-4, etc. were derived from parental clone 5; clones 6-1, 6-2, etc. were derived from parental clone 6). Asterisk: clone 5-13 was not tested for binding to Jeko-1, Raji-CD19 k.o. or Jurkat cell lines.

Individual phage clones from enriched phage panning pools, named as variant clones, were tested for enhanced binding to cell-surface human CD19 compared to their respective parental clones. As shown in FIG. 6A, multiple variant phage clones specifically recognized human CD19 positive cancer cell lines, including Raji and Jeko-1 cells. None of the clones demonstrated binding to human CD19 negative cell lines, such as Raji-CD19 k.o. or Jurkat cells. Notably, multiple clones demonstrated enhanced binding to Raji and Jeko-1 cells as compared to respective parental clones.

Figure 6B:
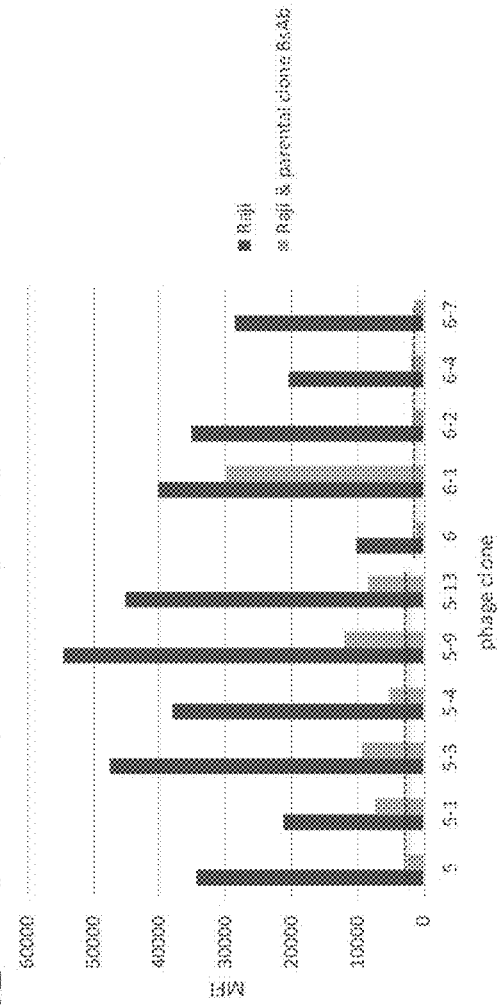
FIG. 6B shows representative cell binding of selected variant antibody phage clones as compared to respective parental clones to Raji cells. Variant clones are noted with a hyphen, i.e., clones 5-1, 5-3, 5-4, etc. were derived from parental clone 5; clones 6-1, 6-2, etc. were derived from parental clone 6. Dashed lines indicate background binding of the respective parental clone under competitive binding of corresponding bi-specific antibody.

A competition cell-binding assay was performed to compare the binding affinities of the variant clones compared to parental clones (FIG. 6B). Briefly, variant phage clones were mixed with Raji cells that have been pre-incubated with their corresponding parental bi-specific antibody clone, followed by staining with anti-M13 mouse antibody and PE-conjugated anti-mouse antibody.

Variant clones 5-1, 5-3, 5-4, 5-9, 5-13, and 6-1 demonstrated improved target-binding compared to their parental clones. In the presence of the parental clone bi-specific antibody, these phage clones exhibited increased binding to Raji cells compared with the parental phage clones, clone 5 or 6. A more accurate measurement of antibody binding affinity was obtained by bi-specific antibody titration flow cytometry (see Table 9 below).

TABLE 7

| Parental Clone | Phage Library name | Library size | Mutation Rate (per 1000 bp) |
|---|---|---|---|
| 4 | ET190-4AM | 3.25E+08 | 4.0 |
| 5 | ET190-5AM | 4.50E+08 | 3.1 |
| 6 | ET190-6AM | 5.70E+08 | 3.3 |

TABLE 8

| Clone | $V_L$ FR1 | $V_L$ CDR1 | $V_L$ FR2 | $V_L$ CDR2 | $V_L$ FR3 | $V_L$ CDR3 | $V_L$ FR4 | $V_H$ FR1 | $V_H$ CDR1 | $V_H$ FR2 | $V_H$ CDR2 | $V_H$ FR3 | $V_H$ CDR3 | $V_H$ FR4 |
|---|---|---|---|---|---|---|---|---|---|---|---|---|---|---|
| 5-1 | | | | | S75N | | | | | | | | | |
| 5-2 | | | | | T69M | | | | | | | | | |
| 5-3 | | | | | D52N | D95E | | | | | | | | |
| 5-4 | V10M | | | | | D95G | | | | | | | | |
| 5-5 | | | | | | S93T | | S17F | | | | T69A | | |
| 5-7 | | | | | N68T | | | | | | | | Y108N | |
| 5-9 | | | | | | | | | | | | S63F | | |
| 5-10 | | | | | | | | Q3R | Y32F | | | | A97V | |
| 5-11 | K16E | | | | | | | | | | | | | |
| 5-13 | | | | | | | | | | | | | M117L | |
| 5-15 | | | | | L72M | | | | S25A | | | | | |
| 6-1 | | | | | | | | | | | | T102S | L116M | |
| 6-2 | S25N | V34I | | | | | | K12E | | | | | D109E | |
| 6-4 | | | | | | | | E16G | | | | | | |
| 6-5 | | | | | L54Q | | | | | | | | M106L | |
| 6-6 | S25N | | | | | | | | | | | | | |
| 6-7 | | | | | | | | | G26A | | | | | Q113L |
| 6-8 | | | | | L54Q | | | | | | | | | |
| 6-9 | | | | | | | | | | | | T102S | | |

Example 5. Generation and Characterization of Bi-Specific Antibody Molecules Based on Anti-Human CD19 Antibody Agent Variants This example demonstrates the construction of multi-specific binding agents using variant human scFv fragments specific for human CD19. In particular, this example specifically demonstrates the construction of bi-specific antibodies having a first antigen-binding site that binds human CD19 in native format (cell-surface expressed) and a second antigen-binding site that binds CD3 on T cells. Thus, the present example illustrates that, in some embodiments, using multi-specific binding agents that contain antibody components as described herein, T cells can be directed to kill target cells that express human CD19.

Generation of Variant Clone Bi-Specific Antibodies.

Figure 7A:
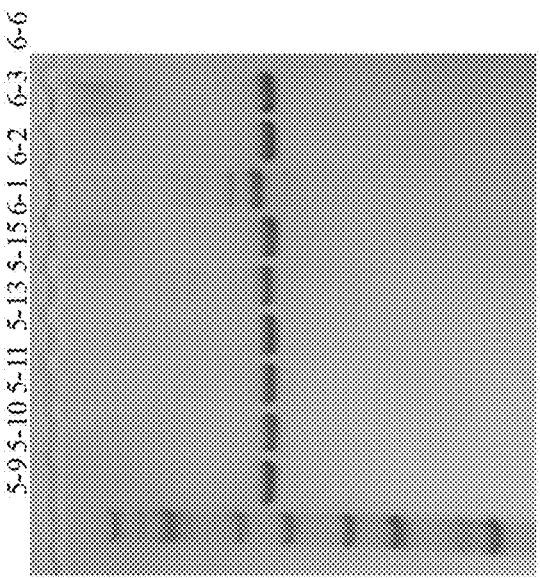
FIGS. 7A and 7B show representative images of SDS-PAGE illustrating selected bi-specific antibodies constructed from affinity-matured antibody phage clones described in Example 4. Clone numbers are indicated above each lane.
Figure 7B:
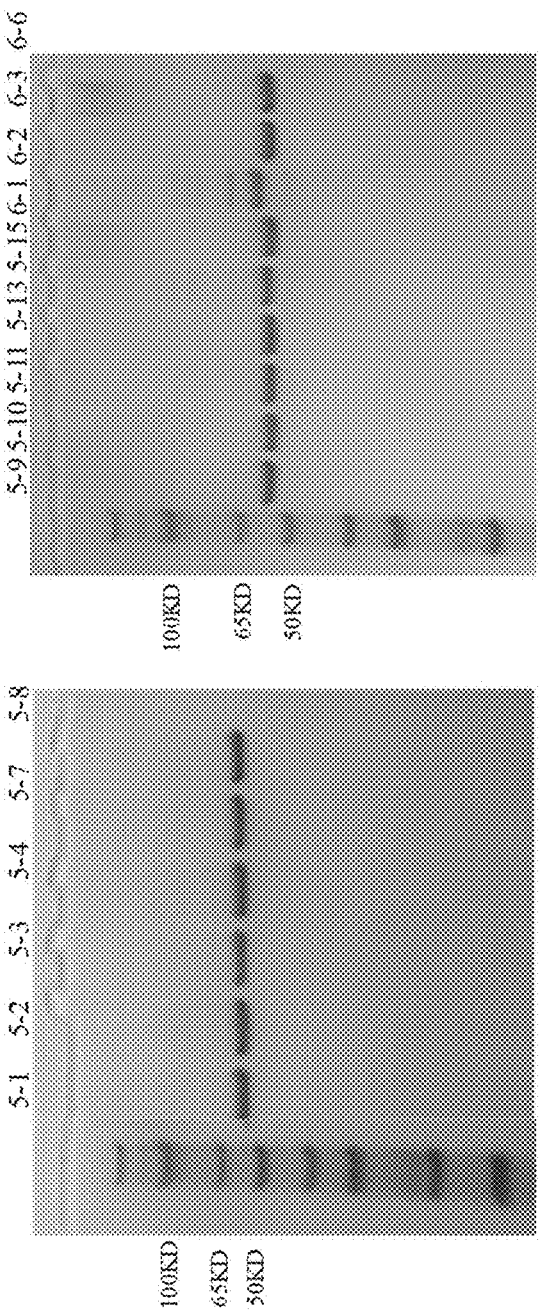

Bi-specific antibodies derived from affinity-improved, variant antibody clones were generated as described in Example 2. Most of the clones demonstrated single bands on SDS-PAGE with >90% purity (FIGS. 7A and 7B).

Binding Affinity Determination for Variant Bi-Specific Antibodies.

Neither the parental antibodies nor their derivatives (variant clones) recognized recombinant human CD19, though they all bound to cell surface expressed human CD19. Thus, the inventors determined relative binding affinity of the variant clones as compared to parental antibodies through antibody titration flow cytometry using human CD19 positive cancer cells (Table 9).

Bi-specific antibody clones, at serially diluted concentrations, were mixed with the same amount of Raji cells. Antibody $EC_{50}$ and apparent $K_D$ were calculated based on flow cytometry binding signals. As shown in Table 9, many of the variant clones based on parent clone 5, with the exception of clone 5-4, demonstrated slightly increased affinity (lower $EC_{50}$ and apparent $K_D$). For variant clones based on parent clone 6, clones 6-1 and 6-4 also demonstrated increased affinity (lower $EC_{50}$ and apparent $K_D$) as compared to their respective parental clone.

T-Cell Killing Assay.

Figure 7C:
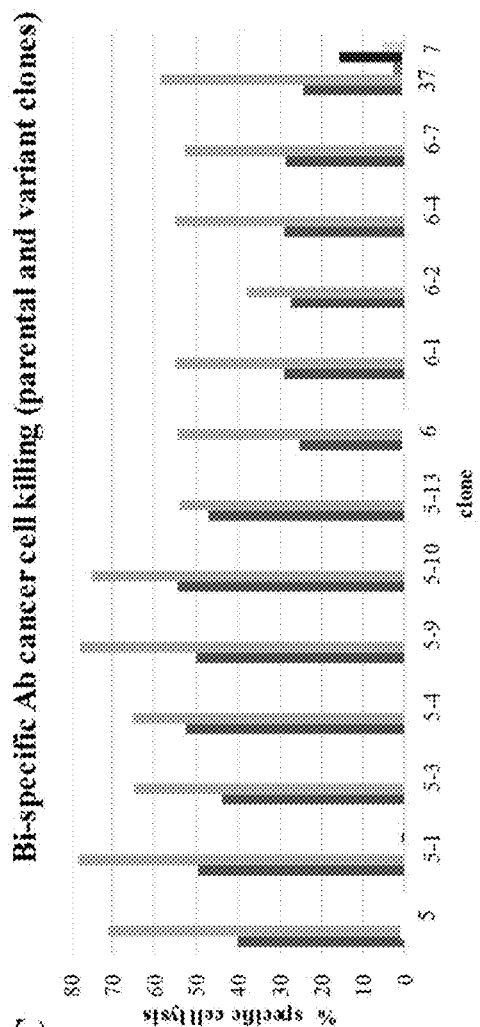
FIG. 7C shows representative cancer cell killing (in % specific cell lysis, y-axis) of various cells lines for selected bi-specific antibody molecules constructed from affinity-matured anti-CD19 human antibody agents.

Tumor cytotoxicity was determined using a LDH Cytotoxicity Assay (Promega). Human T cells were activated and expanded with CD3/CD28 Dynabeads (Invitrogen) according to manufacturer's specifications. Activated T cells were cultured and maintained in RPMI1640 medium with 10% FBS plus 100 U/mL IL-2, and used at day 7-14 post-activation. T cells were >99% CD3+ by FACS analysis. Activated T cells and target cells were co-cultured at a 5:1 ratio with bi-specific antibodies for 16 hours. Cytotoxicity was determined by measuring LDH activity in culture supernatants (FIG. 7C).

Figure 8:
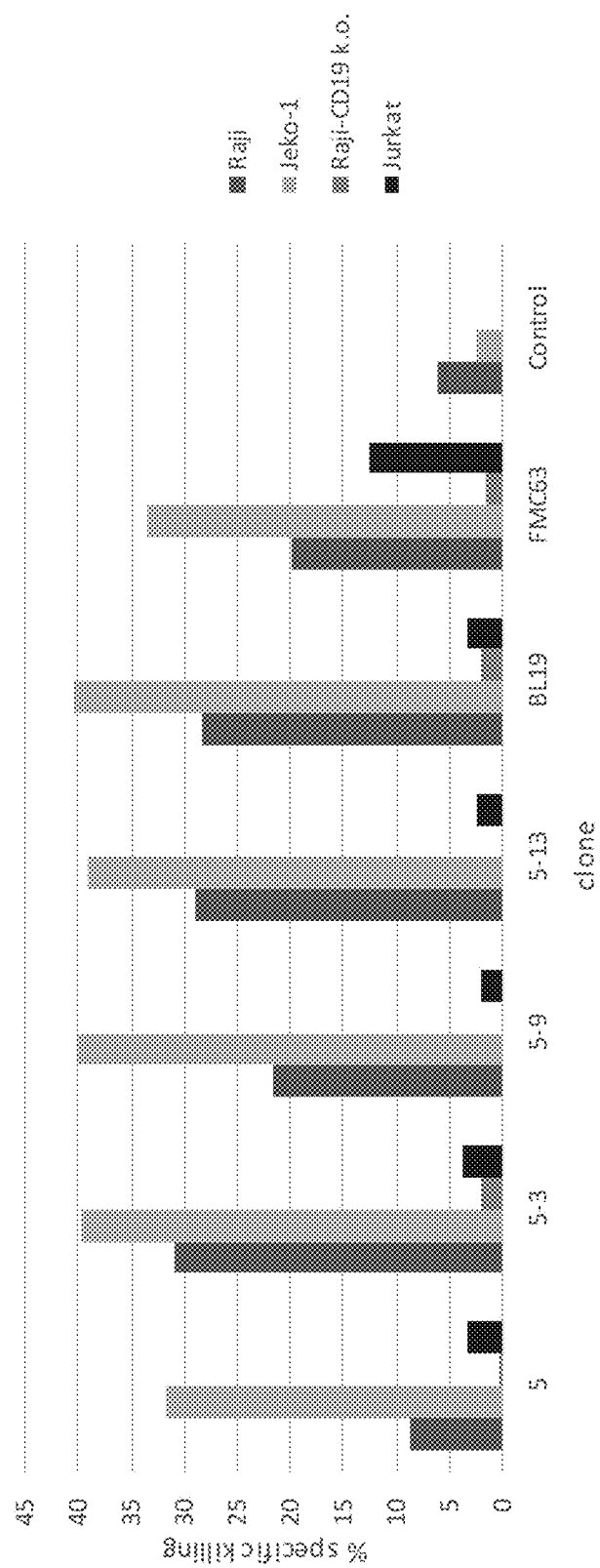
FIG. 8 shows representative cancer cell killing (in % specific cell lysis, y-axis) of various cell lines for selected chimeric antigen receptor expressing T cells (CAR-Ts) generated from anti-CD19 human antibody agents. Target cell lines (CD19$^+$) include Raji and Jeko-1; negative control cell lines (CD19$^-$) include Jurkat and Raji-CD19 k.o. cells; BL19: comparator CAR based on SEQ ID NO:30 of U.S. Pat. No. 7,635,472; FMC63: comparator CAR based on GenBank accession DD064902, U.S. Pat. No. 7,446,179; Control: mock-transduced T cells.

As shown in FIG. 8, variant clones tested maintained the original binding specificity as their parental antibodies. For the cell killing assay shown in FIGS. 11A and 11B, exemplary variant clones were tested along with clone 37 (used as a positive control bi-specific antibody as this clone demonstrated detectable non-specific cytotoxicity against human CD19-negative cells, Raji-CD19 k.o., Jurkat and THP-1). Multiple variant clones tested demonstrated equivalent or increased cell killing efficiency against one or both of the human CD19 positive cell lines (Raji and Jeko-1) as compared to their respective parental clones.

TABLE 9

| Clone | $EC_{50}$ (µg/mL) | Apparent $K_D$ (nM) |
|---|---|---|
| #5 | 0.101 | 1.9 |
| 5-1 | 0.097 | 1.9 |
| 5-3 | 0.081 | 1.6 |
| 5-4 | 0.124 | 2.4 |
| 5-9 | 0.075 | 1.4 |
| 5-10 | 0.097 | 1.9 |
| 5-13 | 0.089 | 1.7 |
| #6 | 0.214 | 4.1 |
| 6-1 | 0.116 | 2.2 |
| 6-2 | 4.02 | 77.3 |
| 6-4 | 0.156 | 3.0 |
| 6-7 | 0.242 | 4.7 |
| NC-ET901 | undetectable | — |

(NC-ET901: control)

Example 6. Characterization of T Cells Expressing Anti-Human CD19 Chimeric Antigen Receptors (CAR-T)

This example demonstrates the construction of chimeric antigen receptors (CARs) using anti-human CD19 antibody agents described in the preceding examples. In particular, this example specifically demonstrates the construction of CARs that include an antigen-binding site of a CD19 human antibody agent and expressed on the surface of T cells. Further, the CARs expressed by T cells were employed in cytotoxicity assays against human lymphoma xenograft models. Thus, the present example illustrates that, in some embodiments, using CARs that include an antigen binding site from human antibody agents described herein are useful for killing target cells that express human CD19 (e.g., lymphoma).

In Vitro Cytotoxicity of Human CD19 Transduced T Cells.

Lenti-viruses containing human CD19 specific chimeric antigen receptors (CARs) were produced by transfection of 293T cells with CAR vectors. Human T cells were used for transduction after one-day stimulation with CD3/CD28 beads (Dynabeads®, Invitrogen) in the presence of IL-2 at 100 U/mL. Concentrated lenti-viruses were applied to T cells in Retronectin (Takara) coated 6-well plates for 72 hours. Functional assessment of transduced T cells (CD19/CAR-T cells) was performed using a LDH Cytotoxicity Assay. Effector-to-target cell ratios were 5:1. Representative results are set forth in FIG. 8.

As shown in FIG. 8, three CARs based on variant antibody clones (clones 5-3, 5-9 and 5-13) demonstrated significantly increased cancer cell killing efficiency against both Raji and Jeko-1 cell lines as compared to parental clone 5. The effector-to-target ratio used in this experiment was 5:1. Killing specificity was confirmed to be CD19-specific as indicated by the low level of killing of human CD19 negative cells (Raji-CD19 k.o. and Jurkat). Further, T cells expressing CARs generated using human antibody agents described herein demonstrated similar or higher cell killing efficiency as CAR-T generated with other anti-CD19 antibodies (BL19, FMC63).

In a similar experiment, human CD19 CAR-Ts (described above) were tested using a large panel of CD19 positive and negative cancer cell lines. Briefly, primary T cells were mock-transduced (Mock) or transduced with selected CAR encoding anti-CD19 antibodies. Transduced T cells were analyzed by FACS using an anti-myc antibody to detect the myc-tag in the extracellular domain of the CAR constructs.

The results demonstrated that anti-CD19 CAR-T cells generated from human antibody agents as described above have ~80% transduction efficiencies (FIGS. 9A-9C). The ability of the CAR-T cells to specifically kill CD19-expressing cancer cells was tested at an effector-to-target ratio at 5:1. As shown in FIG. 9D, CAR-T cells expressing both anti-CD19 clones tested specifically killed CD19+ cells (Raji, CA46, Jeko-1 and Daudi), but not CD19" cells (Raji-CD19 k.o., Jurkat, THP-1, HeLa, MDA-MB-231, MCF-7, SK-Hep-1 and HepG2).

In another similar experiment, CAR-Ts generated from selected human antibody agents described herein and a non-human (e.g., murine) antibody were tested using a panel of CD19 positive and negative cancer cell lines as described above. Briefly, primary T cells were mock-transduced (Mock) or transduced with selected CAR encoding anti-human CD19 scFvs described herein (CAR-T 5, CAR-T 5-9, or CAR-T 5-13) or CAR encoding anti-human CD19 scFv which has variable region sequences from anti-human CD19 murine antibody mAb FMC63 (Zola, H. et al., 1991, Immunol. Cell Biol. 69(Pt 6):411-22). The sequence of the murine anti-CD19 scFv is provided below having a format of $V_L$-linker-$V_H$. Transduced T cells were analyzed by FACs as described above.

| | |
|---|---|
| murine anti-CD19 scFv (SEQ ID NO: 296) | DIQMTQTTSSLSASLGDRVTISCRASQDISKYLN WYQQKPDGTVKLLIYHTSRLHSGVPSRFSGSGSG TDYSLTISNLEQEDIATYFCQQGNTLPYTFGGGT KLEITGSTSGSGKPGSGEGSTKGEVKLQESGPGL VAPSQSLSVTCTVSGVSLPDYGVSWIRQPPRKGL EWLGVIWGSETTYYNSALKSRLTIIKDNSKSQVF LKMNSLQTDDTAIYYCAKHYYYGGSYAMDYWGQG TSVTVSS |

The CDR sequences of the murine anti-CD19 scFv set forth in SEQ ID NO:296 are:

```
    LC-CDR1
                              (SEQ ID NO: 297)
    QDISKY

LC-CDR2
                              (SEQ ID NO: 298)
    HTS

LC-CDR3
                              (SEQ ID NO: 299)
    QQGNTLPYT

HC-CDR1
                              (SEQ ID NO: 300)
    GVSLPDYG

HC-CDR2
                              (SEQ ID NO: 301)
    IWGSETT

HC-CDR3
                              (SEQ ID NO: 302)
    AKHYYYGGSYAMDY
```

Figure 15A:
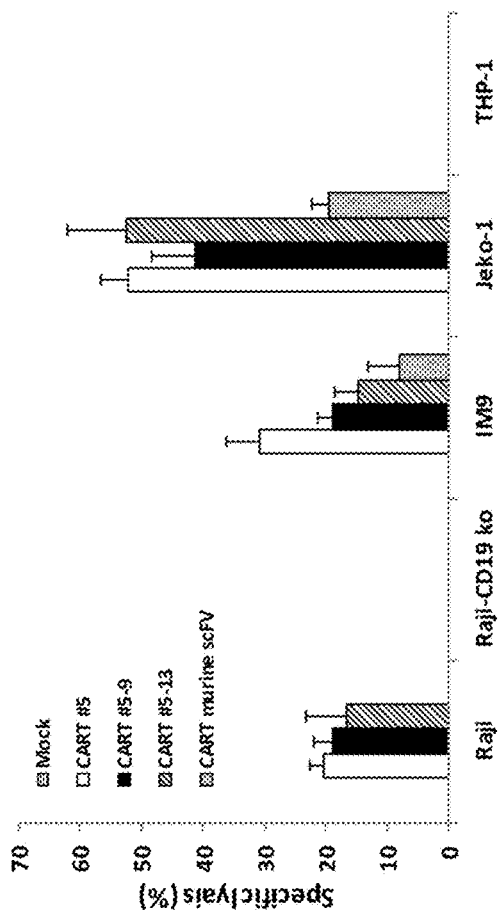
FIGS. 15A and 15B show representative CAR expression (bottom panel.
Figure 15B:
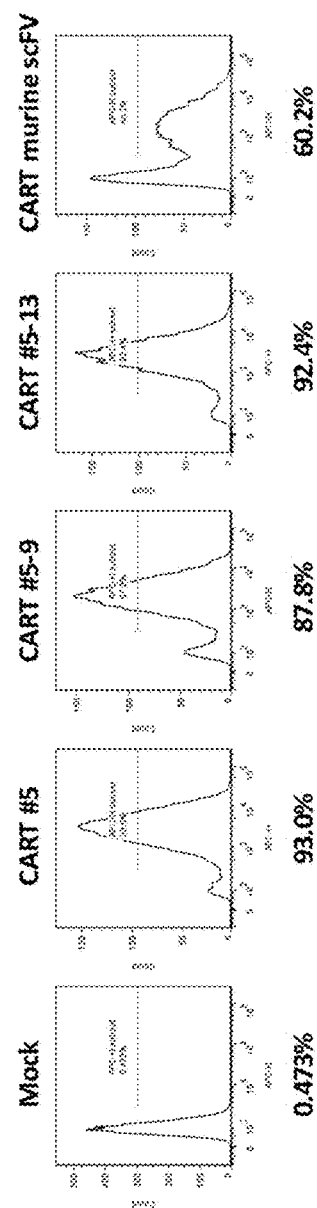

The results showed that anti-CD19 CAR-T cells generated from human scFv clone 5 and two affinity matured variants (5-9, 5-13) demonstrated higher transduction efficiencies and significantly higher CD19-specific cancer cell lysis than anti-CD19 CAR-T cells generated from the murine anti-CD19 antibody (FIGS. 15A and 15B).

In another experiment, exemplary cytokine release profile of activated human CD19 CAR-T cells was determined. Mock-transduced T cells (mock) or a selected anti-CD19 CAR-T (clone 5-3 shown) were co-incubated with target cells. Release of IL-2, IL-4, IL-6, IL-8, IL-10, GM-CSF, IFN-γ and TNF-α into the media after in vitro killing was measured using the Magpix multiplex system (Luminex) with the Bio-plex Pro Human Cytokine 8-plex Assays (BioRad). Cytokine concentrations were determined using a known standard curve, after subtracting release from media, target cell alone and clone 5-3 transduced T cell alone. Representative results are set forth in FIGS. 10A and 10B.

Figure 10B:
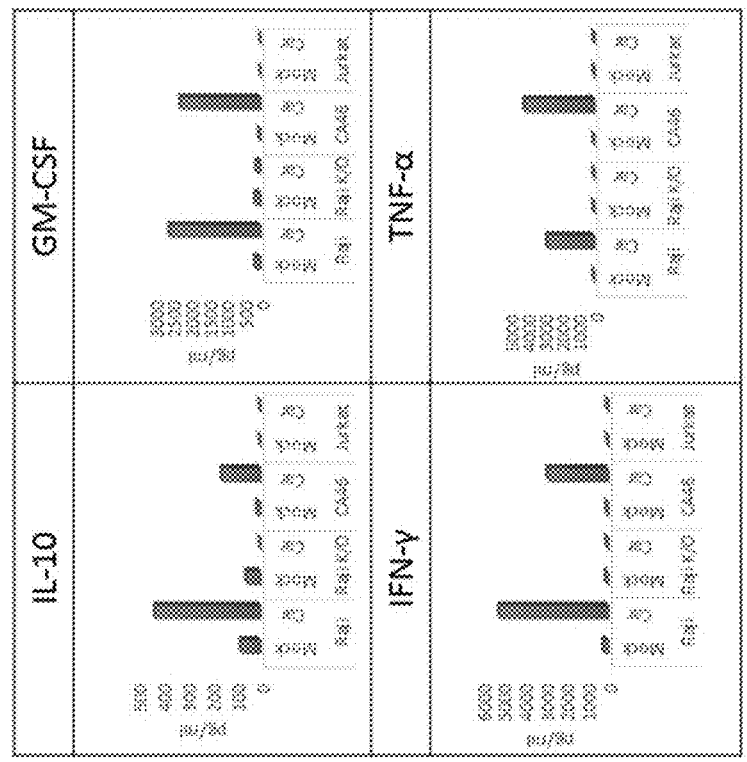
FIGS. 10A and 10B show representative cytokine release of mock-transduced T cells (mock) or T cells transduced with anti-CD19 CAR (Car, based on clone 5-3) after co-culture with various CD19$^+$ (Raji, CA46) and CD19$^-$ (Raji-K/O, i.e., Raji-CD19 k.o., Jurkat) cell lines.
Figure 10A:
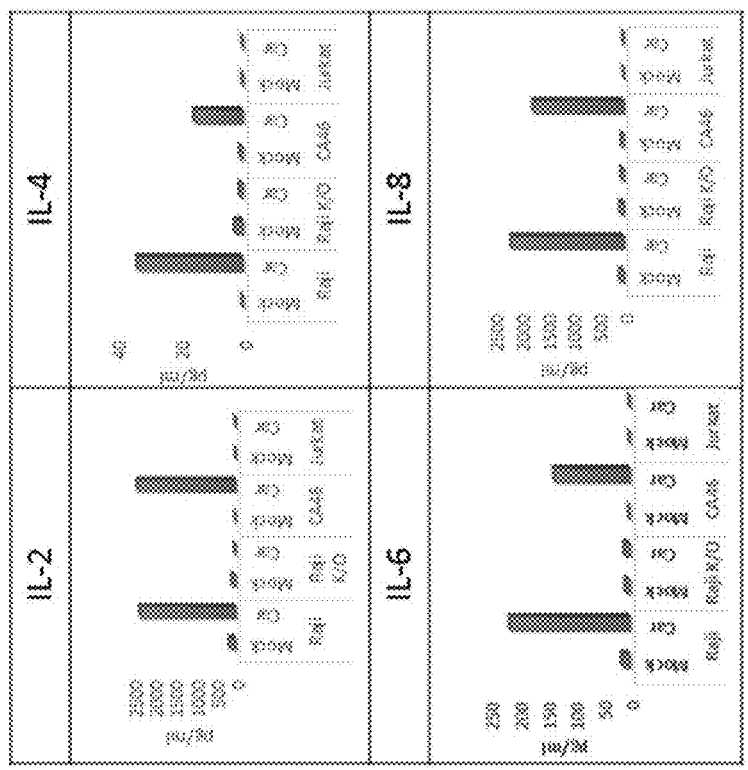

As shown in FIGS. 10A and 10B, cytokine release was detected only when anti-CD19 CAR-T cells were co-incubated with CD19$^+$ cells (Raji and CA46), but not CD19$^-$ cells (Raji-CD19 k.o. and Jurkat). Mock-transduced T cells co-cultured with CD19$^+$ cancer cells released only minimal amount of cytokines. Similarly, the cytokine release profile of activated human CD19 CAR-T cells based on clone 5-13 demonstrated release of cytokines (IL-2, GM-CSF, IFN-γ and TNF-α) only when anti-CD19 CAR-T cells were co-incubated with CD19$^+$ cells (Raji and JeKo-1), but not CD19$^-$ cells (Raji-CD19 k.o.). Also, mock-transduced T cells co-cultured with CD19$^+$ cancer cells released minimal to no cytokines.

In Vivo Efficacy of CD19 CAR-T Cells in Human Lymphoma Xenografts.

The in vivo antitumor activity of an exemplary CAR-T cell (based on clone 5-9) was tested in a CD19-positive human lymphoma xenograft model in NOD SCID gamma (NSG) mice. Briefly, Raji-luc-GFP cells were purchased from Comparative Biosciences, Inc. (Sunnyville, Calif. 94085) and cultured in RPMI Medium+10% FBS and 1% L-Glutamine at 37° C. in a humidified atmosphere with 5% $CO_2$. Raji-luc-GFP cells were derived from the CD19-positive Burkitt lymphoma cell line, Raji, after stable transfection with dual reporter genes encoding both firefly luciferase (luc) and green fluorescent protein, which resulted in cells that can be traced in vivo using bioluminescent imaging. NSG mice were purchased from Jackson Laboratories (Bar Harbor, Me. USA 04609) and were acclimated for at least 7 days before experiment. Raji-luc-GFP cells were re-suspended in PBS and implanted intravenously (i.v.) into NSG mice through tail vein at $1 \times 10^6$ cells/100 µL/mouse. Five days post-implantation, animals were imaged using Xenogen IVIS imaging system for assessment of tumor burden. Mice were randomized based on the photon emission into three groups (n=6 mice per group) at average photon emission of $6.7 \times 10^5$ photons: (i) No treatment, (ii) Mock (non-transduced activated human T cells from the same donor of CAR-T cells), and (iii) 5-9 CAR-T. Animals were treated i.v. with Mock or clone 5-9 CAR-T cells immediately after randomization at a dose of $10^7$ T cells per mouse (comprising 6-8×$10^6$ CAR+ T cells per dose for group (iii)), once every two weeks for 3 doses. Animals were closely monitored after dosing. Bioluminescent imaging using Xenogen IVIS system was taken once a week. Animals with the following conditions were euthanized and recorded as "conditional death": (i) Body weight loss more than 25% initial body weight and (ii) limb paralysis that affects mouse movement. Representative results are set forth in FIGS. 11A and 11B.

Figure 11A:
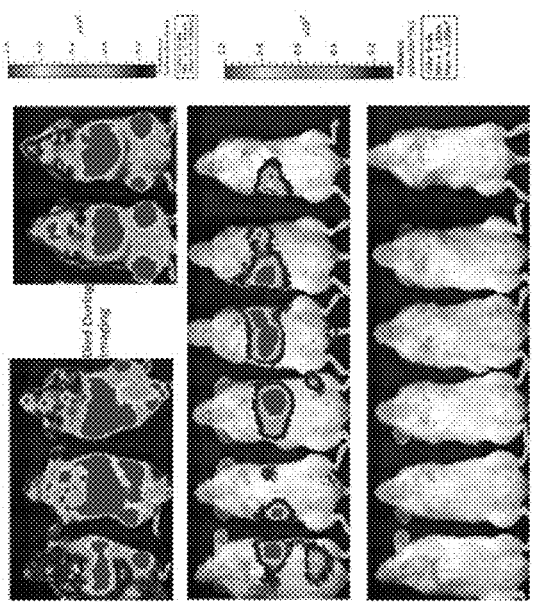
FIGS. 11A and 11B show representative inhibition of in vivo tumor growth in NSG mice by an exemplary anti-CD19 CAR-T based on anti-CD19 human antibody agent clone 5-9. Left: representative kinetics of photon emission from tumor-bearing NSG mice, presented and analyzed by area under the curve (AUC); Right: representative photon emission images of the Raji-luc-GFP tumor-bearing mice at week 3 from each treatment group.
Figure 11B:
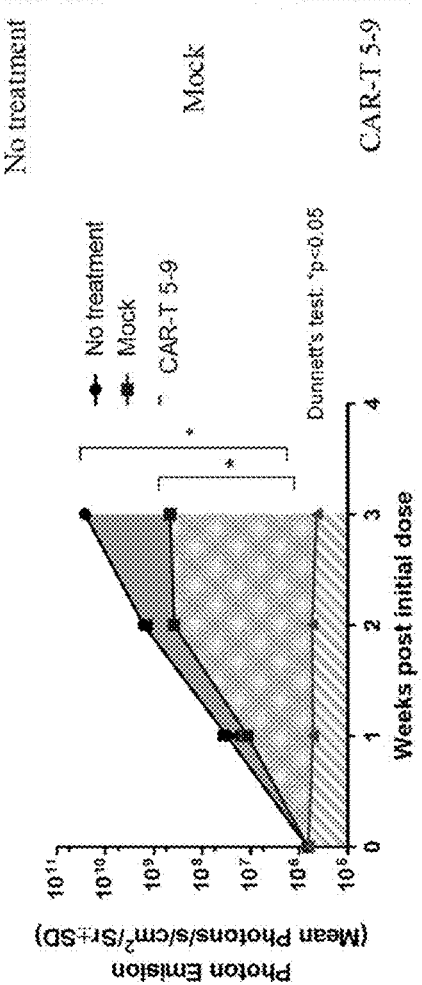

Both mock and the 5-9 CAR-T cells were well tolerated at the current dose and schedule (FIGS. 11A and 11B). No dosing-related adverse health effects were observed throughout the study. Treatment with Mock T cells slowed the growth of the Raji-luc-GFP tumors (p<0.05), however, treatment with CAR-T 5-9 significantly inhibited tumor growth (p<0.05; FIG. 11B).

Figure 13B:
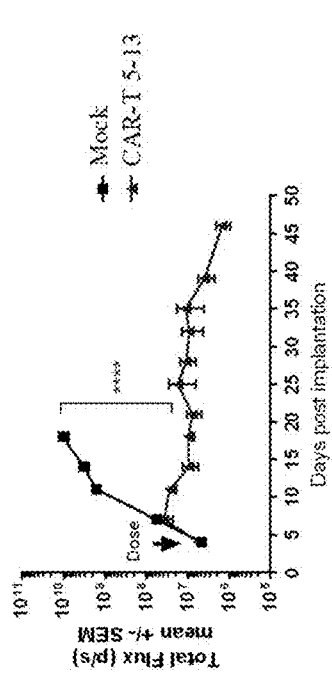
FIGS. 13A-13C show representative tumor-derived bioluminescence from Raji lymphoma xenografts in NSG mice treated with an exemplary anti-CD19 CAR-T based on anti-CD19 human antibody agent clone 5-13.

In a similar experiment, in vivo antitumor activity of another exemplary CAR-T cell (based on clone 5-13) was tested in a CD19-positive human lymphoma xenograft model (Raji) in NSG mice. Experiments were performed as described above for clone 5-9 with the exception that only one dose of anti-CD19 CAR-transduced T cells (5×$10^6$ CAR$^+$ T cells based on clone 5-13) was administered to each mouse. Representative results are set forth in FIGS. 13A-13C.

Figure 13C:
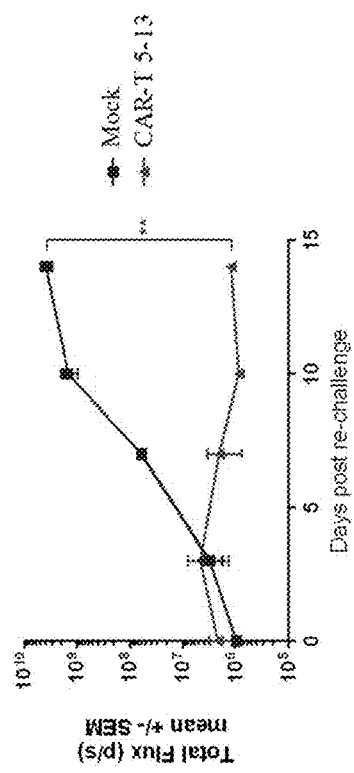
Figure 13A:
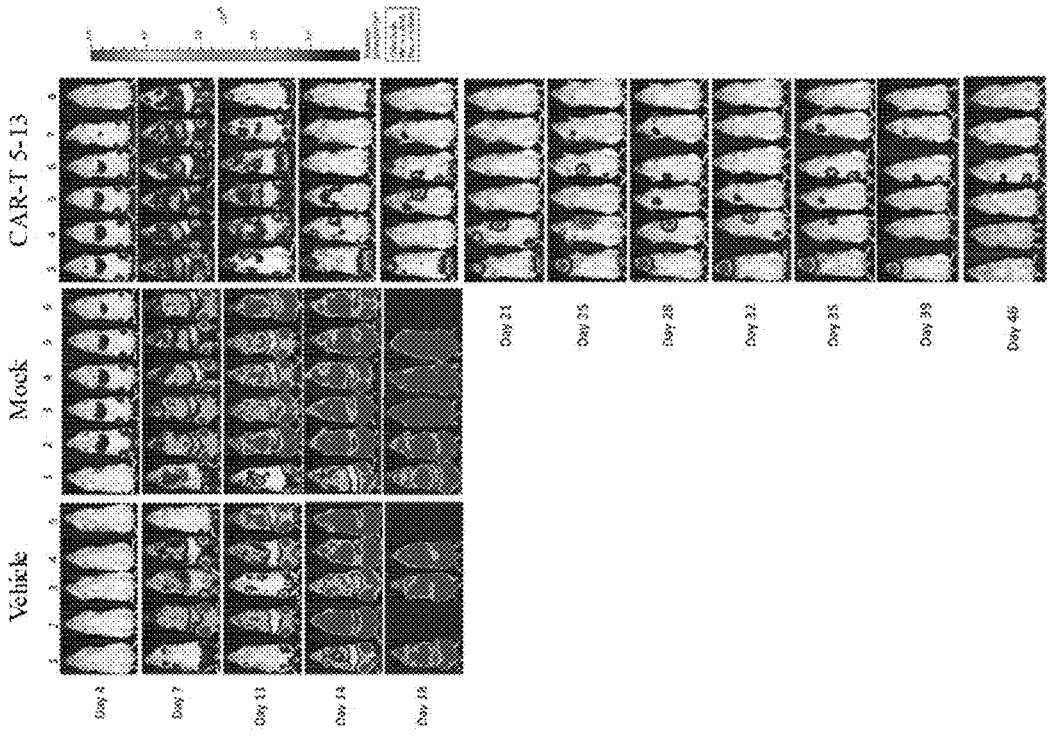

As shown in FIG. 13A, while tumors grew rapidly in mice from vehicle and mock treatment groups, NSG mice treated with anti-CD19 CAR 5-13-transduced T cells demonstrated inhibition of tumor growth. Indeed, a significant difference in tumor growth between treatment groups was detectable as early as day 11 (p<0.0001, Dunnett's tests, FIG. 13B). Further, NSG mice treated with anti-CD19 CAR 5-13-transduced T cells demonstrated regression of tumors as far out as 45 days post implantation.

At 35 days post tumor implantation, three representative mice from the anti-CD19 CAR 5-13-transduced T cell treatment group were re-challenged by i.v. implantation with 5×10⁵ Raji lymphoma cells to determine if the anti-CD19-CAR-transduced T cells persisted and maintained the capacity to respond to antigen (CD19). Naïve NSG mice (i.e., mice not implanted with Raji lymphoma cells or previously treated with T cells, n=2) were implanted with 5×10⁵ Raji lymphoma cells one-day post injection of 1×10⁶ mock-transduced T cells (injected on day 34) as a control. The inventors reasoned that such mock-transduced T cells would mimic a condition of low level circulating T cells in the mice prior to implantation of Raji lymphoma cells. Tumor burden in each group was measured by luciferase activity (as described above). Representative results are set forth in FIG. 13C.

As shown in FIG. 13C, tumors grew rapidly in the mock treatment group. In contrast, prior treatment with anti-CD19 CAR 5-13-transduced T cells prevented the growth of tumors following re-challenge with Raji lymphoma cells (p<0.01). Thus, these data indicated the anti-CD19-CAR-transduced T cells persisted in these mice even at 35 days post implantation, and maintained the capacity to respond to CD19 and kill CD19⁺-tumor cells thereby providing protection against a reoccurring tumor burden.

In another similar experiment, in vivo antitumor activity of an exemplary CAR-T cell (based on clone 5-13) was tested in a CD19-positive human leukemia xenograft model in NSG mice (NALM). NALM-6-luc-GFP cells (a kind gift from Dr. Eric Smith of Memorial Sloan Kettering Cancer Center) were derived from the CD19-positive acute lymphoblastic leukemia cell line NALM-6 after stable transfection with dual reporter genes encoding both firefly luciferase (luc) and green fluorescent protein (GFP), resulting in cells traceable in vivo using bioluminescent imaging.

Briefly, NALM-6-luc-GFP were cultured in RPMI Medium+10% FBS at 37° C. in a humidified atmosphere with 5% $CO_2$. NSG mice were purchased from Jackson Laboratories (Bar Harbor, Me. USA 04609) and acclimated for at least three days prior to experimentation. NALM-6-luc-GFP cells were re-suspended in phosphate-buffered saline (PBS) and intravenously (i.v.) implanted into female NSG mice (n=20, 6-8 weeks old) at 5×10⁵ cells/100 μL/mouse via tail vein injection. At four days post implantation, animals were imaged using Xenogen IVIS imaging system for tumor burden assessment. NSG mice were randomized based on photon emission into three groups: (i) Vehicle (PBS, n=6); (ii) 10⁷ mock-transduced human T cells (n=6); and (iii) 5×10⁶ clone 5-13 anti-CD19 CAR-transduced T cells (CAR-T 5-13, n=8). Animals were closely monitored after implantation and dosing with T cells or vehicle as described above. Representative results are set forth in FIGS. 14A and 14B.

Figure 14B:
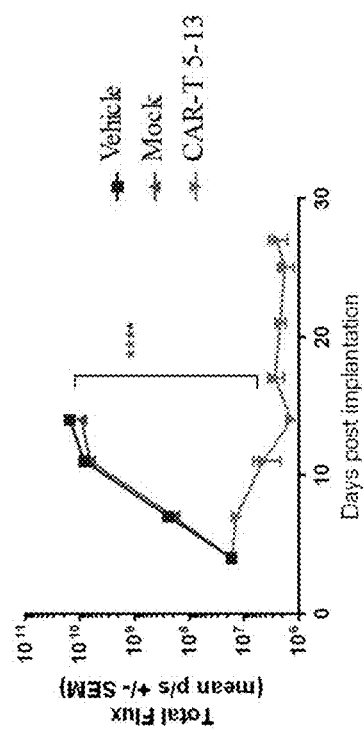
FIGS. 14A and 14B show representative tumor-derived bioluminescence from NALM-6 leukemia xenografts in NSG mice treated with an exemplary anti-CD19 CAR-T based on anti-CD19 human antibody agent clone 5-13.
Figure 14A:
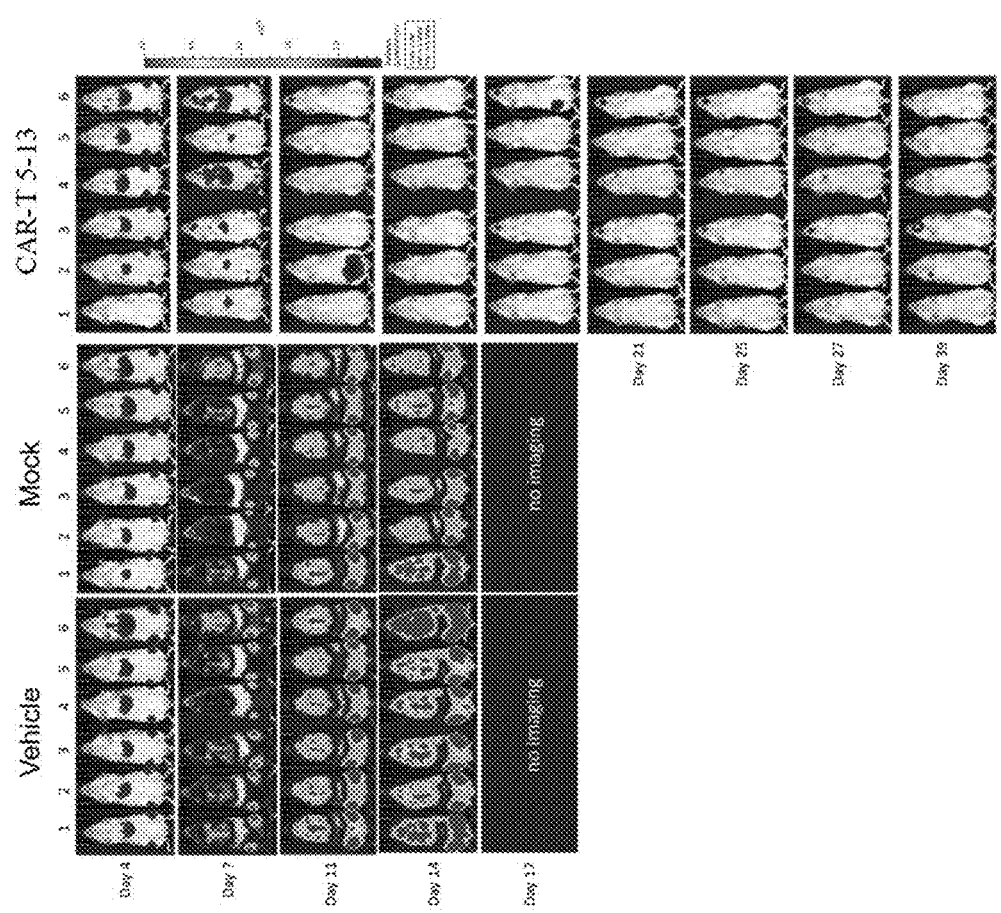

As shown in FIGS. 14A and 14B, vehicle and mock treatment groups demonstrated a rapid progression of growth of the NALM-6 tumors. In contrast, treatment with anti-CD19 CAR-T cells (based on clone 5-13) significantly (p<0.0001) inhibited and even reverted tumor growth as early as day 11. These data establish that CAR-T 5-13 cells targeted and lysed CD19⁺ NALM-6 tumors in vivo thereby demonstrating the efficacy of anti-CD19 antibodies provided herein in an exemplary CAR format to inhibit tumor growth in multiple cancer models.

Taken together this example demonstrates the successful generation and use of chimeric antigen receptor (CAR) expressing T cells, based on anti-CD19 human antibody agents made according to the preceding examples. Further, such anti-CD19 CAR-T cells demonstrated efficient cell killing of various cancer cell lines in a CD19-specific manner. Thus, human antibody agents described herein can be employed in the treatment and diagnosis of various B cell diseases and malignancies, in particular, those characterized by CD19 expression.

Methods

Cell lines Raji, Jeko-1, Jurkat, THP-1 and NIH/3T3 were obtained from the American Type Culture Collection. Raji is a CD19 positive Burkitt's lymphoma cell line (ATCC CCL-86). Jeko-1 is a CD19 positive mantle cell lymphoma cell line (ATCC CRL-3006). Jurkat is a human T lymphocyte cell line derived from T cell leukemia, and is CD19 negative. THP-1, an acute monocytic leukemia cell line, is also CD19 negative (ATCC TIB-202). NIH/3T3 is a mouse embryonic fibroblast cell line (ATCC CRL-1658). Raji-CD19 knock out cell line (Raji-CD19 k.o.) was generated by knocking out CD19 using a commercial CRISPR-Cas9 vector (Origene). The Raji-CD19 k.o. cells were confirmed to be CD19 negative by sequencing and by FACS (FIGS. 12A-12C), using a commercial mouse anti-human CD19 antibody (Biolegend). 3T3-CD19 was generated by transducing NIH/3T3 cell line with a human CD19 (hCD19) expressing mammalian vector, which results in a high level of cell surface expression of hCD19. Other cell lines tested in CAR-T killing assays, such as CA46, Daudi, Hela, HepG2, SK-Hep1, MDA-MB-231 and MCF7, were also purchased from ATCC. Cell lines were cultured in RPMI 1640 or DMEM supplemented with 10% FBS at 37° C./5% $CO_2$.

Mouse monoclonal antibody against phage M13 was purchased from GE (Cat 27-9421-01). PE-labeled anti-mouse IgG secondary antibody was purchased from Vector labs (Cat EI-2007). PE-conjugated mouse anti-hCD19 antibody was purchased from Biolegend (Cat 302208). 901-Fc and NC-ET901 bi-specific antibody are negative control antibodies having a format of human IgG1 and bi-specific antibody, respectively, generated at Eureka Therapeutics, Inc. The antibody does not recognize any human antigen. FITC-labeled anti-His antibody was purchased from Thermo Fisher Scientific (Cat MA1-81891) for detection of bi-specific antibody, which bears a 6×His tag at the C-terminus. PerCP-conjugated anti-human CD20 antibody was purchased from BD (9Cat 302208) for detection of human B cells.

Recombinant human CD19 ECD-Fc fusion protein includes the extracellular domain of human CD19 fused to the Fc of human IgG1 lacking the $C_H1$ domain and including the hinge region. HEK293 (Invitrogen) cells were transfected with a vector encoding the human CD19 ECD-Fc fusion protein by lipofectamine 3000 (Invitrogen). Fusion protein was purified from culture supernatants by protein A affinity chromatography.

Specific Enumerated Aspects

The present invention also provides the following numbered aspects:

1. A human antibody agent that specifically binds human CD19, wherein the human antibody agent comprises one or more heavy chain CDRs that each have a sequence that is at least 95% identical to one or more heavy chain CDRs selected from Table 2, and/or one or more light chain CDRs that each have a sequence that is at least 95% identical to one or more light chain CDRs selected from Table 3.

2. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:73, SEQ ID NO:74 and SEQ ID NO:75, and a light chain CDR1, light chain CDR2 and light chain CDR3 that each have a sequence that is at least 95% identical to each of light chain CDR1, light chain CDR2 and light chain CDR3 set forth in SEQ ID NO:181, SEQ ID NO:182 and SEQ ID NO:183.

3. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:76, SEQ ID NO:77 and SEQ ID NO:78, and a light chain CDR1, light chain CDR2 and light chain CDR3 that each have a sequence that is at least 95% identical to each of light chain CDR1, light chain CDR2 and light chain CDR3 set forth in SEQ ID NO:184, SEQ ID NO:185 and SEQ ID NO:186.

4. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:79, SEQ ID NO:80 and SEQ ID NO:81, and a light chain CDR1, light chain CDR2 and light chain CDR3 that each have a sequence that is at least 95% identical to each of light chain CDR1, light chain CDR2 and light chain CDR3 set forth in SEQ ID NO:187, SEQ ID NO:188 and SEQ ID NO:189.

5. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:82, SEQ ID NO:83 and SEQ ID NO:84, and a light chain CDR1, light chain CDR2 and light chain CDR3 that each have a sequence that is at least 95% identical to each of light chain CDR1, light chain CDR2 and light chain CDR3 set forth in SEQ ID NO:190, SEQ ID NO:191 and SEQ ID NO:192.

6. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:85, SEQ ID NO:86 and SEQ ID NO:87, and a light chain CDR1, light chain CDR2 and light chain CDR3 that each have a sequence that is at least 95% identical to each of light chain CDR1, light chain CDR2 and light chain CDR3 set forth in SEQ ID NO:193, SEQ ID NO:194 and SEQ ID NO:195.

7. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:88, SEQ ID NO:89 and SEQ ID NO:90, and a light chain CDR1, light chain CDR2 and light chain CDR3 that each have a sequence that is at least 95% identical to each of light chain CDR1, light chain CDR2 and light chain CDR3 set forth in SEQ ID NO:196, SEQ ID NO:197 and SEQ ID NO:198.

8. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:91, SEQ ID NO:92 and SEQ ID NO:93, and a light chain CDR1, light chain CDR2 and light chain CDR3 that each have a sequence that is at least 95% identical to each of light chain CDR1, light chain CDR2 and light chain CDR3 set forth in SEQ ID NO:199, SEQ ID NO:200 and SEQ ID NO:201.

9. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:94, SEQ ID NO:95 and SEQ ID NO:96, and a light chain CDR1, light chain CDR2 and light chain CDR3 that each have a sequence that is at least 95% identical to each of light chain CDR1, light chain CDR2 and light chain CDR3 set forth in SEQ ID NO:202, SEQ ID NO:203 and SEQ ID NO:204.

10. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:97, SEQ ID NO:98 and SEQ ID NO:99, and a light chain CDR1, light chain CDR2 and light chain CDR3 that each have a sequence that is at least 95% identical to each of light chain CDR1, light chain CDR2 and light chain CDR3 set forth in SEQ ID NO:205, SEQ ID NO:206 and SEQ ID NO:207.

11. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:100, SEQ ID NO:101 and SEQ ID NO:102, and a light chain CDR1, light chain CDR2 and light chain CDR3 that each have a sequence that is at least 95% identical to each of light chain CDR1, light chain CDR2 and light chain CDR3 set forth in SEQ ID NO:208, SEQ ID NO:209 and SEQ ID NO:210.

12. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:103, SEQ ID NO:104 and SEQ ID NO:105, and a light chain CDR1, light chain CDR2 and light chain CDR3 that each have a sequence that is at least 95% identical to each of light chain CDR1, light chain CDR2 and light chain CDR3 set forth in SEQ ID NO:211, SEQ ID NO:212 and SEQ ID NO:213.

13. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:106, SEQ ID NO:107 and SEQ ID NO:108, and a light chain CDR1, light chain CDR2 and light chain CDR3 that each have a sequence that is at least 95% identical to each of light chain CDR1, light chain CDR2 and light chain CDR3 set forth in SEQ ID NO:214, SEQ ID NO:215 and SEQ ID NO:216.

14. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:109, SEQ ID NO:110 and SEQ ID NO:111, and a light chain CDR1, light chain CDR2 and light chain CDR3 that each have a sequence that is at least 95% identical to each of light chain CDR1, light chain CDR2 and light chain CDR3 set forth in SEQ ID NO:217, SEQ ID NO:218 and SEQ ID NO:219.

15. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:112, SEQ ID NO:113 and SEQ ID NO:114, and a light chain CDR1, light chain CDR2 and light chain CDR3 that each have a sequence that is at least 95% identical to each of light chain CDR1, light chain CDR2 and light chain CDR3 set forth in SEQ ID NO:220, SEQ ID NO:221 and SEQ ID NO:222.

16. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:115, SEQ ID NO:116 and SEQ ID NO:117, and a light chain CDR1, light chain CDR2 and light chain CDR3 that each have a sequence that is at least 95% identical to each of light chain CDR1, light chain CDR2 and light chain CDR3 set forth in SEQ ID NO:223, SEQ ID NO:224 and SEQ ID NO:225.

17. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:118, SEQ ID NO:119 and SEQ ID NO:120, and a light chain CDR1, light chain CDR2 and light chain CDR3 that each have a sequence that is at least 95% identical to each of light chain CDR1, light chain CDR2 and light chain CDR3 set forth in SEQ ID NO:226, SEQ ID NO:227 and SEQ ID NO:228.

18. The human antibody agent of aspect 1, wherein the human antibody agent comprises a heavy chain CDR1, heavy chain CDR2 and heavy chain CDR3 that each have a sequence that is at least 95% identical to each of heavy chain CDR1, heavy chain CDR2 and heavy chain CDR3 set forth in SEQ ID NO:121, SEQ ID NO:122 and SEQ ID NO:123, and a light chain CDR1, light chain CDR2 and light chain CDR3 that each have a sequence that is at least 95% identical to each of light chain CDR1, light chain CDR2 and light chain CDR3 set forth in SEQ ID NO:229, SEQ ID NO:230 and SEQ ID NO:231.

19. The human antibody agent of aspect 2, wherein the human antibody agent comprises the heavy chain CDRs of SEQ ID NO:73, SEQ ID NO:74 and SEQ ID NO:75, and the light chain CDRs of SEQ ID NO:181, SEQ ID NO:182 and SEQ ID NO:183.

20. The human antibody agent of aspect 3, wherein the human antibody agent comprises the heavy chain CDRs of SEQ ID NO:76, SEQ ID NO:77 and SEQ ID NO:78, and the light chain CDRs of SEQ ID NO:184, SEQ ID NO:185 and SEQ ID NO:186.

21. The human antibody agent of aspect 4, wherein the human antibody agent comprises the heavy chain CDRs of SEQ ID NO:79, SEQ ID NO:80 and SEQ ID NO:81 and the light chain CDRs of SEQ ID NO:187, SEQ ID NO:188 and SEQ ID NO:189.

22. The human antibody agent of aspect 5, wherein the human antibody agent comprises the heavy chain CDRs of SEQ ID NO:82, SEQ ID NO:83 and SEQ ID NO:84, and the light chain CDRs of SEQ ID NO:190, SEQ ID NO:191 and SEQ ID NO:192.

23. The human antibody agent of aspect 6, wherein the human antibody agent comprises the heavy chain CDRs of SEQ ID NO:85, SEQ ID NO:86 and SEQ ID NO:87, and the light chain CDRs of SEQ ID NO:193, SEQ ID NO:194 and SEQ ID NO:195.

24. The human antibody agent of aspect 7, wherein the human antibody agent comprises the heavy chain CDRs of SEQ ID NO:88, SEQ ID NO:89 and SEQ ID NO:90 and the light chain CDRs of SEQ ID NO:196, SEQ ID NO:197 and SEQ ID NO:198.

25. The human antibody agent of aspect 8, wherein the human antibody agent comprises the heavy chain CDRs of SEQ ID NO:91, SEQ ID NO:92 and SEQ ID NO:93, and the light chain CDRs of SEQ ID NO:199, SEQ ID NO:200 and SEQ ID NO:201.

26. The human antibody agent of aspect 9, wherein the human antibody agent comprises the heavy chain CDRs of SEQ ID NO:94, SEQ ID NO:95 and SEQ ID NO:96, and the light chain CDRs of SEQ ID NO:202, SEQ ID NO:203 and SEQ ID NO:204.

27. The human antibody agent of aspect 10, wherein the human antibody agent comprises the heavy chain CDRs of SEQ ID NO:97, SEQ ID NO:98 and SEQ ID NO:99, and the light chain CDRs of SEQ ID NO:205, SEQ ID NO:206 and SEQ ID NO:207.

28. The human antibody agent of aspect 11, wherein the human antibody agent comprises the heavy chain CDRs of SEQ ID NO:100, SEQ ID NO:101 and SEQ ID NO:102, and the light chain CDRs of SEQ ID NO:208, SEQ ID NO:209 and SEQ ID NO:210.

29. The human antibody agent of aspect 12, wherein the human antibody agent comprises the heavy chain CDRs of SEQ ID NO:103, SEQ ID NO:104 and SEQ ID NO:105, and the light chain CDRs of SEQ ID NO:211, SEQ ID NO:212 and SEQ ID NO:213.

30. The human antibody agent of aspect 13, wherein the human antibody agent comprises the heavy chain CDRs of SEQ ID NO:106, SEQ ID NO:107 and SEQ ID NO:108, and the light chain CDRs of SEQ ID NO:214, SEQ ID NO:215 and SEQ ID NO:216.

31. The human antibody agent of aspect 14, wherein the human antibody agent comprises the heavy chain CDRs of SEQ ID NO:109, SEQ ID NO:110 and SEQ ID NO:111, and the light chain CDRs of SEQ ID NO:217, SEQ ID NO:218 and SEQ ID NO:219.

32. The human antibody agent of aspect 15, wherein the human antibody agent comprises the heavy chain CDRs of SEQ ID NO:112, SEQ ID NO:113 and SEQ ID NO:114, and the light chain CDRs of SEQ ID NO:220, SEQ ID NO:221 and SEQ ID NO:222.

33. The human antibody agent of aspect 16, wherein the human antibody agent comprises the heavy chain CDRs of SEQ ID NO:115, SEQ ID NO:116 and SEQ ID NO:117, and the light chain CDRs of SEQ ID NO:223, SEQ ID NO:224 and SEQ ID NO:225.

34. The human antibody agent of aspect 17, wherein the human antibody agent comprises the heavy chain CDRs of SEQ ID NO:118, SEQ ID NO:119 and SEQ ID NO:120, and the light chain CDRs of SEQ ID NO:226, SEQ ID NO:227 and SEQ ID NO:228.

35. The human antibody agent of aspect 18, wherein the human antibody agent comprises the heavy chain CDRs of SEQ ID NO:121, SEQ ID NO:122 and SEQ ID NO:123, and the light chain CDRs of SEQ ID NO:229, SEQ ID NO:230 and SEQ ID NO:231.

36. A human antibody agent that competes for binding CD19 with a human antibody agent that comprises (a) the heavy chain CDRs of SEQ ID NO:73, SEQ ID NO:74 and SEQ ID NO:75, and the light chain CDRs of SEQ ID NO:181, SEQ ID NO:182 and SEQ ID NO:183; (b) the heavy chain CDRs of SEQ ID NO:76, SEQ ID NO:77 and SEQ ID NO:78, and the light chain CDRs of SEQ ID NO:184, SEQ ID NO:185 and SEQ ID NO:186; (c) the heavy chain CDRs of SEQ ID NO:79, SEQ ID NO:80 and SEQ ID NO:81 and the light chain CDRs of SEQ ID NO:187, SEQ ID NO:188 and SEQ ID NO:189; (d) the heavy chain CDRs of SEQ ID NO:82, SEQ ID NO:83 and SEQ ID NO:84, and the light chain CDRs of SEQ ID NO:190, SEQ ID NO:191 and SEQ ID NO:192; (e) the heavy chain CDRs of SEQ ID NO:85, SEQ ID NO:86 and SEQ ID NO:87, and the light chain CDRs of SEQ ID NO:193, SEQ ID NO:194 and SEQ ID NO:195; (f) the heavy chain CDRs of SEQ ID NO:88, SEQ ID NO:89 and SEQ ID NO:90 and the light chain CDRs of SEQ ID NO:196, SEQ ID NO:197 and SEQ ID NO:198; (g) the heavy chain CDRs of SEQ ID NO:91, SEQ ID NO:92 and SEQ ID NO:93, and the light chain CDRs of SEQ ID NO:199, SEQ ID NO:200 and SEQ ID NO:201; (h) the heavy chain CDRs of SEQ ID NO:94, SEQ ID NO:95 and SEQ ID NO:96, and the light chain CDRs of SEQ ID NO:202, SEQ ID NO:203 and SEQ ID NO:204; (i) the heavy chain CDRs of SEQ ID NO:97, SEQ ID NO:98 and SEQ ID NO:99, and the light chain CDRs of SEQ ID NO:205, SEQ ID NO:206 and SEQ ID NO:207; (j) the heavy chain CDRs of SEQ ID NO:100, SEQ ID NO:101 and SEQ ID NO:102, and the light chain CDRs of SEQ ID NO:208, SEQ ID NO:209 and SEQ ID NO:210; (k) the heavy chain CDRs of SEQ ID NO:103, SEQ ID NO:104 and SEQ ID NO:105, and the light chain CDRs of SEQ ID NO:211, SEQ ID NO:212 and SEQ ID NO:213; (l) the heavy chain CDRs of SEQ ID NO:106, SEQ ID NO:107 and SEQ ID NO:108, and the light chain CDRs of SEQ ID NO:214, SEQ ID NO:215 and SEQ ID NO:216; (m) the heavy chain CDRs of SEQ ID NO:109, SEQ ID NO:110 and SEQ ID NO:111, and the light chain CDRs of SEQ ID NO:217, SEQ ID NO:218 and SEQ ID NO:219; (n) the heavy chain CDRs of SEQ ID NO:112, SEQ ID NO:113 and SEQ ID NO:114, and the light chain CDRs of SEQ ID NO:220, SEQ ID NO:221 and SEQ ID NO:222; (o) the heavy chain CDRs of SEQ ID NO:115, SEQ ID NO:116 and SEQ ID NO:117, and the light chain CDRs of SEQ ID NO:223, SEQ ID NO:224 and SEQ ID NO:225; (p) the heavy chain CDRs of SEQ ID NO:118, SEQ ID NO:119 and SEQ ID NO:120, and the light chain CDRs of SEQ ID NO:226, SEQ ID NO:227 and SEQ ID NO:228; or (q) the heavy chain CDRs of SEQ ID NO:121, SEQ ID NO:122 and SEQ ID NO:123, and the light chain CDRs of SEQ ID NO:229, SEQ ID NO:230 and SEQ ID NO:231.

37. The human antibody agent of any one of aspects 1-36, wherein the human antibody agent further comprises one or more amino acid substitutions in a heavy chain CDR and/or light chain CDR.

38. The human antibody agent of aspect 37, wherein the human antibody agent further comprises at least one or up to five amino acid substitutions in a heavy chain CDR and/or light chain CDR.

39. The human antibody agent of aspect 38, wherein the human antibody agent further comprises at least one or up to three amino acid substitutions in a heavy chain CDR and/or light chain CDR.

40. A human antibody agent that specifically binds human CD19, wherein the human antibody agent comprises a heavy chain variable region having a sequence that is at least 95% identical to a heavy chain variable region sequence that appears in Table 1, and a light chain variable region having a sequence that is at least 95% identical to a light chain variable region sequence that appears in Table 1.

41. The human antibody agent of aspect 40, wherein the human antibody agent comprises a heavy chain variable region having a sequence that is at least 95% identical to the heavy chain variable region sequence that appears in SEQ ID NO:2, and a light chain variable region having a sequence that is at least 95% identical to the light chain variable region sequence that appears in SEQ ID NO:2.

42. The human antibody agent of aspect 40, wherein the human antibody agent comprises a heavy chain variable region having a sequence that is at least 95% identical to the heavy chain variable region sequence that appears in SEQ ID NO:4, and a light chain variable region having a sequence that is at least 95% identical to the light chain variable region sequence that appears in SEQ ID NO:4.

43. The human antibody agent of aspect 40, wherein the human antibody agent comprises a heavy chain variable region having a sequence that is at least 95% identical to the heavy chain variable region sequence that appears in SEQ ID NO:6, and a light chain variable region having a sequence that is at least 95% identical to the light chain variable region sequence that appears in SEQ ID NO:6.

44. The human antibody agent of aspect 40, wherein the human antibody agent comprises a heavy chain variable region having a sequence that is at least 95% identical to the heavy chain variable region sequence that appears in SEQ ID NO:8, and a light chain variable region having a sequence that is at least 95% identical to the light chain variable region sequence that appears in SEQ ID NO:8.

45. The human antibody agent of aspect 40, wherein the human antibody agent comprises a heavy chain variable region having a sequence that is at least 95% identical to the heavy chain variable region sequence that appears in SEQ ID NO:10, and a light chain variable region having a sequence that is at least 95% identical to the light chain variable region sequence that appears in SEQ ID NO:10.

46. The human antibody agent of aspect 40, wherein the human antibody agent comprises a heavy chain variable region having a sequence that is at least 95% identical to the heavy chain variable region sequence that appears in SEQ ID NO:12, and a light chain variable region having a sequence that is at least 95% identical to the light chain variable region sequence that appears in SEQ ID NO:12.

47. The human antibody agent of aspect 40, wherein the human antibody agent comprises a heavy chain variable region having a sequence that is at least 95% identical to the heavy chain variable region sequence that appears in SEQ ID NO:14, and a light chain variable region having a sequence that is at least 95% identical to the light chain variable region sequence that appears in SEQ ID NO:14.

48. The human antibody agent of aspect 40, wherein the human antibody agent comprises a heavy chain variable region having a sequence that is at least 95% identical to the heavy chain variable region sequence that appears in SEQ ID NO:16, and a light chain variable region having a sequence that is at least 95% identical to the light chain variable region sequence that appears in SEQ ID NO:16.

49. The human antibody agent of aspect 40, wherein the human antibody agent comprises a heavy chain variable region having a sequence that is at least 95% identical to the heavy chain variable region sequence that appears in SEQ ID NO:18, and a light chain variable region having a sequence that is at least 95% identical to the light chain variable region sequence that appears in SEQ ID NO:18.

50. The human antibody agent of aspect 40, wherein the human antibody agent comprises a heavy chain variable region having a sequence that is at least 95% identical to the heavy chain variable region sequence that appears in SEQ ID NO:20, and a light chain variable region having a sequence that is at least 95% identical to the light chain variable region sequence that appears in SEQ ID NO:20.

51. The human antibody agent of aspect 40, wherein the human antibody agent comprises a heavy chain variable region having a sequence that is at least 95% identical to the heavy chain variable region sequence that appears in SEQ ID NO:22, and a light chain variable region having a sequence that is at least 95% identical to the light chain variable region sequence that appears in SEQ ID NO:22.

52. The human antibody agent of aspect 40, wherein the human antibody agent comprises a heavy chain variable region having a sequence that is at least 95% identical to the heavy chain variable region sequence that appears in SEQ ID NO:24, and a light chain variable region having a sequence that is at least 95% identical to the light chain variable region sequence that appears in SEQ ID NO:24.

53. The human antibody agent of aspect 40, wherein the human antibody agent comprises a heavy chain variable region having a sequence that is at least 95% identical to the heavy chain variable region sequence that appears in SEQ ID NO:26, and a light chain variable region having a sequence that is at least 95% identical to the light chain variable region sequence that appears in SEQ ID NO:26.

54. The human antibody agent of aspect 40, wherein the human antibody agent comprises a heavy chain variable region having a sequence that is at least 95% identical to the heavy chain variable region sequence that appears in SEQ ID NO:28, and a light chain variable region having a sequence that is at least 95% identical to the light chain variable region sequence that appears in SEQ ID NO:28.

55. The human antibody agent of aspect 40, wherein the human antibody agent comprises a heavy chain variable region having a sequence that is at least 95% identical to the heavy chain variable region sequence that appears in SEQ ID NO:30, and a light chain variable region having a sequence that is at least 95% identical to the light chain variable region sequence that appears in SEQ ID NO:30.

56. The human antibody agent of aspect 40, wherein the human antibody agent comprises a heavy chain variable region having a sequence that is at least 95% identical to the heavy chain variable region sequence that appears in SEQ ID NO:32, and a light chain variable region having a sequence that is at least 95% identical to the light chain variable region sequence that appears in SEQ ID NO:32.

57. The human antibody agent of aspect 40, wherein the human antibody agent comprises a heavy chain variable region having a sequence that is at least 95% identical to the heavy chain variable region sequence that appears in SEQ ID NO:34, and a light chain variable region having a sequence that is at least 95% identical to the light chain variable region sequence that appears in SEQ ID NO:34.

58. The human antibody agent of any one of aspects 40-57, wherein the human antibody agent comprises the heavy and light chain variable region sequences that appear in any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32 and SEQ ID NO:34.

59. A human antibody agent that specifically binds human CD19, wherein the human antibody agent comprises one or more amino acid substitutions as compared to a parental human antibody agent, and wherein the human antibody agent comprises (a) the heavy chain CDRs of SEQ ID NO:124, SEQ ID NO:125 and SEQ ID NO:126, and the light chain CDRs of SEQ ID NO:232, SEQ ID NO:233 and SEQ ID NO:234; (b) the heavy chain CDRs of SEQ ID NO:127, SEQ ID NO:128 and SEQ ID NO:129, and the light chain CDRs of SEQ ID NO:235, SEQ ID NO:236 and SEQ ID NO:237; (c) the heavy chain CDRs of SEQ ID NO:130, SEQ ID NO:131 and SEQ ID NO:132, and the light chain CDRs of SEQ ID NO:238, SEQ ID NO:239 and SEQ ID NO:240; (d) the heavy chain CDRs of SEQ ID NO:133, SEQ ID NO:134 and SEQ ID NO:135, and the light chain CDRs of SEQ ID NO:241, SEQ ID NO:242 and SEQ ID NO:243; (e) the heavy chain CDRs of SEQ ID NO:136, SEQ ID NO:137 and SEQ ID NO:138, and the light chain CDRs of SEQ ID NO:244, SEQ ID NO:245 and SEQ ID NO:246; (f) the heavy chain CDRs of SEQ ID NO:139, SEQ ID NO:140 and SEQ ID NO:141, and the light chain CDRs of SEQ ID NO:247, SEQ ID NO:248 and SEQ ID NO:249; (g) the heavy chain CDRs of SEQ ID NO:142, SEQ ID NO:143 and SEQ ID NO:144, and the light chain CDRs of SEQ ID NO:250, SEQ ID NO:251 and SEQ ID NO:252; (h) the heavy chain CDRs of SEQ ID NO:145, SEQ ID NO:146 and SEQ ID NO:147, and the light chain CDRs of SEQ ID NO:253, SEQ ID NO:254 and SEQ ID NO:255; (i) the heavy chain CDRs of SEQ ID NO:148, SEQ ID NO:149 and SEQ ID NO:150, and the light chain CDRs of SEQ ID NO:256, SEQ ID NO:257 and SEQ ID NO:258; (j) the heavy chain CDRs of SEQ ID NO:151, SEQ ID NO:152 and SEQ ID NO:153, and the light chain CDRs of SEQ ID NO:259, SEQ ID NO:260 and SEQ ID NO:261; (k) the heavy chain CDRs of SEQ ID NO:154, SEQ ID NO:155 and SEQ ID NO:156, and the light chain CDRs of SEQ ID NO:262, SEQ ID NO:263 and SEQ ID NO:264; (l) the heavy chain CDRs of SEQ ID NO:157, SEQ ID NO:158 and SEQ ID NO:159, and the light chain CDRs of SEQ ID NO:265, SEQ ID NO:266 and SEQ ID NO:267; (m) the heavy chain CDRs of SEQ ID NO:160, SEQ ID NO:161 and SEQ ID NO:163, and the light chain CDRs of SEQ ID NO:268, SEQ ID NO:269 and SEQ ID NO:270; (n) the heavy chain CDRs of SEQ ID NO:163, SEQ ID NO:164 and SEQ ID NO:165, and the light chain CDRs of SEQ ID NO:271, SEQ ID NO:272 and SEQ ID NO:273; (o) the heavy chain CDRs of SEQ ID NO:166, SEQ ID NO:167 and SEQ ID NO:168, and the light chain CDRs of SEQ ID NO:274, SEQ ID NO:275 and SEQ ID NO:276; (p) the heavy chain CDRs of SEQ ID NO:169, SEQ ID NO:170 and SEQ ID NO:171, and the light chain CDRs of SEQ ID NO:277, SEQ ID NO:278 and SEQ ID NO:279; (q) the heavy chain CDRs of SEQ ID NO:172, SEQ ID NO:173 and SEQ ID NO:174, and the light chain CDRs of SEQ ID NO:280, SEQ ID NO:281 and SEQ ID NO:282; (r) the heavy chain CDRs of SEQ ID NO:175, SEQ ID NO:176 and SEQ ID NO:177, and the light chain CDRs of SEQ ID NO:283, SEQ ID NO:284 and SEQ ID NO:285; or (s) the heavy chain CDRs of SEQ ID NO:178, SEQ ID NO:179 and SEQ ID NO:180, and the light chain CDRs of SEQ ID NO:286, SEQ ID NO:287 and SEQ ID NO:288.

60. The human antibody agent of aspect 59, wherein the human antibody agent comprises a light chain variable region that comprises one or more amino acid substitutions at any of amino acid positions selected from the group consisting of 10, 16, 25, 34, 52, 54, 68, 69, 72, 75, 93, 95 and combinations thereof.

61. The human antibody agent of aspect 60, wherein the one or more amino acid substitutions includes V10M, K16E, S25N, V34I, D52N, L54Q, N68T, T69M, L72M, S75N, S93T, D95E, D95G or a combination thereof.

62. The human antibody agent of any one of aspects 59-61, wherein the human antibody agent comprises a heavy chain variable region that comprises one or more amino acid substitutions at any of amino acid positions selected from the group consisting of 3, 12, 16, 17, 25, 26, 32, 63, 69, 97, 102, 106, 108, 109, 113, 116, 117 and combinations thereof.

63. The human antibody agent of aspect 62, wherein the one or more amino acid substitutions includes Q3R, K12E, E16G, S17F, S25A, G26A, Y32F, S63F, T69A, A97V, T102S, M106L, Y108N, D109E, Q113L, L116M, M117L or a combination thereof.

64. The human antibody agent of any one of aspects 59-63, wherein the human antibody agent comprises a light chain variable region with amino acid substitution S75N.

65. The human antibody agent of any one of aspects 59-63, wherein the human antibody agent comprises a light chain variable region with amino acid substitution T69M.

66. The human antibody agent of any one of aspects 59-63, wherein the human antibody agent comprises a light chain variable region with amino acid substitutions D52N and D95E.

67. The human antibody agent of any one of aspects 59-63, wherein the human antibody agent comprises a light chain variable region with amino acid substitutions V10M and D95G.

68. The human antibody agent of any one of aspects 59-63, wherein the human antibody agent comprises a light chain variable region with amino acid substitution S93T, and a heavy chain variable region with amino acid substitutions S17F and T69A.

69. The human antibody agent of any one of aspects 59-63, wherein the human antibody agent comprises a light chain variable region with amino acid substitution N68T, and a heavy chain variable region with amino acid substitutions S17F and Y108N.

70. The human antibody agent of any one of aspects 59-63, wherein the human antibody agent comprises a heavy chain variable region with amino acid substitution S63F.

71. The human antibody agent of any one of aspects 59-63, wherein the human antibody agent comprises a heavy chain variable region with amino acid substitutions Q3R, Y32F and A97V.

72. The human antibody agent of any one of aspects 59-63, wherein the human antibody agent comprises a light chain variable region with amino acid substitution K16E.

73. The human antibody agent of any one of aspects 59-63, wherein the human antibody agent comprises a heavy chain variable region with amino acid substitution M117L.

74. The human antibody agent of any one of aspects 59-63, wherein the human antibody agent comprises a light chain variable region with amino acid substitution L72M, and a heavy chain variable region with amino acid substitution S25A.

75. The human antibody agent of any one of aspects 59-63, wherein the human antibody agent comprises a heavy chain variable region with amino acid substitutions T102S and L116M.

76. The human antibody agent of any one of aspects 59-63, wherein the human antibody agent comprises a light chain variable region with amino acid substitutions S25N and V34I, and a heavy chain variable region with amino acid substitutions K12E and D109E.

77. The human antibody agent of any one of aspects 59-63, wherein the human antibody agent comprises a heavy chain variable region with amino acid substitution E16G.

78. The human antibody agent of any one of aspects 59-63, wherein the human antibody agent comprises a light chain variable region with amino acid substitution L54Q, and a heavy chain variable region with amino acid substitution M106L.

79. The human antibody agent of any one of aspects 59-63, wherein the human antibody agent comprises a light chain variable region with amino acid substitution S25N.

80. The human antibody agent of any one of aspects 59-63, wherein the human antibody agent comprises a heavy chain variable region with amino acid substitutions G26A and Q113L.

81. The human antibody agent of any one of aspects 59-63, wherein the human antibody agent comprises a light chain variable region with amino acid substitution L54Q.

82. The human antibody agent of any one of aspects 59-63, wherein the human antibody agent comprises a heavy chain variable region with amino acid substitution T102S.

83. The human antibody agent of any one of aspects 59-82, wherein the human antibody agent comprises the heavy and light chain variable region sequences that appear in any one of SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

84. The human antibody agent of any one of aspects 1-83, wherein the human antibody agent is a human monoclonal antibody that comprises a variant Fc region.

85. The human antibody agent of aspect 84, wherein the human monoclonal antibody comprises a variant glycosylation pattern as compared to a parental human monoclonal antibody that comprises a wild-type Fc region.

86. The human antibody agent of any one of aspects 1-85, wherein the human antibody agent is conjugated to a therapeutic agent or detection agent.

87. The human antibody agent of any one of aspects 1-85, wherein the human antibody agent is conjugated to a cytotoxic agent or moiety.

88. The human antibody agent of any one of aspects 1-85, wherein the human antibody agent is conjugated to a radioisotope.

89. The human antibody agent of any one of aspects 1-88, wherein the human antibody agent is or comprises an immunoglobulin, Fab, F(ab')$_2$, Fd, Fv, single chain Fv (scFv) or a dAb.

90. The human antibody agent of aspect 89, wherein the human antibody agent is or comprises an scFv.

91. The human antibody agent of aspect 90, wherein the scFv comprises a linker sequence.

92. The human antibody agent of aspect 90 or 91, wherein the scFv is conjugated to a therapeutic agent or detection agent.

93. The human antibody agent of aspect 90 or 91, wherein the scFv is part of a chimeric antigen receptor.

94. The human antibody agent of any one of aspects 1-93, for use in therapy or diagnosis.

95. The human antibody agent of any one of aspects 1-93, for use in the treatment, prevention or amelioration of a disease characterized by CD19 expression.

96. The use of a human antibody agent of any one of aspects 1-93, for use in the treatment, prevention or amelioration of cancer.

97. An isolated nucleic acid molecule encoding a human antibody agent of any one of aspects 1-93.

98. The isolated nucleic acid molecule of aspect 97, wherein the isolated nucleic acid molecule includes a sequence that is codon-optimized.

99. The isolated nucleic acid molecule of aspect 97, wherein the isolated nucleic acid molecule is or comprises a sequence that appears in any one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69 and SEQ ID NO:71.

100. A vector comprising the isolated nucleic acid molecule of any one of aspects 97-99.

101. A cell comprising the vector of aspect 100.

102. A kit comprising a human antibody agent of any one of aspects 1-93, the isolated nucleic acid molecule of any one of aspects 97-99, the vector of aspect 100 or the cell of aspect 101.

103. A vaccine comprising the isolated nucleic acid molecule of any one of aspects 97-99.

104. A method for producing a human antibody agent according to any one of aspects 1-93 comprising a step of culturing the cell according to aspect 101 in a culture medium under conditions allowing the expression of the human antibody agent and separating the human antibody agent from the culture medium.

105. A composition comprising the human antibody agent of any of aspects 1-93.

106. The composition of aspect 105, wherein the human antibody agent is conjugated to a cytotoxic agent or moiety.

107. A pharmaceutical composition comprising the composition of aspect 105 or 106 or the human antibody agent of any one of aspects 1-93, and further comprising a pharmaceutically acceptable carrier or diluent.

108. A method of treating a medical condition characterized by CD19 expression in a subject, comprising a step of administering a therapeutically effective amount of a human antibody agent of any one of aspects 1-93 to said subject.

109. The method of aspect 108, wherein the medical condition characterized by CD19 expression is B cell lymphoma, acute lymphoblastic leukemia, chronic lymphocytic leukemia, Burkitt lymphoma, non-Hodgkin's lymphoma or acute myeloid leukemia.

110. The method of aspect 108, wherein the medical condition characterized by CD19 expression is rheumatoid arthritis (RA), systemic lupus erythematosus (SLE), diabetes or scleroderma.

111. A method of treating cancer, the method comprising a step of administering to a subject a human antibody agent of any one of aspects 1-93.

112. Use of an antibody agent of any one of aspects 1-93 for the treatment or detection of a condition related to CD19 expression.

113. A bi-specific antibody comprising a first antigen-binding site from a human antibody agent of any one of aspects 1-93 and a second antigen-binding site.

114. The bi-specific antibody of aspect 113, wherein the first and second antigen binding sites are scFvs.

115. The bi-specific antibody of aspect 113, wherein the first antigen-binding site is composed of an immunoglobulin molecule and the second antigen-binding site is composed of an scFv, scFab, Fab or Fv.

116. The bi-specific antibody of any one of aspects 113-115, wherein the second antigen-binding site binds an immune cell selected from the group consisting of a T cell, NK cell, B cell, dendritic cell, monocyte, macrophage, neutrophil, mesenchymal stem cell and neural stem cell.

117. The bi-specific antibody of aspect 116, wherein the second antigen-binding site binds CD3 on T cells.

118. A bi-specific T cell engaging monoclonal antibody comprising an antigen-binding site of a human antibody agent of any one of aspects 1-93.

119. The bi-specific antibody of any one of aspects 113-118, for use in therapy or diagnosis.

120. An isolated nucleic acid molecule that encodes, in whole or in part, a polypeptide chain of the bi-specific antibody of any one of aspects 113-118.

121. The isolated nucleic acid molecule of aspect 120, wherein the nucleic acid molecule includes a sequence that is codon-optimized.

122. A vector comprising the nucleic acid sequence of aspect 120 or 121.

123. A cell comprising the vector of aspect 122.

124. A kit comprising a bi-specific antibody of any one of aspects 113-118, the isolated nucleic acid molecule of aspect 120 or 121, the vector of aspect 122 or the cell of aspect 123.

125. A composition comprising the bi-specific antibody of any one of aspects 113-118.

126. A pharmaceutical composition comprising the composition of aspect 125 or the bi-specific antibody of any one of aspects 113-118, and further comprising a pharmaceutically acceptable carrier or diluent.

127. A chimeric antigen receptor comprising an antigen-binding site of a human antibody agent of any one of aspects 1-93.

128. The chimeric antigen receptor of aspect 127, wherein the antigen-binding site is or comprises an scFv.

129. The chimeric antigen receptor of aspect 127, wherein the antigen-binding site is or comprises a $V_L$ region.

130. The chimeric antigen receptor of aspect 129, wherein the $V_L$ region comprises the light chain CDRs of (a) SEQ ID NO:181, SEQ ID NO:182 and SEQ ID NO:183; (b) SEQ ID NO:184, SEQ ID NO:185 and SEQ ID NO:186; (c) SEQ ID NO:187, SEQ ID NO:188 and SEQ ID NO:189; (d) SEQ ID NO:190, SEQ ID NO:191 and SEQ ID NO:192; (e) SEQ ID NO:193, SEQ ID NO:194 and SEQ ID NO:195; (f) SEQ ID NO:196, SEQ ID NO:197 and SEQ ID NO:198; (g) SEQ ID NO:199, SEQ ID NO:200 and SEQ ID NO:201; (h) SEQ ID NO:202, SEQ ID NO:203 and SEQ ID NO:204; (i) SEQ ID NO:205, SEQ ID NO:206 and SEQ ID NO:207; (j) SEQ ID NO:208, SEQ ID NO:209 and SEQ ID NO:210; (k) SEQ ID NO:211, SEQ ID NO:212 and SEQ ID NO:213; (l) SEQ ID NO:214, SEQ ID NO:215 and SEQ ID NO:216; (m) SEQ ID NO:217, SEQ ID NO:218 and SEQ ID NO:219; (n) SEQ ID NO:220, SEQ ID NO:221 and SEQ ID NO:222; (o) SEQ ID NO:223, SEQ ID NO:224 and SEQ ID NO:225; (p) SEQ ID NO:226, SEQ ID NO:227 and SEQ ID NO:228; (q) SEQ ID NO:229, SEQ ID NO:230 and SEQ ID NO:231; (r) SEQ ID NO:232, SEQ ID NO:233 and SEQ ID NO:234; (s) SEQ ID NO:235, SEQ ID NO:236 and SEQ ID NO:237; (t) SEQ ID NO:238, SEQ ID NO:239 and SEQ ID NO:240; (u) SEQ ID NO:241, SEQ ID NO:242 and SEQ ID NO:243; (v) SEQ ID NO:244, SEQ ID NO:245 and SEQ ID NO:246; (w) SEQ ID NO:247, SEQ ID NO:248 and SEQ ID NO:249; (x) SEQ ID NO:250, SEQ ID NO:251 and SEQ ID NO:252; (y) SEQ ID NO:253, SEQ ID NO:254 and SEQ ID NO:255; (z) SEQ ID NO:256, SEQ ID NO:257 and SEQ ID NO:258; (ab) SEQ ID NO:259, SEQ ID NO:260 and SEQ ID NO:261; (ac) SEQ ID NO:262, SEQ ID NO:263 and SEQ ID NO:264; (ad) SEQ ID NO:265, SEQ ID NO:266 and SEQ ID NO:267; (ae) SEQ ID NO:268, SEQ ID NO:269 and SEQ ID NO:270; (af) SEQ ID NO:271, SEQ ID NO:272 and SEQ ID NO:273; (ag) SEQ ID NO:274, SEQ ID NO:275 and SEQ ID NO:276; (ah) SEQ ID NO:277, SEQ ID NO:278 and SEQ ID NO:279; (ai) SEQ ID NO:280, SEQ ID NO:281 and SEQ ID NO:282; (aj) SEQ ID NO:283, SEQ ID NO:284 and SEQ ID NO:285; or (ak) SEQ ID NO:286, SEQ ID NO:287 and SEQ ID NO:288.

131. The chimeric antigen receptor of aspect 129, wherein the $V_L$ region comprises a sequence that appears in any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

132. The chimeric antigen receptor of aspect 127, wherein the antigen-binding site is or comprises a $V_H$ region.

133. The chimeric antigen receptor of aspect 132, wherein the $V_H$ region comprises the heavy chain CDRs of (a) SEQ ID NO:73, SEQ ID NO:74 and SEQ ID NO:75; (b) SEQ ID NO:76, SEQ ID NO:77 and SEQ ID NO:78; (c) SEQ ID NO:79, SEQ ID NO:80 and SEQ ID NO:81; (d) SEQ ID NO:82, SEQ ID NO:83 and SEQ ID NO:84; (e) SEQ ID NO:85, SEQ ID NO:86 and SEQ ID NO:87; (f) SEQ ID NO:88, SEQ ID NO:89 and SEQ ID NO:90; (g) SEQ ID NO:91, SEQ ID NO:92 and SEQ ID NO:93; (h) SEQ ID NO:94, SEQ ID NO:95 and SEQ ID NO:96; (i) SEQ ID NO:97, SEQ ID NO:98 and SEQ ID NO:99; (j) SEQ ID NO:100, SEQ ID NO:101 and SEQ ID NO:102; (k) SEQ ID NO:103, SEQ ID NO:104 and SEQ ID NO:105; (l) SEQ ID NO:106, SEQ ID NO:107 and SEQ ID NO:108; (m) SEQ ID NO:109, SEQ ID NO:110 and SEQ ID NO:111; (n) SEQ ID NO:112, SEQ ID NO:113 and SEQ ID NO:114; (o) SEQ ID NO:115, SEQ ID NO:116 and SEQ ID NO:117; (p) SEQ ID NO:118, SEQ ID NO:119 and SEQ ID NO:120; (q) SEQ ID NO:121, SEQ ID NO:122 and SEQ ID NO:123; (r) SEQ ID NO:124, SEQ ID NO:125 and SEQ ID NO:126; (s) SEQ ID NO:127, SEQ ID NO:128 and SEQ ID NO:129; (t) SEQ ID NO:130, SEQ ID NO:131 and SEQ ID NO:132; (u) SEQ ID NO:133, SEQ ID NO:134 and SEQ ID NO:135; (v) SEQ ID NO:136, SEQ ID NO:137 and SEQ ID NO:138; (w) SEQ ID NO:139, SEQ ID NO:140 and SEQ ID NO:141; (x) SEQ ID NO:142, SEQ ID NO:143 and SEQ ID NO:144; (y) SEQ ID NO:145, SEQ ID NO:146 and SEQ ID NO:147; (z) SEQ ID NO:148, SEQ ID NO:149 and SEQ ID NO:150; (ab) SEQ ID NO:151, SEQ ID NO:152 and SEQ ID NO:153; (ac) SEQ ID NO:154, SEQ ID NO:155 and SEQ ID NO:156; (ad) SEQ ID NO:157, SEQ ID NO:158 and SEQ ID NO:159; (ae) SEQ ID NO:160, SEQ ID NO:161 and SEQ ID NO:163; (af) SEQ ID NO:163, SEQ ID NO:164 and SEQ ID NO:165; (ag) SEQ ID NO:166, SEQ ID NO:167 and SEQ ID NO:168; (ah) SEQ ID NO:169, SEQ ID NO:170 and SEQ ID NO:171; (ai) SEQ ID NO:172, SEQ ID NO:173 and SEQ ID NO:174; (aj) SEQ ID NO:175, SEQ ID NO:176 and SEQ ID NO:177; or (ak) SEQ ID NO:178, SEQ ID NO:179 and SEQ ID NO:180.

134. The chimeric antigen receptor of aspect 132, wherein the $V_H$ region comprises a sequence that appears in any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

135. The chimeric antigen receptor of any one of aspects 127-134, for use in therapy or diagnosis.

136. The chimeric antigen receptor of any one of aspects 127-134, for use in the treatment, prevention or amelioration of a disease characterized by CD19 expression.

137. An isolated nucleic acid molecule that encodes the chimeric antigen receptor of any one of aspects 127-134.

138. The isolated nucleic acid molecule of aspect 137, wherein the nucleic acid molecule includes a sequence that is codon-optimized.

139. An immune effector cell that expresses the chimeric antigen receptor of any one of aspects 127-134.

140. The immune effector cell of aspect 139, wherein the cell is a T cell or an NK cell.

141. The immune effector cell of aspect 139 or 140, for use in therapy or diagnosis.

142. The immune effector cell of aspect 139 or 140, for use in the treatment, prevention or amelioration of a disease characterized by CD19 expression.

143. A kit comprising a chimeric antigen receptor of any one of aspects 127-134, the isolated nucleic acid molecule of aspect 137 or 138, or the immune effector cell of aspect 139 or 140.

144. Use of the chimeric antigen receptor of any one of aspects 127-134 for the treatment or detection of a medical condition related to CD19 expression.

145. A method of inhibiting tumor growth, the method comprising a step of contacting tumor cells with a bi-specific antibody, which bi-specific antibody is composed of a first antigen-binding site based on a human antibody agent of any one of aspects 1-93 and a second antigen-binding site that binds an immune cell, the contacting being performed under conditions and for a time sufficient so that tumor cell killing is observed.

146. A method of killing tumor cells, the method comprising a step of contacting tumor cells with a bi-specific antibody, which bi-specific antibody is composed of a first antigen-binding site based on a human antibody agent of any one of aspects 1-93 and a second antigen-binding site that binds an immune cell, the contacting being performed under conditions and for a time sufficient so that inhibition of tumor cell growth is observed.

147. The method of aspect 145 or 146, wherein the immune cell is a T cell or an NK cell.

148. The method of any one of aspects 145-147, wherein the first and second antigen binding sites are scFvs.

149. The method of aspect 148, wherein the second antigen-binding site binds CD3 on T cells.

150. A bi-specific antibody composed of a first antigen-binding site based on a human antibody agent of any one of aspects 1-93 and a second antigen-binding site that binds an immune cell, for use in inhibiting tumor growth.

151. A bi-specific antibody composed of a first antigen-binding site based on a human antibody agent of any one of aspects 1-93 and a second antigen-binding site that binds an immune cell, for use in killing tumor cells.

152. A method of directing T cells to kill target cells expressing CD19, the method comprising a step of contacting one or more target cells expressing CD19 with a bi-specific antibody, which bi-specific antibody comprises a first antigen-binding site of a human antibody agent of any one of aspects 1-93 and a second antigen-binding site that binds CD3 on T cells, the contacting being performed under conditions and for a time sufficient that T cells to which the bi-specific antibody has bound mediate killing of target cells expressing CD19.

153. The method of aspect 152, wherein the first and second antigen binding sites are scFvs.

154. A bi-specific antibody composed of a first antigen-binding site based on a human antibody agent of any one of aspects 1-93 and a second antigen-binding site that binds CD3 on T cells, for use in directing T cells to kill target cells expressing CD19.

155. A bi-specific antibody comprised of a first scFv that specifically binds CD19 and a second scFv that specifically binds CD3 on T cells, wherein the N-terminal end of the first scFv is linked to the C-terminal end of the second scFv, and wherein the first scFv comprises any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70 and SEQ ID NO:72.

156. The bi-specific antibody of aspect 155, wherein the N-terminal end of the first scFv is linked to the C-terminal end of the second scFv via a linker sequence.

157. The bi-specific antibody of aspect 156, wherein the linker sequence comprises a $(G_4S)_n$ linker.

158. The bi-specific antibody of aspect 157, wherein n is equal to 1, 2, 3, 4 or 5.

159. The bi-specific antibody of aspect 156, wherein the linker sequence is or comprises SRGGGGSGGGGSGGGGSLEMA (SEQ ID NO:289).

160. A pharmaceutical composition comprising the bi-specific antibody of any one of aspects 155-159, and further comprising a pharmaceutically acceptable carrier or diluent.

161. The bi-specific antibody of any one of aspects 155-159, for use in therapy or diagnosis.

162. An antibody-drug conjugate comprising an antigen-binding site of a human antibody agent of any one of aspects 1-93, and a cytotoxic agent or moiety.

163. A kit for diagnosing a subject suffering from a CD19-related disease, or a pre-disposition thereto, or for providing a prognosis of the subject's condition, the kit comprising detection means for detecting the concentration of CD19 present in a sample from a test subject, wherein the detection means comprises an antigen-binding site of a human antibody agent of any one of aspects 1-93, a bi-specific binding agent of any one of aspects 113-118 and 155-159, a chimeric antigen receptor of any one of aspects 127-134, or an immune effector cell of aspect 138 or 139, each being optionally derivatized, wherein presence of CD19 in the sample indicates that the subject suffers from a CD19-related disease.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

Having thus described several aspects of at least one embodiment of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

The invention claimed is:

1. An antibody agent that specifically binds human cluster of differentiation 19 (CD19), wherein the antibody agent comprises heavy chain variable region (HCVR) of 131-260 segment of SEQ ID NO:42 and light chain variable region (LCVR) of 1-109 segment of SEQ ID NO:42.

2. The antibody agent of claim 1, wherein the antibody agent comprises a sequence comprising a heavy chain variable region (HCVR) and a light chain variable region (LCVR), wherein the sequence comprises the sequence of SEQ ID NO: 42.

3. The antibody agent of claim 1, wherein the antibody agent is or comprises an immunoglobulin, Fab, F(ab')$_2$, Fd, Fv, single chain Fv (scFv), or a dAb.

4. The antibody agent of claim 1, wherein the antibody agent is conjugated to a therapeutic agent, a detection agent, a cytotoxic agent or moiety, or a radio-isotope.

5. The antibody agent of claim 1, wherein the antibody agent is a human antibody agent.

6. A bi-specific antibody comprising a first antigen-binding site and a second antigen-binding site, wherein the first antigen-binding site is from an antibody agent of claim 1.

7. The bi-specific antibody of claim 6, wherein the second antigen-binding site binds an immune cell selected from the group consisting of a T cell, NK cell, B cell, dendritic cell, monocyte, macrophage, neutrophil, mesenchymal stem cell and neural stem cell.

8. A chimeric antigen receptor comprising an antigen-binding site of an antibody agent of claim 1.

9. The chimeric antigen receptor of claim 8, further comprising a transmembrane domain and an intracellular signaling domain, wherein the intracellular signaling domain comprises a CD3 intracellular signaling sequence and a CD28 intracellular signaling sequence.

10. A nucleic acid molecule encoding, in whole, the antibody agent of claim 1.

11. A vector comprising the nucleic acid molecule of claim 10.

12. A cell comprising the nucleic acid molecule of claim 10.

13. An effector cell expressing the antibody agent of claim 1.

14. The effector cell of claim 13, wherein the effector cell is a T cell.

15. A composition comprising the effector cell of claim 14, and a carrier or diluent.

16. A method of treating a CD19-expressing B cell malignancy in a subject, comprising a step of administering to the subject (1) a bi-specific antibody having a first antigen-binding site that is from the antibody agent of claim 1 and a second antigen-binding site that binds a T cell; or (2) T cells expressing a chimeric antigen receptor comprising (a) the antigen-binding site that is from the antibody agent of claim 1, (b) a transmembrane domain, and (c) an intracelluar signaling domain.

17. The method of claim 16, wherein the CD19-expressing B cell malignancy is B cell lymphoma, acute lymphoblastic leukemia, chronic lymphocytic leukemia, Burkitt lymphoma, non-Hodgkin's lymphoma, or acute myeloid leukemia.

18. The method of claim 16, wherein the second antigen-binding site binds CD3.

19. The method of claim 16, wherein the intracellular signaling domain comprises a CD3ζ intracellular signaling sequence.

* * * * *

SEQUENCE LISTING

<160> NUMBER OF SEQ ID NOS: 302

<210> SEQ ID NO 1

<211> LENGTH: 747
<212> TYPE: DNA
<213> ORGANISM: Artificial Sequence
<220> FEATURE:
<223> OTHER INFORMATION: Synthetic Construct

<400> SEQUENCE: 1

```
cagactgtgg tgactcagga gccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctc agggattcct    180
gaccgattct ctggctccaa gtctggcacg tcagccaccc tgggcatcac cggactccag   240
actggggacg aggccgatta ttactgcgga acatgggata gcagcctgag tgctggtgtc   300
ttcggaactg ggaccaagct gaccgtccta ggttctagag gtggtggtgg tagcggcggc   360
ggcggctctg gtggtggtgg atccctcgag atggcccagg tgcagctggt ggagactggg   420
ggaggcttgg tacagcctgg ggggtccctg agactctcct gtgcagcctc tggattcacc   480
tttagcagct atgccatgag ctgggtccgc caggctccag gaaggggct ggagtgggtc    540
tcagctatta gtggtagtgg tggtagcaca tactacgcag actccgtgaa gggccggttc   600
accatctcca gagacaattc caagaacacg ctgtatctgc aaatgaacag cctgagagcc   660
gaggacacgg ccgtatatta ctgtgcgcgc tactactact ctcgtctgga ttactggggt   720
caaggtactc tggtgaccgt ctcctca                                       747
```

<210> SEQ ID NO 2
<211> LENGTH: 249
<212> TYPE: PRT
<213> ORGANISM: Artificial Sequence
<220> FEATURE:
<223> OTHER INFORMATION: Synthetic Construct

<400> SEQUENCE: 2

```
Gln Thr Val Val Thr Gln Glu Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Thr Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Glu Thr Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Ala Ile Ser Gly Ser Gly Gly Ser Thr Tyr Tyr
            180                 185                 190
```

Ala Asp Ser Val Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
    210                 215                 220

Val Tyr Tyr Cys Ala Arg Tyr Tyr Tyr Ser Arg Leu Asp Tyr Trp Gly
225                 230                 235                 240

Gln Gly Thr Leu Val Thr Val Ser Ser
                245

<210> SEQ ID NO 3
<211> LENGTH: 747
<212> TYPE: DNA
<213> ORGANISM: Artificial Sequence
<220> FEATURE:
<223> OTHER INFORMATION: Synthetic Construct

<400> SEQUENCE: 3

```
cagtctgtgc tgacgcagcc gcccctcagtg tctgcggccc caggacagaa ggtcaccatc      60
tcctgctctg gaagcagctc caacattggg aataattatg tatcctggta ccggcaactc     120
ccaggaacag ccccccaaact cctcatctat gaaaataata agcgaccctc agggattcct     180
gaccgattct ctggctccaa gtctggcacg tcagccaccc tgggcatcac cggactccag     240
actggggacg aggccgatta ttactgcgga acatgggata gcagcctgcg tgctggggtc     300
ttcggaactg gaccaaggt caccgtccta ggttctagag gtggtggtgg tagcggcggc     360
ggcggctctg gtggtggtgg atccctcgag atggcccagg tgcagctggt ggagtctggg     420
ggaggcttgg tacagcctgg ggggtccctg agactctcct gtgcagcctc tggattcacc     480
tttagcagct atgccatgag ctgggtccgc caggctccgg ggaagggcct ggagtgggtc     540
tcaggtatta gtgctagtgg tggtagcaca tactacgcag actccgtgaa gggccgcttc     600
accatctcca gagacaattc caagaatacg ctgtatctgc aaatgaacag cctgagagcc     660
gaggacacgg ccgtatatta ctgtgcgcgc tactacctgt ctcagatcga ttcttggggt     720
caaggtactc tggtgaccgt ctcctca                                         747
```

<210> SEQ ID NO 4
<211> LENGTH: 249
<212> TYPE: PRT
<213> ORGANISM: Artificial Sequence
<220> FEATURE:
<223> OTHER INFORMATION: Synthetic Construct

<400> SEQUENCE: 4

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Arg Gln Leu Pro Gly Thr Ala Pro Lys Leu Leu
        35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Arg Ala Gly Val Phe Gly Thr Gly Thr Lys Val Thr Val Leu Gly Ser
            100                 105                 110

Arg Gly Gly Gly Gly Ser Gly Gly Gly Ser Gly Gly Gly Ser
    115                 120                 125

Leu Glu Met Ala Gln Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Gly Ile Ser Ala Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Tyr Tyr Leu Ser Gln Ile Asp Ser Trp Gly
225                 230                 235                 240

Gln Gly Thr Leu Val Thr Val Ser Ser
                245

<210> SEQ ID NO 5
<211> LENGTH: 753
<212> TYPE: DNA
<213> ORGANISM: Artificial Sequence
<220> FEATURE:
<223> OTHER INFORMATION: Synthetic Construct

<400> SEQUENCE: 5
cagtctgtgt tgactcagcc accctcagcg tctgggaccc ccgggcagag ggtcaccatc      60
tcttgttctg gaagcagctc aacatcgga agtaatactg taaactggta ccagcagctc     120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggccatgtg    300
gtattcggcg gagggaccaa gctgaccgtc ctaggttcta gaggtggtgg tggtagcggc    360
ggcggcggct ctggtggtgg tggatccctc gagatggccg aggtccagct ggtgcagtct    420
ggggctgagg tgaagaagcc tggggctaca gtgaaaatct cctgcaaggt ttctggatac    480
accttcaccg actactacat gcactgggtg caacaggccc ctggaaaagg gcttgagtgg    540
atgggacttg ttgatcctga agatggtgaa acaatatacg cagagaagtt ccagggcaga    600
gtcaccataa ccgcggacac gtctacagac acagcctaca tggagctgag cagcctgaga    660
tctgaggaca cggccgtgta ttactgtgca accggaatct atagcagacc tctgggctac    720
tggggccagg gaaccctggt caccgtctcc tca                                  753

<210> SEQ ID NO 6
<211> LENGTH: 251
<212> TYPE: PRT
<213> ORGANISM: Artificial Sequence
<220> FEATURE:
<223> OTHER INFORMATION: Synthetic Construct

<400> SEQUENCE: 6

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly His Val Val Phe Gly Gly Thr Lys Leu Thr Val Leu Gly
            100                 105                 110

Ser Arg Gly Gly Gly Ser Gly Gly Gly Ser Gly Gly Gly
            115                 120                 125

Ser Leu Glu Met Ala Glu Val Gln Leu Val Gln Ser Gly Ala Glu Val
    130                 135                 140

Lys Lys Pro Gly Ala Thr Val Lys Ile Ser Cys Lys Val Ser Gly Tyr
145                 150                 155                 160

Thr Phe Thr Asp Tyr Tyr Met His Trp Val Gln Gln Ala Pro Gly Lys
                165                 170                 175

Gly Leu Glu Trp Met Gly Leu Val Asp Pro Glu Asp Gly Glu Thr Ile
            180                 185                 190

Tyr Ala Glu Lys Phe Gln Gly Arg Val Thr Ile Thr Ala Asp Thr Ser
        195                 200                 205

Thr Asp Thr Ala Tyr Met Glu Leu Ser Ser Leu Arg Ser Glu Asp Thr
    210                 215                 220

Ala Val Tyr Tyr Cys Ala Thr Gly Ile Tyr Ser Arg Pro Leu Gly Tyr
225                 230                 235                 240

Trp Gly Gln Gly Thr Leu Val Thr Val Ser Ser
                245                 250

<210> SEQ ID NO 7
<211> LENGTH: 759
<212> TYPE: DNA
<213> ORGANISM: Artificial Sequence
<220> FEATURE:
<223> OTHER INFORMATION: Synthetic Construct

<400> SEQUENCE: 7
tcctatgtgc tgactcagcc accctcagcg tctgggaccc ccgggcagag ggtcaccatc       60
tcttgttctg gaagcagctc caacatcgga agtcatactg taaactggta ccagcagctc      120
ccaggaacgg cccccaaact cctcatctat agtaataatc agcggccctc aggggtccct      180
gaccgattct ctggctccaa gtctggcacc tcagcctccc tggccatcag tgggctccag      240
tctgaggatg aggctgatta ttactgtgca gcatgggatg acagcctgaa tggttatgtc      300
ttcggaactg ggaccaaggt caccgtccta ggttctagag gtggtggtgg tagcggcggc      360
ggcggctctg gtggtggtgg atccctcgag atggccgagg tgcagctggt ggagactggg      420
ggaggcttgg tacagcctgg gggtccctg agactctcct gtgcagcctc tggattcacc      480
tttagcagct atgccatgag ctgggtccgc caggctccag ggaaggggct ggagtgggtc      540
tcagctatta gtggtagtgg tggtagcaca tactacgcag actccgtgaa gggccgattc      600
accatctcca gagacaattc caagaacacg ctgtatcttc aaatgaacag cctgagagct      660
gaggacacgg ccgtgtatta ctgtgcgcgc tctgacggta acatttctgt gcagcagtac      720
gatgcttggg gtcaaggtac tctggtgacc gtctcctca                             759

<210> SEQ ID NO 8
<211> LENGTH: 253
<212> TYPE: PRT
<213> ORGANISM: Artificial Sequence
<220> FEATURE:
<223> OTHER INFORMATION: Synthetic Construct

<400> SEQUENCE: 8

```
Ser Tyr Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser His
            20                  25                  30

Thr Val Asn Trp Tyr Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
            100                 105                 110

Arg Gly Gly Gly Ser Gly Gly Gly Ser Gly Gly Gly Ser
        115                 120                 125

Leu Glu Met Ala Glu Val Gln Leu Val Glu Thr Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Ala Ile Ser Gly Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Ser Asp Gly Lys His Phe Trp Gln Gln Tyr
225                 230                 235                 240

Asp Ala Trp Gly Gln Gly Thr Leu Val Thr Val Ser Ser
            245                 250
```

<210> SEQ ID NO 9
<211> LENGTH: 729
<212> TYPE: DNA
<213> ORGANISM: Artificial Sequence
<220> FEATURE:
<223> OTHER INFORMATION: Synthetic Construct

<400> SEQUENCE: 9

```
gacatccagt tgacccagtc tccatcctcc ctgtctgcat atgtgggaga cagagtcacc    60
atcacttgtc gggcgagtca gggcattacc aattctttag cctggtatca gcagaagcca   120
gggaaagccc ctaagctcct gctacatgct gcatccagat tggagtctgg ggtcccatcc   180
aggttcagtg gcagtggatt tgggacggat ttcactctca ccatcagcag cctgcagcct   240
gaagattttg cagtttatta ctgtcaacac tatttaggta ccccgtactc ttttggccag   300
gggaccaagg tggagatcaa acgttctaga ggtggtggtg gtagcggcgg cggcggctct   360
```

```
ggtggtggtg gatccctcga gatggccgag gtgcagctgg tggagtctgg aggaggcttg    420
gtccagcctg gggggtccct gagactctcc tgtgcagcct ctgggttcac cgtcagtagc    480
aactacatga gctgggtccg ccaggctcca gggaaggggc tggagtgggt ctcagctatt    540
agtggtagtg gtggtagcac atactacgca gactccgtga agggccggtt caccatctcc    600
agagacaatt ccaagaacac gctgtatctg caaatgaaca gcctgagagc cgaggacacg    660
gccgtatatt actgtgcgcg catgaacatc gattactggg gtcaaggtac tctggtgacc    720
gtctcctca                                                             729
```

\<210\> SEQ ID NO 10
\<211\> LENGTH: 243
\<212\> TYPE: PRT
\<213\> ORGANISM: Artificial Sequence
\<220\> FEATURE:
\<223\> OTHER INFORMATION: Synthetic Construct

\<400\> SEQUENCE: 10

```
Asp Ile Gln Leu Thr Gln Ser Pro Ser Ser Leu Ser Ala Tyr Val Gly
1               5                   10                  15

Asp Arg Val Thr Ile Thr Cys Arg Ala Ser Gln Gly Ile Thr Asn Ser
            20                  25                  30

Leu Ala Trp Tyr Gln Gln Lys Pro Gly Lys Ala Pro Lys Leu Leu Leu
        35                  40                  45

His Ala Ala Ser Arg Leu Glu Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Val Tyr Tyr Cys Gln His Tyr Leu Gly Thr Pro Tyr
                85                  90                  95

Ser Phe Gly Gln Gly Thr Lys Val Glu Ile Lys Arg Ser Arg Gly Gly
            100                 105                 110

Gly Gly Ser Gly Gly Gly Gly Ser Gly Gly Gly Gly Ser Leu Glu Met
        115                 120                 125

Ala Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Val Ser Ser
145                 150                 155                 160

Asn Tyr Met Ser Trp Val Arg Gln Ala Pro Gly Lys Gly Leu Glu Trp
                165                 170                 175

Val Ser Ala Ile Ser Gly Ser Gly Gly Ser Thr Tyr Tyr Ala Asp Ser
            180                 185                 190

Val Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Ala Arg Met Asn Ile Asp Tyr Trp Gly Gln Gly Thr Leu Val Thr
225                 230                 235                 240

Val Ser Ser
```

\<210\> SEQ ID NO 11
\<211\> LENGTH: 759
\<212\> TYPE: DNA
\<213\> ORGANISM: Artificial Sequence
\<220\> FEATURE:
\<223\> OTHER INFORMATION: Synthetic Construct

<400> SEQUENCE: 11

```
gaaattgtgc tgactcagtc tccatcctcc ctgtctgcat ctgtaggaga cagagtcacc      60
atctcttgcc gggcaagtca gagcgttagc agatttttaa attggtatca gcagaaaccg     120
ggtaaagccc ctaagctcct gatctatggt gtatccactt tggaacgtgg ggtcccttca     180
aggttcagtg gcagtggatc tgggacagat ttcactctca ccatcagcag tctgcaacct     240
gaagattttg caacttacta ctgtcaagag agttacatta tcccgctcac tttcggcgga     300
gggaccaagc tggagatcaa acgttctaga ggtggtggtg gtagcggcgg cggcggctct     360
ggtggtggtg gatccctcga gatggccgag gtgcagctgg tgcagtctgg agcagaggtg     420
aaaaggcccg gggagtctct gacgatctcc tgtaagggtt ctgaatacag ctttgccagc     480
tactggatca cctgggtgcg ccagatgccc gggaaaggcc tggagtggat ggggaggatt     540
gatcctagtg actcttatac caactacagc ccgtccttcc aaggccacgt caccatctca     600
gctgacaagt ccatcagcac tgcctacttg cagtggagca gcctgaaggc ctcggacacc     660
gccatatatt actgtgcgag accttttcag tacgactacg tggttactc cgatgctttt      720
gatatctggg gccaagggac aatggtcacc gtctcttca                            759
```

<210> SEQ ID NO 12
<211> LENGTH: 253
<212> TYPE: PRT
<213> ORGANISM: Artificial Sequence
<220> FEATURE:
<223> OTHER INFORMATION: Synthetic Construct

<400> SEQUENCE: 12

```
Glu Ile Val Leu Thr Gln Ser Pro Ser Leu Ser Ala Ser Val Gly
1               5                   10                  15

Asp Arg Val Thr Ile Ser Cys Arg Ala Ser Gln Ser Val Ser Arg Phe
            20                  25                  30

Leu Asn Trp Tyr Gln Gln Lys Pro Gly Lys Ala Pro Lys Leu Leu Ile
        35                  40                  45

Tyr Gly Val Ser Thr Leu Glu Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Ser Tyr Ile Ile Pro Leu
                85                  90                  95

Thr Phe Gly Gly Gly Thr Lys Leu Glu Ile Lys Arg Ser Arg Gly Gly
            100                 105                 110

Gly Gly Ser Gly Gly Gly Gly Ser Gly Gly Gly Gly Ser Leu Glu Met
        115                 120                 125

Ala Glu Val Gln Leu Val Gln Ser Gly Ala Glu Val Lys Arg Pro Gly
    130                 135                 140

Glu Ser Leu Thr Ile Ser Cys Lys Gly Ser Glu Tyr Ser Phe Ala Ser
145                 150                 155                 160

Tyr Trp Ile Thr Trp Val Arg Gln Met Pro Gly Lys Gly Leu Glu Trp
                165                 170                 175

Met Gly Arg Ile Asp Pro Ser Asp Ser Tyr Thr Asn Tyr Ser Pro Ser
            180                 185                 190

Phe Gln Gly His Val Thr Ile Ser Ala Asp Lys Ser Ile Ser Thr Ala
        195                 200                 205

Tyr Leu Gln Trp Ser Ser Leu Lys Ala Ser Asp Thr Ala Ile Tyr Tyr
```

```
                  210                 215                 220
Cys Ala Arg Pro Phe Gln Tyr Asp Tyr Gly Gly Tyr Ser Asp Ala Phe
225                 230                 235                 240

Asp Ile Trp Gly Gln Gly Thr Met Val Thr Val Ser Ser
                245                 250

<210> SEQ ID NO 13
<211> LENGTH: 753
<212> TYPE: DNA
<213> ORGANISM: Artificial Sequence
<220> FEATURE:
<223> OTHER INFORMATION: Synthetic Construct

<400> SEQUENCE: 13
gaaattgtga tgacgcagtc tccactctcc ctgtccgtca cccctggaga gccggcctcc      60
atctcctgca ggtctagtca gagcctcttg acagcaatg gattcaactc tttggattgg     120
tacctgcaga agccagggca gtctccacaa ctcctgatcc atttaggttc tgatcgggcc     180
tccggggtcc ctgacaggtt cagcggcagt ggatcaggca cagattttac actgaaaatc     240
agcagagtgg aggctgagga tgttggaatt tattactgca tgcagtctct acaaattccg     300
acgttcggcc aagggaccaa ggtggaaatc aaacgttcta gaggtggtgg tggtagcggc     360
ggcggcggct ctggtggtgg tggatccctc gagatggccc agatgcagct ggtgcaatct     420
ggggctgagg tgaagaaggc tgggtcctcg gtgaaggtct cctgcgagac ttctggaggc     480
accttcagca gctctagtgt caactgggtg cgacaggccc ctggacaagg gcttgagtgg     540
atgggaggaa tcatccctat cgttggaaca ccaaactacg cacagaagtt ccaggacaga     600
gtcacgatta ccgcggtcga atccaccttt acagcctaca tggagctgag cggcctgaga     660
tctgaggaca cggccgttta ttactgtgcg cgggggggat atcgcgacta tatggatgtc     720
tggggcagag ggaccacggt caccgtctcc tca                                 753

<210> SEQ ID NO 14
<211> LENGTH: 251
<212> TYPE: PRT
<213> ORGANISM: Artificial Sequence
<220> FEATURE:
<223> OTHER INFORMATION: Synthetic Construct

<400> SEQUENCE: 14

Glu Ile Val Met Thr Gln Ser Pro Leu Ser Leu Ser Val Thr Pro Gly
1               5                  10                  15

Glu Pro Ala Ser Ile Ser Cys Arg Ser Ser Gln Ser Leu Leu Asp Ser
            20                  25                  30

Asn Gly Phe Asn Ser Leu Asp Trp Tyr Leu Gln Lys Pro Gly Gln Ser
        35                  40                  45

Pro Gln Leu Leu Ile His Leu Gly Ser Asp Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Leu Gln Ile Pro Thr Phe Gly Gln Gly Thr Lys Val Glu Ile Lys Arg
            100                 105                 110

Ser Arg Gly Gly Gly Gly Ser Gly Gly Gly Gly Ser Gly Gly Gly Gly
        115                 120                 125

Ser Leu Glu Met Ala Gln Met Gln Leu Val Gln Ser Gly Ala Glu Val
```

```
                    130                 135                 140
Lys Lys Ala Gly Ser Ser Val Lys Val Ser Cys Glu Thr Gly Gly
145                 150                 155                 160

Thr Phe Ser Ser Ser Val Asn Trp Val Arg Gln Ala Pro Gly Gln
                165                 170                 175

Gly Leu Glu Trp Met Gly Gly Ile Ile Pro Ile Val Gly Thr Pro Asn
                180                 185                 190

Tyr Ala Gln Lys Phe Gln Asp Arg Val Thr Ile Thr Ala Val Glu Ser
                195                 200                 205

Thr Phe Thr Ala Tyr Met Glu Leu Ser Gly Leu Arg Ser Glu Asp Thr
                210                 215                 220

Ala Val Tyr Tyr Cys Ala Arg Gly Gly Tyr Arg Asp Tyr Met Asp Val
225                 230                 235                 240

Trp Gly Arg Gly Thr Thr Val Thr Val Ser Ser
                245                 250

<210> SEQ ID NO 15
<211> LENGTH: 747
<212> TYPE: DNA
<213> ORGANISM: Artificial Sequence
<220> FEATURE:
<223> OTHER INFORMATION: Synthetic Construct

<400> SEQUENCE: 15
tcctatgagc tgactcagcc accctcagcg tctgggaccc ccgggcagag ggtcaccatc     60
tcttgttctg gaagcagctc caacatcgga agtaattatg tatactggta ccagcagctc    120
ccaggaacgg cccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag tggttatgtc    300
ttcggaactg ggaccaaggt caccgtccta ggttctagag gtggtggtgg tagcggcggc    360
ggcggctctg gtggtggtgg atccctcgag atggccgagg tgcagctggt ggagtctgga    420
ggaggcttga tccagcctgg ggggtccctg agactctcct gtgcagcctc tgggttcacc    480
gtcagtagca actacatgag ctgggtccgc caggctccag gaaggggct ggagtgggtc    540 tcagttattt atagcggtgg tagcacatac tacgcagact ccgtgaaggg ccgattcacc    600
atctccagag acaattccaa gaacacgctg tatcttcaaa tgaacagcct gagagccgag    660
gacacggccg tgtattactg tgcgaggggg gggtttggag ctgaatttga ctactgggc    720 cagggaaccc tggtcaccgt ctcctca                                        747

<210> SEQ ID NO 16
<211> LENGTH: 249
<212> TYPE: PRT
<213> ORGANISM: Artificial Sequence
<220> FEATURE:
<223> OTHER INFORMATION: Synthetic Construct

<400> SEQUENCE: 16

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
                35                  40                  45

Ile Tyr Arg Asn Asn Gln Arg Pro Ser Gly Val Pro Asp Arg Phe Ser
```

```
                   50                  55                  60
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Tyr Val Phe Gly Thr Gly Thr Lys Val Thr Val Leu Gly Ser
            100                 105                 110

Arg Gly Gly Gly Ser Gly Gly Gly Ser Gly Gly Gly Ser
            115                 120                 125

Leu Glu Met Ala Glu Val Gln Leu Val Glu Ser Gly Gly Gly Leu Ile
            130                 135                 140

Gln Pro Gly Gly Ser Leu Arg Leu Ser Cys Ala Ala Ser Gly Phe Thr
145                 150                 155                 160

Val Ser Ser Asn Tyr Met Ser Trp Val Arg Gln Ala Pro Gly Lys Gly
                165                 170                 175

Leu Glu Trp Val Ser Val Ile Tyr Ser Gly Gly Ser Thr Tyr Tyr Ala
            180                 185                 190

Asp Ser Val Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
210                 215                 220

Tyr Tyr Cys Ala Arg Gly Gly Phe Gly Ala Glu Phe Asp Tyr Trp Gly
225                 230                 235                 240

Gln Gly Thr Leu Val Thr Val Ser Ser
                245
```

<210> SEQ ID NO 17
<211> LENGTH: 756
<212> TYPE: DNA
<213> ORGANISM: Artificial Sequence
<220> FEATURE:
<223> OTHER INFORMATION: Synthetic Construct

<400> SEQUENCE: 17

```
tcctatgtgc tgactcagcc accctcagtg tccgtgtccc caggacagac agccagcatc    60
acctgctctg gagataaaatt gggggataaa tatgcttcct ggtatcagca aagccaggc   120
cagtcccctg tactggtcat ctatcaagat aacaagcggc cctcagggat ccctgagcga   180
ttctctggct ccaactctgg aacacagcc actctgacca tcagcgggac ccaggctatg   240
gatgaggctg actattactg tcaggcgtgg acagcagca ctgaggatgt cttcggacct   300
gggaccaagg tcaccgtcct aggttctaga ggtggtggtg gtagcggcgg cggcggctct   360
ggtggtggtg gatccctcga gatggccgag gtgcagctgg tggagtctgg aggaggcttg   420
atccagcctg gggggtccct gagactctcc tgtgcagcct ctgggttcac cgtcagtagc   480
aactacatga gctgggtccg ccaggctcca gggaaggggc tggagtgggt ctcagttatt   540
tatagcggtg gtagcacata ctacgcagac tccgtgaagg gccgattcac catctccaga   600
gacaattcca agaacacgct gtatcttcaa atgaacagcc tgagagccga ggacacggcc   660
gtgtattact gtgcgagagg tggtatttcg gacgattact atggttcggg gagttatgat   720
aactgggggcc agggaaccct ggtcaccgtc tcctca                            756
```

<210> SEQ ID NO 18
<211> LENGTH: 252
<212> TYPE: PRT
<213> ORGANISM: Artificial Sequence
<220> FEATURE:
<223> OTHER INFORMATION: Synthetic Construct

<400> SEQUENCE: 18

Ser Tyr Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Glu Asp
                85                  90                  95

Val Phe Gly Pro Gly Thr Lys Val Thr Val Leu Gly Ser Arg Gly Gly
            100                 105                 110

Gly Gly Ser Gly Gly Gly Gly Ser Gly Gly Gly Gly Ser Leu Glu Met
        115                 120                 125

Ala Glu Val Gln Leu Val Glu Ser Gly Gly Gly Leu Ile Gln Pro Gly
    130                 135                 140

Gly Ser Leu Arg Leu Ser Cys Ala Ala Ser Gly Phe Thr Val Ser Ser
145                 150                 155                 160

Asn Tyr Met Ser Trp Val Arg Gln Ala Pro Gly Lys Gly Leu Glu Trp
                165                 170                 175

Val Ser Val Ile Tyr Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Gly Gly Ile Ser Asp Asp Tyr Tyr Gly Ser Gly Ser Tyr Asp
225                 230                 235                 240

Asn Trp Gly Gln Gly Thr Leu Val Thr Val Ser Ser
                245                 250

<210> SEQ ID NO 19
<211> LENGTH: 741
<212> TYPE: DNA
<213> ORGANISM: Artificial Sequence
<220> FEATURE:
<223> OTHER INFORMATION: Synthetic Construct

<400> SEQUENCE: 19
gacatccagt tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccccttca cttcggcgga     300
gggaccaagg tggagatcaa acgttctaga ggtggtggtg gtagcggcgg cggcggctct     360
ggtggtggtg gatccctcga gatggccgag gtgcagctgg tggagtctgg gggaggcttg     420
gtccagcctg gggggtccct gagactctcc tgtgcagcct ctggattcac cgtcagtagc     480

-continued

```
aactacatga gctgggtccg ccaggctcca gggaaggggc tggagtgggt ctcagttatt    540
tatagcggtg gtagcacata ctacgcagac tccgtgaagg gccgattcac catctccaga    600
gacaattcca agaacacgct gtatcttcaa atgaacagcc tgagagctga ggacacggct    660
gtgtattact gtgcgagaga aaggggatg ggatatgctt ttgatatctg gggccaaggg     720
acaatggtca ccgtctcttc a                                              741
```

<210> SEQ ID NO 20
<211> LENGTH: 247
<212> TYPE: PRT
<213> ORGANISM: Artificial Sequence
<220> FEATURE:
<223> OTHER INFORMATION: Synthetic Construct

<400> SEQUENCE: 20

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gly Gly Thr Lys Val Glu Ile Lys Arg Ser Arg Gly Gly
            100                 105                 110

Gly Gly Ser Gly Gly Gly Gly Ser Gly Gly Gly Gly Ser Leu Glu Met
        115                 120                 125

Ala Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Val Ser Ser
145                 150                 155                 160

Asn Tyr Met Ser Trp Val Arg Gln Ala Pro Gly Lys Gly Leu Glu Trp
                165                 170                 175

Val Ser Val Ile Tyr Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Glu Arg Gly Met Gly Tyr Ala Phe Asp Ile Trp Gly Gln Gly
225                 230                 235                 240

Thr Met Val Thr Val Ser Ser
                245
```

<210> SEQ ID NO 21
<211> LENGTH: 720
<212> TYPE: DNA
<213> ORGANISM: Artificial Sequence
<220> FEATURE:
<223> OTHER INFORMATION: Synthetic Construct

<400> SEQUENCE: 21

```
gacatccaga tgacccagtc tccatcctcc ctgtctgcat ctgtaggaga cagagtcacc    60
```

-continued

```
atcacttgcc gggccagtca gggcattggc agttatttag cctggtatca gcaaaaacca    120
gggaaagccc ctaaactcct gatctatcct gcatccacgt tgcaaagtgg ggtcccatca    180
agattcagcg gcagtggatc tgggacagaa ttcactctca caatcagcag cctgcagcct    240
gaagattttg caacttatta ctgtcaacaa cttaatagtc tcttcggcca agggacacga    300
ctggagatta aacgttctag aggtggtggt ggtagcggcg gcggcggctc tggtggtggt    360
ggatccctcg agatggccca gctgcagctg caggagtcgg gcccaggact ggtgaagcct    420
tcggagaccc tgtccctcac ctgctctgtc tctggtgtct ccatgagtga aaactactgg    480
agctggatcc ggcagccccc agggaagcga ctggagtgga ttgggtgtgc cattacact    540 ggggacaccc actacaaccc ctccctcaag gtcgagtca ccatatcact agacacgtcc    600
atgaaccagt tctccctgag gctgaactct gtgaccgctg cggacacggc cgtctattac    660
tgtgcgagtt atcatccctt taactactgg ggccaggaa ccctggtcac cgtctcctca    720
```

<210> SEQ ID NO 22
<211> LENGTH: 240
<212> TYPE: PRT
<213> ORGANISM: Artificial Sequence
<220> FEATURE:
<223> OTHER INFORMATION: Synthetic Construct

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Tyr
            20                  25                  30

Leu Ala Trp Tyr Gln Gln Lys Pro Gly Lys Ala Pro Lys Leu Leu Ile
        35                  40                  45

Tyr Pro Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Leu Phe Gly
                85                  90                  95

Gln Gly Thr Arg Leu Glu Ile Lys Arg Ser Arg Gly Gly Gly Gly Ser
            100                 105                 110

Gly Gly Gly Gly Ser Gly Gly Gly Ser Leu Glu Met Ala Gln Leu
        115                 120                 125

Gln Leu Gln Glu Ser Gly Pro Gly Leu Val Lys Pro Ser Glu Thr Leu
    130                 135                 140

Ser Leu Thr Cys Ser Val Ser Gly Val Ser Met Ser Glu Asn Tyr Trp
145                 150                 155                 160

Ser Trp Ile Arg Gln Pro Pro Gly Lys Arg Leu Glu Trp Ile Gly Cys
                165                 170                 175

Ala His Tyr Thr Gly Asp Thr His Tyr Asn Pro Ser Leu Lys Gly Arg
            180                 185                 190

Val Thr Ile Ser Leu Asp Thr Ser Met Asn Gln Phe Ser Leu Arg Leu
        195                 200                 205

Asn Ser Val Thr Ala Ala Asp Thr Ala Val Tyr Tyr Cys Ala Ser Tyr
    210                 215                 220

His Pro Phe Asn Tyr Trp Gly Gln Gly Thr Leu Val Thr Val Ser Ser
225                 230                 235                 240
```

```
<210> SEQ ID NO 23
<211> LENGTH: 774
<212> TYPE: DNA
<213> ORGANISM: Artificial Sequence
<220> FEATURE:
<223> OTHER INFORMATION: Synthetic Construct

<400> SEQUENCE: 23
caggctgtgc tgactcagcc accctcggcg tctgggaccc ccgggcagag ggtcaccatc      60
tcttgttctg gaagcagctc caacatcgga actaaaactg taaactggta tcaggtgctc     120
ccaggaacgg ccccaaaact cctcatctat agtaattatc gccggccctc agggggtccct   180 gaccgattct ctggctccaa gtctggcacc tcagcctccc tggccatcag tgggctccag    240
tctgacgatg aggctgatta ttactgtgca ctatgggatg acagcctgga tggttatgtc    300
ttcggaactg gaccaaggt caccgtccta ggttctagag gtggtggtgg tagcggcggc      360
ggcggctctg gtggtggtgg atccctcgag atggccgagg tccagctggt gcagtctggg    420
gctgaggtga ggaggcctgg ggctacagtg aaaatctcct gcaaggtttc tggatacacc    480
ttcaacgact tctacttaca ctgggtgcga caggcccctg gaaagggct tgagtggatg     540 ggacgtattg atcctgaaga tggtaaaaca agatatgcag agaagttcca gggcagactc    600
accattaccg cggacacgtc tacagacact ctttacatgc aactgggcgg cctgacatct    660
gacgacacgg ccgtctatta ctgtacaact gattggggct atagcagttc cctacgtgag   720
gaggacatct ggtacgactg ctggggccag ggaaccctgg tcaccgtctc ctca          774

<210> SEQ ID NO 24
<211> LENGTH: 258
<212> TYPE: PRT
<213> ORGANISM: Artificial Sequence
<220> FEATURE:
<223> OTHER INFORMATION: Synthetic Construct

<400> SEQUENCE: 24

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Lys
                20                  25                  30

Thr Val Asn Trp Tyr Gln Val Leu Pro Gly Thr Ala Pro Lys Leu Leu
            35                  40                  45

Ile Tyr Ser Asn Tyr Arg Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Asp Asp Glu Ala Asp Tyr Tyr Cys Ala Leu Trp Asp Asp Ser Leu
                85                  90                  95

Asp Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Arg
    130                 135                 140

Arg Pro Gly Ala Thr Val Lys Ile Ser Cys Lys Val Ser Gly Tyr Thr
145                 150                 155                 160

Phe Asn Asp Phe Tyr Leu His Trp Val Arg Gln Ala Pro Gly Lys Gly
                165                 170                 175

Leu Glu Trp Met Gly Arg Ile Asp Pro Glu Asp Gly Lys Thr Arg Tyr
```

```
                180                 185                 190
Ala Glu Lys Phe Gln Gly Arg Leu Thr Ile Thr Ala Asp Thr Ser Thr
            195                 200                 205

Asp Thr Leu Tyr Met Gln Leu Gly Gly Leu Thr Ser Asp Asp Thr Ala
        210                 215                 220

Val Tyr Tyr Cys Thr Thr Asp Trp Gly Tyr Ser Ser Leu Arg Glu
225                 230                 235                 240

Glu Asp Ile Trp Tyr Asp Cys Trp Gly Gln Gly Thr Leu Val Thr Val
                245                 250                 255

Ser Ser

<210> SEQ ID NO 25
<211> LENGTH: 756
<212> TYPE: DNA
<213> ORGANISM: Artificial Sequence
<220> FEATURE:
<223> OTHER INFORMATION: Synthetic Construct

<400> SEQUENCE: 25
tcctatgagc tgactcagcc accctcagtg tcagtggccc caggaaagac ggccaggatt    60
acctgtgggg gaaacaacat tggaagtaaa agtgtgcact ggtaccagca gaagccaggc   120
caggcccctg tgctggtcat ctattatgat agcgaccggc cctcagggat ccctgagcga   180
ttctctggct ccaactctgg gaacacggcc accctgacca tcagcagggt cgaagccggg   240
gatgaggccg actattactg tcaggtgtgg atagtagta gtgatcatta tgtcttcgga    300
actgggacca aggtcaccgt cctaggttct agaggtggtg gtggtagcgg cggcggcggc   360
tctggtggtg gtggatcccc tcgagatggc gaggtgcagc tggtgcagtc tggggctgag   420
gtgaagaagc ctgggtcctc ggtgaaggtc tcctgcaagg cttctggagg caccttcagc   480
agctatgcta tcagctgggt gcgacaggcc cctggacaag gcttgagtg atgggaggg    540 atcatccta tctttggtac agcaaactac gcacagaagt tccagggcag agtcacgatt   600
accgcggacg aatccacgag cacagcctac atggagctga gcagcctgag atctgaggac   660
acggccgtgt attactgtgc gagagattat gggtacggtg actacggtga tgcttttgat   720
atctggggcc aagggacaat ggtcaccgtc tcttca                             756

<210> SEQ ID NO 26
<211> LENGTH: 252
<212> TYPE: PRT
<213> ORGANISM: Artificial Sequence
<220> FEATURE:
<223> OTHER INFORMATION: Synthetic Construct

<400> SEQUENCE: 26

Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95
```

```
Tyr Val Phe Gly Thr Gly Thr Lys Val Thr Val Leu Gly Ser Arg Gly
            100                 105                 110

Gly Gly Gly Ser Gly Gly Gly Ser Gly Gly Gly Ser Leu Glu
        115                 120                 125

Met Ala Glu Val Gln Leu Val Gln Ser Gly Ala Glu Val Lys Lys Pro
    130                 135                 140

Gly Ser Ser Val Lys Val Ser Cys Lys Ala Ser Gly Gly Thr Phe Ser
145                 150                 155                 160

Ser Tyr Ala Ile Ser Trp Val Arg Gln Ala Pro Gly Gln Gly Leu Glu
                165                 170                 175

Trp Met Gly Gly Ile Ile Pro Ile Phe Gly Thr Ala Asn Tyr Ala Gln
            180                 185                 190

Lys Phe Gln Gly Arg Val Thr Ile Thr Ala Asp Glu Ser Thr Ser Thr
        195                 200                 205

Ala Tyr Met Glu Leu Ser Ser Leu Arg Ser Glu Asp Thr Ala Val Tyr
    210                 215                 220

Tyr Cys Ala Arg Asp Tyr Gly Tyr Gly Asp Tyr Gly Asp Ala Phe Asp
225                 230                 235                 240

Ile Trp Gly Gln Gly Thr Met Val Thr Val Ser Ser
                245                 250
```

<210> SEQ ID NO 27
<211> LENGTH: 753
<212> TYPE: DNA
<213> ORGANISM: Artificial Sequence
<220> FEATURE:
<223> OTHER INFORMATION: Synthetic Construct

<400> SEQUENCE: 27

```
tcctatgtgc tgactcagcc accctcggtg tcagtggccc caggaaagac ggccaggatt      60
acctgtgggg gaaacaacat tggaagtaaa agtgtgcact ggtaccagca gaggccaggc     120
caggcccctg tgctggtcgt ctatgatgat agcgaccggc cctcagggat ccctgagcga     180
ttctctggct ccaactctgg aaacacggcc accctgacca tcagcagggt cgaagccggg     240
gatgaggccg actattcctg tcaggtgtgg gatagcagta gtgatcatta tgtcttcgga     300
cctgggacca aggtcaccgt cctaggttct agaggtggtg gtggtagcgg cggcggcggc     360
tctggtggtg gtggatccct cgagatggcc gaagtgcagc tggtgcagtc tggagcagag     420
gtgaaaaagc ccggggagtc tctgaagatc tcctgtaagg gttctggata cagctttacc     480
agctactgga tcggctgggt gcgccagatg cccgggaaag gcctggagtg gatgggggatc     540
atctatcctg gtgactctga taccagatac agcccgtcct tccaaggcca ggtcaccatc     600
tcagccgaca gtccatcagc accgcctac ctgcagtgga gcagcctgaa ggcctcggac     660
accgccatgt attactgtgc gcgcgttgtt ggtactatct actctatgca gtacgatgtt     720
tggggtcaag gtactctggt gaccgtctcc tca                                  753
```

<210> SEQ ID NO 28
<211> LENGTH: 251
<212> TYPE: PRT
<213> ORGANISM: Artificial Sequence
<220> FEATURE:
<223> OTHER INFORMATION: Synthetic Construct

<400> SEQUENCE: 28

```
Ser Tyr Val Leu Thr Gln Pro Pro Ser Val Ser Val Ala Pro Gly Lys
1               5                   10                  15
```

```
Thr Ala Arg Ile Thr Cys Gly Gly Asn Asn Ile Gly Ser Lys Ser Val
            20                  25                  30

His Trp Tyr Gln Gln Arg Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Ser Cys Gln Val Trp Asp Ser Ser Asp His
                85                  90                  95

Tyr Val Phe Gly Pro Gly Thr Lys Val Thr Val Leu Gly Ser Arg Gly
            100                 105                 110

Gly Gly Gly Ser Gly Gly Gly Ser Gly Gly Gly Gly Ser Leu Glu
            115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Val Val Gly Thr Ile Tyr Ser Met Gln Tyr Asp Val
225                 230                 235                 240

Trp Gly Gln Gly Thr Leu Val Thr Val Ser Ser
                245                 250

<210> SEQ ID NO 29
<211> LENGTH: 780
<212> TYPE: DNA
<213> ORGANISM: Artificial Sequence
<220> FEATURE:
<223> OTHER INFORMATION: Synthetic Construct

<400> SEQUENCE: 29
ctgcctgtgc tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgattatgt ggtattcggc     300
ggagggacca agctgaccgt cctaggttct agaggtggtg gtggtagcgg cggcggcggc     360
tctggtggtg gtggatccct cgagatggcc gaagtgcagc tggtgcagtc tggagcagag     420
gtgaaaaagc ccggggagtc tctgaagatc tcctgtaagg gttctggata cagctttacc     480
agctactgga tcggctgggt gcgccagatg cccgggaaag cctggagtg atggggatc     540 atctatcctg gtgactctga taccagatac agcccgtcct tccaaggcca ggtcaccatc     600
tcagccgaca gtccatcag caccgcctac ctgcagtgga gcagcctgaa ggcctcggac     660
accgccatgt attactgtgc gcgccaggtt tggggttggc agggtggtat gtacccgcgt     720
```
tctaactggt ggtacaacat ggattcttgg ggtcaaggta ctctggtgac cgtctcctca    780

<210> SEQ ID NO 30
<211> LENGTH: 260
<212> TYPE: PRT
<213> ORGANISM: Artificial Sequence
<220> FEATURE:
<223> OTHER INFORMATION: Synthetic Construct

<400> SEQUENCE: 30

```
Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260
```

<210> SEQ ID NO 31
<211> LENGTH: 759
<212> TYPE: DNA
<213> ORGANISM: Artificial Sequence
<220> FEATURE:
<223> OTHER INFORMATION: Synthetic Construct

<400> SEQUENCE: 31
caggctgtgc tgactcagcc accctcggtg tctgaagccc ccaggcagag ggtcaccatc    60
tcctgttctg gaagcagctc caacgtcgga aataatgctg taaactggta ccagcaggtc   120
ccaggaaagg ctcccaaact cctcatctat tatgatgatc tgctgtcctc agggtctct   180

```
gaccgattct ctggctccaa gtctggcacc tcagcctccc tggccatcag tgggctccag    240
tctgaggatg aggccgatta ttattgtgca gcatgggatg acagcctgaa tggtccggta    300
ttcggcggag ggaccaagct gaccgtccta ggttctagag gtggtggtgg tagcggcggc    360
ggcggctctg gtggtggtgg atccctcgag atggccgaag tgcagctggt gcagtctgga    420
gcagaggtga aaaagcccgg ggagtctctg aagatctcct gtaagggttc tggatacagc    480
tttaccagct actggatcgg ctgggtgcgc cagatgcccg ggaaaggcct ggagtggatg    540
gggatcatct atcctggtga ctctgatacc agatacagcc cgtccttcca aggccaggtc    600
accatctcag ccgacaagtc catcagcacc gcctacctgc agtggagcag cctgaaggcc    660
tcggacaccg ccatgtatta ctgtgcgcgc tggtcttcta cttgggactc tatgtacatg    720
gattactggg gtcaaggtac tctggtgacc gtctcctca                          759
```

```
<210> SEQ ID NO 32
<211> LENGTH: 253
<212> TYPE: PRT
<213> ORGANISM: Artificial Sequence
<220> FEATURE:
<223> OTHER INFORMATION: Synthetic Construct

<400> SEQUENCE: 32

Gln Ala Val Leu Thr Gln Pro Pro Ser Val Ser Glu Ala Pro Arg Gln
1               5                   10                  15

Arg Val Thr Ile Ser Cys Ser Gly Ser Ser Asn Val Gly Asn Asn
            20                  25                  30

Ala Val Asn Trp Tyr Gln Gln Val Pro Gly Lys Ala Pro Lys Leu Leu
        35                  40                  45

Ile Tyr Tyr Asp Asp Leu Leu Ser Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Trp Ser Ser Thr Trp Asp Ser Met Tyr Met
225                 230                 235                 240

Asp Tyr Trp Gly Gln Gly Thr Leu Val Thr Val Ser Ser
                245                 250
```

<210> SEQ ID NO 33
<211> LENGTH: 756
<212> TYPE: DNA
<213> ORGANISM: Artificial Sequence
<220> FEATURE:
<223> OTHER INFORMATION: Synthetic Construct

<400> SEQUENCE: 33

```
cagcctgtgc tgactcagcc accctcagtg tcagtggccc caggaaagac ggccaggatc      60
acctgtggag gaaacaacat tggaagtgaa agtgtgcact ggtaccagca gaagccaggc     120
caggccccta tggtggtcat ctattatgat agcaaccggc cctcagggat ccctgagcga     180
ttctctggct ccaactctgg gaacacggcc accctgaccg tcagcagggt cgaagccgag     240
gatgaggccg actattactg tcaggtgtgg aatagtagta gtgatcatcg aggagtgttc     300
ggcggaggga ccaagctgac cgtcctaggt tctagaggtg gtggtggtag cggcggcggc     360
ggctctggtg gtggtggatc cctcgagatg gccgaagtgc agctggtgca gtctggagca     420
gaggtgaaaa agcccgggga gtctctgagg atctcctgta agggttctgg atacagcttt     480
accagctact ggatcggctg ggtgcgccag atgcccggga aggcctgga gtggatgggg     540
atcatctatc ctggtgactc tgataccaga tacagcccgt ccttccaagg ccaggtcacc     600
atctcagccg acaagtccat cagcaccgcc tacctgcagt ggagcagcct gaaggcctcg     660
gacaccgcca tgtattactg tgcgcgcgtt acttactcta tggactctta ctacttcgat     720
tcttggggtc aaggtactct ggtgaccgtc tcctca                               756
```

<210> SEQ ID NO 34
<211> LENGTH: 252
<212> TYPE: PRT
<213> ORGANISM: Artificial Sequence
<220> FEATURE:
<223> OTHER INFORMATION: Synthetic Construct

<400> SEQUENCE: 34

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Glu Ser Val
            20                  25                  30

His Trp Tyr Gln Gln Lys Pro Gly Gln Ala Pro Met Val Val Ile Tyr
        35                  40                  45

Tyr Asp Ser Asn Arg Pro Ser Gly Ile Pro Glu Arg Phe Ser Gly Ser
    50                  55                  60

Asn Ser Gly Asn Thr Ala Thr Leu Thr Val Ser Arg Val Glu Ala Glu
65                  70                  75                  80

Asp Glu Ala Asp Tyr Tyr Cys Gln Val Trp Asn Ser Ser Ser Asp His
                85                  90                  95

Arg Gly Val Phe Gly Gly Gly Thr Lys Leu Thr Val Leu Gly Ser Arg
            100                 105                 110

Gly Gly Gly Gly Ser Gly Gly Gly Ser Gly Gly Gly Gly Ser Leu
            115                 120                 125

Glu Met Ala Glu Val Gln Leu Val Gln Ser Gly Ala Glu Val Lys Lys
        130                 135                 140

Pro Gly Glu Ser Leu Arg Ile Ser Cys Lys Gly Ser Gly Tyr Ser Phe
145                 150                 155                 160

Thr Ser Tyr Trp Ile Gly Trp Val Arg Gln Met Pro Gly Lys Gly Leu
                165                 170                 175

```
Glu Trp Met Gly Ile Ile Tyr Pro Gly Asp Ser Asp Thr Arg Tyr Ser
            180                 185                 190
Pro Ser Phe Gln Gly Gln Val Thr Ile Ser Ala Asp Lys Ser Ile Ser
            195                 200                 205
Thr Ala Tyr Leu Gln Trp Ser Ser Leu Lys Ala Ser Asp Thr Ala Met
            210                 215                 220
Tyr Tyr Cys Ala Arg Val Thr Tyr Ser Met Asp Ser Tyr Tyr Phe Asp
225                 230                 235                 240
Ser Trp Gly Gln Gly Thr Leu Val Thr Val Ser Ser
                245                 250
```

<210> SEQ ID NO 35
<211> LENGTH: 780
<212> TYPE: DNA
<213> ORGANISM: Artificial Sequence
<220> FEATURE:
<223> OTHER INFORMATION: Synthetic Construct

<400> SEQUENCE: 35

```
ctgcctgtgc ttactcagcc accctcggtg tcagtggccc caggaaagac ggccaggatt    60
acctgtgggg gaaacaacat tggaagtaaa agtgtgcact ggtaccagca gaagccaggc   120
caggccctg tgctggtcgt ctatgatgat agcgaccggc cctcagggat ccctgagcga   180
ttctctggct ccaactctgg gaacacggcc accctgacca tcaacagggt cgaagccggg   240
gatgaggccg actattactg tcaggtgtgg gatagtagta gtgattatgt ggtattcggc   300
ggagggacca gctgaccgt cctaggttct agaggtggtg gtggtagcgg cggcggcggc   360
tctggtggtg gtggatccct cgagatggcc gaagtgcagc tggtgcagtc tggagcagag   420
gtgaaaaagc ctggggagtc tctgaagatc cctgtaagg gttctggata cagctttacc   480
agctactgga tcggctgggt gcgccagatg cccgggaaag gcctggagtg gatggggatc   540
atctatcctg gtgactctga taccagatac agcccgtcct ccaaggcca ggtcaccatc   600
tcagccgaca agtccatcag caccgcctac ctgcagtgga gcagcctgaa ggcctcggac   660
accgccatgt attactgtgc gcgccaggtt tggggttggc agggtggtat gtacccgcgt   720
tctaactggg ggtacaacat ggattcttgg ggtcaaggta ctctggtgac tgtctcctca   780
```

<210> SEQ ID NO 36
<211> LENGTH: 260
<212> TYPE: PRT
<213> ORGANISM: Artificial Sequence
<220> FEATURE:
<223> OTHER INFORMATION: Synthetic Construct

<400> SEQUENCE: 36

```
Leu Pro Val Leu Thr Gln Pro Pro Ser Val Ser Val Ala Pro Gly Lys
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Val Tyr
            35                  40                  45
Asp Asp Ser Asp Arg Pro Ser Gly Ile Pro Glu Arg Phe Ser Gly Ser
        50                  55                  60
Asn Ser Gly Asn Thr Ala Thr Leu Thr Ile Asn Arg Val Glu Ala Gly
65                  70                  75                  80
Asp Glu Ala Asp Tyr Tyr Cys Gln Val Trp Asp Ser Ser Ser Asp Tyr
                85                  90                  95
```

```
Val Val Phe Gly Gly Gly Thr Lys Leu Thr Val Leu Gly Ser Arg Gly
                100                 105                 110

Gly Gly Gly Ser Gly Gly Gly Ser Gly Gly Gly Ser Leu Glu
            115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
            195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260

<210> SEQ ID NO 37
<211> LENGTH: 780
<212> TYPE: DNA
<213> ORGANISM: Artificial Sequence
<220> FEATURE:
<223> OTHER INFORMATION: Synthetic Construct

<400> SEQUENCE: 37
ctgcctgtgc tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgattatgt ggtatttggc     300
ggagggacca agctgaccgt cctaggttct agaggtggtg gtggtagcgg cggcggcggc     360
tctggtggtg gtggatccct cgagatggcc gaagtgcggc tggtgcagtc tggagcagag     420
gtgaaaaagc ccggggagtc tctgaagatc tcctgcaagg gttctggata cagctttacc     480
agcttctgga tcggctgggt gcgccagatg cccgggaaag gcctggagtg gatggggatc     540
atctatcctg gtgactctga taccagatac agcccgtcct tccaaggcca ggtcaccatc     600
tcagccgaca agtccatcag caccgcctac ctgcagtgga gcagcctgaa ggcctcggac     660
accgcgatgt attactgtgt gcgccaggtt tggggttggc agggtggtat gtacccgcgt     720
tctaactggt ggtacaacat ggattcttgg ggtcaaggta ctctggtaac cgtctcctca     780

<210> SEQ ID NO 38
<211> LENGTH: 260
<212> TYPE: PRT
<213> ORGANISM: Artificial Sequence
<220> FEATURE:
<223> OTHER INFORMATION: Synthetic Construct

<400> SEQUENCE: 38
```

-continued

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
                35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Gly Gly Ser Leu Glu
                115                 120                 125

Met Ala Glu Val Arg Leu Val Gln Ser Gly Ala Glu Val Lys Lys Pro
        130                 135                 140

Gly Glu Ser Leu Lys Ile Ser Cys Lys Gly Ser Gly Tyr Ser Phe Thr
145                 150                 155                 160

Ser Phe Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
                195                 200                 205

Ala Tyr Leu Gln Trp Ser Ser Leu Lys Ala Ser Asp Thr Ala Met Tyr
        210                 215                 220

Tyr Cys Val Arg Gln Val Trp Gly Trp Gln Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260

<210> SEQ ID NO 39
<211> LENGTH: 780
<212> TYPE: DNA
<213> ORGANISM: Artificial Sequence
<220> FEATURE:
<223> OTHER INFORMATION: Synthetic Construct

<400> SEQUENCE: 39
ctgcctgtgc tgactcagcc accctcggtg tcagtggccc caggagagac ggccaggatt      60
acctgtgggg gaaacaacat tggaagtaaa agtgtgcact ggtaccagca gaagccaggc     120
caggcccctg tgctggtcgt ctatgatgat agcgaccggc cctcaggat ccctgagcga      180
ttctctggct ccaactctgg gaacacggcc accctgacca tcagcagggt cgaagccggg     240
gatgaggccg actattactg tcaggtgtgg gatagtagta gtgattatgt ggtattcggc     300
ggagggacca agctgaccgt cctaggttct agaggtggtg gtggtagcgg cggcggcggc     360
tctggtggtg gtggatcccc gagatggca gaagtgcagc tggtgcagtc tggagcagag     420
gtgaaaaagc ccggggagtc tctgaagatc tcctgtaagg gttctggata cagctttacc     480
agctactgga tcggctgggt gcgccagatg cccgggaaag gcctggagtg gatggggatc     540

```
atctatcctg gtgactctga taccagatac agcccgtcct tccaaggcca ggtcaccatc    600
tcagccgaca gtccatcag caccgcctac ctgcagtgga gcagcctgaa ggcctcggac     660
accgccatgt attactgtgc gcgccaggtt tggggttggc agggtggtat gtacccgcgt    720
tctaactggt ggtacaacat ggattcttgg ggtcaaggta ctctggtgac cgtctcctca    780
```

<210> SEQ ID NO 40
<211> LENGTH: 260
<212> TYPE: PRT
<213> ORGANISM: Artificial Sequence
<220> FEATURE:
<223> OTHER INFORMATION: Synthetic Construct

<400> SEQUENCE: 40

```
Leu Pro Val Leu Thr Gln Pro Pro Ser Val Ser Val Ala Pro Gly Glu
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260
```

<210> SEQ ID NO 41
<211> LENGTH: 780
<212> TYPE: DNA
<213> ORGANISM: Artificial Sequence
<220> FEATURE:
<223> OTHER INFORMATION: Synthetic Construct

<400> SEQUENCE: 41

```
ctgcctgtgc tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgattatgt ggtattcggc     300
ggagggacca agctgaccgt cctaggttct agaggtggtg gtggtagcgg cggcggcggc     360
tctggcggtg gtggatccct cgagatggcc gaagtgcagc tggtgcagtc tggagcagag     420
gtgaaaaagc ccggggagtc tctgaagatc tcctgtaagg gttctggata cagctttacc     480
agctactgga tcggctgggt gcgccagatg cccgggaaag gcctggagtg gatggggatc     540
atctatcctg gtgactctga taccagatac agcccgtcct ccaaggcca ggtcaccatc      600
tcagccgaca gtccatcag caccgcctac ctgcagtgga gcagcctgaa ggcctcggac       660
accgccatgt attactgtgc gcgccaggtt tggggttggc agggtggtat gtacccgcgt     720
tctaactggt ggtacaactt ggattcttgg ggtcaaggta ctctggtgac cgtctcctca     780
```

<210> SEQ ID NO 42
<211> LENGTH: 260
<212> TYPE: PRT
<213> ORGANISM: Artificial Sequence
<220> FEATURE:
<223> OTHER INFORMATION: Synthetic Construct

<400> SEQUENCE: 42

```
Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Tyr Pro Arg
```

```
                225                 230                 235                 240
Ser Asn Trp Trp Tyr Asn Leu Asp Ser Trp Gly Gln Gly Thr Leu Val
                    245                 250                 255

Thr Val Ser Ser
            260

<210> SEQ ID NO 43
<211> LENGTH: 780
<212> TYPE: DNA
<213> ORGANISM: Artificial Sequence
<220> FEATURE:
<223> OTHER INFORMATION: Synthetic Construct

<400> SEQUENCE: 43
ctgcctgtgc tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accatgacca tcagcagggt cgaagccggg     240
gatgaggccg actattactg tcaggtgtgg gatagtagta gtgattatgt ggtattcggc     300
ggagggacca agctgaccgt cctaggttct agaggtggtg gtggtagcgg cggcggcggc     360
tctggtggtg gtggatccct cgagatggcc gaagtgcagc tggtgcagtc tggagcagag     420
gtgaaaaagc ccggggagtc tctgaagatc tcctgtaagg gtgctggata cagctttacc     480
agctactgga tcggctgggt gcgccagatg cccgggaaag gcctggagtg gatggggatc     540
atctatcctg gtgactctga taccagatac agcccgtcct tccaaggcca ggtcaccatc     600
tcagccgaca gtccatcagc accgcctac ctgcagtgga gcagctgaa ggcctcggac     660 accgccatgt attactgtgc gcgccaggtt tggggttggc agggtggtat gtacccgcgt     720
tctaactggt ggtacaacat ggattcttgg ggtcaaggta ctctggtgac cgtctcctca     780

<210> SEQ ID NO 44
<211> LENGTH: 260
<212> TYPE: PRT
<213> ORGANISM: Artificial Sequence
<220> FEATURE:
<223> OTHER INFORMATION: Synthetic Construct

<400> SEQUENCE: 44

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Met Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
```

```
                    130                 135                 140
Gly Glu Ser Leu Lys Ile Ser Cys Lys Gly Ala Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Met Tyr Pro Arg
225                 230                 235                 240

Ser Asn Trp Trp Tyr Asn Met Asp Ser Trp Gln Gly Thr Leu Val
                245                 250                 255

Thr Val Ser Ser
            260

<210> SEQ ID NO 45
<211> LENGTH: 780
<212> TYPE: DNA
<213> ORGANISM: Artificial Sequence
<220> FEATURE:
<223> OTHER INFORMATION: Synthetic Construct

<400> SEQUENCE: 45
ctgcctgtgc tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcgaccggc cctcaggggat ccctgagcga    180 ttctctggct ccaactctgg gaacatggcc accctgacca tcagcagggt cgaagccggg    240
gatgaggccg actattactg tcaggtgtgg gatagtagta gtgattatgt ggtattcggc    300
ggagggacca agctgaccgt cctaggttct agaggtggtg gtggtagcgg cggcggcggc    360
tctggtggtg gtggatccct cgagatggcc gaagtgcagc tggtgcagtc tggagcagag    420
gtgaaaaagc ccggggagtc tctgaagatc tcctgtaagg gttctggata cagctttacc    480
agctactgga tcgctgggt gcgccagatg cccgggaaag gcctgagtg atggggatc       540 atctatcctg gtgactctga taccagatac agcccgtcct ccaaggcca ggtcaccatc    600 tcagccgaca gtccatcag caccgcctac ctgcagtgga gcagcctgaa ggcctcggac    660
accgccatgt attactgtgc gcgccaggtt tggggttggc agggtggtat gtacccgcgt    720
tctaactggt ggtacaacat ggattcttgg ggtcaaggta ctctggtgac cgtctcctca    780

<210> SEQ ID NO 46
<211> LENGTH: 260
<212> TYPE: PRT
<213> ORGANISM: Artificial Sequence
<220> FEATURE:
<223> OTHER INFORMATION: Synthetic Construct

<400> SEQUENCE: 46

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
```

```
            35                  40                  45
Asp Asp Ser Asp Arg Pro Ser Gly Ile Pro Glu Arg Phe Ser Gly Ser
 50                  55                  60

Asn Ser Gly Asn Met Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp Tyr
                 85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Gly Gly Ser Leu Glu
            115                 120                 125

Met Ala Glu Val Gln Leu Val Gln Ser Gly Ala Glu Val Lys Lys Pro
            130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
            195                 200                 205

Ala Tyr Leu Gln Trp Ser Ser Leu Lys Ala Ser Asp Thr Ala Met Tyr
210                 215                 220

Tyr Cys Ala Arg Gln Val Trp Gly Trp Gln Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260

<210> SEQ ID NO 47
<211> LENGTH: 780
<212> TYPE: DNA
<213> ORGANISM: Artificial Sequence
<220> FEATURE:
<223> OTHER INFORMATION: Synthetic Construct

<400> SEQUENCE: 47
ctgcctgtgc tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcaaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgagtatgt ggtattcggc     300
ggagggacca agctgaccgt cctaggttct agaggtggtg gtggtagcgg cggcggcggc     360
tctggtggtg gtggatccct cgagatggcc gaagtgcagc tggtgcagtc tggagcagag     420
gtgaaaaagc ccggggagtc tctgaagatc tcctgtaagg gttctggata cagctttacc     480
agctactgga tcggctgggt cgcgcagatg cccgggaaag gcctgagtg atggggatc       540
atctatcctg gtgactctga taccagatac agcccgtcct ccaaggcca ggtcaccatc      600
tcagccgaca gtccatcag caccgcctac ctgcagtgga gcagcctgaa ggcctcggac      660
accgccatgt attactgtgc gcgtcaggtt tggggttggc agggtggtat gtacccgcgt     720
tctaactggt ggtacaacat ggattcttgg ggtcaaggta ctctggtgac cgtctcctca     780
```

<210> SEQ ID NO 48
<211> LENGTH: 260
<212> TYPE: PRT
<213> ORGANISM: Artificial Sequence
<220> FEATURE:
<223> OTHER INFORMATION: Synthetic Construct

<400> SEQUENCE: 48

```
Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Glu Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260
```

<210> SEQ ID NO 49
<211> LENGTH: 780
<212> TYPE: DNA
<213> ORGANISM: Artificial Sequence
<220> FEATURE:
<223> OTHER INFORMATION: Synthetic Construct

<400> SEQUENCE: 49

```
ctgcctgtgc tgactcagcc accctcgatg tcagtggccc caggaaagac ggccaggatt     60
acctgtgggg gaaacaacat tggaagtaaa agtgtgcact ggtaccagca gaagccaggc    120
caggcccctg tgctggtcgt ctatgatgat agcgaccggc cctcaggat ccctgagcga    180
ttctctggct ccaactctgg gaacacggcc accctgacca tcagcagggt cgaagccggg    240
```

```
gatgaggccg actattactg tcaggtgtgg gatagtagta gtggttatgt ggtattcggc    300
ggagggacca agctgaccgt cctaggttct agaggtggtg gtggtagcgg cggcggcggc    360
tctggtggtg gtggatccct cgagatggcc gaagtgcagc tggtgcagtc tggagcagag    420
gtgaaaaagc ccggggagtc tctgaagatc tcctgtaagg gttctggata cagctttacc    480
agctactgga tcggctgggt gcgccagatg cccgggaaag gcctggagtg gatggggatc    540
atctatcctg gtgactctga taccagatac agcccgtcct ccaaggcca ggtcaccatc     600
tcagccgaca gtccatcag caccgcctac ctgcagtgga gcagctgaa ggcctcggac      660
accgccatgt attactgtgc gcgccaggtt tggggttggc agggtggtat gtacccgcgt    720
tctaactggt ggtacaacat ggattcttgg ggtcaaggta ctctggtgac cgtctcctca    780
```

<210> SEQ ID NO 50
<211> LENGTH: 260
<212> TYPE: PRT
<213> ORGANISM: Artificial Sequence
<220> FEATURE:
<223> OTHER INFORMATION: Synthetic Construct

<400> SEQUENCE: 50

```
Leu Pro Val Leu Thr Gln Pro Pro Ser Met Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Gly Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260
```

<210> SEQ ID NO 51
<211> LENGTH: 780
<212> TYPE: DNA
<213> ORGANISM: Artificial Sequence
<220> FEATURE:
<223> OTHER INFORMATION: Synthetic Construct

<400> SEQUENCE: 51

```
ctgcctgtgc tgactcagcc accctcggtg tcagtggccc caggaaagac ggccaggatt    60
acctgtgggg gaaacaacat tggaagtaaa agtgtgcact ggtaccagca gaagccaggc   120
caggcccctg tgctggtcgt ctacgatgat agcgaccggc cctcaggat ccctgagcga    180
ttctctggct ccaactctgg gaacacggcc accctgacca tcagcagggt cgaagccggg   240
gatgaggccg actattactg tcaggtgtgg atagtacta gtgattatgt ggtattcggc    300
ggagggacca agctgaccgt cctaggttct agaggtggtg gtggtagcgg cggcggcggc   360
tctggtggtg gtggatccct cgagatggcc gaagtgcagc tggtgcagtc tggagcagag   420
gtgaaaaagc ccggggagtt tctgaagatc tcctgtaagg gttctggata cagcttcacc   480
agctactgga tcggctgggt gcgccagatg cccgggaaag gcctgagtg gatggggatc    540
atctatcctg gtgactctga taccagatac agcccgtcct tccaaggcca ggtcgccatc   600
tcagccgaca gtccatcag caccgcctac ctgcagtgga gcagcctgaa ggcctcggac    660
accgccatgt attactgtgc gcgccaggtt tggggttggc agggtggtat gtacccgcgt   720
tctaactggt ggtacaacat ggattcttgg ggtcaaggta ctctggtgac cgtctcctca   780
```

<210> SEQ ID NO 52
<211> LENGTH: 260
<212> TYPE: PRT
<213> ORGANISM: Artificial Sequence
<220> FEATURE:
<223> OTHER INFORMATION: Synthetic Construct

<400> SEQUENCE: 52

```
Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Ser Leu Glu
        115                 120                 125

Met Ala Glu Val Gln Leu Val Gln Ser Gly Ala Glu Val Lys Lys Pro
    130                 135                 140

Gly Glu Phe Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175
```

```
Trp Met Gly Ile Ile Tyr Pro Gly Asp Ser Asp Thr Arg Tyr Ser Pro
            180                 185                 190

Ser Phe Gln Gly Gln Val Ala Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260

<210> SEQ ID NO 53
<211> LENGTH: 780
<212> TYPE: DNA
<213> ORGANISM: Artificial Sequence
<220> FEATURE:
<223> OTHER INFORMATION: Synthetic Construct

<400> SEQUENCE: 53
ctgcctgtgc tgactcagcc accctcggtg tcagtggccc caggaaagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaccactgcc accctgacca tcagcagggt cgaagccggg     240
gatgaggccg actattactg tcaggtgtgg gatagtagta gtgattatgt ggtattcggc     300
ggagggacca gctgaccgt cctaggttct agaggtggtg gtggtagcgg cggcggcggc     360
tctggtggtg gtggatccct cgagatggcc gaagtgcagc tagtgcagtc tggagcagag     420
gtgaaaaagc ccggggagtc tctgaagatc tcctgtaagg gttctggata cagctttacc     480
agctactgga tcggctgggt gcgccagatg cccgggaaag gcctggagtg gatggggatc     540
atctatcctg gtgactccga taccagatac agcccgtcct tccaaggcca ggtcaccatc     600
tcagccgaca agtccatcag caccgcctac ctgcagtgga gcagcctgaa ggcctcggac     660
accgccatgt attactgtgc gcgccaggtt tggggttggc agggtggtat gaacccgcgt     720
tctaactggt ggtacaacat ggattcttgg ggtcaaggta ctctggtgac cgtctcctca     780

<210> SEQ ID NO 54
<211> LENGTH: 260
<212> TYPE: PRT
<213> ORGANISM: Artificial Sequence
<220> FEATURE:
<223> OTHER INFORMATION: Synthetic Construct

<400> SEQUENCE: 54

Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Thr Thr Ala Thr Leu Thr Ile Ser Arg Val Glu Ala Gly
65                  70                  75                  80
```

Asp Glu Ala Asp Tyr Tyr Cys Gln Val Trp Asp Ser Ser Asp Tyr
                85                  90                  95

Val Val Phe Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125

Met Ala Glu Val Gln Leu Val Gln Ser Gly Ala Glu Val Lys Lys Pro
130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Ser Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Asn Pro Arg
225                 230                 235                 240

Ser Asn Trp Trp Tyr Asn Met Asp Ser Trp Gly Gln Gly Thr Leu Val
                245                 250                 255

Thr Val Ser Ser
            260

<210> SEQ ID NO 55
<211> LENGTH: 780
<212> TYPE: DNA
<213> ORGANISM: Artificial Sequence
<220> FEATURE:
<223> OTHER INFORMATION: Synthetic Construct

<400> SEQUENCE: 55
ctgcctgtgc tgactcagcc accctcggtg tcagtggccc caggaaagac ggccaggatt    60
acctgtgggg gaaacaacat tggaagtaaa agtgtgcact ggtaccagca gaagccaggc   120
caggcccctg tgctggtcgt ctatgatgat agcgaccggc cctcagggat ccctgagcga   180
ttctctggct ccaactctgg gaacacggcc accttgacca tcagcagggt cgaagccggg   240
gatgaggccg actattactg tcaggtgtgg gatagtagta gtgattatgt ggtattcggc   300
ggagggacca gctgaccgt cctaggttct agaggtggtg gtggtagtgg cggcggcggc   360
tctggtggtg gtggatccct cgagatggcc gaagtgcagc tggtgcagtc tggagcagag   420
gtgaaaaagc ccggggagtc tctgaagatc tcctgtaagg gttctggata cagctttacc   480
agctactgga tcggctgggt gcgccagatg cccgggaaag gcctggagtg gatggggatc   540
atctatcctg gtgactctga taccagatac agcccgttct ccaaggcca ggtcaccatc   600 tcagccgaca gtccatcag caccgcctac ctgcagtgga gcagcctgaa ggcctcggac   660
accgccatgt attactgtgc gcgccaggtt tggggttggc agggtggtat gtacccgcgt   720
tctaactggt ggtacaacat ggattcttgg ggtcaaggta ctctggtgac cgtctcctca   780

<210> SEQ ID NO 56
<211> LENGTH: 260
<212> TYPE: PRT
<213> ORGANISM: Artificial Sequence
<220> FEATURE:

<223> OTHER INFORMATION: Synthetic Construct

<400> SEQUENCE: 56

```
Leu Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Tyr
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Gln Ser Gly Ala Glu Val Lys Lys Pro
    130                 135                 140

Gly Glu Ser Leu Lys Ile Ser Cys Lys Gly Ser Gly Tyr Ser Phe Thr
145                 150                 155                 160

Ser Tyr Trp Ile Gly Trp Val Arg Gln Met Pro Gly Lys Gly Leu Glu
                165                 170                 175

Trp Met Gly Ile Ile Tyr Pro Gly Asp Ser Asp Thr Arg Tyr Ser Pro
            180                 185                 190

Phe Phe Gln Gly Gln Val Thr Ile Ser Ala Asp Lys Ser Ile Ser Thr
        195                 200                 205

Ala Tyr Leu Gln Trp Ser Ser Leu Lys Ala Ser Asp Thr Ala Met Tyr
    210                 215                 220

Tyr Cys Ala Arg Gln Val Trp Gly Trp Gln Gly Gly Met Tyr Pro Arg
225                 230                 235                 240

Ser Asn Trp Trp Tyr Asn Met Asp Ser Trp Gly Gln Gly Thr Leu Val
                245                 250                 255

Thr Val Ser Ser
            260
```

<210> SEQ ID NO 57
<211> LENGTH: 759
<212> TYPE: DNA
<213> ORGANISM: Artificial Sequence
<220> FEATURE:
<223> OTHER INFORMATION: Synthetic Construct

<400> SEQUENCE: 57

```
caggctgtgc tgactcagcc accctcggtg tctgaagccc ccaggcagag ggtcaccatc    60
tcctgttctg gaagcagctc caacgtcgga aataatgctg taaactggta ccagcaggtc   120
ccaggaaagg ctcccaaact cctcatctat tatgatgatc tgctgtcctc aggggtctct   180
gaccgattct ctggctccaa gtctggcacc tcagcctccc tggccatcag tgggctccag   240
tctgaggatg aggccgatta ttattgtgca gcatgggatg acagcctgaa tggtccggta   300
ttcggcggag ggaccaagct gaccgtccta ggttctagag gtggtggtgg tagcggcggc   360
ggcggctctg gtggtggtgg atccctcgag atggccgaag tgcagctggt gcagtccgga   420
```

```
gcagaggtga aaaagcccgg ggagtctctg aagatctcct gtaagggttc tggatacagc    480
tttaccagct actggatcgg ctgggtgcgc cagatgcccg ggaaaggcct ggagtggatg    540
gggatcatct atcctggtga ctctgatacc agatacagcc cgtccttcca aggccaggtc    600
accatctcag ccgacaagtc catcagcacc gcctacctgc agtggagcag cctgaaggcc    660
tcggacaccg ccatgtatta ctgtgcgcgc tggtcttctt cttgggactc tatgtacatg    720
gattactggg gtcaaggtac tatggtgacc gtctcctca                           759
```

<210> SEQ ID NO 58
<211> LENGTH: 253
<212> TYPE: PRT
<213> ORGANISM: Artificial Sequence
<220> FEATURE:
<223> OTHER INFORMATION: Synthetic Construct

<400> SEQUENCE: 58

```
Gln Ala Val Leu Thr Gln Pro Pro Ser Val Ser Glu Ala Pro Arg Gln
1               5                   10                  15

Arg Val Thr Ile Ser Cys Ser Gly Ser Ser Asn Val Gly Asn Asn
            20                  25                  30

Ala Val Asn Trp Tyr Gln Gln Val Pro Gly Lys Ala Pro Lys Leu Leu
        35                  40                  45

Ile Tyr Tyr Asp Asp Leu Leu Ser Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Ser Leu
                85                  90                  95

Asn Gly Pro Val Phe Gly Gly Gly Thr Lys Leu Thr Val Leu Gly Ser
            100                 105                 110

Arg Gly Gly Gly Ser Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Trp Ser Ser Ser Trp Asp Ser Met Tyr Met
225                 230                 235                 240

Asp Tyr Trp Gly Gln Gly Thr Met Val Thr Val Ser Ser
                245                 250
```

<210> SEQ ID NO 59
<211> LENGTH: 759
<212> TYPE: DNA
<213> ORGANISM: Artificial Sequence
<220> FEATURE:
<223> OTHER INFORMATION: Synthetic Construct

<400> SEQUENCE: 59

-continued

```
caggctgtgc ttactcagcc accctcggtg tctgaagccc ccaggcagag ggtcaccatc    60
tcctgttctg gaaacagctc caacgtcgga ataatgctat aaactggtac cagcaggtc    120 ccaggaaagg ctcccaaact cctcatctat tatgatgatc tgctgtcctc agggqtctct    180 gaccgattct ctggctccaa gtctggcacc tcagcctccc tggccatcag tgggctccag    240
tctgaggatg aggccgatta ttattgtgca gcatgggatg acagcctgaa tggtccggta    300
ttcggcggag ggaccaagct gaccgtccta ggttctagag gtggtggtgg tagcggcggc    360
ggcggctctg gtggtggtgg atccctcgag atggccgaag tgcagctggt gcagtctgga    420
gcagaggtgg aaaagcccgg ggagtctctg aagatctcct gtaagggttc tggatacagc    480
tttaccagct actggatcgg ctgggtgcgc cagatgcccg ggaaaggcct ggagtggatg    540
gggatcatct atcctggtga ctctgatacc agatacagcc cgtccttcca aggccaggtc    600
accatctcag ccgacaagtc catcagcacc gcctacctgc agtggagcag cctgaaggcc    660
tcggacaccg ccatgtatta ctgtgcgcgc tggtcttcta cttgggactc tatgtacatg    720
gaatactggg gtcaaggtac tctggtgacc gtctcctca    759
```

<210> SEQ ID NO 60
<211> LENGTH: 253
<212> TYPE: PRT
<213> ORGANISM: Artificial Sequence
<220> FEATURE:
<223> OTHER INFORMATION: Synthetic Construct

<400> SEQUENCE: 60

```
Gln Ala Val Leu Thr Gln Pro Pro Ser Val Ser Glu Ala Pro Arg Gln
1               5                   10                  15

Arg Val Thr Ile Ser Cys Ser Gly Asn Ser Ser Asn Val Gly Asn Asn
            20                  25                  30

Ala Ile Asn Trp Tyr Gln Gln Val Pro Gly Lys Ala Pro Lys Leu Leu
        35                  40                  45

Ile Tyr Tyr Asp Asp Leu Leu Ser Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
            100                 105                 110

Arg Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Glu
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220
```

```
Met Tyr Tyr Cys Ala Arg Trp Ser Ser Thr Trp Asp Ser Met Tyr Met
225                 230                 235                 240

Glu Tyr Trp Gly Gln Gly Thr Leu Val Thr Val Ser Ser
                245                 250
```

<210> SEQ ID NO 61
<211> LENGTH: 760
<212> TYPE: DNA
<213> ORGANISM: Artificial Sequence
<220> FEATURE:
<223> OTHER INFORMATION: Synthetic Construct

<400> SEQUENCE: 61

```
caggctgtgc tgactcagcc accctcggtg tctgaagccc caggcagag ggtcaccatc    60
tcctgttctg gaagcagctc caacgtcgga ataatgctg taaactggta ccagcaggtc   120
ccaggaaagg ctcccaaact cctcatctat tatgatgatc tgctgtcctc aggggtctct   180
gaccgattct ctggctccaa gtctggcacc tcagcctccc tggccatcag tgggctccag   240
tctgaggatg aggccgatta ttattgtgca gcatgggatg acagcctgaa tggtccggta   300
ttcggcggag ggaccaagct gaccgtccta ggttctagag gtggtggtgg tagcggcggc   360
ggcggctctg gtggtggtgg atccctcgag atggccgaag tgcagctggt gcagtctgga   420
gcagaggtga aaaagcccgg ggggtctctg aagatctcct gtaagggttc tggatacagc   480
tttaccagct actggatcgg ctgggtgcgc cagatgcccg ggaaaggcct ggagtggatg   540
gggatcatct atcctggtga ctctgatacc agatacagcc cgtccttcca aggccaggtc   600
accatctcag ccgacaagtc catcagcacc gcctacctgc agtggagcag cctgaaggcc   660
tcggacaccg ccatgtatta ctgtgcgcgc tggtcttcta cttgggactc tatgtacatg   720
gattactggg gtcaaggtac tctggtgacc gtctcctcaa                        760
```

<210> SEQ ID NO 62
<211> LENGTH: 253
<212> TYPE: PRT
<213> ORGANISM: Artificial Sequence
<220> FEATURE:
<223> OTHER INFORMATION: Synthetic Construct

<400> SEQUENCE: 62

```
Gln Ala Val Leu Thr Gln Pro Pro Ser Val Ser Glu Ala Pro Arg Gln
1               5                   10                  15

Arg Val Thr Ile Ser Cys Ser Gly Ser Ser Asn Val Gly Asn Asn
            20                  25                  30

Ala Val Asn Trp Tyr Gln Gln Val Pro Gly Lys Ala Pro Lys Leu Leu
        35                  40                  45

Ile Tyr Tyr Asp Asp Leu Leu Ser Ser Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
                100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Val Lys
        130                 135                 140
```

```
Lys Pro Gly Gly Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
            165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
            195                 200                 205

Ser Thr Ala Tyr Leu Gln Trp Ser Ser Leu Lys Ala Ser Asp Thr Ala
            210                 215                 220

Met Tyr Tyr Cys Ala Arg Trp Ser Ser Thr Trp Asp Ser Met Tyr Met
225                 230                 235                 240

Asp Tyr Trp Gly Gln Gly Thr Leu Val Thr Val Ser Ser
            245                 250
```

<210> SEQ ID NO 63
<211> LENGTH: 759
<212> TYPE: DNA
<213> ORGANISM: Artificial Sequence
<220> FEATURE:
<223> OTHER INFORMATION: Synthetic Construct

<400> SEQUENCE: 63

```
caggctgtgc tgactcagcc accctcggtg tctgaagccc ccaggcagag ggtcaccatc    60
tcctgttctg gaagcagctc caacgtcgga aataatgctg taaactggta ccagcaggtc   120
ccaggaaagg ctcccaaact cctcatctat tatgatgatc agctgtcctc agggttctct   180
gaccgattct ctggctccaa gtctggcacc tcagcctccc tggccatcag tgggctccag   240
tctgaggatg aggccgatta ttattgtgca gcatgggatg acagcctgaa tggtccggta   300
ttcggcggag ggaccaagct gaccgtccta ggttctagag tggtggtggt agcggcggc   360
ggcggctctg gtggtggtgg atccctcgag atggccgaag tgcagctggt gcagtctgga   420
gcagaggtga aaaagcccgg ggagtctctg aagatctcct gtaagggttc tggatacagc   480
tttaccagct actggatcgg ctgggtgcgc cagatgcccg ggaaaggcct ggagtggatg   540
gggatcatct atcctggtga ctctgatacc agatacagcc cgtccttcca aggccaggtc   600
accatctcag ccgacaagtc catcagcacc gcctacctgc agtggagcag cctgaaggcc   660
tcggacaccg ccatgtatta ctgtgcgcgc tggtcttcta cttgggactc tttgtacatg   720
gattactggg gtcaaggtac tctggtgacc gtctcctca                         759
```

<210> SEQ ID NO 64
<211> LENGTH: 253
<212> TYPE: PRT
<213> ORGANISM: Artificial Sequence
<220> FEATURE:
<223> OTHER INFORMATION: Synthetic Construct

<400> SEQUENCE: 64

```
Gln Ala Val Leu Thr Gln Pro Pro Ser Val Ser Glu Ala Pro Arg Gln
1               5                   10                  15

Arg Val Thr Ile Ser Cys Ser Gly Ser Ser Ser Asn Val Gly Asn Asn
            20                  25                  30

Ala Val Asn Trp Tyr Gln Gln Val Pro Gly Lys Ala Pro Lys Leu Leu
            35                  40                  45

Ile Tyr Tyr Asp Asp Gln Leu Ser Ser Gly Val Ser Asp Arg Phe Ser
50                  55                  60
```

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
            100                 105                 110

Arg Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
210                 215                 220

Met Tyr Tyr Cys Ala Arg Trp Ser Ser Thr Trp Asp Ser Leu Tyr Met
225                 230                 235                 240

Asp Tyr Trp Gly Gln Gly Thr Leu Val Thr Val Ser Ser
            245                 250

<210> SEQ ID NO 65
<211> LENGTH: 759
<212> TYPE: DNA
<213> ORGANISM: Artificial Sequence
<220> FEATURE:
<223> OTHER INFORMATION: Synthetic Construct

<400> SEQUENCE: 65
caggctgtgc tgactcagcc accctcggtg tctgaagccc caggcagag ggtcaccatc      60 tcctgttctg gaaacagctc caacgtcgga aataatgctg taaactggta ccagcaggtc     120
ccaggaaagg ctcccaaact tctcatctat tatgatgatc tgctgtcctc agggtctct     180 gaccgattct ctggctccaa gtctggcacc tcagcctccc tggccatcag tgggctccag    240
tctgaggatg aggccgatta ttattgtgca gcatgggatg acagcctgaa tggtccggta    300
ttcggcggag ggaccaagct gaccgtccta ggttctagag gtggtggtgg tagcggcggc    360
ggcggctctg gtggtggtgg atccctcgag atggccgaag tgcagctggt gcagtctgga    420
gcagaggtga aaaagcccgg ggagtctctg aagatctcct gtaagggttc tggatacagc    480
tttaccagct actggatcgg ctgggtgcgc cagatgcccg gaaaggcct ggagtggatg     540 gggatcatct atcctggtga ctctgatacc agatacagcc cgtccttcca aggccaggtc    600
accatctcag ccgacaagtc catcagcacc gcctacctgc agtggagcag cctgaaggcc    660
tcggacaccg ccatgtatta ctgtgcgcgc tggtcttcta cttgggactc tatgtacatg    720
gattactggg gtcaaggtac tctggtgacc gtctcctca                           759

<210> SEQ ID NO 66
<211> LENGTH: 253
<212> TYPE: PRT
<213> ORGANISM: Artificial Sequence
<220> FEATURE:
<223> OTHER INFORMATION: Synthetic Construct

<400> SEQUENCE: 66

Gln Ala Val Leu Thr Gln Pro Pro Ser Val Ser Glu Ala Pro Arg Gln
1               5                   10                  15

Arg Val Thr Ile Ser Cys Ser Gly Asn Ser Ser Asn Val Gly Asn Asn
            20                  25                  30

Ala Val Asn Trp Tyr Gln Gln Val Pro Gly Lys Ala Pro Lys Leu Leu
        35                  40                  45

Ile Tyr Tyr Asp Asp Leu Leu Ser Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Thr Lys Leu Thr Val Leu Gly Ser
            100                 105                 110

Arg Gly Gly Gly Ser Gly Gly Gly Ser Gly Gly Gly Ser
            115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Trp Ser Ser Thr Trp Asp Ser Met Tyr Met
225                 230                 235                 240

Asp Tyr Trp Gly Gln Gly Thr Leu Val Thr Val Ser Ser
                245                 250

<210> SEQ ID NO 67
<211> LENGTH: 759
<212> TYPE: DNA
<213> ORGANISM: Artificial Sequence
<220> FEATURE:
<223> OTHER INFORMATION: Synthetic Construct

<400> SEQUENCE: 67
caggctgtgc tgactcagcc accctcggtg tccgaagccc ccaggcagag ggtcaccatc      60
tcctgttctg gaagcagctc caacgtcgga aataatgctg taaactggta ccagcaggtc     120
ccaggaaagg ctcccaaact cctcatctat tatgatgatc tgctgtcctc agggtctct      180
gaccgattct ctggctccaa gtctggcacc tcagcctccc tggccatcag tgggctccag    240
tctgaggatg aggccgatta ttattgtgca gcatgggatg acagcctgaa tggtccggta    300
ttcggcggag ggaccaagct gaccgtccta ggttctagag gtggtggtgg tagcggcggc    360
ggcggctctg gtggtggtgg ttccctcgag atggccgaag tacagctggt gcagtcagga    420
gcagaggtga aaaagcccgg ggaatctctg aagatctcct gtaagggttc tgcatacagc    480
tttaccagct actggatcgg ctgggtgcgc cagatgcccg ggaaaggcct ggagtggatg    540

```
gggatcatct atcctggtga ctctgatacc agatacagcc cgtccttcca aggccaggtc    600
accatctcag ccgacaagtc catcagcacc gcctacctgc agtggagcag cctgaaggcc    660
tcggacaccg ccatgtatta ctgtgcgcgc tggtcttcta cttgggactc tatgtacatg    720
gattactggg gtctaggtac tctggtgacc gtctcctca                          759
```

<210> SEQ ID NO 68
<211> LENGTH: 253
<212> TYPE: PRT
<213> ORGANISM: Artificial Sequence
<220> FEATURE:
<223> OTHER INFORMATION: Synthetic Construct

<400> SEQUENCE: 68

```
Gln Ala Val Leu Thr Gln Pro Pro Ser Val Ser Glu Ala Pro Arg Gln
1               5                   10                  15

Arg Val Thr Ile Ser Cys Ser Gly Ser Ser Asn Val Gly Asn Asn
            20                  25                  30

Ala Val Asn Trp Tyr Gln Gln Val Pro Gly Lys Ala Pro Lys Leu Leu
        35                  40                  45

Ile Tyr Tyr Asp Asp Leu Leu Ser Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Ala Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Trp Ser Ser Thr Trp Asp Ser Met Tyr Met
225                 230                 235                 240

Asp Tyr Trp Gly Leu Gly Thr Leu Val Thr Val Ser Ser
                245                 250
```

<210> SEQ ID NO 69
<211> LENGTH: 759
<212> TYPE: DNA
<213> ORGANISM: Artificial Sequence
<220> FEATURE:
<223> OTHER INFORMATION: Synthetic Construct

<400> SEQUENCE: 69

```
caggctgtgc tgactcaacc accctcggtg tctgaagccc ccaggcagag ggtcaccatc     60
tcctgttctg gaagcagctc caacgtcgga ataatgctg taaactggta ccagcaggtc    120
```

```
ccaggaaagg ctcccaaact cctcatctat tatgatgatc agctgtcctc aggggtctct    180
gaccgattct ctggctccaa gtctggcacc tcagcctccc tggccatcag tgggctccag    240
tctgaggatg aggccgatta ttattgtgca gcatgggatg acagcctgaa tggtccggta    300
ttcggcggag ggaccaagct gaccgtccta ggttctagag gtggtggtgg tagcggcggc    360
ggcggctctg gtggtggtgg atccctcggg atggccgaag tgcagctggt gcagtctgga    420
gcagaggtga aaaagcccgg ggagtctctg aagatctcct gtaagggttc tggatacagc    480
tttaccagct actggatcgg ctgggtgcgc cagatgcccg ggaaaggcct ggagtggatg    540
gggatcatct atcctggtga ctctgatacc agatacagcc cgtccttcca aggccaggtt    600
accatctcag ccgacaagtc catcagcacc gcctacctgc agtggagcag cctgaaggcc    660
tcggacaccg ccatgtatta ctgtgcgcgc tggtcttcta cttgggactc tatgtacatg    720
gattactggg gtcaaggtac tctggtaacc gtctcctca                           759
```

<210> SEQ ID NO 70
<211> LENGTH: 253
<212> TYPE: PRT
<213> ORGANISM: Artificial Sequence
<220> FEATURE:
<223> OTHER INFORMATION: Synthetic Construct

<400> SEQUENCE: 70

```
Gln Ala Val Leu Thr Gln Pro Pro Ser Val Ser Glu Ala Pro Arg Gln
1               5                   10                  15

Arg Val Thr Ile Ser Cys Ser Gly Ser Ser Ser Asn Val Gly Asn Asn
            20                  25                  30

Ala Val Asn Trp Tyr Gln Gln Val Pro Gly Lys Ala Pro Lys Leu Leu
        35                  40                  45

Ile Tyr Tyr Asp Asp Gln Leu Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Gly Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Trp Ser Ser Thr Trp Asp Ser Met Tyr Met
225                 230                 235                 240

Asp Tyr Trp Gly Gln Gly Thr Leu Val Thr Val Ser Ser
                245                 250
```

<210> SEQ ID NO 71
<211> LENGTH: 759
<212> TYPE: DNA
<213> ORGANISM: Artificial Sequence
<220> FEATURE:
<223> OTHER INFORMATION: Synthetic Construct

<400> SEQUENCE: 71

```
caggctgtgc tgactcagcc accctcggtg tctgaagccc caggcagag ggtcaccatc        60
tcctgttctg gaagcagctc caacgtcggt aataatgctg taaactggta ccagcaggtc       120
ccaggaaagg ctcccaaact cctcatctat tatgatgatc tgctgtcctc aggggtctct       180
gaccgattct ctggctccaa gtctggcacc tcagcctccc tggccatcag tgggctccag       240
tctgaggatg aggccgatta ttattgtgca gcatgggatg acagcctgaa tggtccggta       300
ttcggcggag ggaccaagct gaccgtccta ggttctagag gtggtggtgg tagcggcggc       360
ggcggctctg gtggtggtgg atccctcgag atggccgaag tgcagctggt gcagtctgga       420
gcagaggtga aaagcccgg ggagtctctg aagatctcct gtaagggttc tggatacagc       480
tttaccagct actggatcgg ctgggtgcgc cagatgcccg gaaaggcct ggagtggatg       540
gggatcatct atcctggtga ctctgatacc agatacagcc cgtccttcca aggccaggtc       600
accatctcag ccgacaagtc catcagcacc gcctacctgc agtggagcag cctgaaggcc       660
tcggacaccg ccatgtatta ctgtgcgcgc tggtcttctt cttgggactc tatgtacatg       720
gattactggg gtcaaggtac tctggtgacc gtctcctca                              759
```

<210> SEQ ID NO 72
<211> LENGTH: 253
<212> TYPE: PRT
<213> ORGANISM: Artificial Sequence
<220> FEATURE:
<223> OTHER INFORMATION: Synthetic Construct

<400> SEQUENCE: 72

```
Gln Ala Val Leu Thr Gln Pro Pro Ser Val Ser Glu Ala Pro Arg Gln
1               5                   10                  15

Arg Val Thr Ile Ser Cys Ser Gly Ser Ser Asn Val Gly Asn Asn
            20                  25                  30

Ala Val Asn Trp Tyr Gln Gln Val Pro Gly Lys Ala Pro Lys Leu Leu
        35                  40                  45

Ile Tyr Tyr Asp Asp Leu Leu Ser Ser Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
```

```
                     165                 170                 175

Leu Glu Trp Met Gly Ile Ile Tyr Pro Gly Asp Ser Asp Thr Arg Tyr
            180                 185                 190

Ser Pro Ser Phe Gln Gly Gln Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Trp Ser Ser Ser Trp Asp Ser Met Tyr Met
225                 230                 235                 240

Asp Tyr Trp Gly Gln Gly Thr Leu Val Thr Val Ser Ser
                245                 250
```

<210> SEQ ID NO 73
<211> LENGTH: 8
<212> TYPE: PRT
<213> ORGANISM: Artificial Sequence
<220> FEATURE:
<223> OTHER INFORMATION: Synthetic Construct

<400> SEQUENCE: 73

```
Gly Phe Thr Phe Ser Ser Tyr Ala
1               5
```

<210> SEQ ID NO 74
<211> LENGTH: 8
<212> TYPE: PRT
<213> ORGANISM: Artificial Sequence
<220> FEATURE:
<223> OTHER INFORMATION: Synthetic Construct

<400> SEQUENCE: 74

```
Ile Ser Gly Ser Gly Gly Ser Thr
1               5
```

<210> SEQ ID NO 75
<211> LENGTH: 10
<212> TYPE: PRT
<213> ORGANISM: Artificial Sequence
<220> FEATURE:
<223> OTHER INFORMATION: Synthetic Construct

<400> SEQUENCE: 75

```
Ala Arg Tyr Tyr Tyr Ser Arg Leu Asp Tyr
1               5                   10
```

<210> SEQ ID NO 76
<211> LENGTH: 8
<212> TYPE: PRT
<213> ORGANISM: Artificial Sequence
<220> FEATURE:
<223> OTHER INFORMATION: Synthetic Construct

<400> SEQUENCE: 76

```
Gly Phe Thr Phe Ser Ser Tyr Ala
1               5
```

<210> SEQ ID NO 77
<211> LENGTH: 8
<212> TYPE: PRT
<213> ORGANISM: Artificial Sequence
<220> FEATURE:
<223> OTHER INFORMATION: Synthetic Construct

<400> SEQUENCE: 77

```
Ile Ser Ala Ser Gly Gly Ser Thr
1               5

<210> SEQ ID NO 78
<211> LENGTH: 10
<212> TYPE: PRT
<213> ORGANISM: Artificial Sequence
<220> FEATURE:
<223> OTHER INFORMATION: Synthetic Construct

<400> SEQUENCE: 78

Ala Arg Tyr Tyr Leu Ser Gln Ile Asp Ser
1               5                   10

<210> SEQ ID NO 79
<211> LENGTH: 8
<212> TYPE: PRT
<213> ORGANISM: Artificial Sequence
<220> FEATURE:
<223> OTHER INFORMATION: Synthetic Construct

<400> SEQUENCE: 79

Gly Tyr Thr Phe Thr Asp Tyr Tyr
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic Construct

<400> SEQUENCE: 80

Val Asp Pro Glu Asp Gly Glu Thr
1               5

<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

Ala Thr Gly Ile Tyr Ser Arg Pro Leu Gly Tyr
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Synthetic Construct

<400> SEQUENCE: 82

Gly Phe Thr Phe Ser Ser Tyr Ala
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic Construct

<400> SEQUENCE: 83

Ile Ser Gly Ser Gly Gly Ser Thr
```

```
<210> SEQ ID NO 84
<211> LENGTH: 14
<212> TYPE: PRT
<213> ORGANISM: Artificial Sequence
<220> FEATURE:
<223> OTHER INFORMATION: Synthetic Construct

<400> SEQUENCE: 84

Ala Arg Ser Asp Gly Lys His Phe Trp Gln Gln Tyr Asp Ala
1               5                   10

<210> SEQ ID NO 85
<211> LENGTH: 8
<212> TYPE: PRT
<213> ORGANISM: Artificial Sequence
<220> FEATURE:
<223> OTHER INFORMATION: Synthetic Construct

<400> SEQUENCE: 85

Gly Phe Thr Val Ser Ser Asn Tyr
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic Construct

<400> SEQUENCE: 86

Ile Ser Gly Ser Gly Gly Ser Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct

<400> SEQUENCE: 87

Ala Arg Met Asn Ile Asp Tyr
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Glu Tyr Ser Phe Ala Ser Tyr Trp
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic Construct

<400> SEQUENCE: 89

Ile Asp Pro Ser Asp Ser Tyr Thr
1               5
```

<210> SEQ ID NO 90
<211> LENGTH: 17
<212> TYPE: PRT
<213> ORGANISM: Artificial Sequence
<220> FEATURE:
<223> OTHER INFORMATION: Synthetic Construct

<400> SEQUENCE: 90

Ala Arg Pro Phe Gln Tyr Asp Tyr Gly Gly Tyr Ser Asp Ala Phe Asp
1               5                   10                  15

Ile

<210> SEQ ID NO 91
<211> LENGTH: 8
<212> TYPE: PRT
<213> ORGANISM: Artificial Sequence
<220> FEATURE:
<223> OTHER INFORMATION: Synthetic Construct

<400> SEQUENCE: 91

Gly Gly Thr Phe Ser Ser Ser Ser
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic Construct

<400> SEQUENCE: 92

Ile Ile Pro Ile Val Gly Thr Pro
1               5

<210> SEQ ID NO 93
<211> LENGTH: 11
<212> TYPE: PRT
<213> ORGANISM: Artificial Sequence
<220> FEATURE:
<223> OTHER INFORMATION: Synthetic Construct

<400> SEQUENCE: 93

Ala Arg Gly Gly Tyr Arg Asp Tyr Met Asp Val
1               5                   10

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct

<400> SEQUENCE: 94

Gly Phe Thr Val Ser Ser Asn Tyr
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic Construct

<400> SEQUENCE: 95

Ile Tyr Ser Gly Gly Ser Thr

```
1               5

<210> SEQ ID NO 96
<211> LENGTH: 11
<212> TYPE: PRT
<213> ORGANISM: Artificial Sequence
<220> FEATURE:
<223> OTHER INFORMATION: Synthetic Construct

<400> SEQUENCE: 96

Ala Arg Gly Gly Phe Gly Ala Glu Phe Asp Tyr
1               5                   10

<210> SEQ ID NO 97
<211> LENGTH: 8
<212> TYPE: PRT
<213> ORGANISM: Artificial Sequence
<220> FEATURE:
<223> OTHER INFORMATION: Synthetic Construct

<400> SEQUENCE: 97

Gly Phe Thr Val Ser Ser Asn Tyr
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic Construct

<400> SEQUENCE: 98

Ile Tyr Ser Gly Gly Ser Thr
1               5

<210> SEQ ID NO 99
<211> LENGTH: 17
<212> TYPE: PRT
<213> ORGANISM: Artificial Sequence
<220> FEATURE:
<223> OTHER INFORMATION: Synthetic Construct

<400> SEQUENCE: 99

Ala Arg Gly Gly Ile Ser Asp Asp Tyr Tyr Gly Ser Gly Ser Tyr Asp
1               5                   10                  15

Asn

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct

<400> SEQUENCE: 100

Gly Phe Thr Val Ser Ser Asn Tyr
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic Construct

<400> SEQUENCE: 101
```

Ile Tyr Ser Gly Gly Ser Thr
1               5

<210> SEQ ID NO 102
<211> LENGTH: 12
<212> TYPE: PRT
<213> ORGANISM: Artificial Sequence
<220> FEATURE:
<223> OTHER INFORMATION: Synthetic Construct

<400> SEQUENCE: 102

Ala Arg Glu Arg Gly Met Gly Tyr Ala Phe Asp Ile
1               5                   10

<210> SEQ ID NO 103
<211> LENGTH: 8
<212> TYPE: PRT
<213> ORGANISM: Artificial Sequence
<220> FEATURE:
<223> OTHER INFORMATION: Synthetic Construct

<400> SEQUENCE: 103

Gly Val Ser Met Ser Glu Asn Tyr
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic Construct

<400> SEQUENCE: 104

Ala His Tyr Thr Gly Asp Thr
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic Construct

<400> SEQUENCE: 105

Ala Ser Tyr His Pro Phe Asn Tyr
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic Construct

<400> SEQUENCE: 106

Gly Tyr Thr Phe Asn Asp Phe Tyr
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic Construct

<400> SEQUENCE: 107

Ile Asp Pro Glu Asp Gly Lys Thr

```
<210> SEQ ID NO 108
<211> LENGTH: 19
<212> TYPE: PRT
<213> ORGANISM: Artificial Sequence
<220> FEATURE:
<223> OTHER INFORMATION: Synthetic Construct

<400> SEQUENCE: 108

Thr Thr Asp Trp Gly Tyr Ser Ser Ser Leu Arg Glu Glu Asp Ile Trp
1               5                   10                  15

Tyr Asp Cys

<210> SEQ ID NO 109
<211> LENGTH: 8
<212> TYPE: PRT
<213> ORGANISM: Artificial Sequence
<220> FEATURE:
<223> OTHER INFORMATION: Synthetic Construct

<400> SEQUENCE: 109

Gly Gly Thr Phe Ser Ser Tyr Ala
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic Construct

<400> SEQUENCE: 110

Ile Ile Pro Ile Phe Gly Thr Ala
1               5

<210> SEQ ID NO 111
<211> LENGTH: 15
<212> TYPE: PRT
<213> ORGANISM: Artificial Sequence
<220> FEATURE:
<223> OTHER INFORMATION: Synthetic Construct

<400> SEQUENCE: 111

Ala Arg Asp Tyr Gly Tyr Gly Asp Tyr Gly Asp Ala Phe Asp Ile
1               5                   10                  15

<210> SEQ ID NO 112
<211> LENGTH: 8
<212> TYPE: PRT
<213> ORGANISM: Artificial Sequence
<220> FEATURE:
<223> OTHER INFORMATION: Synthetic Construct

<400> SEQUENCE: 112

Gly Tyr Ser Phe Thr Ser Tyr Trp
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic Construct

<400> SEQUENCE: 113
```

```
Ile Tyr Pro Gly Asp Ser Asp Thr
1               5
```

<210> SEQ ID NO 114
<211> LENGTH: 14
<212> TYPE: PRT
<213> ORGANISM: Artificial Sequence
<220> FEATURE:
<223> OTHER INFORMATION: Synthetic Construct

<400> SEQUENCE: 114

```
Ala Arg Val Val Gly Thr Ile Tyr Ser Met Gln Tyr Asp Val
1               5                   10
```

<210> SEQ ID NO 115
<211> LENGTH: 8
<212> TYPE: PRT
<213> ORGANISM: Artificial Sequence
<220> FEATURE:
<223> OTHER INFORMATION: Synthetic Construct

<400> SEQUENCE: 115

```
Gly Tyr Ser Phe Thr Ser Tyr Trp
1               5
```

<210> SEQ ID NO 116
<211> LENGTH: 8
<212> TYPE: PRT
<213> ORGANISM: Artificial Sequence
<220> FEATURE:
<223> OTHER INFORMATION: Synthetic Construct

<400> SEQUENCE: 116

```
Ile Tyr Pro Gly Asp Ser Asp Thr
1               5
```

<210> SEQ ID NO 117
<211> LENGTH: 23
<212> TYPE: PRT
<213> ORGANISM: Artificial Sequence
<220> FEATURE:
<223> OTHER INFORMATION: Synthetic Construct

<400> SEQUENCE: 117

```
Ala Arg Gln Val Trp Gly Trp Gln Gly Gly Met Tyr Pro Arg Ser Asn
1               5                   10                  15

Trp Trp Tyr Asn Met Asp Ser
            20
```

<210> SEQ ID NO 118
<211> LENGTH: 8
<212> TYPE: PRT
<213> ORGANISM: Artificial Sequence
<220> FEATURE:
<223> OTHER INFORMATION: Synthetic Construct

<400> SEQUENCE: 118

```
Gly Tyr Ser Phe Thr Ser Tyr Trp
1               5
```

<210> SEQ ID NO 119
<211> LENGTH: 8
<212> TYPE: PRT
<213> ORGANISM: Artificial Sequence
<220> FEATURE:
<223> OTHER INFORMATION: Synthetic Construct

```
<400> SEQUENCE: 119

Ile Tyr Pro Gly Asp Ser Asp Thr
1               5

<210> SEQ ID NO 120
<211> LENGTH: 14
<212> TYPE: PRT
<213> ORGANISM: Artificial Sequence
<220> FEATURE:
<223> OTHER INFORMATION: Synthetic Construct

<400> SEQUENCE: 120

Ala Arg Trp Ser Ser Thr Trp Asp Ser Met Tyr Met Asp Tyr
1               5                   10

<210> SEQ ID NO 121
<211> LENGTH: 8
<212> TYPE: PRT
<213> ORGANISM: Artificial Sequence
<220> FEATURE:
<223> OTHER INFORMATION: Synthetic Construct

<400> SEQUENCE: 121

Gly Tyr Ser Phe Thr Ser Tyr Trp
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic Construct

<400> SEQUENCE: 122

Ile Tyr Pro Gly Asp Ser Asp Thr
1               5

<210> SEQ ID NO 123
<211> LENGTH: 14
<212> TYPE: PRT
<213> ORGANISM: Artificial Sequence
<220> FEATURE:
<223> OTHER INFORMATION: Synthetic Construct

<400> SEQUENCE: 123

Ala Arg Val Thr Tyr Ser Met Asp Ser Tyr Tyr Phe Asp Ser
1               5                   10

<210> SEQ ID NO 124
<211> LENGTH: 8
<212> TYPE: PRT
<213> ORGANISM: Artificial Sequence
<220> FEATURE:
<223> OTHER INFORMATION: Synthetic Construct

<400> SEQUENCE: 124

Gly Tyr Ser Phe Thr Ser Tyr Trp
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic Construct

<400> SEQUENCE: 125
```

```
Ile Tyr Pro Gly Asp Ser Asp Thr
1               5

<210> SEQ ID NO 126
<211> LENGTH: 23
<212> TYPE: PRT
<213> ORGANISM: Artificial Sequence
<220> FEATURE:
<223> OTHER INFORMATION: Synthetic Construct

<400> SEQUENCE: 126

Ala Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 127
<211> LENGTH: 8
<212> TYPE: PRT
<213> ORGANISM: Artificial Sequence
<220> FEATURE:
<223> OTHER INFORMATION: Synthetic Construct

<400> SEQUENCE: 127

Gly Tyr Ser Phe Thr Ser Tyr Trp
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic Construct

<400> SEQUENCE: 128

Ile Tyr Pro Gly Asp Ser Asp Thr
1               5

<210> SEQ ID NO 129
<211> LENGTH: 23
<212> TYPE: PRT
<213> ORGANISM: Artificial Sequence
<220> FEATURE:
<223> OTHER INFORMATION: Synthetic Construct

<400> SEQUENCE: 129

Ala Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 130
<211> LENGTH: 8
<212> TYPE: PRT
<213> ORGANISM: Artificial Sequence
<220> FEATURE:
<223> OTHER INFORMATION: Synthetic Construct

<400> SEQUENCE: 130

Gly Tyr Ser Phe Thr Ser Tyr Trp
1               5

<210> SEQ ID NO 131
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 131

Ile Tyr Pro Gly Asp Ser Asp Thr
1               5

<210> SEQ ID NO 132
<211> LENGTH: 23
<212> TYPE: PRT
<213> ORGANISM: Artificial Sequence
<220> FEATURE:
<223> OTHER INFORMATION: Synthetic Construct

<400> SEQUENCE: 132

Ala Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 133
<211> LENGTH: 8
<212> TYPE: PRT
<213> ORGANISM: Artificial Sequence
<220> FEATURE:
<223> OTHER INFORMATION: Synthetic Construct

<400> SEQUENCE: 133

Gly Tyr Ser Phe Thr Ser Tyr Trp
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic Construct

<400> SEQUENCE: 134

Ile Tyr Pro Gly Asp Ser Asp Thr
1               5

<210> SEQ ID NO 135
<211> LENGTH: 23
<212> TYPE: PRT
<213> ORGANISM: Artificial Sequence
<220> FEATURE:
<223> OTHER INFORMATION: Synthetic Construct

<400> SEQUENCE: 135

Ala Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 136
<211> LENGTH: 8
<212> TYPE: PRT
<213> ORGANISM: Artificial Sequence
<220> FEATURE:
<223> OTHER INFORMATION: Synthetic Construct

<400> SEQUENCE: 136

Gly Tyr Ser Phe Thr Ser Tyr Trp
1               5
```

```
<210> SEQ ID NO 137
<211> LENGTH: 8
<212> TYPE: PRT
<213> ORGANISM: Artificial Sequence
<220> FEATURE:
<223> OTHER INFORMATION: Synthetic Construct

<400> SEQUENCE: 137

Ile Tyr Pro Gly Asp Ser Asp Thr
1               5

<210> SEQ ID NO 138
<211> LENGTH: 23
<212> TYPE: PRT
<213> ORGANISM: Artificial Sequence
<220> FEATURE:
<223> OTHER INFORMATION: Synthetic Construct

<400> SEQUENCE: 138

Ala Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 139
<211> LENGTH: 8
<212> TYPE: PRT
<213> ORGANISM: Artificial Sequence
<220> FEATURE:
<223> OTHER INFORMATION: Synthetic Construct

<400> SEQUENCE: 139

Gly Tyr Ser Phe Thr Ser Tyr Trp
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic Construct

<400> SEQUENCE: 140

Ile Tyr Pro Gly Asp Ser Asp Thr
1               5

<210> SEQ ID NO 141
<211> LENGTH: 23
<212> TYPE: PRT
<213> ORGANISM: Artificial Sequence
<220> FEATURE:
<223> OTHER INFORMATION: Synthetic Construct

<400> SEQUENCE: 141

Ala Arg Gln Val Trp Gly Trp Gln Gly Gly Met Asn Pro Arg Ser Asn
1               5                   10                  15

Trp Trp Tyr Asn Met Asp Ser
            20

<210> SEQ ID NO 142
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 142

Gly Tyr Ser Phe Thr Ser Tyr Trp
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic Construct

<400> SEQUENCE: 143

Ile Tyr Pro Gly Asp Ser Asp Thr
1               5

<210> SEQ ID NO 144
<211> LENGTH: 23
<212> TYPE: PRT
<213> ORGANISM: Artificial Sequence
<220> FEATURE:
<223> OTHER INFORMATION: Synthetic Construct

<400> SEQUENCE: 144

Ala Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 145
<211> LENGTH: 8
<212> TYPE: PRT
<213> ORGANISM: Artificial Sequence
<220> FEATURE:
<223> OTHER INFORMATION: Synthetic Construct

<400> SEQUENCE: 145

Gly Tyr Ser Phe Thr Ser Phe Trp
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic Construct

<400> SEQUENCE: 146

Ile Tyr Pro Gly Asp Ser Asp Thr
1               5

<210> SEQ ID NO 147
<211> LENGTH: 23
<212> TYPE: PRT
<213> ORGANISM: Artificial Sequence
<220> FEATURE:
<223> OTHER INFORMATION: Synthetic Construct

<400> SEQUENCE: 147

Val Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 148

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 148

Gly Tyr Ser Phe Thr Ser Tyr Trp
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic Construct

<400> SEQUENCE: 149

Ile Tyr Pro Gly Asp Ser Asp Thr
1               5

<210> SEQ ID NO 150
<211> LENGTH: 23
<212> TYPE: PRT
<213> ORGANISM: Artificial Sequence
<220> FEATURE:
<223> OTHER INFORMATION: Synthetic Construct

<400> SEQUENCE: 150

Ala Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 151
<211> LENGTH: 8
<212> TYPE: PRT
<213> ORGANISM: Artificial Sequence
<220> FEATURE:
<223> OTHER INFORMATION: Synthetic Construct

<400> SEQUENCE: 151

Gly Tyr Ser Phe Thr Ser Tyr Trp
1               5

<210> SEQ ID NO 152
<211> LENGTH: 8
<212> TYPE: PRT
<213> ORGANISM: Artificial Sequence
<220> FEATURE:
<223> OTHER INFORMATION: Synthetic Construct

<400> SEQUENCE: 152

Ile Tyr Pro Gly Asp Ser Asp Thr
1               5

<210> SEQ ID NO 153
<211> LENGTH: 23
<212> TYPE: PRT
<213> ORGANISM: Artificial Sequence
<220> FEATURE:
<223> OTHER INFORMATION: Synthetic Construct

<400> SEQUENCE: 153

Ala Arg Gln Val Trp Gly Trp Gln Gly Gly Met Tyr Pro Arg Ser Asn
1               5                   10                  15
```

Trp Trp Tyr Asn Leu Asp Ser
            20

<210> SEQ ID NO 154
<211> LENGTH: 8
<212> TYPE: PRT
<213> ORGANISM: Artificial Sequence
<220> FEATURE:
<223> OTHER INFORMATION: Synthetic Construct

<400> SEQUENCE: 154

Gly Tyr Ser Phe Thr Ser Tyr Trp
1               5

<210> SEQ ID NO 155
<211> LENGTH: 8
<212> TYPE: PRT
<213> ORGANISM: Artificial Sequence
<220> FEATURE:
<223> OTHER INFORMATION: Synthetic Construct

<400> SEQUENCE: 155

Ile Tyr Pro Gly Asp Ser Asp Thr
1               5

<210> SEQ ID NO 156
<211> LENGTH: 23
<212> TYPE: PRT
<213> ORGANISM: Artificial Sequence
<220> FEATURE:
<223> OTHER INFORMATION: Synthetic Construct

<400> SEQUENCE: 156

Ala Arg Gln Val Trp Gly Trp Gln Gly Gly Met Tyr Pro Arg Ser Asn
1               5                   10                  15

Trp Trp Tyr Asn Met Asp Ser
            20

<210> SEQ ID NO 157
<211> LENGTH: 8
<212> TYPE: PRT
<213> ORGANISM: Artificial Sequence
<220> FEATURE:
<223> OTHER INFORMATION: Synthetic Construct

<400> SEQUENCE: 157

Gly Tyr Ser Phe Thr Ser Tyr Trp
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic Construct

<400> SEQUENCE: 158

Ile Tyr Pro Gly Asp Ser Asp Thr
1               5

<210> SEQ ID NO 159
<211> LENGTH: 14
<212> TYPE: PRT
<213> ORGANISM: Artificial Sequence
<220> FEATURE:
<223> OTHER INFORMATION: Synthetic Construct

```
<400> SEQUENCE: 159

Ala Arg Trp Ser Ser Trp Asp Ser Met Tyr Met Asp Tyr
1               5                   10

<210> SEQ ID NO 160
<211> LENGTH: 8
<212> TYPE: PRT
<213> ORGANISM: Artificial Sequence
<220> FEATURE:
<223> OTHER INFORMATION: Synthetic Construct

<400> SEQUENCE: 160

Gly Tyr Ser Phe Thr Ser Tyr Trp
1               5

<210> SEQ ID NO 161
<211> LENGTH: 8
<212> TYPE: PRT
<213> ORGANISM: Artificial Sequence
<220> FEATURE:
<223> OTHER INFORMATION: Synthetic Construct

<400> SEQUENCE: 161

Ile Tyr Pro Gly Asp Ser Asp Thr
1               5

<210> SEQ ID NO 162
<211> LENGTH: 14
<212> TYPE: PRT
<213> ORGANISM: Artificial Sequence
<220> FEATURE:
<223> OTHER INFORMATION: Synthetic Construct

<400> SEQUENCE: 162

Ala Arg Trp Ser Ser Thr Trp Asp Ser Met Tyr Met Glu Tyr
1               5                   10

<210> SEQ ID NO 163
<211> LENGTH: 8
<212> TYPE: PRT
<213> ORGANISM: Artificial Sequence
<220> FEATURE:
<223> OTHER INFORMATION: Synthetic Construct

<400> SEQUENCE: 163

Gly Tyr Ser Phe Thr Ser Tyr Trp
1               5

<210> SEQ ID NO 164
<211> LENGTH: 8
<212> TYPE: PRT
<213> ORGANISM: Artificial Sequence
<220> FEATURE:
<223> OTHER INFORMATION: Synthetic Construct

<400> SEQUENCE: 164

Ile Tyr Pro Gly Asp Ser Asp Thr
1               5

<210> SEQ ID NO 165
<211> LENGTH: 14
<212> TYPE: PRT
<213> ORGANISM: Artificial Sequence
<220> FEATURE:
<223> OTHER INFORMATION: Synthetic Construct

<400> SEQUENCE: 165
```

Ala Arg Trp Ser Ser Thr Trp Asp Ser Met Tyr Met Asp Tyr
1               5                   10

<210> SEQ ID NO 166
<211> LENGTH: 8
<212> TYPE: PRT
<213> ORGANISM: Artificial Sequence
<220> FEATURE:
<223> OTHER INFORMATION: Synthetic Construct

<400> SEQUENCE: 166

Gly Tyr Ser Phe Thr Ser Tyr Trp
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic Construct

<400> SEQUENCE: 167

Ile Tyr Pro Gly Asp Ser Asp Thr
1               5

<210> SEQ ID NO 168
<211> LENGTH: 14
<212> TYPE: PRT
<213> ORGANISM: Artificial Sequence
<220> FEATURE:
<223> OTHER INFORMATION: Synthetic Construct

<400> SEQUENCE: 168

Ala Arg Trp Ser Ser Thr Trp Asp Ser Leu Tyr Met Asp Tyr
1               5                   10

<210> SEQ ID NO 169
<211> LENGTH: 8
<212> TYPE: PRT
<213> ORGANISM: Artificial Sequence
<220> FEATURE:
<223> OTHER INFORMATION: Synthetic Construct

<400> SEQUENCE: 169

Gly Tyr Ser Phe Thr Ser Tyr Trp
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic Construct

<400> SEQUENCE: 170

Ile Tyr Pro Gly Asp Ser Asp Thr
1               5

<210> SEQ ID NO 171
<211> LENGTH: 14
<212> TYPE: PRT
<213> ORGANISM: Artificial Sequence
<220> FEATURE:
<223> OTHER INFORMATION: Synthetic Construct

<400> SEQUENCE: 171

Ala Arg Trp Ser Ser Thr Trp Asp Ser Met Tyr Met Asp Tyr
1               5                   10

<210> SEQ ID NO 172
<211> LENGTH: 8
<212> TYPE: PRT
<213> ORGANISM: Artificial Sequence
<220> FEATURE:
<223> OTHER INFORMATION: Synthetic Construct

<400> SEQUENCE: 172

Ala Tyr Ser Phe Thr Ser Tyr Trp
1               5

<210> SEQ ID NO 173
<211> LENGTH: 8
<212> TYPE: PRT
<213> ORGANISM: Artificial Sequence
<220> FEATURE:
<223> OTHER INFORMATION: Synthetic Construct

<400> SEQUENCE: 173

Ile Tyr Pro Gly Asp Ser Asp Thr
1               5

<210> SEQ ID NO 174
<211> LENGTH: 14
<212> TYPE: PRT
<213> ORGANISM: Artificial Sequence
<220> FEATURE:
<223> OTHER INFORMATION: Synthetic Construct

<400> SEQUENCE: 174

Ala Arg Trp Ser Ser Thr Trp Asp Ser Met Tyr Met Asp Tyr
1               5                   10

<210> SEQ ID NO 175
<211> LENGTH: 8
<212> TYPE: PRT
<213> ORGANISM: Artificial Sequence
<220> FEATURE:
<223> OTHER INFORMATION: Synthetic Construct

<400> SEQUENCE: 175

Gly Tyr Ser Phe Thr Ser Tyr Trp
1               5

<210> SEQ ID NO 176
<211> LENGTH: 8
<212> TYPE: PRT
<213> ORGANISM: Artificial Sequence
<220> FEATURE:
<223> OTHER INFORMATION: Synthetic Construct

<400> SEQUENCE: 176

Ile Tyr Pro Gly Asp Ser Asp Thr
1               5

<210> SEQ ID NO 177
<211> LENGTH: 14
<212> TYPE: PRT
<213> ORGANISM: Artificial Sequence
<220> FEATURE:
<223> OTHER INFORMATION: Synthetic Construct

<400> SEQUENCE: 177

Ala Arg Trp Ser Ser Thr Trp Asp Ser Met Tyr Met Asp Tyr

```
1               5                   10

<210> SEQ ID NO 178
<211> LENGTH: 8
<212> TYPE: PRT
<213> ORGANISM: Artificial Sequence
<220> FEATURE:
<223> OTHER INFORMATION: Synthetic Construct

<400> SEQUENCE: 178

Gly Tyr Ser Phe Thr Ser Tyr Trp
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic Construct

<400> SEQUENCE: 179

Tyr Pro Gly Asp Ser Asp Thr
1               5

<210> SEQ ID NO 180
<211> LENGTH: 14
<212> TYPE: PRT
<213> ORGANISM: Artificial Sequence
<220> FEATURE:
<223> OTHER INFORMATION: Synthetic Construct

<400> SEQUENCE: 180

Ala Arg Trp Ser Ser Ser Trp Asp Ser Met Tyr Met Asp Tyr
1               5                   10

<210> SEQ ID NO 181
<211> LENGTH: 8
<212> TYPE: PRT
<213> ORGANISM: Artificial Sequence
<220> FEATURE:
<223> OTHER INFORMATION: Synthetic Construct

<400> SEQUENCE: 181

Ser Ser Asn Ile Gly Asn Asn Tyr
1               5

<210> SEQ ID NO 182
<211> LENGTH: 3
<212> TYPE: PRT
<213> ORGANISM: Artificial Sequence
<220> FEATURE:
<223> OTHER INFORMATION: Synthetic Construct

<400> SEQUENCE: 182

Asp Asn Asn
1

<210> SEQ ID NO 183
<211> LENGTH: 11
<212> TYPE: PRT
<213> ORGANISM: Artificial Sequence
<220> FEATURE:
<223> OTHER INFORMATION: Synthetic Construct

<400> SEQUENCE: 183

Gly Thr Trp Asp Ser Ser Leu Ser Ala Gly Val
1               5                   10
```

```
<210> SEQ ID NO 184
<211> LENGTH: 8
<212> TYPE: PRT
<213> ORGANISM: Artificial Sequence
<220> FEATURE:
<223> OTHER INFORMATION: Synthetic Construct

<400> SEQUENCE: 184

Ser Ser Asn Ile Gly Asn Asn Tyr
1               5

<210> SEQ ID NO 185
<211> LENGTH: 3
<212> TYPE: PRT
<213> ORGANISM: Artificial Sequence
<220> FEATURE:
<223> OTHER INFORMATION: Synthetic Construct

<400> SEQUENCE: 185

Glu Asn Asn
1

<210> SEQ ID NO 186
<211> LENGTH: 11
<212> TYPE: PRT
<213> ORGANISM: Artificial Sequence
<220> FEATURE:
<223> OTHER INFORMATION: Synthetic Construct

<400> SEQUENCE: 186

Gly Thr Trp Asp Ser Ser Leu Arg Ala Gly Val
1               5                   10

<210> SEQ ID NO 187
<211> LENGTH: 8
<212> TYPE: PRT
<213> ORGANISM: Artificial Sequence
<220> FEATURE:
<223> OTHER INFORMATION: Synthetic Construct

<400> SEQUENCE: 187

Ser Ser Asn Ile Gly Ser Asn Thr
1               5

<210> SEQ ID NO 188
<211> LENGTH: 3
<212> TYPE: PRT
<213> ORGANISM: Artificial Sequence
<220> FEATURE:
<223> OTHER INFORMATION: Synthetic Construct

<400> SEQUENCE: 188

Ser Asn Asn
1

<210> SEQ ID NO 189
<211> LENGTH: 12
<212> TYPE: PRT
<213> ORGANISM: Artificial Sequence
<220> FEATURE:
<223> OTHER INFORMATION: Synthetic Construct

<400> SEQUENCE: 189

Ala Ala Trp Asp Asp Ser Leu Asn Gly His Val Val
1               5                   10
```

<210> SEQ ID NO 190
<211> LENGTH: 8
<212> TYPE: PRT
<213> ORGANISM: Artificial Sequence
<220> FEATURE:
<223> OTHER INFORMATION: Synthetic Construct

<400> SEQUENCE: 190

Ser Ser Asn Ile Gly Ser His Thr
1               5

<210> SEQ ID NO 191
<211> LENGTH: 3
<212> TYPE: PRT
<213> ORGANISM: Artificial Sequence
<220> FEATURE:
<223> OTHER INFORMATION: Synthetic Construct

<400> SEQUENCE: 191

Ser Asn Asn
1

<210> SEQ ID NO 192
<211> LENGTH: 11
<212> TYPE: PRT
<213> ORGANISM: Artificial Sequence
<220> FEATURE:
<223> OTHER INFORMATION: Synthetic Construct

<400> SEQUENCE: 192

Ala Ala Trp Asp Asp Ser Leu Asn Gly Tyr Val
1               5                   10

<210> SEQ ID NO 193
<211> LENGTH: 6
<212> TYPE: PRT
<213> ORGANISM: Artificial Sequence
<220> FEATURE:
<223> OTHER INFORMATION: Synthetic Construct

<400> SEQUENCE: 193

Gln Gly Ile Thr Asn Ser
1               5

<210> SEQ ID NO 194
<211> LENGTH: 3
<212> TYPE: PRT
<213> ORGANISM: Artificial Sequence
<220> FEATURE:
<223> OTHER INFORMATION: Synthetic Construct

<400> SEQUENCE: 194

Ala Ala Ser
1

<210> SEQ ID NO 195
<211> LENGTH: 9
<212> TYPE: PRT
<213> ORGANISM: Artificial Sequence
<220> FEATURE:
<223> OTHER INFORMATION: Synthetic Construct

<400> SEQUENCE: 195

Gln His Tyr Leu Gly Thr Pro Tyr Ser
1               5

<210> SEQ ID NO 196
<211> LENGTH: 6
<212> TYPE: PRT
<213> ORGANISM: Artificial Sequence
<220> FEATURE:
<223> OTHER INFORMATION: Synthetic Construct

<400> SEQUENCE: 196

Gln Ser Val Ser Arg Phe
1               5

<210> SEQ ID NO 197
<211> LENGTH: 3
<212> TYPE: PRT
<213> ORGANISM: Artificial Sequence
<220> FEATURE:
<223> OTHER INFORMATION: Synthetic Construct

<400> SEQUENCE: 197

Gly Val Ser
1

<210> SEQ ID NO 198
<211> LENGTH: 9
<212> TYPE: PRT
<213> ORGANISM: Artificial Sequence
<220> FEATURE:
<223> OTHER INFORMATION: Synthetic Construct

<400> SEQUENCE: 198

Gln Glu Ser Tyr Ile Ile Pro Leu Thr
1               5

<210> SEQ ID NO 199
<211> LENGTH: 11
<212> TYPE: PRT
<213> ORGANISM: Artificial Sequence
<220> FEATURE:
<223> OTHER INFORMATION: Synthetic Construct

<400> SEQUENCE: 199

Gln Ser Leu Leu Asp Ser Asn Gly Phe Asn Ser
1               5                   10

<210> SEQ ID NO 200
<211> LENGTH: 3
<212> TYPE: PRT
<213> ORGANISM: Artificial Sequence
<220> FEATURE:
<223> OTHER INFORMATION: Synthetic Construct

<400> SEQUENCE: 200

Leu Gly Ser
1

<210> SEQ ID NO 201
<211> LENGTH: 8
<212> TYPE: PRT
<213> ORGANISM: Artificial Sequence
<220> FEATURE:
<223> OTHER INFORMATION: Synthetic Construct

<400> SEQUENCE: 201

Met Gln Ser Leu Gln Ile Pro Thr
1               5

<210> SEQ ID NO 202

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 202

Ser Ser Asn Ile Gly Ser Asn Tyr
1               5

<210> SEQ ID NO 203
<211> LENGTH: 3
<212> TYPE: PRT
<213> ORGANISM: Artificial Sequence
<220> FEATURE:
<223> OTHER INFORMATION: Synthetic Construct

<400> SEQUENCE: 203

Arg Asn Asn
1

<210> SEQ ID NO 204
<211> LENGTH: 11
<212> TYPE: PRT
<213> ORGANISM: Artificial Sequence
<220> FEATURE:
<223> OTHER INFORMATION: Synthetic Construct

<400> SEQUENCE: 204

Ala Ala Trp Asp Asp Ser Leu Ser Gly Tyr Val
1               5                   10

<210> SEQ ID NO 205
<211> LENGTH: 6
<212> TYPE: PRT
<213> ORGANISM: Artificial Sequence
<220> FEATURE:
<223> OTHER INFORMATION: Synthetic Construct

<400> SEQUENCE: 205

Lys Leu Gly Asp Lys Tyr
1               5

<210> SEQ ID NO 206
<211> LENGTH: 3
<212> TYPE: PRT
<213> ORGANISM: Artificial Sequence
<220> FEATURE:
<223> OTHER INFORMATION: Synthetic Construct

<400> SEQUENCE: 206

Gln Asp Asn
1

<210> SEQ ID NO 207
<211> LENGTH: 10
<212> TYPE: PRT
<213> ORGANISM: Artificial Sequence
<220> FEATURE:
<223> OTHER INFORMATION: Synthetic Construct

<400> SEQUENCE: 207

Gln Ala Trp Asp Ser Ser Thr Glu Asp Val
1               5                   10

<210> SEQ ID NO 208
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 208

Gln Ser Ile Ser Ser Tyr
1               5

<210> SEQ ID NO 209
<211> LENGTH: 3
<212> TYPE: PRT
<213> ORGANISM: Artificial Sequence
<220> FEATURE:
<223> OTHER INFORMATION: Synthetic Construct

<400> SEQUENCE: 209

Ala Ala Ser
1

<210> SEQ ID NO 210
<211> LENGTH: 9
<212> TYPE: PRT
<213> ORGANISM: Artificial Sequence
<220> FEATURE:
<223> OTHER INFORMATION: Synthetic Construct

<400> SEQUENCE: 210

Gln Gln Ser Tyr Ser Thr Pro Phe Thr
1               5

<210> SEQ ID NO 211
<211> LENGTH: 6
<212> TYPE: PRT
<213> ORGANISM: Artificial Sequence
<220> FEATURE:
<223> OTHER INFORMATION: Synthetic Construct

<400> SEQUENCE: 211

Gln Gly Ile Gly Ser Tyr
1               5

<210> SEQ ID NO 212
<211> LENGTH: 3
<212> TYPE: PRT
<213> ORGANISM: Artificial Sequence
<220> FEATURE:
<223> OTHER INFORMATION: Synthetic Construct

<400> SEQUENCE: 212

Pro Ala Ser
1

<210> SEQ ID NO 213
<211> LENGTH: 6
<212> TYPE: PRT
<213> ORGANISM: Artificial Sequence
<220> FEATURE:
<223> OTHER INFORMATION: Synthetic Construct

<400> SEQUENCE: 213

Gln Gln Leu Asn Ser Leu
1               5

<210> SEQ ID NO 214
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 214

Ser Ser Asn Ile Gly Thr Lys Thr
1               5

<210> SEQ ID NO 215
<211> LENGTH: 3
<212> TYPE: PRT
<213> ORGANISM: Artificial Sequence
<220> FEATURE:
<223> OTHER INFORMATION: Synthetic Construct

<400> SEQUENCE: 215

Ser Asn Tyr
1

<210> SEQ ID NO 216
<211> LENGTH: 11
<212> TYPE: PRT
<213> ORGANISM: Artificial Sequence
<220> FEATURE:
<223> OTHER INFORMATION: Synthetic Construct

<400> SEQUENCE: 216

Ala Leu Trp Asp Asp Ser Leu Asp Gly Tyr Val
1               5                   10

<210> SEQ ID NO 217
<211> LENGTH: 6
<212> TYPE: PRT
<213> ORGANISM: Artificial Sequence
<220> FEATURE:
<223> OTHER INFORMATION: Synthetic Construct

<400> SEQUENCE: 217

Asn Ile Gly Ser Lys Ser
1               5

<210> SEQ ID NO 218
<211> LENGTH: 3
<212> TYPE: PRT
<213> ORGANISM: Artificial Sequence
<220> FEATURE:
<223> OTHER INFORMATION: Synthetic Construct

<400> SEQUENCE: 218

Tyr Asp Ser
1

<210> SEQ ID NO 219
<211> LENGTH: 11
<212> TYPE: PRT
<213> ORGANISM: Artificial Sequence
<220> FEATURE:
<223> OTHER INFORMATION: Synthetic Construct

<400> SEQUENCE: 219

Gln Val Trp Asp Ser Ser Ser Asp His Tyr Val
1               5                   10

<210> SEQ ID NO 220
<211> LENGTH: 6
<212> TYPE: PRT
<213> ORGANISM: Artificial Sequence
```

```
<220> FEATURE:
<223> OTHER INFORMATION: Synthetic Construct

<400> SEQUENCE: 220

Asn Ile Gly Ser Lys Ser
1               5

<210> SEQ ID NO 221
<211> LENGTH: 3
<212> TYPE: PRT
<213> ORGANISM: Artificial Sequence
<220> FEATURE:
<223> OTHER INFORMATION: Synthetic Construct

<400> SEQUENCE: 221

Asp Asp Ser
1

<210> SEQ ID NO 222
<211> LENGTH: 11
<212> TYPE: PRT
<213> ORGANISM: Artificial Sequence
<220> FEATURE:
<223> OTHER INFORMATION: Synthetic Construct

<400> SEQUENCE: 222

Gln Val Trp Asp Ser Ser Ser Asp His Tyr Val
1               5                   10

<210> SEQ ID NO 223
<211> LENGTH: 6
<212> TYPE: PRT
<213> ORGANISM: Artificial Sequence
<220> FEATURE:
<223> OTHER INFORMATION: Synthetic Construct

<400> SEQUENCE: 223

Asn Ile Gly Ser Lys Ser
1               5

<210> SEQ ID NO 224
<211> LENGTH: 3
<212> TYPE: PRT
<213> ORGANISM: Artificial Sequence
<220> FEATURE:
<223> OTHER INFORMATION: Synthetic Construct

<400> SEQUENCE: 224

Asp Asp Ser
1

<210> SEQ ID NO 225
<211> LENGTH: 11
<212> TYPE: PRT
<213> ORGANISM: Artificial Sequence
<220> FEATURE:
<223> OTHER INFORMATION: Synthetic Construct

<400> SEQUENCE: 225

Gln Val Trp Asp Ser Ser Ser Asp Tyr Val Val
1               5                   10

<210> SEQ ID NO 226
<211> LENGTH: 8
<212> TYPE: PRT
<213> ORGANISM: Artificial Sequence
<220> FEATURE:
```

<223> OTHER INFORMATION: Synthetic Construct

<400> SEQUENCE: 226

Ser Ser Asn Val Gly Asn Asn Ala
1               5

<210> SEQ ID NO 227
<211> LENGTH: 3
<212> TYPE: PRT
<213> ORGANISM: Artificial Sequence
<220> FEATURE:
<223> OTHER INFORMATION: Synthetic Construct

<400> SEQUENCE: 227

Tyr Asp Asp
1

<210> SEQ ID NO 228
<211> LENGTH: 11
<212> TYPE: PRT
<213> ORGANISM: Artificial Sequence
<220> FEATURE:
<223> OTHER INFORMATION: Synthetic Construct

<400> SEQUENCE: 228

Ala Ala Trp Asp Asp Ser Leu Asn Gly Pro Val
1               5                   10

<210> SEQ ID NO 229
<211> LENGTH: 6
<212> TYPE: PRT
<213> ORGANISM: Artificial Sequence
<220> FEATURE:
<223> OTHER INFORMATION: Synthetic Construct

<400> SEQUENCE: 229

Asn Ile Gly Ser Glu Ser
1               5

<210> SEQ ID NO 230
<211> LENGTH: 3
<212> TYPE: PRT
<213> ORGANISM: Artificial Sequence
<220> FEATURE:
<223> OTHER INFORMATION: Synthetic Construct

<400> SEQUENCE: 230

Tyr Asp Ser
1

<210> SEQ ID NO 231
<211> LENGTH: 12
<212> TYPE: PRT
<213> ORGANISM: Artificial Sequence
<220> FEATURE:
<223> OTHER INFORMATION: Synthetic Construct

<400> SEQUENCE: 231

Gln Val Trp Asn Ser Ser Ser Asp His Arg Gly Val
1               5                   10

<210> SEQ ID NO 232
<211> LENGTH: 6
<212> TYPE: PRT
<213> ORGANISM: Artificial Sequence
<220> FEATURE:
<223> OTHER INFORMATION: Synthetic Construct

```
<400> SEQUENCE: 232

Asn Ile Gly Ser Lys Ser
1               5

<210> SEQ ID NO 233
<211> LENGTH: 3
<212> TYPE: PRT
<213> ORGANISM: Artificial Sequence
<220> FEATURE:
<223> OTHER INFORMATION: Synthetic Construct

<400> SEQUENCE: 233

Asp Asp Ser
1

<210> SEQ ID NO 234
<211> LENGTH: 11
<212> TYPE: PRT
<213> ORGANISM: Artificial Sequence
<220> FEATURE:
<223> OTHER INFORMATION: Synthetic Construct

<400> SEQUENCE: 234

Gln Val Trp Asp Ser Ser Ser Asp Tyr Val Val
1               5                   10

<210> SEQ ID NO 235
<211> LENGTH: 6
<212> TYPE: PRT
<213> ORGANISM: Artificial Sequence
<220> FEATURE:
<223> OTHER INFORMATION: Synthetic Construct

<400> SEQUENCE: 235

Asn Ile Gly Ser Lys Ser
1               5

<210> SEQ ID NO 236
<211> LENGTH: 3
<212> TYPE: PRT
<213> ORGANISM: Artificial Sequence
<220> FEATURE:
<223> OTHER INFORMATION: Synthetic Construct

<400> SEQUENCE: 236

Asp Asp Ser
1

<210> SEQ ID NO 237
<211> LENGTH: 11
<212> TYPE: PRT
<213> ORGANISM: Artificial Sequence
<220> FEATURE:
<223> OTHER INFORMATION: Synthetic Construct

<400> SEQUENCE: 237

Gln Val Trp Asp Ser Ser Ser Asp Tyr Val Val
1               5                   10

<210> SEQ ID NO 238
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 238

Asn Ile Gly Ser Lys Ser
1               5

<210> SEQ ID NO 239
<211> LENGTH: 3
<212> TYPE: PRT
<213> ORGANISM: Artificial Sequence
<220> FEATURE:
<223> OTHER INFORMATION: Synthetic Construct

<400> SEQUENCE: 239

Asp Asp Ser
1

<210> SEQ ID NO 240
<211> LENGTH: 11
<212> TYPE: PRT
<213> ORGANISM: Artificial Sequence
<220> FEATURE:
<223> OTHER INFORMATION: Synthetic Construct

<400> SEQUENCE: 240

Gln Val Trp Asp Ser Ser Ser Glu Tyr Val Val
1               5                   10

<210> SEQ ID NO 241
<211> LENGTH: 6
<212> TYPE: PRT
<213> ORGANISM: Artificial Sequence
<220> FEATURE:
<223> OTHER INFORMATION: Synthetic Construct

<400> SEQUENCE: 241

Asn Ile Gly Ser Lys Ser
1               5

<210> SEQ ID NO 242
<211> LENGTH: 3
<212> TYPE: PRT
<213> ORGANISM: Artificial Sequence
<220> FEATURE:
<223> OTHER INFORMATION: Synthetic Construct

<400> SEQUENCE: 242

Asp Asp Ser
1

<210> SEQ ID NO 243
<211> LENGTH: 11
<212> TYPE: PRT
<213> ORGANISM: Artificial Sequence
<220> FEATURE:
<223> OTHER INFORMATION: Synthetic Construct

<400> SEQUENCE: 243

Gln Val Trp Asp Ser Ser Ser Gly Tyr Val Val
1               5                   10

<210> SEQ ID NO 244
<211> LENGTH: 6
<212> TYPE: PRT
<213> ORGANISM: Artificial Sequence
<220> FEATURE:
<223> OTHER INFORMATION: Synthetic Construct

<400> SEQUENCE: 244
```

```
Asn Ile Gly Ser Lys Ser
1               5

<210> SEQ ID NO 245
<211> LENGTH: 3
<212> TYPE: PRT
<213> ORGANISM: Artificial Sequence
<220> FEATURE:
<223> OTHER INFORMATION: Synthetic Construct

<400> SEQUENCE: 245

Asp Asp Ser
1

<210> SEQ ID NO 246
<211> LENGTH: 11
<212> TYPE: PRT
<213> ORGANISM: Artificial Sequence
<220> FEATURE:
<223> OTHER INFORMATION: Synthetic Construct

<400> SEQUENCE: 246

Gln Val Trp Asp Ser Thr Ser Asp Tyr Val Val
1               5                   10

<210> SEQ ID NO 247
<211> LENGTH: 6
<212> TYPE: PRT
<213> ORGANISM: Artificial Sequence
<220> FEATURE:
<223> OTHER INFORMATION: Synthetic Construct

<400> SEQUENCE: 247

Asn Ile Gly Ser Lys Ser
1               5

<210> SEQ ID NO 248
<211> LENGTH: 3
<212> TYPE: PRT
<213> ORGANISM: Artificial Sequence
<220> FEATURE:
<223> OTHER INFORMATION: Synthetic Construct

<400> SEQUENCE: 248

Asp Asp Ser
1

<210> SEQ ID NO 249
<211> LENGTH: 11
<212> TYPE: PRT
<213> ORGANISM: Artificial Sequence
<220> FEATURE:
<223> OTHER INFORMATION: Synthetic Construct

<400> SEQUENCE: 249

Gln Val Trp Asp Ser Ser Ser Asp Tyr Val Val
1               5                   10

<210> SEQ ID NO 250
<211> LENGTH: 6
<212> TYPE: PRT
<213> ORGANISM: Artificial Sequence
<220> FEATURE:
<223> OTHER INFORMATION: Synthetic Construct

<400> SEQUENCE: 250
```

Asn Ile Gly Ser Lys Ser
1               5

<210> SEQ ID NO 251
<211> LENGTH: 3
<212> TYPE: PRT
<213> ORGANISM: Artificial Sequence
<220> FEATURE:
<223> OTHER INFORMATION: Synthetic Construct

<400> SEQUENCE: 251

Asp Asp Ser
1

<210> SEQ ID NO 252
<211> LENGTH: 11
<212> TYPE: PRT
<213> ORGANISM: Artificial Sequence
<220> FEATURE:
<223> OTHER INFORMATION: Synthetic Construct

<400> SEQUENCE: 252

Gln Val Trp Asp Ser Ser Ser Asp Tyr Val Val
1               5                   10

<210> SEQ ID NO 253
<211> LENGTH: 6
<212> TYPE: PRT
<213> ORGANISM: Artificial Sequence
<220> FEATURE:
<223> OTHER INFORMATION: Synthetic Construct

<400> SEQUENCE: 253

Asn Ile Gly Ser Lys Ser
1               5

<210> SEQ ID NO 254
<211> LENGTH: 3
<212> TYPE: PRT
<213> ORGANISM: Artificial Sequence
<220> FEATURE:
<223> OTHER INFORMATION: Synthetic Construct

<400> SEQUENCE: 254

Asp Asp Ser
1

<210> SEQ ID NO 255
<211> LENGTH: 11
<212> TYPE: PRT
<213> ORGANISM: Artificial Sequence
<220> FEATURE:
<223> OTHER INFORMATION: Synthetic Construct

<400> SEQUENCE: 255

Gln Val Trp Asp Ser Ser Ser Asp Tyr Val Val
1               5                   10

<210> SEQ ID NO 256
<211> LENGTH: 6
<212> TYPE: PRT
<213> ORGANISM: Artificial Sequence
<220> FEATURE:
<223> OTHER INFORMATION: Synthetic Construct

<400> SEQUENCE: 256

Asn Ile Gly Ser Lys Ser

```
1               5
```

<210> SEQ ID NO 257
<211> LENGTH: 3
<212> TYPE: PRT
<213> ORGANISM: Artificial Sequence
<220> FEATURE:
<223> OTHER INFORMATION: Synthetic Construct

<400> SEQUENCE: 257

```
Asp Asp Ser
1
```

<210> SEQ ID NO 258
<211> LENGTH: 11
<212> TYPE: PRT
<213> ORGANISM: Artificial Sequence
<220> FEATURE:
<223> OTHER INFORMATION: Synthetic Construct

<400> SEQUENCE: 258

```
Gln Val Trp Asp Ser Ser Ser Asp Tyr Val Val
1               5                   10
```

<210> SEQ ID NO 259
<211> LENGTH: 6
<212> TYPE: PRT
<213> ORGANISM: Artificial Sequence
<220> FEATURE:
<223> OTHER INFORMATION: Synthetic Construct

<400> SEQUENCE: 259

```
Asn Ile Gly Ser Lys Ser
1               5
```

<210> SEQ ID NO 260
<211> LENGTH: 3
<212> TYPE: PRT
<213> ORGANISM: Artificial Sequence
<220> FEATURE:
<223> OTHER INFORMATION: Synthetic Construct

<400> SEQUENCE: 260

```
Asp Asp Ser
1
```

<210> SEQ ID NO 261
<211> LENGTH: 11
<212> TYPE: PRT
<213> ORGANISM: Artificial Sequence
<220> FEATURE:
<223> OTHER INFORMATION: Synthetic Construct

<400> SEQUENCE: 261

```
Gln Val Trp Asp Ser Ser Ser Asp Tyr Val Val
1               5                   10
```

<210> SEQ ID NO 262
<211> LENGTH: 6
<212> TYPE: PRT
<213> ORGANISM: Artificial Sequence
<220> FEATURE:
<223> OTHER INFORMATION: Synthetic Construct

<400> SEQUENCE: 262

```
Asn Ile Gly Ser Lys Ser
1               5
```

<210> SEQ ID NO 263
<211> LENGTH: 3
<212> TYPE: PRT
<213> ORGANISM: Artificial Sequence
<220> FEATURE:
<223> OTHER INFORMATION: Synthetic Construct

<400> SEQUENCE: 263

Asp Asp Ser
1

<210> SEQ ID NO 264
<211> LENGTH: 11
<212> TYPE: PRT
<213> ORGANISM: Artificial Sequence
<220> FEATURE:
<223> OTHER INFORMATION: Synthetic Construct

<400> SEQUENCE: 264

Gln Val Trp Asp Ser Ser Ser Asp Tyr Val Val
1               5                   10

<210> SEQ ID NO 265
<211> LENGTH: 8
<212> TYPE: PRT
<213> ORGANISM: Artificial Sequence
<220> FEATURE:
<223> OTHER INFORMATION: Synthetic Construct

<400> SEQUENCE: 265

Ser Ser Asn Val Gly Asn Asn Ala
1               5

<210> SEQ ID NO 266
<211> LENGTH: 3
<212> TYPE: PRT
<213> ORGANISM: Artificial Sequence
<220> FEATURE:
<223> OTHER INFORMATION: Synthetic Construct

<400> SEQUENCE: 266

Tyr Asp Asp
1

<210> SEQ ID NO 267
<211> LENGTH: 11
<212> TYPE: PRT
<213> ORGANISM: Artificial Sequence
<220> FEATURE:
<223> OTHER INFORMATION: Synthetic Construct

<400> SEQUENCE: 267

Ala Ala Trp Asp Asp Ser Leu Asn Gly Pro Val
1               5                   10

<210> SEQ ID NO 268
<211> LENGTH: 8
<212> TYPE: PRT
<213> ORGANISM: Artificial Sequence
<220> FEATURE:
<223> OTHER INFORMATION: Synthetic Construct

<400> SEQUENCE: 268

Ser Ser Asn Val Gly Asn Asn Ala
1               5

<210> SEQ ID NO 269
<211> LENGTH: 3
<212> TYPE: PRT
<213> ORGANISM: Artificial Sequence
<220> FEATURE:
<223> OTHER INFORMATION: Synthetic Construct

<400> SEQUENCE: 269

Tyr Asp Asp
1

<210> SEQ ID NO 270
<211> LENGTH: 11
<212> TYPE: PRT
<213> ORGANISM: Artificial Sequence
<220> FEATURE:
<223> OTHER INFORMATION: Synthetic Construct

<400> SEQUENCE: 270

Ala Ala Trp Asp Asp Ser Leu Asn Gly Pro Val
1               5                   10

<210> SEQ ID NO 271
<211> LENGTH: 8
<212> TYPE: PRT
<213> ORGANISM: Artificial Sequence
<220> FEATURE:
<223> OTHER INFORMATION: Synthetic Construct

<400> SEQUENCE: 271

Ser Ser Asn Val Gly Asn Asn Ala
1               5

<210> SEQ ID NO 272
<211> LENGTH: 3
<212> TYPE: PRT
<213> ORGANISM: Artificial Sequence
<220> FEATURE:
<223> OTHER INFORMATION: Synthetic Construct

<400> SEQUENCE: 272

Tyr Asp Asp
1

<210> SEQ ID NO 273
<211> LENGTH: 11
<212> TYPE: PRT
<213> ORGANISM: Artificial Sequence
<220> FEATURE:
<223> OTHER INFORMATION: Synthetic Construct

<400> SEQUENCE: 273

Ala Ala Trp Asp Asp Ser Leu Asn Gly Pro Val
1               5                   10

<210> SEQ ID NO 274
<211> LENGTH: 8
<212> TYPE: PRT
<213> ORGANISM: Artificial Sequence
<220> FEATURE:
<223> OTHER INFORMATION: Synthetic Construct

<400> SEQUENCE: 274

Ser Ser Asn Val Gly Asn Asn Ala
1               5

```
<210> SEQ ID NO 275
<211> LENGTH: 3
<212> TYPE: PRT
<213> ORGANISM: Artificial Sequence
<220> FEATURE:
<223> OTHER INFORMATION: Synthetic Construct

<400> SEQUENCE: 275

Tyr Asp Asp
1

<210> SEQ ID NO 276
<211> LENGTH: 11
<212> TYPE: PRT
<213> ORGANISM: Artificial Sequence
<220> FEATURE:
<223> OTHER INFORMATION: Synthetic Construct

<400> SEQUENCE: 276

Ala Ala Trp Asp Asp Ser Leu Asn Gly Pro Val
1               5                   10

<210> SEQ ID NO 277
<211> LENGTH: 8
<212> TYPE: PRT
<213> ORGANISM: Artificial Sequence
<220> FEATURE:
<223> OTHER INFORMATION: Synthetic Construct

<400> SEQUENCE: 277

Ser Ser Asn Val Gly Asn Asn Ala
1               5

<210> SEQ ID NO 278
<211> LENGTH: 3
<212> TYPE: PRT
<213> ORGANISM: Artificial Sequence
<220> FEATURE:
<223> OTHER INFORMATION: Synthetic Construct

<400> SEQUENCE: 278

Tyr Asp Asp
1

<210> SEQ ID NO 279
<211> LENGTH: 11
<212> TYPE: PRT
<213> ORGANISM: Artificial Sequence
<220> FEATURE:
<223> OTHER INFORMATION: Synthetic Construct

<400> SEQUENCE: 279

Ala Ala Trp Asp Asp Ser Leu Asn Gly Pro Val
1               5                   10

<210> SEQ ID NO 280
<211> LENGTH: 8
<212> TYPE: PRT
<213> ORGANISM: Artificial Sequence
<220> FEATURE:
<223> OTHER INFORMATION: Synthetic Construct

<400> SEQUENCE: 280

Ser Ser Asn Val Gly Asn Asn Ala
1               5

<210> SEQ ID NO 281
```

```
<211> LENGTH: 3
<212> TYPE: PRT
<213> ORGANISM: Artificial Sequence
<220> FEATURE:
<223> OTHER INFORMATION: Synthetic Construct

<400> SEQUENCE: 281

Tyr Asp Asp
1

<210> SEQ ID NO 282
<211> LENGTH: 11
<212> TYPE: PRT
<213> ORGANISM: Artificial Sequence
<220> FEATURE:
<223> OTHER INFORMATION: Synthetic Construct

<400> SEQUENCE: 282

Ala Ala Trp Asp Asp Ser Leu Asn Gly Pro Val
1               5                   10

<210> SEQ ID NO 283
<211> LENGTH: 8
<212> TYPE: PRT
<213> ORGANISM: Artificial Sequence
<220> FEATURE:
<223> OTHER INFORMATION: Synthetic Construct

<400> SEQUENCE: 283

Ser Ser Asn Val Gly Asn Asn Ala
1               5

<210> SEQ ID NO 284
<211> LENGTH: 3
<212> TYPE: PRT
<213> ORGANISM: Artificial Sequence
<220> FEATURE:
<223> OTHER INFORMATION: Synthetic Construct

<400> SEQUENCE: 284

Tyr Asp Asp
1

<210> SEQ ID NO 285
<211> LENGTH: 11
<212> TYPE: PRT
<213> ORGANISM: Artificial Sequence
<220> FEATURE:
<223> OTHER INFORMATION: Synthetic Construct

<400> SEQUENCE: 285

Ala Ala Trp Asp Asp Ser Leu Asn Gly Pro Val
1               5                   10

<210> SEQ ID NO 286
<211> LENGTH: 8
<212> TYPE: PRT
<213> ORGANISM: Artificial Sequence
<220> FEATURE:
<223> OTHER INFORMATION: Synthetic Construct

<400> SEQUENCE: 286

Ser Ser Asn Val Gly Asn Asn Ala
1               5

<210> SEQ ID NO 287
<211> LENGTH: 3
```

```
<212> TYPE: PRT
<213> ORGANISM: Artificial Sequence
<220> FEATURE:
<223> OTHER INFORMATION: Synthetic Construct

<400> SEQUENCE: 287

Tyr Asp Asp
1

<210> SEQ ID NO 288
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid

<400> SEQUENCE: 288

Ile Xaa Pro Xaa Xaa Xaa Xaa Thr
1               5

<210> SEQ ID NO 289
<211> LENGTH: 556
<212> TYPE: PRT
<213> ORGANISM: Homo sapeins

<400> SEQUENCE: 289

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30

Asn Ala Val Leu Gln Cys Leu Lys Gly Thr Ser Asp Gly Pro Thr Gln
            35                  40                  45

Gln Leu Thr Trp Ser Arg Glu Ser Pro Leu Lys Pro Phe Leu Lys Leu
        50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
```

```
                    210                 215                 220
Leu Leu Ser Leu Glu Leu Lys Asp Asp Arg Pro Ala Arg Asp Met Trp
225                 230                 235                 240

Val Met Glu Thr Gly Leu Leu Pro Arg Ala Thr Ala Gln Asp Ala
                    245                 250                 255

Gly Lys Tyr Tyr Cys His Arg Gly Asn Leu Thr Met Ser Phe His Leu
                    260                 265                 270

Glu Ile Thr Ala Arg Pro Val Leu Trp His Trp Leu Leu Arg Thr Gly
                275                 280                 285

Gly Trp Lys Val Ser Ala Val Thr Leu Ala Tyr Leu Ile Phe Cys Leu
290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
                355                 360                 365

Ala Gly Leu Gly Gly Thr Ala Pro Ser Tyr Gly Asn Pro Ser Ser Asp
370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                    405                 410                 415

Asp Ser Glu Phe Tyr Glu Asn Asp Ser Asn Leu Gly Gln Asp Gln Leu
                    420                 425                 430

Ser Gln Asp Gly Ser Gly Tyr Glu Asn Pro Glu Asp Glu Pro Leu Gly
                435                 440                 445

Pro Glu Asp Glu Asp Ser Phe Ser Asn Ala Glu Ser Tyr Glu Asn Glu
450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
                515                 520                 525

Asp Ser Tyr Glu Asn Met Asp Asn Pro Asp Gly Pro Asp Pro Ala Trp
                530                 535                 540

Gly Gly Gly Gly Arg Met Gly Thr Trp Ser Thr Arg
545                 550                 555

<210> SEQ ID NO 290
<211> LENGTH: 488
<212> TYPE: PRT
<213> ORGANISM: Homo sapiens

<400> SEQUENCE: 290

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
                20                  25                  30
```

-continued

```
Asn Ala Val Leu Gln Cys Leu Lys Gly Thr Ser Asp Gly Pro Thr Gln
         35                  40                  45
Gln Leu Thr Trp Ser Arg Glu Ser Pro Leu Lys Pro Phe Leu Lys Leu
 50                  55                  60
Ser Leu Gly Leu Pro Gly Leu Gly Ile His Met Arg Pro Leu Ala Ile
 65                  70                  75                  80
Trp Leu Phe Ile Phe Asn Val Ser Gln Gln Met Gly Gly Phe Tyr Leu
                 85                  90                  95
Cys Gln Pro Gly Pro Pro Ser Glu Lys Ala Trp Gln Pro Gly Trp Thr
             100                 105                 110
Val Asn Val Glu Gly Ser Gly Glu Leu Phe Arg Trp Asn Val Ser Asp
         115                 120                 125
Leu Gly Gly Leu Gly Cys Gly Leu Lys Asn Arg Ser Ser Glu Gly Pro
130                 135                 140
Ser Ser Pro Ser Gly Lys Leu Met Ser Pro Lys Leu Tyr Val Trp Ala
145                 150                 155                 160
Lys Asp Arg Pro Glu Ile Trp Glu Gly Glu Pro Pro Cys Leu Pro Pro
                 165                 170                 175
Arg Asp Ser Leu Asn Gln Ser Leu Ser Gln Asp Leu Thr Met Ala Pro
             180                 185                 190
Gly Ser Thr Leu Trp Leu Ser Cys Gly Val Pro Pro Asp Ser Val Ser
         195                 200                 205
Arg Gly Pro Leu Ser Trp Thr His Val His Pro Lys Gly Pro Lys Ser
         210                 215                 220
Leu Leu Ser Leu Glu Leu Lys Asp Asp Arg Pro Ala Arg Asp Met Trp
225                 230                 235                 240
Val Met Glu Thr Gly Leu Leu Leu Pro Arg Ala Thr Ala Gln Asp Ala
                 245                 250                 255
Gly Lys Tyr Tyr Cys His Arg Gly Asn Leu Thr Met Ser Phe His Leu
             260                 265                 270
Glu Ile Thr Ala Arg Pro Val Leu Trp His Trp Leu Leu Arg Thr Gly
         275                 280                 285
Gly Trp Lys Val Ser Ala Val Thr Leu Ala Tyr Leu Ile Phe Cys Leu
290                 295                 300
Cys Ser Leu Val Gly Ile Leu His Leu Gln Arg Ala Leu Val Leu Arg
305                 310                 315                 320
Arg Lys Arg Lys Arg Met Thr Asp Pro Thr Arg Arg Phe Phe Lys Val
                 325                 330                 335
Thr Pro Pro Pro Gly Ser Gly Pro Gln Asn Gln Tyr Gly Asn Val Leu
             340                 345                 350
Ser Leu Pro Thr Pro Thr Ser Gly Leu Gly Arg Ala Gln Arg Trp Ala
         355                 360                 365
Ala Gly Leu Gly Gly Thr Ala Pro Ser Tyr Gly Asn Pro Ser Ser Asp
         370                 375                 380
Val Gln Ala Asp Gly Ala Leu Gly Ser Arg Ser Pro Pro Gly Val Gly
385                 390                 395                 400
Pro Glu Glu Glu Glu Gly Glu Gly Tyr Glu Glu Pro Asp Ser Glu Glu
                 405                 410                 415
Asp Ser Glu Phe Tyr Glu Asn Asp Ser Asn Leu Gly Gln Asp Gln Leu
             420                 425                 430
Ser Gln Asp Gly Ser Gly Tyr Glu Asn Pro Glu Asp Glu Pro Leu Gly
         435                 440                 445
Pro Glu Asp Glu Asp Ser Phe Ser Asn Ala Glu Ser Tyr Glu Asn Glu
```

```
                450               455               460
Asp Glu Glu Leu Thr Gln Pro Val Ala Arg Thr Met Asp Phe Leu Ser
465                 470               475                 480

Pro His Gly Ser Ala Trp Asp Pro
                485
```

<210> SEQ ID NO 291
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(8)
<223> OTHER INFORMATION: X2 is F, G, Y or V, X3 is S or T, X5 is S or T,
      X7 is N or Y, and X8 is A, W or Y

<400> SEQUENCE: 291

```
Gly Xaa Xaa Phe Xaa Ser Xaa Xaa
1               5
```

<210> SEQ ID NO 292
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(7)
<223> OTHER INFORMATION: X2 is S, D or Y, X4 is E, S, G or I, X5 is D, F
      or V, X6 is G or S, and X7 is K, E, Y, D or T

<400> SEQUENCE: 292

```
Ile Xaa Pro Xaa Xaa Xaa Xaa Thr
1               5
```

<210> SEQ ID NO 293
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feaure
<222> LOCATION: (4)..(8)
<223> OTHER INFORMATION: X4 is I or V, X6 is N, S or T, X7 is N, H or K,
      X8 is Y, A or T

<400> SEQUENCE: 293

```
Ser Ser Asn Xaa Gly Xaa Xaa Xaa
1               5
```

<210> SEQ ID NO 294
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: X5 is K or E

<400> SEQUENCE: 294

```
Asn Ile Gly Ser Xaa Ser
1               5
```

```
<210> SEQ ID NO 295
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: X1 is D, E, S, R or Y, X2 is N or D, X3 is N,
      Y, S or D

<400> SEQUENCE: 295

Xaa Xaa Xaa
1

<210> SEQ ID NO 296
<211> LENGTH: 245
<212> TYPE: PRT
<213> ORGANISM: Artificial Sequence
<220> FEATURE:
<223> OTHER INFORMATION: Synthetic Construct

<400> SEQUENCE: 296

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 297
<211> LENGTH: 6
```

```
<212> TYPE: PRT
<213> ORGANISM: Mus musculus

<400> SEQUENCE: 297

Gln Asp Ile Ser Lys Tyr
1               5

<210> SEQ ID NO 298
<211> LENGTH: 3
<212> TYPE: PRT
<213> ORGANISM: Mus musculus

<400> SEQUENCE: 298

His Thr Ser
1

<210> SEQ ID NO 299
<211> LENGTH: 9
<212> TYPE: PRT
<213> ORGANISM: Mus musculus

<400> SEQUENCE: 299

Gln Gln Gly Asn Thr Leu Pro Tyr Thr
1               5

<210> SEQ ID NO 300
<211> LENGTH: 8
<212> TYPE: PRT
<213> ORGANISM: Mus musculus

<400> SEQUENCE: 300

Gly Val Ser Leu Pro Asp Tyr Gly
1               5

<210> SEQ ID NO 301
<211> LENGTH: 7
<212> TYPE: PRT
<213> ORGANISM: Mus musculus

<400> SEQUENCE: 301

Ile Trp Gly Ser Glu Thr Thr
1               5

<210> SEQ ID NO 302
<211> LENGTH: 14
<212> TYPE: PRT
<213> ORGANISM: Mus musculus

<400> SEQUENCE: 302

Ala Lys His Tyr Tyr Gly Gly Ser Tyr Ala Met Asp Tyr
1               5                   10
```